(12) United States Patent
Bös

(10) Patent No.: US 8,815,892 B2
(45) Date of Patent: *Aug. 26, 2014

(54) P2X7R ANTAGONISTS AND THEIR USE

(75) Inventor: Michael Bös, Munich (DE)

(73) Assignee: Affectis Pharmaceuticals AG, Martinsried (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/556,988

(22) Filed: Jul. 24, 2012

(65) Prior Publication Data

US 2013/0197046 A1   Aug. 1, 2013

Related U.S. Application Data

(63) Continuation-in-part of application No. 12/411,090, filed on Mar. 25, 2009, now Pat. No. 8,232,290.

(60) Provisional application No. 61/041,050, filed on Mar. 31, 2008.

(30) Foreign Application Priority Data

Mar. 25, 2008  (EP) ..................................... 08005532

(51) Int. Cl.
*A61K 31/44*   (2006.01)

(52) U.S. Cl.
USPC ........................................... 514/300; 548/469

(58) Field of Classification Search
USPC ........................................... 514/300; 548/469
See application file for complete search history.

(56) References Cited

U.S. PATENT DOCUMENTS

| | | | |
|---|---|---|---|
| 3,705,175 A | 12/1972 | Magdanyi | |
| 7,402,602 B2 | 7/2008 | Bigg | |
| 7,919,503 B2 | 4/2011 | Boes | |
| 8,232,290 B2* | 7/2012 | Bos .............................. | 514/300 |
| 2012/0190680 A1* | 7/2012 | Bakthavatchalam et al. ........................ | 514/234.5 |

FOREIGN PATENT DOCUMENTS

| | | |
|---|---|---|
| JP | 2005-534669 A | 11/2005 |
| WO | 99/29660 A1 | 6/1999 |
| WO | 01/58869 A2 | 8/2001 |
| WO | 03/106462 A1 | 12/2003 |
| WO | 2004/074275 A1 | 9/2004 |

OTHER PUBLICATIONS

Bakthavatchalam et al. CAS: 150: 260207, 2009.*
European Search Report mailed Aug. 4, 2009, issued in related Application No. EP 09004301.9, filed Mar. 25, 2009, 3 pages.
International Search Report mailed Aug. 20, 2009, in related International Application No. PCT/EP2009/002189, filed Mar. 25, 2009, 5 pages.
Romagnoli, R., et al., "Recent Progress in the Discovery of Antagonists Acting at P2X$_7$ Receptor," Expert Opinion on Therapeutic Patents 15(3):271-287, Mar. 2005.
Agresti, C., et al., "ATP Regulates Oligodendrocyte Progenitor Migration, Proliferation, and Differentiation: Involvement of Metabotropic P2 Receptors," Brain Research Reviews 48(2):157-165, Apr. 2005.
Carroll, W.A., et al., "Novel and Potent 3-(2,3-Dichlorophenyl)-4-(benzyl)-4H-1,2,4-triazole P2X$_7$ Antagonists," Bioorganic & Medicinal Chemistry Letters 17(14):4044-4048, Jul. 15, 2007.
Chen, L., and C.F. Brosnan, "Exacerbation of Experimental Autoimmune Encephalomyelitis in P2X$_7$R-/- Mice: Evidence for Loss of Apoptotic Activity in Lymphocytes," Journal of Immunology 176(5):3115-3126, Mar. 1, 2006.
Cherian, P.P., et al., "Mechanical Strain Opens Connexin 43 Hemichannels in Osteocytes: A Novel Mechanism for the Release of Prostaglandin," Molecular Biology of the Cell 16(7):3100-3106, Jul. 2005.
Chessell, I.P., et al., "Disruption of the P2X7 Purinoceptor Gene Abolishes Chronic Inflammatory and Neuropathic Pain," Pain 114(3):386-396, Apr. 2005.
Collo, G., et al., "Tissue Distribution of the P2X$_7$ Receptor," Neuropharmacology 36(9):1277-1283, Sep. 1997.
Donnelly-Roberts, D.L., and M.F. Jarvis, "Discovery of P2X$_7$ Receptor-Selective Antagonists Offers New Insights Into P2X$_7$ Receptor Function and Indicates a Role in Chronic Pain States," British Journal of Pharmacology 151(5):571-579, Jul. 2007.
Frankish, H., "Boosting Brain Endocannabinoids in Multiple Sclerosis," Lancet Neurology 5(5):388, May 2006.
Fulgenzi, A., et al., "Periodate Oxidized ATP (oATP) Reduces Hyperalgesia in Mice: Involvement of P2X$_7$ Receptors and Implications for Therapy," International Journal of Immunopathology & Pharmacology 21(1):61-71, Jan.-Mar. 2008.
Gallagher, J.A., "ATP P2 Receptors and Regulation of Bone Effector Cells," Journal of Musculoskeletal Neuronal Interactions 4(2):125-127, Jun. 2004.
Gartland, A., et al., "Blockade of the Pore-Forming P2X$_7$ Receptor Inhibits Formation of Multinucleated Human Osteoclasts In Vitro," Calcified Tissue International 73(4):361-369, Oct. 2003.
Gartland, A., et al., "Expression of a P2X$_7$ Receptor by a Subpopulation of Human Osteoblasts," Journal of Bone & Mineral Research 16(5):846-856, May 2001.
Gartland, A., et al., "Multinucleated Osteoclast Formation In Vivo and In Vitro by P2X$_7$ Receptor-Deficient Mice," Critical Reviews in Eukaryotic Gene Expression 13(2-4):243-253, 2003.
Gartland, A., et al., "P2 Receptors in Bone—Modulation of Osteoclast Formation and Activity via P2X$_7$ Activation," Critical Reviews in Eukaryotic Gene Expression 13(2-4):237-242, 2003.

(Continued)

Primary Examiner — Rei-tsang Shiao
(74) Attorney, Agent, or Firm — Christensen O'Connor Johnson Kindness PLLC

(57) ABSTRACT

The present application is directed to novel P2X7R antagonists that are indol-3-carboxamide or azaindole-3-carboxamide compounds, pharmaceutical compositions comprising the same and their use for the prophylactic or therapeutic treatment of diseases mediated by P2X7R activity.

16 Claims, 5 Drawing Sheets

(56) References Cited

OTHER PUBLICATIONS

Gunosewoyo, H., et al., "Molecular Probes for $P2X_7$ Receptor Studies," Current Medicinal Chemistry 14(14):1505-1523, 2007.

Honore, P., et al., "A-740003 [N-(1-{[(cyanoimino)(5-quinolinylamino) methyl]amino}-2,2-dimethylpropyl)-2-(3,4-dimethoxyphenyl)acetamide], a Novel and Selective $P2X_7$ Receptor Antagonist, Dose-Dependently Reduces Neuropathic Pain in the Rat," Journal of Pharmacology & Experimental Therapeutics 319(3):1376-1385, Dec. 2006.

Jørgensen, N.R., "Short-Range Intercellular Calcium Signaling in Bone," APMIS Supplementum (118):1-36, 2005.

Jørgensen, N.R., et al., "Intercellular Calcium Signaling Occurs Between Human Osteoblasts and Osteoclasts and Requires Activation of Osteoclast P2X7 Receptors," Journal of Biological Chemistry 277(9):7574-7580, Mar. 1, 2002.

Ke, H.Z., "In Vivo Characterization of Skeletal Phenotype of Genetically Modified Mice," Journal of Bone & Mineral Metabolism 23(Suppl):84-89, 2005.

Ke, H.Z., et al., "Deletion of the $P2X_7$ Nucleotide Receptor Reveals Its Regulatory Roles in Bone Formation and Resorption," Molecular Endocrinology 17(7):1356-67, Jul. 2003.

Korcok, J., et al., "Extracellular Nucleotides Act Through $P2X_7$ Receptors to Activate NF-κB in Osteoclasts," Journal of Bone and Mineral Research 19(4):642-651, Apr. 2004.

Li, J. et al., "The $P2X_7$ Nucleotide Receptor Mediates Skeletal Mechanotransduction," Journal of Biological Chemistry 280(52):42952-42959, Dec. 2005.

Matute, C., et al., "$P2X_7$ Receptor Blockade Prevents ATP Excitotoxicity in Oligodendrocytes and Ameliorates Experimental Autoimmune Encephalomyelitis," Journal of Neuroscience 27(35):9525-9533, Aug. 2007.

McGaraughty, S., et al., "$P2X_7$-Related Modulation of Pathological Nociception in Rats," Neuroscience 146(4):1817-1828, Jun. 2007.

Naemsch, L.N., et al., "Activity-Dependent Development of $P2X_7$ Current and $Ca^{2+}$•Entry in Rabbit Osteoclasts," Journal of Biological Chemistry 276(42):39107-39114, Oct. 2001.

Narcisse, L., et al., "The Cytokine IL-1β Transiently Enhances $P2X_7$ Receptor Expression and Function in Human Astrocytes," Glia 49(2):245-258, Jan. 2005.

Nelson, D.W., et al., "Structure—Activity Relationship Studies on a Series of Novel, Substituted 1-Benzyl-5-phenyltetrazole $P2X_7$ Antagonists," Journal of Medicinal Chemistry 49(12):3659-3666, Jun. 2006.

Ohlendorff, S.D., et al., "Single Nucleotide Polymorphisms in the $P2x_7$ Gene Are Associated to Fracture Risk and to Effect of Estrogen Treatment," Pharmacogenetics and Genomics 17(7):555-567, Jul. 2007.

Panupinthu, N., et al., "P2X7 Nucleotide Receptors Mediate Blebbing in Osteoblasts Through a Pathway Involving Lysophosphatidic Acid," Journal of Biological Chemistry 282(5):3403-3412, Feb. 2007.

Penolazzi, L., et al., "N-Arylpiperazine Modified Analogues of the $P2X_7$ Receptor KN-62 Antagonist Are Potent Inducers of Apoptosis of Human Primary Osteoclasts," Journal of Biomedical Science 12(6):1013-1020, Dec. 2005.

Raouf, R., et al., "Differential Regulation of Microglial P2X4 and P2X7 ATP Receptors Following LPS-Induced Activation," Neuropharmacology 53(4):496-504, Sep. 2007.

Sharp, A.J., et al., "P2x7 Deficiency Suppresses Development of Experimental Autoimmune Encephalomyelitis," Journal of Neuroinflammation 5:33, Aug. 2008,13 pages.

Witting, A., et al., "Experimental Autoimmune Encephalomyelitis Disrupts Endocannabinoid-Mediated Neuroprotection," Proceedings of the National Academy of Sciences of the United States of America (PNAS) 103(16):6362-6367, Apr. 2006.

Yiangou, Y., et al., "COX-2, CB2 and $P2X_7$-Immunoreactivities Are Increased in Activated Microglial Cells/Macrophages of Multiple Sclerosis and Amyotrophic Lateral Sclerosis Spinal Cord," BMC Neurology 6:12, Mar. 2006, 14 pages.

Notice of Rejection mailed Jul. 8, 2013, issued in corresponding Japanese Patent Application No. 2011-501146, filed Mar. 25, 2009, 4 pages.

\* cited by examiner

P2X7R ANTAGONISTS AND THEIR USE

CROSS-REFERENCES TO RELATED APPLICATIONS

This application is a continuation-in-part of U.S. patent application Ser. No. 12/411,090, filed Mar. 25, 2009, now U.S. Pat. No. 8,232,290, which claims the benefit of U.S. Provisional Application No. 61/041,050, filed Mar. 31, 2008, and claims priority to European Application No. 08 00 5532.0, filed Mar. 25, 2008, each expressly incorporated herein by reference in its entirety.

The present application relates to novel P2X7R antagonists that are indol-3 carboxamide and azaindol-3 carboxamide compounds, pharmaceutical compositions comprising these compounds and to their use in the prophylactic and therapeutic treatment of diseases and disorders mediated by P2X7R.

BACKGROUND

P2X7R is an ATP-gated ion channel belonging to the P2X ionotropic channel family. The gene was first isolated from rat brain (Surprenant et al. (1996) 272:735-738) and subsequently from a human monocyte library (Rassendren et al. (1997) J. Biol. Chem. 272:5482-5486; Genbank accession numbers NM_002562, Y09561) by virtue of its sequence homology with the other members of the P2X family. It was later found that P2X7R corresponded to the unidentified P2Z receptor which mediates the permeabilising action of ATP on mast cells and macrophages (Dahlqvist and Diamant (1974) Acta Physiol. Scand. 34:368-384; Steinberg and Silverstein (1987) J. Biol. Chem. 262:3118-3122; Gordon (1986) Biochem. J. 233:309-319). The P2X7R has two hydrophobic membrane-spanning domains, an extracellular loop, and forms transmembrane ion channels. P2X7R bears a pharmacological profile markedly different from other P2X homo- or heteromers (North and Surprenant (2000) Annual Rev. Pharmacology Toxicology 40:563-580). P2X7R requires levels of ATP in excess of 1 mM to achieve activation, whereas other P2X receptors activate at ATP concentrations of ≤100 µM (Steinberg et al. (1987) J. Biol. Chem. 262:8884-8888; Greenberg et al. (1988) J. Biol. Chem. 263:10337-10343). While all P2X receptors demonstrate non-selective channel-like properties following ligation, the channels formed by the P2X7R can rapidly transform into pores that can allow the passage of molecules of up to 900 Dalton (Virginio et al. (1999) J. Physiol. 519:335-346).

P2X7R is expressed in haematopoietic cells, mast cells, lymphocytes, erythrocytes, fibroblast, Langerhans cells, and macrophages (Surprenant et al., 1996, Science 272:3118-3122). In the central nervous system, P2X7R expression has been reported in glial cells, Schwann cells, astrocytes, as well as in neurons (Ferrari et al. (1996) J. Immunol. 156:1531-1539; Collo et al. (1997) Neuropharmacology 36: 1277-1283; Anderson and Nedergaard (2006) Trends Neuroscien 29: 257-262).

P2X7R is involved in the regulation of the immune function and inflammatory response. Activation of P2X7R by ATP in macrophages is associated with mitogenic stimulation of T cells (Baricordi et al. (1996) Blood 87:682-690), the release of cytokines (Griffiths et al. (1995) J. Immol. 154:2821-2828), and formation of macrophage polykarions (Falzoni et al. (1995) J. Clin. Invest. 95:1207-1216). P2X7R is involved in the processing and release of active interleukin-1beta (IL-1β) from proinflammatory cells (Perregaux and Gabel (1998) J Biol Chem 269:15195-15203; Ferrari et al., (2006) J Immunol 176: 3877-3883). Stimulation of the P2X7R by ATP can also result in apoptosis and cell death by triggering the formation of non-selective plasma membrane pores (Di Virgilio et al. (1998) Cell Death Differ. 5:191-199).

Upregulation of P2X7R has been observed during ischemic damage and necrosis induced by occlusion of middle cerebral artery in rat brain (Collo et al. (1997) Neuropharmacol 36:1277-1283). Recent studies indicate a role of P2X7R in the generation of superoxide in microglia, and upregulation of P2X7R has been detected around amyloid plaques in a transgenic mouse models for Alzheimer's disease (Parvathenani et al. (2003) J Biol Chem 278:13300-13317) and in multiple sclerosis lesions from autopsy brain sections (Narcisse et al. (2005) Glia, 49:245-258).

Studies from mice lacking P2X7R resulted in absence of inflammatory and neuropathic hypersensitivity to mechanical and thermal stimuli, indicating a link between P2X7R and inflammatory and neuropathic pain (Chessell et al. (2005) Pain 114:386-396). Antagonists of P2X7R significantly improved functional recovery and decreased cell death in spinal cord injury in animal models (Wang et al. (2004) Nature Med 10:B21-B27).

Compounds which modulate P2X7R have been reported. For example, Brilliant Blue (Jiang et al., Mol. Pharmacol. 58 (2000), 82-88), the isoquinolines 1-[N,O-Bis(5-isoquinolinesulfonyl)-N-methyl-L-tyrosyl]-4-phenylpiperazine and N-[1-[N-methyl-p-(5 isoquinolinesulfonyl)benzyl]-2-(4 phenylpiperazine)ethyl]-5-isoquinolinesulfonamide (Humphreys et al., Mol. Pharmacol., 54 (1998), 22-32), adamantane derivatives (WO 99/29660, WO 99/29661, WO 00/61569, WO 01/42194, WO 01/44170, WO 01/44213, WO 01/94338, WO 03/041707, WO 03/042190, WO 03/080579, WO 04/074224, WO 05/014529, WO 06/025783, WO 06/059945), piperidine and piperazine compounds (WO 01/44213, WO 01/46200, WO 08/005,368), benzamide and heteroarylamide compounds (WO 03/042191, WO 04/058731, WO 04/058270, WO 04/099146, WO 05/019182, WO 06/003500, WO 06/003513, WO 06/067444), substituted tyrosine derivatives (WO 00/71529, WO 03/047515, WO 03/059353), imidazole compounds (WO 05/014555), amino-tetrazoles compounds (WO 05/111003), cyanoamidine (WO 06/017406), bicycloheteroaryl derivatives (WO 05/009968, WO 06/102588, WO 06/102610, WO 07/028, 022, WO 07/109,154, WO 07/109,160, WO 07/109,172, WO 07/109,182, WO 07/109,192, WO 07/109,201), acylhydrazide (WO 06/110516), and other examples (WO 99/29686, WO 04/106305, WO 05/039590, WO 06/080884, WO 06/086229, WO 06/136004, WO 07/025,366, WO 07/056,046, WO 07/056,091, WO 07/141,267, WO 07/141, 269, WO 08/003,697) are antagonists of P2X7R while Oxidized ATP (oATP) acts as an irreversible inhibitor of the receptor (Chen et al., J. Biol. Chem., 268 (1993), 8199-8203).

Consequently, there is strong evidence that compounds acting on P2X7R can be used in the treatment of pain, inflammatory processes, and degenerative conditions associated with disease states such as rheumatoid arthritis, osteoarthritis, psoriasis, allergic dermatitis, asthma, chronic obstructive pulmonary disease, airways hyper-responsiveness, septic shock, glomerulonephritis, irritable bowel disease, inflammatory bowel disease, Crohn's disease, ulcerative colitis, atherosclerosis, growth and metastases of malignant cells, myoblastic leukaemia, diabetes, Alzheimer's disease, Parkinson's disease, multiple sclerosis, glaucoma, depression, bipolar affective disorders, anxiety, meningitis, traumatic brain injury, acute spinal cord injury, neuropathic pain, osteoporosis, burn injury, ischemic heart disease, myocardial infarction, stroke, and varicose veins.

Thus, the object on the present invention is to provide a novel series of compound which can inhibit P2X7R activity and can be used in the treatment of the above mentioned diseases.

DETAILED DESCRIPTION OF THE INVENTION

The present invention relates to novel P2X7R antagonists that are indol-3 carboxamide and azaindol-3 carboxamide compounds represented by the general formula (I):

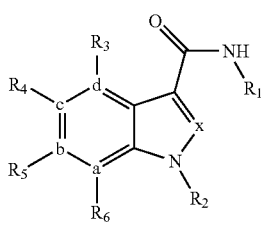

wherein,
$R_1$ is a mono- or bicycloalkylalkyl group;
$R_2$ is selected from straight or branched $C_1$-$C_5$ alkyl which may optionally substituted with —OH, $C_1$-$C_5$ alkoxy, $NH_2$—, $N(R_a)_2$—, $NHR_a$—, CN—, $CF_3$, halogen (i.e. Cl, F, Br or I), piperidino, morpholino, pyrrolidino, 5H-tetrazolylpropyl, methylcarbamoyl, dimethylcarbamoyl, or ethylmethylcarbamoyl, wherein Ra is hydrogen or $C_1$-$C_5$ alkyl;
$R_3$, $R_4$, $R_5$, $R_6$ are at each occurrence independently selected from hydrogen, halogen (i.e. Cl, F, Br or I), methyl, hydroxy, methoxy, cyano, or trifluoromethyl;
a, b, c, d, x are at each occurrence independently selected from carbon, or nitrogen; or a pharmaceutically acceptable salt or solvate thereof.

Compounds of Formula (I), wherein $R_1$ is a mono- or bicycloalkylalkyl group selected from cyclopentylmethyl, cyclopentylethyl, cyclohexylmethyl, cyclohexylethyl, cycloheptylmethyl, cycloheptylethyl, bicyclo[2.2.2]octan-1-ylmethyl and bicyclo[2.2.2]octan-1-ylethyl are preferred.

Compounds as disclosed above, wherein $R_2$ is $C_1$-$C_5$ alkyl or $C_2$-$C_5$ hydroxyalkyl are also preferred.

Furthermore, it is preferred that at least two of $R_3$, $R_4$, $R_5$ and $R_6$ are hydrogen. Additionally, it is preferred that a, b, c, and d are C or one of a, b, c and d is N. Examples of novel indol-3 carboxamide and azaindol-3 carboxamide compounds are disclosed in examples 6-295.

The invention further relates to a compound of Formula (I) or a pharmaceutically acceptable salt or solvate thereof, being:
N-(cyclopentylmethyl)-1-methyl-1H-indole-3-carboxamide,
4-chloro-N-(cyclopentylmethyl)-1-methyl-1H-indole-3-carboxamide,
N-(cyclopentylmethyl)-4-fluoro-1-methyl-1H-indole-3-carboxamide,
4-bromo-N-(cyclopentylmethyl)-1-methyl-1H-indole-3-carboxamide,
N-(cyclopentylmethyl)-1,4-dimethyl-1H-indole-3-carboxamide,
N-(cyclopentylmethyl)-4-fluoro-1-(2-hydroxyethyl)-1H-indole-3-carboxamide,
4-chloro-N-(cyclopentylmethyl)-1-(2-hydroxyethyl)-1H-indole-3-carboxamide,
4-bromo-N-(cyclopentylmethyl)-1-(2-hydroxyethyl)-1H-indole-3-carboxamide,
N-(cyclohexylmethyl)-1-methyl-1H-indole-3-carboxamide,
4-chloro-N-(cyclohexylmethyl)-1-methyl-1H-indole-3-carboxamide,
N-(cyclohexylmethyl)-4-fluoro-1-methyl-1H-indole-3-carboxamide,
4-bromo-N-(cyclohexylmethyl)-1-methyl-1H-indole-3-carboxamide,
N-(cyclohexylmethyl)-1,4-dimethyl-1H-indole-3-carboxamide,
N-(cyclohexylmethyl)-4-fluoro-1-(2-hydroxyethyl)-1H-indole-3-carboxamide,
4-chloro-N-(cyclohexylmethyl)-1-(2-hydroxyethyl)-1H-indole-3-carboxamide,
4-bromo-N-(cyclohexylmethyl)-1-(2-hydroxyethyl)-1H-indole-3-carboxamide,
N-(cycloheptylmethyl)-1-methyl-1H-indole-3-carboxamide,
4-chloro-N-(cycloheptylmethyl)-1-methyl-1H-indole-3-carboxamide,
N-(cycloheptylmethyl)-4-fluoro-1-methyl-1H-indole-3-carboxamide,
4-bromo-N-(cycloheptylmethyl)-1-methyl-1H-indole-3-carboxamide,
N-(cycloheptylmethyl)-1,4-dimethyl-1H-indole-3-carboxamide,
N-(cycloheptylmethyl)-4-methoxy-1-methyl-1H-indole-3-carboxamide,
4-cyano-N-(cycloheptylmethyl)-1-methyl-1H-indole-3-carboxamide,
N-(cycloheptylmethyl)-1-methyl-4-(trifluoromethyl)-1H-indole-3-carboxamide,
N-(cycloheptylmethyl)-1-ethyl-1H-indole-3-carboxamide,
N-(cycloheptylmethyl)-1-ethyl-4-fluoro-1H-indole-3-carboxamide,
4-chloro-N-(cycloheptylmethyl)-1-ethyl-1H-indole-3-carboxamide,
4-bromo-N-(cycloheptylmethyl)-1-ethyl-1H-indole-3-carboxamide,
N-(cycloheptylmethyl)-1-ethyl-4-methyl-1H-indole-3-carboxamide,
N-(cycloheptylmethyl)-1-ethyl-4-methoxy-1H-indole-3-carboxamide,
4-cyano-N-(cycloheptylmethyl)-1-ethyl-1H-indole-3-carboxamide,
N-(cycloheptylmethyl)-1-ethyl-4-(trifluoromethyl)-1H-indole-3-carboxamide,
N-(cycloheptylmethyl)-1-propyl-1H-indole-3-carboxamide,
N-(cycloheptylmethyl)-4-fluoro-1-propyl-1H-indole-3-carboxamide,
4-chloro-N-(cycloheptylmethyl)-1-propyl-1H-indole-3-carboxamide,
4-bromo-N-(cycloheptylmethyl)-1-propyl-1H-indole-3-carboxamide,
N-(cycloheptylmethyl)-4-methyl-1-propyl-1H-indole-3-carboxamide,
N-(cycloheptylmethyl)-4-methoxy-1-propyl-1H-indole-3-carboxamide,
4-cyano-N-(cycloheptylmethyl)-1-propyl-1H-indole-3-carboxamide,
N-(cycloheptylmethyl)-1-propyl-4-(trifluoromethyl)-1H-indole-3-carboxamide,
4-chloro-N-(cycloheptylmethyl)-1-isopropyl-1H-indole-3-carboxamide, 4-bromo-N-(cycloheptylmethyl)-1-isopropyl-1H-indole-3-carboxamide,
N-(cycloheptylmethyl)-1-isopropyl-4-methyl-1H-indole-3-carboxamide,
4-chloro-N-(cycloheptylmethyl)-1-isopropyl-1H-indole-3-carboxamide,
4-bromo-N-(cycloheptylmethyl)-1-isopropyl-1H-indole-3-carboxamide,
N-(cycloheptylmethyl)-1-isopropyl-4-methyl-1H-indole-3-carboxamide,
4-chloro-N-(cycloheptylmethyl)-1-isobutyl-1H-indole-3-carboxamide,
4-bromo-N-(cycloheptylmethyl)-1-isobutyl-1H-indole-3-carboxamide,
N-(cycloheptylmethyl)-1-isobutyl-4-methyl-1H-indole-3-carboxamide,
N-(cycloheptylmethyl)-1-(2-hydroxyethyl)-1H-indole-3-carboxamide,
N-(cycloheptylmethyl)-4-fluoro-1-(2-hydroxyethyl)-1H-indole-3-carboxamide,
4-chloro-N-(cycloheptylmethyl)-1-(2-hydroxyethyl)-1H-indole-3-carboxamide,
4-bromo-N-(cycloheptylmethyl)-1-(2-hydroxyethyl)-1H-indole-3-carboxamide,
N-(cycloheptylmethyl)-1-(2-hydroxyethyl)-4-methyl-1H-indole-3-carboxamide,
N-(cycloheptylmethyl)-1-(2-hydroxyethyl)-4-methoxy-1H-indole-3-carboxamide,
4-cyano-N-(cycloheptylmethyl)-1-(2-hydroxyethyl)-1H-indole-3-carboxamide,
N-(cycloheptylmethyl)-1-(2-hydroxyethyl)-4-(trifluoromethyl)-1H-indole-3-carboxamide,
1-butyl-N-(cycloheptylmethyl)-1H-indole-3-carboxamide,
1-butyl-N-(cycloheptylmethyl)-4-fluoro-1H-indole-3-carboxamide,
1-butyl-4-chloro-N-(cycloheptylmethyl)-1H-indole-3-carboxamide,
4-bromo-1-butyl-N-(cycloheptylmethyl)-1H-indole-3-carboxamide,
1-butyl-N-(cycloheptylmethyl)-4-methyl-1H-indole-3-carboxamide,
N-(cycloheptylmethyl)-4-fluoro-1-(3-hydroxypropyl)-1H-indole-3-carboxamide,
4-chloro-N-(cycloheptylmethyl)-1-(3-hydroxypropyl)-1H-indole-3-carboxamide,
4-bromo-N-(cycloheptylmethyl)-1-(3-hydroxypropyl)-1H-indole-3-carboxamide,
N-(bicyclo[2.2.2]octan-1-ylmethyl)-1-methyl-1H-indole-3-carboxamide,
N-(bicyclo[2.2.2]octan-1-ylmethyl)-4-chloro-1-methyl-1H-indole-3-carboxamide,
N-(bicyclo[2.2.2]octan-1-ylmethyl)-4-fluoro-1-methyl-1H-indole-3-carboxamide,
N-(bicyclo[2.2.2]octan-1-ylmethyl)-4-bromo-1-methyl-1H-indole-3-carboxamide,
N-(bicyclo[2.2.2]octan-1-ylmethyl)-1,4-dimethyl-1H-indole-3-carboxamide,
N-(bicyclo[2.2.2]octan-1-ylmethyl)-4-methoxy-1-methyl-1H-indole-3-carboxamide,
N-(bicyclo[2.2.2]octan-1-ylmethyl)-4-cyano-1-methyl-1H-indole-3-carboxamide,
N-(bicyclo[2.2.2]octan-1-ylmethyl)-1-methyl-4-(trifluoromethyl)-1H-indole-3-carboxamide,
N-(bicyclo[2.2.2]octan-1-ylmethyl)-1-ethyl-1H-indole-3-carboxamide,
N-(bicyclo[2.2.2]octan-1-ylmethyl)-1-ethyl-4-fluoro-1H-indole-3-carboxamide,
N-(bicyclo[2.2.2]octan-1-ylmethyl)-4-chloro-1-ethyl-1H-indole-3-carboxamide,
N-(bicyclo[2.2.2]octan-1-ylmethyl)-4-bromo-1-ethyl-1H-indole-3-carboxamide,
N-(bicyclo[2.2.2]octan-1-ylmethyl)-1-ethyl-4-methyl-1H-indole-3-carboxamide,
N-(bicyclo[2.2.2]octan-1-ylmethyl)-1-ethyl-4-methoxy-1H-indole-3-carboxamide,
N-(bicyclo[2.2.2]octan-1-ylmethyl)-4-cyano-1-ethyl-1H-indole-3-carboxamide,
N-(bicyclo[2.2.2]octan-1-ylmethyl)-1-ethyl-4-(trifluoromethyl)-1H-indole-3-carboxamide,
N-(bicyclo[2.2.2]octan-1-ylmethyl)-1-propyl-1H-indole-3-carboxamide,
N-(bicyclo[2.2.2]octan-1-ylmethyl)-4-fluoro-1-propyl-1H-indole-3-carboxamide,
N-(bicyclo[2.2.2]octan-1-ylmethyl)-4-chloro-1-propyl-1H-indole-3-carboxamide,
N-(bicyclo[2.2.2]octan-1-ylmethyl)-4-bromo-1-propyl-1H-indole-3-carboxamide,
N-(bicyclo[2.2.2]octan-1-ylmethyl)-4-methyl-1-propyl-1H-indole-3-carboxamide,
N-(bicyclo[2.2.2]octan-1-ylmethyl)-4-methoxy-1-propyl-1H-indole-3-carboxamide,
N-(bicyclo[2.2.2]octan-1-ylmethyl)-4-cyano-1-propyl-1H-indole-3-carboxamide,
N-(bicyclo[2.2.2]octan-1-ylmethyl)-1-propyl-4-(trifluoromethyl)-1H-indole-3-carboxamide,
N-(bicyclo[2.2.2]octan-1-ylmethyl)-1-isopropyl-1H-indole-3-carboxamide,
N-(bicyclo[2.2.2]octan-1-ylmethyl)-4-fluoro-1-isopropyl-1H-indole-3-carboxamide,
N-(bicyclo[2.2.2]octan-1-ylmethyl)-4-chloro-1-isopropyl-1H-indole-3-carboxamide,
N-(bicyclo[2.2.2]octan-1-ylmethyl)-4-bromo-1-isopropyl-1H-indole-3-carboxamide,
N-(bicyclo[2.2.2]octan-1-ylmethyl)-1-isopropyl-4-methyl-1H-indole-3-carboxamide,
N-(bicyclo[2.2.2]octan-1-ylmethyl)-4-fluoro-1-isobutyl-1H-indole-3-carboxamide,
N-(bicyclo[2.2.2]octan-1-ylmethyl)-4-chloro-1-isobutyl-1H-indole-3-carboxamide,
N-(bicyclo[2.2.2]octan-1-ylmethyl)-4-bromo-1-isobutyl-1H-indole-3-carboxamide,
N-(bicyclo[2.2.2]octan-1-ylmethyl)-1-isobutyl-4-methyl-1H-indole-3-carboxamide,
N-(bicyclo[2.2.2]octan-1-ylmethyl)-1-(2-hydroxyethyl)-1H-indole-3-carboxamide,
N-(bicyclo[2.2.2]octan-1-ylmethyl)-4-fluoro-1-(2-hydroxyethyl)-1H-indole-3-carboxamide,
N-(bicyclo[2.2.2]octan-1-ylmethyl)-4-chloro-1-(2-hydroxyethyl)-1H-indole-3-carboxamide,
N-(bicyclo[2.2.2]octan-1-ylmethyl)-4-bromo-1-(2-hydroxyethyl)-1H-indole-3-carboxamide,
N-(bicyclo[2.2.2]octan-1-ylmethyl)-1-(2-hydroxyethyl)-4-methyl-1H-indole-3-carboxamide,
N-(bicyclo[2.2.2]octan-1-ylmethyl)-1-(2-hydroxyethyl)-4-methoxy-1H-indole-3-carboxamide,
N-(bicyclo[2.2.2]octan-1-ylmethyl)-4-cyano-1-(2-hydroxyethyl)-1H-indole-3-carboxamide,
N-(bicyclo[2.2.2]octan-1-ylmethyl)-1-(2-hydroxyethyl)-4-(trifluoromethyl)-1H-indole-3-carboxamide,
N-(bicyclo[2.2.2]octan-1-ylmethyl)-1-butyl-4-fluoro-1H-indole-3-carboxamide,
N-(bicyclo[2.2.2]octan-1-ylmethyl)-1-butyl-4-chloro-1H-indole-3-carboxamide, N-(bicyclo[2.2.2]octan-1-ylmethyl)-4-bromo-1-butyl-1H-indole-3-carboxamide,
N-(bicyclo[2.2.2]octan-1-ylmethyl)-1-butyl-4-methyl-1H-indole-3-carboxamide,
N-(bicyclo[2.2.2]octan-1-ylmethyl)-4-fluoro-1-(3-hydroxypropyl)-1H-indole-3-carboxamide,
N-(bicyclo[2.2.2]octan-1-ylmethyl)-4-chloro-1-(3-hydroxypropyl)-1H-indole-3-carboxamide,
N-(bicyclo[2.2.2]octan-1-ylmethyl)-4-bromo-1-(3-hydroxypropyl)-1H-indole-3-carboxamide,
N-(bicyclo[2.2.2]octan-1-ylmethyl)-1-(3-hydroxypropyl)-4-methyl-1H-indole-3-carboxamide,
4-chloro-N-(2-cyclohexylethyl)-1-methyl-1H-indole-3-carboxamide,
N-(2-cyclohexylethyl)-4-fluoro-1-methyl-1H-indole-3-carboxamide,
4-bromo-N-(2-cyclohexylethyl)-1-methyl-1H-indole-3-carboxamide,
N-(2-cyclohexylethyl)-1,4-dimethyl-1H-indole-3-carboxamide,
N-(2-cyclohexylethyl)-1-ethyl-4-fluoro-1H-indole-3-carboxamide,
4-chloro-N-(2-cyclohexylethyl)-1-ethyl-1H-indole-3-carboxamide,
4-bromo-N-(2-cyclohexylethyl)-1-ethyl-1H-indole-3-carboxamide,
N-(2-cyclohexylethyl)-1,4-dimethyl-1H-indole-3-carboxamide,
N-(2-cyclohexylethyl)-1-ethyl-4-fluoro-1H-indole-3-carboxamide,
4-chloro-N-(2-cyclohexylethyl)-1-ethyl-1H-indole-3-carboxamide,
4-bromo-N-(2-cyclohexylethyl)-1-ethyl-1H-indole-3-carboxamide,
N-(2-cyclohexylethyl)-1-ethyl-4-methyl-1H-indole-3-carboxamide,
N-(2-cyclohexylethyl)-4-fluoro-1-(2-hydroxyethyl)-1H-indole-3-carboxamide,
4-chloro-N-(2-cyclohexylethyl)-1-(2-hydroxyethyl)-1H-indole-3-carboxamide,
4-bromo-N-(2-cyclohexylethyl)-1-(2-hydroxyethyl)-1H-indole-3-carboxamide,
N-(2-cyclohexylethyl)-1-(2-hydroxyethyl)-4-methyl-1H-indole-3-carboxamide,
4-chloro-N-(2-cycloheptylethyl)-1-methyl-1H-indole-3-carboxamide,
4-bromo-N-(2-cycloheptylethyl)-1-methyl-1H-indole-3-carboxamide,
N-(2-cycloheptylethyl)-1,4-dimethyl-1H-indole-3-carboxamide,
4-chloro-N-(2-cycloheptylethyl)-1-ethyl-1H-indole-3-carboxamide,
4-bromo-N-(2-cycloheptylethyl)-1-ethyl-1H-indole-3-carboxamide,
N-(2-cycloheptylethyl)-1-ethyl-4-methyl-1H-indole-3-carboxamide,
4-chloro-N-(2-cycloheptylethyl)-1-(2-hydroxyethyl)-1H-indole-3-carboxamide,
4-bromo-N-(2-cycloheptylethyl)-1-(2-hydroxyethyl)-1H-indole-3-carboxamide,
N-(2-cycloheptylethyl)-1-(2-hydroxyethyl)-4-methyl-1H-indole-3-carboxamide,
5-chloro-N-(cycloheptylmethyl)-1-methyl-1H-indole-3-carboxamide,
5-bromo-N-(cycloheptylmethyl)-1-methyl-1H-indole-3-carboxamide,
N-(cycloheptylmethyl)-1,5-dimethyl-1H-indole-3-carboxamide,
5-chloro-N-(cycloheptylmethyl)-1-ethyl-1H-indole-3-carboxamide,
5-bromo-N-(cycloheptylmethyl)-1-ethyl-1H-indole-3-carboxamide,
N-(cycloheptylmethyl)-1-ethyl-5-methyl-1H-indole-3-carboxamide,
5-chloro-N-(cycloheptylmethyl)-1-(2-hydroxyethyl)-1H-indole-3-carboxamide,
5-bromo-N-(cycloheptylmethyl)-1-(2-hydroxyethyl)-1H-indole-3-carboxamide,
N-(cycloheptylmethyl)-1-(2-hydroxyethyl)-5-methyl-1H-indole-3-carboxamide,
6-chloro-N-(cycloheptylmethyl)-1-methyl-1H-indole-3-carboxamide,
6-bromo-N-(cycloheptylmethyl)-1-methyl-1H-indole-3-carboxamide,
N-(cycloheptylmethyl)-1,6-dimethyl-1H-indole-3-carboxamide,
6-chloro-N-(cycloheptylmethyl)-1-ethyl-1H-indole-3-carboxamide,
6-bromo-N-(cycloheptylmethyl)-1-ethyl-1H-indole-3-carboxamide,
N-(cycloheptylmethyl)-1-ethyl-6-methyl-1H-indole-3-carboxamide,
6-chloro-N-(cycloheptylmethyl)-1-(2-hydroxyethyl)-1H-indole-3-carboxamide),
6-bromo-N-(cycloheptylmethyl)-1-(2-hydroxyethyl)-1H-indole-3-carboxamide,
N-(cycloheptylmethyl)-1-(2-hydroxyethyl)-6-methyl-1H-indole-3-carboxamide,
7-chloro-N-(cycloheptylmethyl)-1-methyl-1H-indole-3-carboxamide,
7-bromo-N-(cycloheptylmethyl)-1-methyl-1H-indole-3-carboxamide,
N-(cycloheptylmethyl)-1,7-dimethyl-1H-indole-3-carboxamide,
7-chloro-N-(cycloheptylmethyl)-1-ethyl-1H-indole-3-carboxamide,
7-bromo-N-(cycloheptylmethyl)-1-ethyl-1H-indole-3-carboxamide,
N-(cycloheptylmethyl)-1-ethyl-7-methyl-1H-indole-3-carboxamide,
7-chloro-N-(cycloheptylmethyl)-1-(2-hydroxyethyl)-1H-indole-3-carboxamide,
7-bromo-N-(cycloheptylmethyl)-1-(2-hydroxyethyl)-1H-indole-3-carboxamide,
N-(cycloheptylmethyl)-1-(2-hydroxyethyl)-7-methyl-1H-indole-3-carboxamide,
N-(bicyclo[2.2.2]octan-1-ylmethyl)-5-chloro-1-methyl-1H-indole-3-carboxamide,
N-(bicyclo[2.2.2]octan-1-ylmethyl)-5-bromo-1-methyl-1H-indole-3-carboxamide,
N-(bicyclo[2.2.2]octan-1-ylmethyl)-1,5-dimethyl-1H-indole-3-carboxamide,
N-(bicyclo[2.2.2]octan-1-ylmethyl)-5-chloro-1-ethyl-1H-indole-3-carboxamide,
N-(bicyclo[2.2.2]octan-1-ylmethyl)-5-bromo-1-ethyl-1H-indole-3-carboxamide,
N-(bicyclo[2.2.2]octan-1-ylmethyl)-1-ethyl-5-methyl-1H-indole-3-carboxamide,
N-(bicyclo[2.2.2]octan-1-ylmethyl)-5-chloro-1-(2-hydroxyethyl)-1H-indole-3-carboxamide,
N-(bicyclo[2.2.2]octan-1-ylmethyl)-5-bromo-1-(2-hydroxyethyl)-1H-indole-3-carboxamide, N-(bicyclo[2.2.2]octan-1-ylmethyl)-1-(2-hydroxyethyl)-5-methyl-1H-indole-3-carboxamide,
N-(bicyclo[2.2.2]octan-1-ylmethyl)-6-chloro-1-methyl-1H-indole-3-carboxamide,
N-(bicyclo[2.2.2]octan-1-ylmethyl)-6-bromo-1-methyl-1H-indole-3-carboxamide,
N-(bicyclo[2.2.2]octan-1-ylmethyl)-1,6-dimethyl-1H-indole-3-carboxamide,
N-(bicyclo[2.2.2]octan-1-ylmethyl)-6-chloro-1-ethyl-1H-indole-3-carboxamide,
N-(bicyclo[2.2.2]octan-1-ylmethyl)-6-bromo-1-ethyl-1H-indole-3-carboxamide,
N-(bicyclo[2.2.2]octan-1-ylmethyl)-1-ethyl-6-methyl-1H-indole-3-carboxamide,
N-(bicyclo[2.2.2]octan-1-ylmethyl)-6-chloro-1-(2-hydroxyethyl)-1H-indole-3-carboxamide,
N-(bicyclo[2.2.2]octan-1-ylmethyl)-6-bromo-1-(2-hydroxyethyl)-1H-indole-3-carboxamide,
N-(bicyclo[2.2.2]octan-1-ylmethyl)-1-(2-hydroxyethyl)-6-methyl-1H-indole-3-carboxamide,
N-(bicyclo[2.2.2]octan-1-ylmethyl)-7-chloro-1-methyl-1H-indole-3-carboxamide,
N-(bicyclo[2.2.2]octan-1-ylmethyl)-7-bromo-1-methyl-1H-indole-3-carboxamide,
N-(bicyclo[2.2.2]octan-1-ylmethyl)-1,7-dimethyl-1H-indole-3-carboxamide,
N-(bicyclo[2.2.2]octan-1-ylmethyl)-7-chloro-1-ethyl-1H-indole-3-carboxamide,
N-(bicyclo[2.2.2]octan-1-ylmethyl)-7-bromo-1-ethyl-1H-indole-3-carboxamide,
N-(bicyclo[2.2.2]octan-1-ylmethyl)-1-ethyl-7-methyl-1H-indole-3-carboxamide,
N-(bicyclo[2.2.2]octan-1-ylmethyl)-7-chloro-1-(2-hydroxyethyl)-1H-indole-3-carboxamide,
N-(bicyclo[2.2.2]octan-1-ylmethyl)-7-bromo-1-(2-hydroxyethyl)-1H-indole-3-carboxamide,
N-(bicyclo[2.2.2]octan-1-ylmethyl)-1-(2-hydroxyethyl)-7-methyl-1H-indole-3-carboxamide,
4-chloro-N-(cycloheptylmethyl)-6-fluoro-1-methyl-1H-indole-3-carboxamide,
4-bromo-N-(cycloheptylmethyl)-6-fluoro-1-methyl-1H-indole-3-carboxamide,
N-(cycloheptylmethyl)-6-fluoro-1,4-dimethyl-1H-indole-3-carboxamide,
4-chloro-N-(cycloheptylmethyl)-1-ethyl-6-fluoro-1H-indole-3-carboxamide,
4-bromo-N-(cycloheptylmethyl)-1-ethyl-6-fluoro-1H-indole-3-carboxamide,
N-(cycloheptylmethyl)-1-ethyl-6-fluoro-4-methyl-1H-indole-3-carboxamide,
4-chloro-N-(cycloheptylmethyl)-6-fluoro-1-isopropyl-1H-indole-3-carboxamide,
4-bromo-N-(cycloheptylmethyl)-6-fluoro-1-isopropyl-1H-indole-3-carboxamide,
4-chloro-N-(cycloheptylmethyl)-6-fluoro-1-(2-hydroxyethyl)-1H-indole-3-carboxamide,
4-bromo-N-(cycloheptylmethyl)-6-fluoro-1-(2-hydroxyethyl)-1H-indole-3-carboxamide,
N-(cycloheptylmethyl)-6-fluoro-1-(2-hydroxyethyl)-4-methyl-1H-indole-3-carboxamide,
4,6-dichloro-N-(cycloheptylmethyl)-1-methyl-1H-indole-3-carboxamide,
6-chloro-N-(cycloheptylmethyl)-4-fluoro-1-methyl-1H-indole-3-carboxamide,
4-bromo-6-chloro-N-(cycloheptylmethyl)-1-methyl-1H-indole-3-carboxamide,
6-chloro-N-(cycloheptylmethyl)-1,4-dimethyl-1H-indole-3-carboxamide,
6-chloro-N-(cycloheptylmethyl)-1-ethyl-4-fluoro-1H-indole-3-carboxamide,
4,6-dichloro-N-(cycloheptylmethyl)-1-ethyl-1H-indole-3-carboxamide,
4-bromo-6-chloro-N-(cycloheptylmethyl)-1-ethyl-1H-indole-3-carboxamide,
6-chloro-N-(cycloheptylmethyl)-1-ethyl-4-methyl-1H-indole-3-carboxamide,
6-chloro-N-(cycloheptylmethyl)-4-fluoro-1-(2-hydroxyethyl)-1H-indole-3-carboxamide,
4,6-dichloro-N-(cycloheptylmethyl)-1-(2-hydroxyethyl)-1H-indole-3-carboxamide,
4-bromo-6-chloro-N-(cycloheptylmethyl)-1-(2-hydroxyethyl)-1H-indole-3-carboxamide,
6-chloro-N-(cycloheptylmethyl)-1-(2-hydroxyethyl)-4-methyl-1H-indole-3-carboxamide,
6-bromo-4-chloro-N-(cycloheptylmethyl)-1-methyl-1H-indole-3-carboxamide,
6-bromo-N-(cycloheptylmethyl)-4-fluoro-1-methyl-1H-indole-3-carboxamide,
4,6-dibromo-N-(cycloheptylmethyl)-1-methyl-1H-indole-3-carboxamide,
6-bromo-N-(cycloheptylmethyl)-1,4-dimethyl-1H-indole-3-carboxamide,
6-bromo-N-(cycloheptylmethyl)-1-ethyl-4-fluoro-1H-indole-3-carboxamide,
6-bromo-4-chloro-N-(cycloheptylmethyl)-1-ethyl-1H-indole-3-carboxamide,
4,6-dibromo-N-(cycloheptylmethyl)-1-ethyl-1H-indole-3-carboxamide,
6-bromo-N-(cycloheptylmethyl)-1-ethyl-4-methyl-1H-indole-3-carboxamide,
6-bromo-N-(cycloheptylmethyl)-4-fluoro-1-(2-hydroxyethyl)-1H-indole-3-carboxamide,
6-bromo-4-chloro-N-(cycloheptylmethyl)-1-(2-hydroxyethyl)-1H-indole-3-carboxamide),
4,6-dibromo-N-(cycloheptylmethyl)-1-(2-hydroxyethyl)-1H-indole-3-carboxamide,
6-bromo-N-(cycloheptylmethyl)-1-(2-hydroxyethyl)-4-methyl-1H-indole-3-carboxamide,
N-(bicyclo[2.2.2]octan-1-ylmethyl)-4-chloro-6-fluoro-1-methyl-1H-indole-3-carboxamide,
N-(bicyclo[2.2.2]octan-1-ylmethyl)-4-bromo-6-fluoro-1-methyl-1H-indole-3-carboxamide,
N-(bicyclo[2.2.2]octan-1-ylmethyl)-6-fluoro-1,4-dimethyl-1H-indole-3-carboxamide,
N-(bicyclo[2.2.2]octan-1-ylmethyl)-4-chloro-1-ethyl-6-fluoro-1H-indole-3-carboxamide,
N-(bicyclo[2.2.2]octan-1-ylmethyl)-4-bromo-1-ethyl-6-fluoro-1H-indole-3-carboxamide,
N-(bicyclo[2.2.2]octan-1-ylmethyl)-1-ethyl-6-fluoro-4-methyl-1H-indole-3-carboxamide,
N-(bicyclo[2.2.2]octan-1-ylmethyl)-4-chloro-6-fluoro-1-(2-hydroxyethyl)-1H-indole-3-carboxamide,
N-(bicyclo[2.2.2]octan-1-ylmethyl)-4-bromo-6-fluoro-1-(2-hydroxyethyl)-1H-indole-3-carboxamide,
N-(bicyclo[2.2.2]octan-1-ylmethyl)-6-fluoro-1-(2-hydroxyethyl)-4-methyl-1H-indole-3-carboxamide,
N-(bicyclo[2.2.2]octan-1-ylmethyl)-4,6-dichloro-1-methyl-1H-indole-3-carboxamide,
N-(bicyclo[2.2.2]octan-1-ylmethyl)-6-chloro-4-fluoro-1-methyl-1H-indole-3-carboxamide,
N-(bicyclo[2.2.2]octan-1-ylmethyl)-4-bromo-6-chloro-1-methyl-1H-indole-3-carboxamide, N-(bicyclo[2.2.2]octan-1-ylmethyl)-6-chloro-1,4-dimethyl-1H-indole-3-carboxamide,
N-(bicyclo[2.2.2]octan-1-ylmethyl)-6-chloro-1-ethyl-4-fluoro-1H-indole-3-carboxamide,
N-(bicyclo[2.2.2]octan-1-ylmethyl)-4,6-dichloro-1-ethyl-1H-indole-3-carboxamide,
N-(bicyclo[2.2.2]octan-1-ylmethyl)-4-bromo-6-chloro-1-ethyl-1H-indole-3-carboxamide,
N-(bicyclo[2.2.2]octan-1-ylmethyl)-6-chloro-1-ethyl-4-methyl-1H-indole-3-carboxamide,
N-(bicyclo[2.2.2]octan-1-ylmethyl)-6-chloro-4-fluoro-1-(2-hydroxyethyl)-1H-indole-3-carboxamide,
N-(bicyclo[2.2.2]octan-1-ylmethyl)-4,6-dichloro-1-(2-hydroxyethyl)-1H-indole-3-carboxamide,
N-(bicyclo[2.2.2]octan-1-ylmethyl)-4-bromo-6-chloro-1-(2-hydroxyethyl)-1H-indole-3-carboxamide,
N-(bicyclo[2.2.2]octan-1-ylmethyl)-6-chloro-1-(2-hydroxyethyl)-4-methyl-1H-indole-3-carboxamide,
N-(bicyclo[2.2.2]octan-1-ylmethyl)-6-bromo-4-chloro-1-methyl-1H-indole-3-carboxamide,
N-(bicyclo[2.2.2]octan-1-ylmethyl)-6-bromo-4-fluoro-1-methyl-1H-indole-3-carboxamide,
N-(bicyclo[2.2.2]octan-1-ylmethyl)-4,6-dibromo-1-methyl-1H-indole-3-carboxamide,
N-(bicyclo[2.2.2]octan-1-ylmethyl)-6-bromo-1,4-dimethyl-1H-indole-3-carboxamide,
N-(bicyclo[2.2.2]octan-1-ylmethyl)-6-bromo-1-ethyl-4-fluoro-1H-indole-3-carboxamide,
N-(bicyclo[2.2.2]octan-1-ylmethyl)-6-bromo-4-chloro-1-ethyl-1H-indole-3-carboxamide,
N-(bicyclo[2.2.2]octan-1-ylmethyl)-4,6-dibromo-1-ethyl-1H-indole-3-carboxamide,
N-(bicyclo[2.2.2]octan-1-ylmethyl)-6-bromo-1-ethyl-4-methyl-1H-indole-3-carboxamide,
N-(bicyclo[2.2.2]octan-1-ylmethyl)-6-bromo-4-fluoro-1-(2-hydroxyethyl)-1H-indole-3-carboxamide,
N-(bicyclo[2.2.2]octan-1-ylmethyl)-6-bromo-4-chloro-1-(2-hydroxyethyl)-1H-indole-3-carboxamide,
N-(bicyclo[2.2.2]octan-1-ylmethyl)-4,6-dibromo-1-(2-hydroxyethyl)-1H-indole-3-carboxamide),
N-(bicyclo[2.2.2]octan-1-ylmethyl)-6-bromo-1-(2-hydroxyethyl)-4-methyl-1H-indole-3-carboxamide,
4-chloro-N-(cycloheptylmethyl)-1-methyl-1H-indazole-3-carboxamide),
4-bromo-N-(cycloheptylmethyl)-1-methyl-1H-indazole-3-carboxamide,
N-(bicyclo[2.2.2]octan-1-ylmethyl)-4-chloro-1-methyl-1H-indazole-3-carboxamide,
N-(bicyclo[2.2.2]octan-1-ylmethyl)-4-bromo-1-methyl-1H-indazole-3-carboxamide,
4-chloro-N-(cycloheptylmethyl)-1-methyl-1H-pyrrolo[2,3-b]pyridine-3-carboxamide),
4-bromo-N-(cycloheptylmethyl)-1-methyl-1H-pyrrolo[2,3-b]pyridine-3-carboxamide,
N-(bicyclo[2.2.2]octan-1-ylmethyl)-4-chloro-1-methyl-1H-pyrrolo[2,3-b]pyridine-3-carboxamide,
N-(bicyclo[2.2.2]octan-1-ylmethyl)-4-bromo-1-methyl-1H-pyrrolo[2,3-b]pyridine-3-carboxamide,
4-chloro-N-(cycloheptylmethyl)-1-methyl-1H-pyrrolo[3,2-c]pyridine-3-carboxamide,
4-bromo-N-(cycloheptylmethyl)-1-methyl-1H-pyrrolo[3,2-c]pyridine-3-carboxamide),
N-(bicyclo[2.2.2]octan-1-ylmethyl)-4-chloro-1-methyl-1H-pyrrolo[3,2-c]pyridine-3-carboxamide,
N-(bicyclo[2.2.2]octan-1-ylmethyl)-4-bromo-1-methyl-1H-pyrrolo[3,2-c]pyridine-3-carboxamide,
4-chloro-N-(cycloheptylmethyl)-1-methyl-1H-pyrrolo[2,3-c]pyridine-3-carboxamide,
4-bromo-N-(cycloheptylmethyl)-1-methyl-1H-pyrrolo[2,3-c]pyridine-3-carboxamide,
N-(bicyclo[2.2.2]octan-1-ylmethyl)-4-chloro-1-methyl-1H-pyrrolo[2,3-c]pyridine-3-carboxamide,
N-(bicyclo[2.2.2]octan-1-ylmethyl)-4-bromo-1-methyl-1H-pyrrolo[2,3-c]pyridine-3-carboxamide,
1-(2-(2H-tetrazol-5-yl)ethyl)-4-chloro-N-(cycloheptylmethyl)-1H-indole-3-carboxamide,
1-(2-(2H-tetrazol-5-yl)ethyl)-4-bromo-N-(cycloheptylmethyl)-1H-indole-3-carboxamide,
1-(2-(2H-tetrazol-5-yl)ethyl)-N-(cycloheptylmethyl)-4-methyl-1H-indole-3-carboxamide,
1-(2-(2H-tetrazol-5-yl)ethyl)-N-(bicyclo[2.2.2]octan-1-ylmethyl)-4-chloro-1H-indole-3-carboxamide,
1-(2-(2H-tetrazol-5-yl)ethyl)-N-(bicyclo[2.2.2]octan-1-ylmethyl)-4-bromo-1H-indole-3-carboxamide,
1-(2-(2H-tetrazol-5-yl)ethyl)-N-(bicyclo[2.2.2]octan-1-ylmethyl)-4-methyl-1H-indole-3-carboxamide,
4-chloro-N-3-(cycloheptylmethyl)-N1-methyl-1H-indole-1,3-dicarboxamide,
4-bromo-N3-(cycloheptylmethyl)-N1-methyl-1H-indole-1,3-dicarboxamide,
N3-(bicyclo[2.2.2]octan-1-ylmethyl)-4-chloro-N1-methyl-1H-indole-1,3-dicarboxamide,
N3-(bicyclo[2.2.2]octan-1-ylmethyl)-4-bromo-N1-methyl-1H-indole-1,3-dicarboxamide,
4-chloro-N3-(cycloheptylmethyl)-N1,N1-dimethyl-1H-indole-1,3-dicarboxamide,
4-bromo-N3-(cycloheptylmethyl)-N1,N1-dimethyl-1H-indole-1,3-dicarboxamide,
N3-(bicyclo[2.2.2]octan-1-ylmethyl)-4-chloro-N1,N1-dimethyl-1H-indole-1,3-dicarboxamide,
N3-(bicyclo[2.2.2]octan-1-ylmethyl)-4-bromo-N1,N1-dimethyl-1H-indole-1,3-dicarboxamide,
4-chloro-N3-(cycloheptylmethyl)-N1-ethyl-N1-methyl-1H-indole-1,3-dicarboxamide,
4-bromo-N3-(cycloheptylmethyl)-N1-ethyl-N1-methyl-1H-indole-1,3-dicarboxamide,
N3-(bicyclo[2.2.2]octan-1-ylmethyl)-4-chloro-N1-ethyl-N1-methyl-1H-indole-1,3-dicarboxamide and
N3-(bicyclo[2.2.2]octan-1-ylmethyl)-4-bromo-N1-ethyl-N1-methyl-1H-indole-1,3-dicarboxamide.

The present invention also includes isotopically-labelled compounds, which are identical to those recited in Formula (I), but for the fact that one or more atoms are replaced by an atom having an atomic mass or mass number different from the atomic mass or mass 25 number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{35}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances.

Isotopically-labelled compounds of Formula (I) of this invention and prodrugs thereof can generally be prepared by carrying out the procedures disclosed in the Examples below, by substituting a readily available isotopically-labelled reagent for a non-isotopically-labelled reagent.

Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine and procaine.

Further Pharmaceutically Acceptable Salts

In an further embodiment the present application is directed to a pharmaceutical composition comprising a compound of Formula (I) of the present invention.

The pharmaceutical composition according to the present invention may further comprise an additional active compound in separate or unit dosage form for simultaneous or sequential administration.

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

The present invention also relates to the treatment of an IL-1 or cytokine mediated condition.

As defined herein, an "IL-1 mediated condition" and "cytokine mediated condition" includes, but is not limited to, a disease or disorder selected from the group consisting of arthritis (including psoriatic arthritis, Reiter's syndrome, rheumatoid arthritis, gout, traumatic arthritis, rubella arthritis, rheumatoid spondylitis, osteoarthritis, gouty arthritis and acute synovitis), inflammatory bowel disease, Crohn's disease, emphysema, acute respiratory distress syndrome, adult respiratory distress syndrome, asthma, bronchitis chronic obstructive pulmonary disease, chronic pulmonary inflammatory disease, silicosis, pulmonary sarcoidosis, allergic reactions, allergic contact hypersensitivity, eczema, contact dermatitis, psoriasis, sunburn, cancer, tissue ulceration, restenosis, periodontal disease, epidermolysis bullosa, osteoporosis, bone resorption disease, loosening of artificial joint implants, atherosclerosis, aortic aneurysm, congestive heart failure, myocardial infarction, stroke, cerebral ischemia, head trauma, neurotrauma, spinal cord injury, neuro-degenerative disorders, Alzheimer's disease, Parkinson's disease, glaucoma, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, corneal scarring, scleritis, abnormal wound healing, burns, autoimmune disorders, Huntington's disease, diabetes, AIDS, cachexia, sepsis, septic shock, endotoxic shock, conjunctivitis shock, gram negative sepsis, toxic shock syndrome, cerebral malaria, cardiac and renal reperfusion injury, thrombosis, glomerularonephritis, graft vs. host reaction, allograft rejection, organ transplant toxicity, ulcerative colitis, or muscle degeneration, in a mammal, including a human, comprising administering to said mammal an amount of a compound to Formula (I), effective in treating such a condition.

The present invention relates to a pharmaceutical composition for the treatment of an IL-1 mediated condition in a mammal, including a human, comprising an amount of a compound of Formula (I), effective in treating such a condition and a pharmaceutically acceptable carrier.

The compounds of the invention are useful for the treatment of rheumatoid arthritis, osteoarthritis, psoriasis, allergic dermatitis, asthma, chronic obstructive pulmonary disease (COPD), hyperresponsiveness of the airway, septic shock, glomerulonephritis, irritable bowel disease, Crohn's disease, ulcerative colitis, atherosclerosis, growth and metastases of malignant cells, myoblastic leukemia, diabetes, Alzheimer's disease, meningitis, osteoporosis, burn injury, ischemic heart disease, stroke and varicose veins.

In another aspect, the invention further provides a pharmaceutical composition for treating osteoarthritis which comprises a therapeutically effective amount of a compound of Formula (I), or a pharmaceutically acceptable salt or solvate thereof, as hereinbefore defined.

The invention further provides a pharmaceutical composition for effecting immunosuppression (e.g. in the treatment of rheumatoid arthritis, irritable bowel disease, atherosclerosis or psoriasis) which comprises a therapeutically effective amount of a compound of Formula (I), or a pharmaceutically acceptable salt or solvate thereof, as hereinbefore defined.

The invention also provides a pharmaceutical composition for treating an obstructive airways disease (e.g. asthma or COPD) which comprises a therapeutically effective amount of a compound of Formula (I), or a pharmaceutically acceptable salt or solvate thereof, as hereinbefore defined.

The present invention yet further provides a pharmaceutical composition for treating a mammal susceptible to or afflicted with conditions that are causally related to abnormal activity of the P2X7 receptor, such as neurodegenerative diseases and disorders including, for example, Parkinson's disease, multiple sclerosis, glaucoma, diseases and disorders which are mediated by or result in neuromflammation such as, for example traumatic brain injury and encephalitis; centrally-mediated neuropsychiatric diseases and disorders such as, for example depression mania, bipolar disease, anxiety, schizophrenia, eating disorders, sleep disorders and cognition disorders, epilepsy and seizure disorders comprising a therapeutically effective amount of a compound of Formula (I), or a pharmaceutically acceptable salt or solvate thereof, as hereinbefore defined.

In particular embodiment the pharmaceutical composition according to the present invention may be used for the treatment of affective disorders. In a preferred embodiment the affective disorder is selected from depression, anxiety, bipolar disorder and schizophrenia.

In an alternative embodiment the pharmaceutical composition according to the present invention is useful for the treatment of neurodegenerative diseases and disorders, diseases and disorders which are mediated by or result in neuroinflammation and centrally-mediated neuropsychiatric diseases and disorders.

Furthermore, the pharmaceutical composition according to the present invention may particularly be useful for the treatment of pain, inflammatory processes, and degenerative conditions. In a more preferred embodiment the inflammatory process is selected from rheumatoid arthritis, osteoporosis and chronic obstructive pulmonary disease.

Moreover, the pharmaceutical composition according to the present invention may be used for the treatment of neuropathic pain.

Dosage, pharmaceutical preparation and delivery of a compound of Formula (I) for use in accordance with the present invention can be formulated in conventional manner according to methods found in the art, using one or more physiological carriers or excipient, see, for example Ansel et al., "Pharmaceutical Dosage Forms and Drug Delivery Systems", 7th edition, Lippincott Williams & Wilkins Publishers, 1999. Thus, the P2X7R modulating agent and its physiologically acceptable salts and solvates can be formulated for administration by inhalation, insufflation (either through the mouth, or nose), oral, buccal, parenteral, or rectal administration.

For oral administration, the pharmaceutical composition of a compound of Formula (I) can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). The pharmaceutical composition can be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium ion, dried skim milk, glycerol, propylene, glycol, water, ethanol and the like. The composition, if desired, can also contain minor amounts of wetting or emulsifying agents, or pH buffering agents. These compositions can be in the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the aforementioned compounds, preferably in purified form, together with a suitable amount of carrier so as to provide the form for proper administration to the patient. The formulation should suit the mode of administration.

Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, soric acids). The preparations can also contain buffer salts, flavouring, coloring and sweetening agents as deemed appropriate. Preparations for oral administration can be suitably formulated to give controlled release of a compound of Formula (I).

For administration by inhalation, a compound of Formula (I) of the present invention is conveniently delivered in the form of an aerosol spray presentation from a pressurised pack or a nebulizer, with the use of a suitable propellant (e.g., dichlorodifluoromethane, trichlorofluoromethane, dichlorotetrafluoroethane, carbon dioxide or other suitable gas). In the case of a pressurised aerosol, the dosage unit can be determined by providing a valve to deliver a metered amount. Capsules and cartridges of, for example, gelatine, for use in an inhaler or insufflator can be formulated containing a powder mix of a compound of Formula (I) and a suitable powder base such as lactose or starch.

A compound of Formula (I) of the present invention can be formulated for parenteral administration by injection, for example, by bolus injection or continuous infusion. Site of injections include intra-venous, intra-peritoneal or sub-cutaneous. Formulations for injection can be presented in units dosage form (e.g., in phial, in multi-dose container), and with an added preservative. A compound of Formula (I) of the present invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

A compound of Formula (I) of the present invention can be formulated for transdermal administration. Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention. The compounds of this invention can also be administered by a transdermal device. Accordingly, transdermal administration can be accomplished using a patch either of the reservoir or porous membrane type, or of a solid matrix variety.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

A compound of Formula (I) of the present invention can also, if desired, be presented in a pack, or dispenser device which can contain one or more unit dosage forms containing the said agent. The pack can for example comprise metal or plastic foil, such as blister pack. The pack or dispenser device can be accompanied with instruction for administration.

A compound of Formula (I) of the present invention can be administered as sole active agent or can be adminstered in combination with other agents. These agents include non-steroidal anti-inflammatory drug (NSAIDS) such as celecoxib, rofecoxib, cimicoxib, etoricoxib, lumiracoxib, valdecoxib, deracoxib, N-(2-cyclohexyloxynitrophenyl)methane sulphonamide, COX189, ABT963, JTE-522, GW-406381, LAS-34475, CS-706, PAC-10649, SVT-2016, GW-644784, tenidap, acetylsalicylic acid (aspirin), amoxiprin, benorilate, choline magnesium salicylate, diflunisal, faislamine, methyl salicylate, magnesium salicylate, salicyl salicylate (salsalatee), diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, oxaprozin, tiaprofenic acid, suprofen, mefenamic acid, meclofenamic acid, phenylbutazone, azapropazone, metamizole, oxyphenbutazone, sulfinpyrazone, piroxicam, lornoxicam, meloxicam, tenoxicam, nimesulide, licofelone, paracetamol.

A compound of Formula (I) of the present invention can be combined with agents such as TNF-α inhibitors such as anti-TNF monoclonal antibodies (such as Remicade, CDP-870 and D2E7) and TNF receptor immunoglobulin molecules (such as Enbrel), low dose methotrexate, lefunomide; ciclesonide; hydroxychloroquine, d-penicillamine, auranofin or parenteral or oral gold.

A compound of Formula (I) of the present invention can also be administered in combination with an inhibitor of proTNFalpha convertase enzyme (TACE) such as 3-Amino-N-hydroxy-α-(2-methylpropyl)-3-[4-[(2-methyl-4-quinolinyl)methoxy]phenyl]-2-oxo-1-pyrrolidineacetamide, 2(S),3 (S)-Piperidinedicarboxamide, N3-hydroxy-1-methyl-N-2-[4-[(2-methyl-4-quinolinyl)methoxy]phenyl], 3-Thiomorpholinecarboxamide, 4-[[4-(2-butynyloxy)phenyl]sulfonyl]-N-hydroxy-2,2-dimethyl, 5-Hexenoic acid, 3-[(hydroxyamino)carbonyl]-2-(2-methylpropyl)-6-phenyl-, 2-(2-methylpropyl)-2-(methylsulfonyl)hydrazide, (2R,3S, 5E), 2-Piperidinecarboxamide, N,5-dihydroxy-1-[[4-(1-naphthalenylmethoxy)phenyl]sulfonyl]-, (2R,5R), Pentanamide, 3-(formylhydroxyamino)-4-methyl-2-(2-methylpropyl)-N-[(1S,2S)-2-methyl-1-[(2-pyridinylamino) carbonyl]butyl]-, (2R,3S),2-Propenamide, N-hydroxy-3-[3-[[(4-methoxyphenyl)sulfonyl](1-methylethyl)amino] phenyl]-3-(3-pyridinyl)-, (2E), Benzamide, N-(2,4-dioxo-1, 3,7-triazaspiro[4.4]non-9-yl)-4-[(2-methyl-4-quinolinyl) methoxy], Benzamide, N-[(1-acetyl-4-piperidinyl)(2,5-dioxo-4-imidazolidinyl)methyl]-4-[(2-methyl-4-quinolinyl) methoxy], or 2,4-Imidazolidinedione, 5-methyl-5-[[[4-[(2-methyl-4-quinolinyl)methoxy]phenyl]sulfonyl]methyl].
Other examples of TACE inhibitors are described in WO 99/18074, WO 99/65867, U.S. Pat. No. 6,225,311, WO 00/00465, WO 00/09485, WO 98/38179, WO 02/18326, WO 02/096426, WO 03/079986, WO 03/055856, WO 03/053941, WO 03/040103, WO 03/031431, WO 03/024899, WO 03/016248, WO 04/096206, WO 04/033632, WO 04/108086, WO 04/043349, WO 04/032846, WO 04/012663, WO 04/006925, WO 07/016,597.

A compound of Formula (I) of the present invention can also be administered in combination with a corticosteroid such as budesonide, corticosterone, cortisol, cortisone acetate, prednisone, prednisolone, methylprednisolone, dexamethasone, betamethasone, triamcinolone, beclometasone, fludrocortisone acetate, deoxycorticosterone acetate (doca), aldosterone.

A compound of Formula (I) of the present invention can further be administered in combination with a β2-adrenergic receptor agonist such as formoterol, salbutamol (albuterol), levalbuterol, terbutaline, pirbuterol, procaterol, metaproterenol, fenoterol, bitolterol mesylate, salmeterol, bambuterol, clenbuterol.

A compound of Formula (I) of the present invention can further be administered in combination with an antidepressant drug such as sertraline, escitalopram, fluoxetine, bupropion, paroxetine, venlafaxine, trazodone, amitriptyline, citalopram, duloxetine, mirtazapine, nortriptyline, imipramine, lithium.

A compound of Formula (I) of the present invention can further be administered in combination with an antipsychotic drug such as chlorpromazine, fluphenazine, perphenazine, prochlorperazine, thioridazine, trifluoperazine, mesoridazine, promazine, triflupromazine, levomepromazine, promethazine, chlorprothixene, flupenthixol, thiothixene, zuclopenthixol, haloperidol, droperidol, pimozide, melperone, benperidol, triperidol, clozapine, olanzapine, risperidone, quetiapine, ziprasidone, amisulpride, paliperidone, bifeprunox, aripiprazole.

A compound of Formula (I) of the present invention can also be administered in combination with a leukotriene biosynthesis inhibitor, 5-lipoxygenase (5-LO) inhibitor or 5-lipoxygenase activating protein (FLAP) antagonist, for example, zileuton; ABT-761; fenleuton; tepoxalin; nicaraven; VIA-2291; etalocib; ketoprofen, Abt-79175; Abt-85761; N-(5-substituted) thiophene-2-alkylsulfonamides; TDT-070; licofelone; PEP-03; tenoxicam; 2,6-di-tert-butylphenol hydrazones; methoxytetrahydropyrans such as Zeneca ZD-2138; the compound SB-210661; pyridinyl-substituted 2-cyanonaphthalene compounds such as L-739-010; 2-cyanoquinoline compounds such as L-746-530; indole and quinoline compounds such as MK-591, MK-886, and BAY x 1005.

A compound of Formula (I) of the present invention can be administered in combination with a receptor antagonists for leukotrienes LTB4, LTC4, LTD4, and LTE, for example, phenothiazin-3-ones such as L-651.392; amidino compounds such as CGS-25019c; benzoxalamines such as ontezolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195; masilukast.

A compound of Formula (I) of the present invention can also be administered in combination with a PDE4 inhibitor including inhibitors of the isoform PDE4D.

A compound of Formula (I) of the present invention can also be administered in combination with a antihistaminic $H_1$ receptor antagonists including cetirizine, loratadine, desloratadine, fexofenadine, astemizole, azelastine, and chlorpheniramine.

A compound of Formula (I) of the present invention can further be administered in combination with a gastroprotective $H_2$ receptor antagonist.

A compound of Formula (I) of the present invention can yet further be administered in combination with an α1- and α2-adrenoceptor agonist vasoconstrictor sympathomimetic agent, including propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

A compound of Formula (I) of the present invention can be administered in combination with anticholinergic agents including ipratropium bromide; tiotropium bromide; oxitropium bromide; pirenzepine; and telenzepine The present invention still further relates to the combination of a compound of the invention together with a $\beta_1$- to $\beta_4$-adrenoceptor agonists including metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

A compound of Formula (I) of the present invention can be administered in combination with an insulin-like growth factor type I (IGF-1) mimetic.

A compound of Formula (I) of the present invention can be administered in combination with an inhaled glucocorticoid with reduced systemic side effects, including, prednisone, prednisolone, flunisolide, triamcinolone acetonide, beclomethasone dipropionate, budesonide, fluticasone propionate, and mometasone furoate.

A compound of Formula (I) of the present invention can be administered in combination with (a) tryptase inhibitors; (b) platelet activating factor (PAF) antagonists; (c) interleukin converting enzyme (ICE) inhibitors; (d) IMPDH inhibitors; (e) adhesion molecule inhibitors including VLA-4 antagonists; (f) cathepsins; (g) MAP kinase inhibitors; (h) glucose-6 phosphate dehydrogenase inhibitors; (i) kinin-$B_1$- and $B_2$-receptor antagonists; j) anti-gout agents, e.g., colchicine; (k) xanthine oxidase inhibitors, e.g., allopurinol; (l) uricosuric agents, e.g., probenecid, sulfinpyrazone, and benzbromarone; (m) growth hormone secretagogues; (n) transforming growth factor (TGFB$\beta$); (o) platelet-derived growth factor (PDGF); (p) fibroblast growth factor, e.g., basic fibroblast growth factor (bFGF); (q) granulocyte macrophage colony stimulating factor (GM-CSF); (r) capsaicin cream; (s) Tachykinin $NK_1$ and $NK_3$ receptor antagonists such as NKP-608C; SB-233412 (talnetant); and D-4418; and (t) elastase inhibitors such as UT-77 and ZD-0892.

A compound of Formula (I) of the present invention can be administered in combination with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11).

A compound of Formula (I) of the present invention can be administered in combination with anticancer agents such as endostatin and angiostatin or cytotoxic drugs such as adriamycin, daunomycin, cis-platinum, etoposide, taxol, taxotere and farnesyl transferase inhibitors, VEGF inhibitors, COX-2 inhibitors and antimetabolites such as methotrexate antineoplastic agents, especially antimitotic drugs including the vinca alkaloids such as vinblastine and vincristine.

A compound of Formula (I) of the present invention can be administered in combination with antiviral agents such as Viracept, AZT, aciclovir and famciclovir, and antisepsis compounds such as Valant.

A compound of Formula (I) of the present invention can be administered in combination with cardiovascular agents such as calcium channel blockers, lipid lowering agents such as stating, fibrates, beta-blockers, ACE inhibitors, Angiotensin-2 receptor antagonists and platelet aggregation inhibitors.

A compound of Formula (I) of the present invention can be administered in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

A compound of Formula (I) of the present invention can be administered in combination with osteoporosis agents such as roloxifene, droloxifene, lasofoxifene or fosomax and immunosuppressant agents such as FK-506, rapamycin, cyclosporine, azathioprine, and methotrexate.

EXAMPLES

Example 1

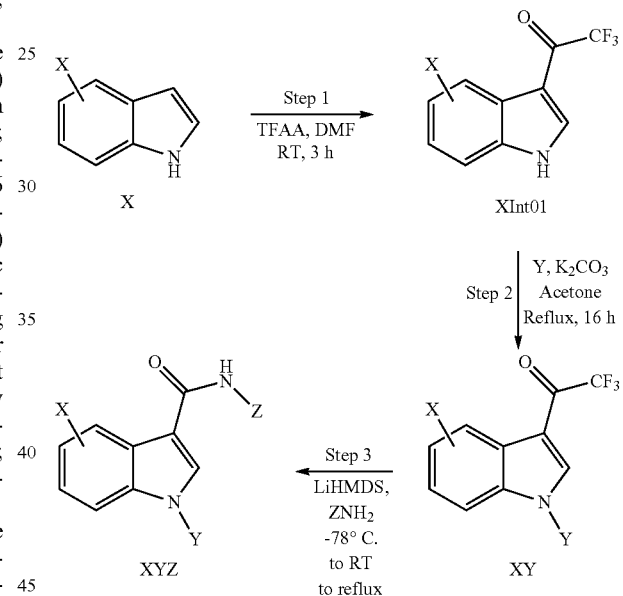

General Synthetic Procedure I
General procedure for preparation of XInt01:
A solution of the indole derivative X (1 eq) in dry dimethylformamide at 0° C. was added to trifluoroacetic anhydride (1.5 eq), stirred, and slowly warmed to room temperature. After completion of the reaction (1 h), the mixture was treated with ice-cold water to obtain a solid. The solid was separated by filtration and washed with water and n-pentane and dried under high vacuum to afford compound XInt01 (80-94% yield).
General Procedure for Preparation of XY:
A solution of XInt01 (1 eq), $K_2CO_3$ (5 eq) and alkyl halides Y such as methyl iodide, ethyl iodide, n-propyl bromide, iso-propyl bromide, n-butyl bromide, isobutyl bromide (1.5 eq, 1 h) or O-t-butyldimethylsilyl-2-chloroethanol (10 eq, 24 h) or O-t-butyldimethylsilyl-2-chloropropanol in acetone was stirred and heated to reflux. After completion of the reaction (monitored by thin layer chromatography (TLC)), the mixture was concentrated in vacuo and the residue treated with dichloromethane. The insoluble impurities were removed by filtration and the filtrate was concentrated to afford compound XY (60-95% yield).

General Procedure for Preparation of AFT20 XYZ:

To a mixture of XY (1 eq) and a cyclic derivative Z (1.5 eq) like cyclopentylmethyl amine, cyclopentylethyl amine, cyclohexylmethyl amine, cyclohexylethyl amine, cycloheptylmethyl amine, cycloheptylethyl amine, bicyclo[2.2.2]octan-1-ylmethyl amine, or bicyclo[2.2.2]octan-1-ylethyl amine, in dry THF at −78° C. was added lithium hexamethyldisilazide (3.5 eq). Bicyclo[2.2.2]octan-1-ylmethyl amine was prepared according to the procedures disclosed in Unig and Kahanek (1957) Chem Ber 90:236, Delany and Berchtold (1988) J Org Chem 53:3262-3265, Grob et al. (1958) Hely Chim Acta 41:1191-1197, Whitney et al. (1970) J Med Chem 13:254-260. The resulting solution was warmed to room temperature and subsequently heated to reflux for 16 h. After completion of the reaction (TLC), the mixture was concentrated in vacuo. In case of the non-silyloxyethyl derivatives, the residue was purified either by trituration, column chromatography or preparative HPLC to afford compound XYZ (40-66% yield). In case of the silyloxyethyl compounds, the residue was used in the deprotection step without further purification.

General Procedure for Deprotection of t-butyldimethylsilyl Group:

To a solution of the silyloxyethyl compound (1 eq) in dry tetrahydrofuran at 0° C. was added tetrabutylammonium fluoride (6 eq) and stirred at room temperature for 4 h. The reaction mixture concentrated in vacuo and the residue was purified by column chromatography to afford XYZ (50-60% yield).

Reagents used in the synthesis of the compounds of this invention are available from commercial suppliers such as Sigma-Aldrich, Alfa Aesar, and Sinova. Chemical properties are evaluated by liquid chromatography-tandem mass spectrometry (MS) and/or calculated using CS Chemdraw 8.0 (CambridgeSoft, USA).

Example 2

General Synthetic Procedure II

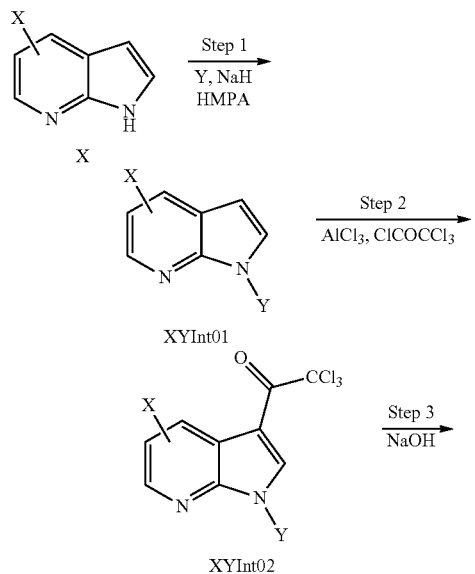

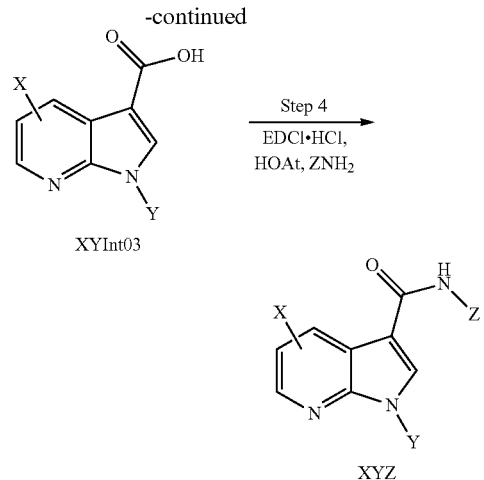

General Procedure for Preparation of XYInt01:

To a solution of azaindole derivative X in hexamethylphosphoramide (HMPA) at 0° C., natrium hydrogen (NaH; 1.2 eq) was added and stirred further. After 1 hour, an alkyl halides Y such as methyl iodide, ethyl iodide, n-propyl bromide, isopropyl bromide, n-butyl bromide, isobutyl bromide (1.5 eq, 1 h) or O-t-butyldimethylsilyl-2-chloroethanol (10 eq, 24 h) or O-t-butyldimethylsilyl-2-chloropropanol (1.5 eq) was added and stirred. After completion of the reaction (monitored by thin layer chromatography (TLC)), the reaction was quenched by ice cold water and extracted with ethyl acetate (EtOAc; 3×). The organic layer was dried over anhydrous $Na_2SO_4$ and concentrated under reduced pressure to leave a residue of crude product. The crude product was purified by column chromatography to afford XYInt01 (75-85% yield).

General Procedure for Preparation of XYInt02:

To a solution of anhydrous $AlCl_3$ (5 eq) in dry dimethylformamide (DMF) at 0° C. (20 mL) a solution of XYInt01 in dimethylformamide and the mixture was stirred further. After 1 hour, trichloroacetyl chloride (5 eq) was added and the mixture was allowed to warm to room temperature. After completion of the reaction (monitored by TLC), the reaction was quenched with ice-cold water and extracted with dimethylformamide (3×). The organic layer was dried over anhydrous $Na_2SO_4$ and concentrated under reduced pressure to leave a residue which was purified by column chromatography to afford XYInt02 (60-70% yield).

General Procedure for Preparation of XYInt03:

To a solution of XYInt02 in THF was added 5N NaOH and the mixture was stirred at room temperature. After completion of the reaction (monitored by TLC), the mixture was concentrated to about ¼th of the reaction volume and neutralized with dil. HCl. The precipitate formed was filtered and dried under vacuum to afford XYInt03 (75-85% yield).

General Procedure for Preparation of XYZ:

To a solution of XYInt02 in dry dimethylformamide, 1-[3-(dimethylamino)propyl]-3-ethylcarbodiimide.hydrochloride (EDCI.HCl; 1.5 eq), 1-hydroxy-7-azabenzotriazole (HOAt; 1.5 eq), triethanolamine (2 eq) and Z (1.4 eq) like cyclopentylmethyl amine, cyclopentylethyl amine, cyclohexylmethyl amine, cyclohexylethyl amine, cycloheptylmethyl amine, cycloheptylethyl amine, bicyclo[2.2.2]octan-1-ylmethyl amine, or bicyclo[2.2.2]octan-1-ylethyl amine were added and the resulting reaction mixture was stirred at room temperature. After completion of the reaction (TLC), the reaction mixture was treated with water and extracted with dimethylformamide (3×). The organic layer was dried over anhydrous Na$_2$SO$_4$ and concentrated under reduced pressure to leave a residue which was purified by column chromatography to afford XYZ (40-55% yield).

General Procedure for Deprotection of t-butyldimethylsilyl Group:

To a solution of the silyloxyethyl compound (1 eq) in dry tetrahydrofuran at 0° C. was added tetrabutylammonium fluoride (6 eq) and stirred at room temperature for 4 hour. The reaction mixture concentrated in vacuo and the residue was purified by column chromatography to afford XYZ (50-60% yield).

Example 3

Indol-3 Carboxamide and Azaindol-3 Carboxamide Compounds Antagonise P2X7R Activity Inhibition of P2X7R activity by indol-3 carboxamide and azaindol-3 carboxamide compounds of the present invention can be assessed by measuring calcium influx in Hek293 cells (ECACC No. 85120602) which have been stably transfected with a cDNA for the human P2X7R.

The Hek293 cells are human embryo kidney cells that do not express endogenous P2X7R (Surprenant et al. (1996) Science 272:735-738). Hek293 cells expressing P2X7R were generated by lipofectamine transfection of the human P2X7R cDNA (Genbank accession number BC011913) under the control of the human cytomegalovirus immediate-early (CMV) promoter and inserted into the pcDNA3.1 vector (Invitrogen). Cells were cultivated at 37° C. with 8.5% CO2 in Dulbecco's modified eagles medium (DMEM; GibcoBRL/Invitrogen) supplemented with heat-inactivated foetal calf serum (10% v/v), 2 mM L-glutamine, 100 units/ml penicillin, 0.1 mg/ml streptomycin, and 750 µg/ml Geneticin G418 (GibcoBRL/Invitrogen).

Inhibition of Bz-ATP-stimulated P2X7R by test compounds was monitored by measuring changes in calcium influx using the Fluo-4-AM fluorescent dye according to the manufacturer's recommendations (Molecular Devices Corporation, U.S.A.). Briefly, Hek293 cells expressing P2X7R were cultured in 96-well plates at a final density of approximately 10,000 cells per well. On the day of the experiment, the culture medium was completely removed from the wells and cells were washed one time in assay buffer (1× Hank's Balanced Salt (HBSS) solution containing 20 mM Hepes buffer pH 7.4 and 250 mM Probenecid; GibcoBRL/Invitrogen). The cells were incubated in 50 µl of assay buffer containing 100 µM Fluo-4 AM fluorescent dye per well for 1 hour at room temperature. The assay buffer containing the Fluo-4 AM fluorescent dye was then removed, the cells were washed once with assay buffer (without Fluo-4 AM), 100 µl of assay buffer (without Fluo-4 AM) containing the test compounds was then added per well. After a 15 minute incubation, 100 µM Bz-ATP was added and fluorescence was measured in a FlexStation II (Molecular Devices, U.S.A.) according to the following parameters: 485 nm Excitation Wavelength; 525 nm Emission Wavelength; 515 nm Emission Cut-off; 100 µl Pipette Height; 25 µl Transfer Volume; 5 fold Compound Concentration; 3 rate Addition Speed. Test compounds were added at concentrations of 0.013 µM up to 60 µM. The fluorescence data were processed using a lag time of 15 seconds, recording 45 seconds, zero baseline calibrated using 2 points, and % baseline multiplier set at 3. Then, the area of the resulting curve was calculated and the half-maximal inhibitory concentration (IC$_{50}$) for each test compound was determined using SoftMax Pro software (Molecular Devices, U.S.A.). Compounds of the present invention can inhibit P2X7R activity with an IC$_{50}$ between 1 µM and 0.001 µM. For example, the IC$_{50}$ of compound from Example 5 is approximately 0.134 µM.

Example 4

Indol-3 Carboxamide and Azaindol-3 Carboxamide Compounds Reduce Interleukin-1 Beta Secretion The effects of indol-3 carboxamide and azaindol-3 carboxamide compounds of the present invention on IL-1 beta secretion is assessed using the human monocyte cell line THP-1 (ATCC Cat #285-IF-100).

Briefly, THP-1 cells are plated in 96 well plates at a concentration of 200.000 cells per well and allowed to differentiate in RPMI-1640 media (ATCC Cat #30-2001) containing 10% FBS, 100 IU/mL penicillin, 100 ug/mL streptomycin, 100 nM PMA (phorbol myristate acetate) for 72 hours. Under these conditions, THP-1 cells differentiate into macrophages expressing endogenous P2X7R. The compounds of the present invention are added to the cells at different concentrations and the differentiated cells are then stimulated for 4 hours with 1 ug/ml LPS (lipopolysaccharide) to activate IL-1 beta transcription (see Humphreys and Dubyak (1998) J Leukoc Biol. 64:265-73). Subsequently, IL-1 beta processing and secretion is stimulated by adding 2 mM ATP for 1 hour. The concentration of IL-1 beta in the supernatants is then quantified by ELISA (R&D system) using specific monoclonal anti-human IL-1 beta antibodies according to the manufacturer instructions. More than 90% of the detected protein is biologically active mature IL-1 beta. Observed results were verified statistically using one-way ANOVA tests. Examples of reduced IL-1 beta secretion by the compounds of the invention are illustrated in FIG. 1.

Example 5

Analgesic and Anti-inflammatory Effects

This example illustrates the analgesic and anti-inflammatory benefits of the compounds of the present invention using a carrageenan-induced paw edema model of inflammation.

Adult male Sprague Dawley rats were challenged by a subcutaneous injection of carrageenan (1% suspension, 0.1 ml), in the plantar side of the right hind paw. A suspension of the compound in 0.5% methyl cellulose or a vehicle (0.5% methyl cellulose) was administered orally one hour after the carrageenan challenge. The paw was then marked with indelible ink at the level of the lateral malleolus so that the paw can be immersed in the Plethysmometer cell up to this mark. A Plethysmometer allows the measurements of small volume changes in the paw. An hour after compound or vehicle administration (or 2 hr of carrageenan challenge), the plantar test was performed followed by the recording of paw volume.

For the plantar test, each rat was place on preheated glass stand. Both of the hind paws of the animal were stimulated with a radiant heat source. The latency of paw withdrawal from the stimuli was recorded. An increase in the response latency of paw withdrawal is interpreted as an analgesic response. Three trials were given to each animal in order to obtain an average withdrawal latency. The mean Paw Withdrawal Latency (PWL) of test group was compared with the vehicle treated group.

For the paw edema test, the increase in paw volume for each animal is calculated by subtracting left hind paw volume from right hind paw volume (Difference in Paw Volume=Right Hind paw volume−Left hind paw volume). An inhibition of the increase in paw volume is interpreted as an anti inflammatory response. Observed results were verified statistically using ANOVA Tukey's multiple comparison tests. Results are illustrated in FIG. 2.

A compound of the present invention was evaluated for increase in the paw withdrawal latency to respond to the heat stimulus which is indicative of an analgesic response.

A compound of the present invention was also evaluated for inhibition of paw edema induced by carrageenan which is interpreted as an anti-inflammatory response.

Example 6

N-(cyclopentylmethyl)-1-methyl-1H-indole-3-carboxamide

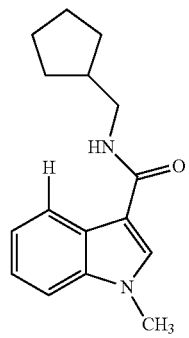

Synthesised according to the procedure disclosed in Example 1 where X is indole, Y is methyl iodide and Z is cyclopentylmethyl amine. Formula: $C_{16}H_{20}N_2O$; Molecular Weight: 256.3; Mass/charge ratio: 256.2 (100.0%), 257.2 (18.3%), 258.2 (1.8%); Elemental analysis: C, 74.97; H, 7.86; N, 10.93; O, 6.24.

Example 7

4-chloro-N-(cyclopentylmethyl)-1-methyl-1H-indole-3-carboxamide

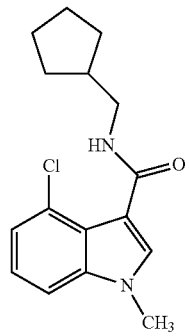 [SMILES: Cn1cc(C(=O)NCC2CCCC2)c2c(Cl)cccc21]

Synthesised according to the procedure disclosed in Example 1 where X is 4-chloro indole, Y is methyl iodide and Z is cyclopentylmethyl amine. Formula: $C_{16}H_{19}ClN_2O$; Molecular Weight: 290.8; Mass/charge ratio: 290.1 (100.0%), 292.1 (33.7%), 291.1 (18.3%), 293.1 (6.0%); Elemental analysis: C, 66.09; H, 6.59; Cl, 12.19; N, 9.63; O, 5.50

Example 8

N-(cyclopentylmethyl)-4-fluoro-1-methyl-1H-indole-3-carboxamide

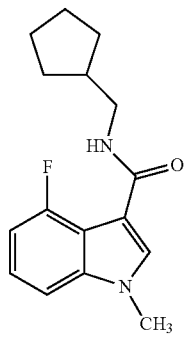 [SMILES: Cn1cc(C(=O)NCC2CCCC2)c2c(F)cccc21]

Synthesised according to the procedure disclosed in Example 1 where X is 4-fluoro indole, Y is methyl iodide and Z is cyclopentylmethyl amine. Formula: $C_{16}H_{19}FN_2O$; Molecular Weight: 274.3; Mass/charge ratio: 274.1 (100.0%), 275.2 (17.6%), 276.2 (1.7%); Elemental analysis: C, 70.05; H, 6.98; F, 6.93; N, 10.21; O, 5.83.

Example 9

4-bromo-N-(cyclopentylmethyl)-1-methyl-1H-indole-3-carboxamide

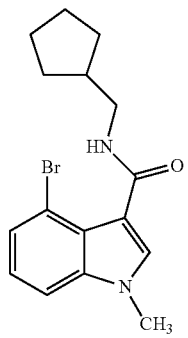 [SMILES: Cn1cc(C(=O)NCC2CCCC2)c2c(Br)cccc21]

Synthesised according to the procedure disclosed in Example 1 where X is 4-bromo indole, Y is methyl iodide and Z is cyclopentylmethyl amine. Formula: $C_{16}H_{19}BrN_2O$; Molecular Weight: 335.2; MS: 335.1/336.1; Mass/charge ratio: 334.1 (100.0%), 336.1 (99.1%), 335.1 (18.3%), 337.1 (17.9%), 338.1 (1.7%); Elemental analysis: C, 57.32; H, 5.71; Br, 23.83; N, 8.36; O, 4.77.

Example 10

N-(cyclopentylmethyl)-1,4-dimethyl-1H-indole-3-carboxamide

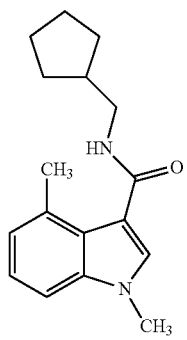 [SMILES: Cc1cccc2c1c(C(=O)NCC1CCCC1)cn2C]

Synthesised according to the procedure disclosed in Example 1 where X is 4-methyl indole, Y is methyl iodide and Z is cyclopentylmethyl amine. Formula: $C_{17}H_{22}N_2O$; Molecular Weight: 270.4; Mass/charge ratio: 270.2 (100.0%), 271.2 (19.4%), 272.2 (2.0%); Elemental analysis: C, 75.52; H, 8.20; N, 10.36; O, 5.92.

Example 11

N-(cyclopentylmethyl)-4-fluoro-1-(2-hydroxyethyl)-1H-indole-3-carboxamide

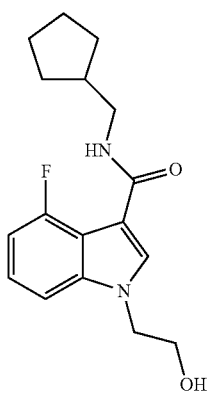 [SMILES: O=C(NCC1CCCC1)c1cn(CCO)c2cccc(F)c12]

Synthesised according to the procedure disclosed in Example 1 where X is 4-fluoro indole, Y is O-TBS-2-chloroethanol and Z is cyclopentylmethyl amine. Formula: $C_{17}H_{21}FN_2O_2$; Molecular Weight: 304.4; Mass/charge ratio: 304.2 (100.0%), 305.2 (19.4%), 306.2 (2.2%); Elemental analysis: C, 67.09; H, 6.95; F, 6.24; N, 9.20; O, 10.51.

Example 12

4-chloro-N-(cyclopentylmethyl)-1-(2-hydroxyethyl)-1H-indole-3-carboxamide

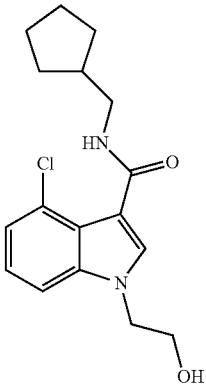 [SMILES: O=C(NCC1CCCC1)c1cn(CCO)c2cccc(Cl)c12]

Synthesised according to the procedure disclosed in Example 1 where X is 4-chloro indole, Y is O-TBS-2-chloroethanol and Z is cyclopentylmethyl amine. Formula: $C_{17}H_{21}ClN_2O_2$; Molecular Weight: 320.8; Mass/charge ratio: 320.1 (100.0%), 322.1 (34.2%), 321.1 (19.4%), 323.1 (6.4%); Elemental analysis: C, 63.64; H, 6.60; Cl, 11.05; N, 8.73; O, 9.97.

Example 13

4-bromo-N-(cyclopentylmethyl)-1-(2-hydroxyethyl)-1H-indole-3-carboxamide

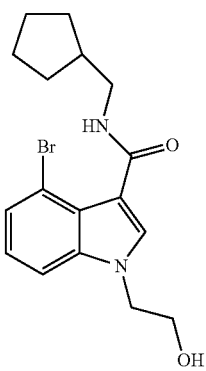 [SMILES: O=C(NCC1CCCC1)c1cn(CCO)c2cccc(Br)c12]

Synthesised according to the procedure disclosed in Example 1 where X is 4-bromo indole, Y is O-TBS-2-chloroethanol and Z is cyclopentylmethyl amine. Formula: $C_{17}H_{21}BrN_2O_2$; Molecular Weight: 365.3; Mass/charge ratio: 364.1 (100.0%), 366.1 (99.5%), 365.1 (19.4%), 367.1 (19.1%), 368.1 (2.2%); Elemental analysis: C, 55.90; H, 5.79; Br, 21.88; N, 7.67; O, 8.76.

Example 14

N-(cyclohexylmethyl)-1-methyl-1H-indole-3-carboxamide

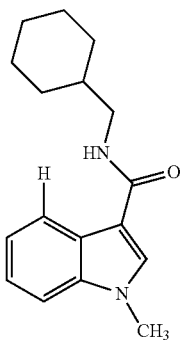

Synthesised according to the procedure disclosed in Example 1 where X is indole, Y is methyl iodide and Z is cyclohexylmethyl amine. Formula: $C_{17}H_{22}N_2O$; Molecular Weight: 270.4; Mass/charge ratio: 270.2 (100.0%), 271.2 (19.4%), 272.2 (2.0%); Elemental analysis: C, 75.52; H, 8.20; N, 10.36; O, 5.92.

Example 15

4-chloro-N-(cyclohexylmethyl)-1-methyl-1H-indole-3-carboxamide

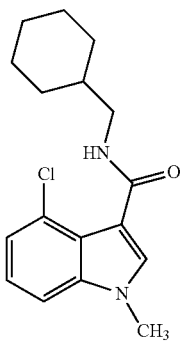 [SMILES: Cn1cc(C(=O)NCC2CCCCC2)c2c(Cl)cccc21]

Synthesised according to the procedure disclosed in Example 1 where X is 4-chloro indole, Y is methyl iodide and Z is cyclohexylmethyl amine. Formula: $C_{17}H_{21}ClN_2O$; Molecular Weight: 304.8; MS: 305.1/306.1; Mass/charge ratio: 304.1 (100.0%), 306.1 (33.9%), 305.1 (19.4%), 307.1 (6.3%); Elemental analysis: C, 66.99; H, 6.94; Cl, 11.63; N, 9.19; O, 5.25.

Example 16

N-(cyclohexylmethyl)-4-fluoro-1-methyl-1H-indole-3-carboxamide

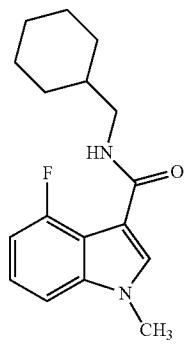 [SMILES: Cn1cc(C(=O)NCC2CCCCC2)c2c(F)cccc21]

Synthesised according to the procedure disclosed in Example 1 where X is 4-fluoro indole, Y is methyl iodide and Z is cyclohexylmethyl amine. Formula: $C_{17}H_{21}FN_2O$; Molecular Weight: 288.4; Mass/charge ratio: 288.2 (100.0%), 289.2 (19.4%), 290.2 (2.0%); Elemental analysis: C, 70.81; H, 7.34; F, 6.59; N, 9.71; O, 5.55.

Example 17

4-bromo-N-(cyclohexylmethyl)-1-methyl-1H-indole-3-carboxamide

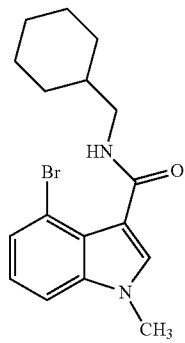 [SMILES: Cn1cc(C(=O)NCC2CCCCC2)c2c(Br)cccc21]

Synthesised according to the procedure disclosed in Example 1 where X is 4-bromo indole, Y is methyl iodide and Z is cyclohexylmethyl amine. Formula: $C_{17}H_{21}BrN_2O$; Molecular Weight: 349.3; MS: 351.1/352.1; Mass/charge ratio: 348.1 (100.0%), 350.1 (99.3%), 349.1 (19.4%), 351.1 (19.0%), 352.1 (1.9%); Elemental analysis: C, 58.46; H, 6.06; Br, 22.88; N, 8.02; O, 4.58.

Example 18

N-(cyclohexylmethyl)-1,4-dimethyl-1H-indole-3-carboxamide

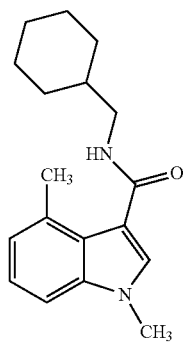 [SMILES: Cc1cccc2c1c(C(=O)NCC1CCCCC1)cn2C]

Synthesised according to the procedure disclosed in Example 1 where X is 4-methyl indole, Y is methyl iodide and Z is cyclohexylmethyl amine. Formula: $C_{18}H_{24}N_2O$; Molecular Weight: 284.4; Mass/charge ratio: 284.2 (100.0%), 285.2 (20.5%), 286.2 (2.2%); Elemental analysis: C, 76.02; H, 8.51; N, 9.85; O, 5.63.

Example 19

N-(cyclohexylmethyl)-4-fluoro-1-(2-hydroxyethyl)-1H-indole-3-carboxamide

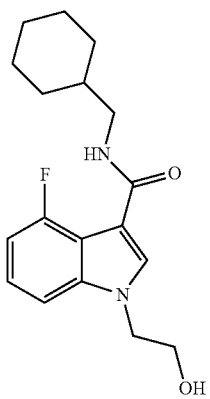 [SMILES: O=C(NCC1CCCCC1)c1cn(CCO)c2cccc(F)c12]

Synthesised according to the procedure disclosed in Example 1 where X is 4-fluoro indole, Y is O-TBS-2-chloroethanol and Z is cyclohexylmethyl amine. Formula: $C_{18}H_{23}FN_2O_2$; Molecular Weight: 318.4; Mass/charge ratio: 318.2 (100.0%), 319.2 (20.5%), 320.2 (2.4%); Elemental analysis: C, 67.90; H, 7.28; F, 5.97; N, 8.80; O, 10.05.

Example 20

4-chloro-N-(cyclohexylmethyl)-1-(2-hydroxyethyl)-1H-indole-3-carboxamide

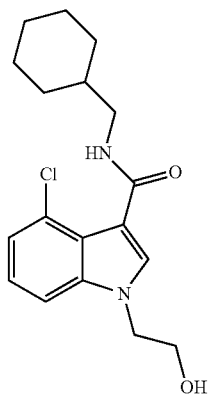 [SMILES: O=C(NCC1CCCCC1)c1cn(CCO)c2cccc(Cl)c12]

Synthesised according to the procedure disclosed in Example 1 where X is 4-chloro indole, Y is O-TBS-2-chloroethanol and Z is cyclohexylmethyl amine. Formula: $C_{18}H_{23}ClN_2O_2$; Molecular Weight: 334.8; Mass/charge ratio: 334.1 (100.0%), 336.1 (32.5%), 335.1 (20.3%), 337.1 (6.6%), 336.2 (1.9%); Elemental analysis: C, 64.57; H, 6.92; Cl, 10.59; N, 8.37; O, 9.56.

Example 21

4-bromo-N-(cyclohexylmethyl)-1-(2-hydroxyethyl)-1H-indole-3-carboxamide

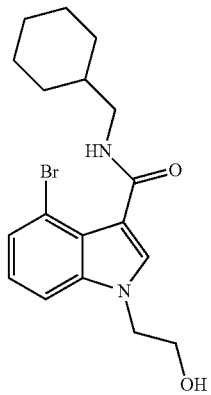 [SMILES: O=C(NCC1CCCCC1)c1cn(CCO)c2cccc(Br)c12]

Synthesised according to the procedure disclosed in Example 1 where X is 4-bromo indole, Y is O-TBS-2-chloroethanol and Z is cyclohexylmethyl amine. Formula: $C_{18}H_{23}BrN_2O_2$; Molecular Weight: 379.3; Mass/charge ratio: 378.1 (100.0%), 380.1 (99.7%), 379.1 (20.5%), 381.1 (20.2%), 382.1 (2.4%); Elemental analysis: C, 57.00; H, 6.11; Br, 21.07; N, 7.39; O, 8.44.

Example 22

N-(cycloheptylmethyl)-1-methyl-1H-indole-3-carboxamide

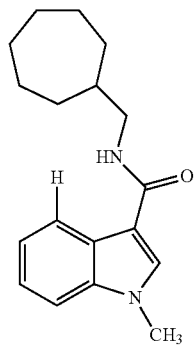

Synthesised according to the procedure disclosed in Example 1 where X is indole, Y is methyl iodide, and Z is cycloheptylmethyl amine. Formula: $C_{18}H_{24}N_2O$; Molecular Weight: 284.4; Mass/charge ratio: 284.2 (100.0%), 285.2 (20.5%), 286.2 (2.2%); Elemental analysis: C, 76.02; H, 8.51; N, 9.85; O, 5.63.

Example 23

4-chloro-N-(cycloheptylmethyl)-1-methyl-1H-indole-3-carboxamide

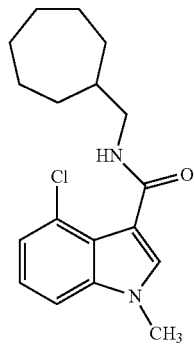 [SMILES: Cn1cc(C(=O)NCC2CCCCCC2)c2c(Cl)cccc21]

Synthesised according to the procedure disclosed in Example 1 where X is 4-chloro indole, Y is methyl iodide, and Z is cycloheptylmethyl amine. Formula: $C_{18}H_{23}ClN_2O$; Molecular Weight: 318.8; MS: 319.2/320.1; Mass/charge ratio: 318.1 (100.0%), 320.1 (32.0%), 319.2 (19.8%), 321.2 (6.5%), 320.2 (2.2%); Elemental analysis: C, 67.81; H, 7.27; Cl, 11.12; N, 8.79; O, 5.02.

Example 24

N-(cycloheptylmethyl)-4-fluoro-1-methyl-1H-indole-3-carboxamide

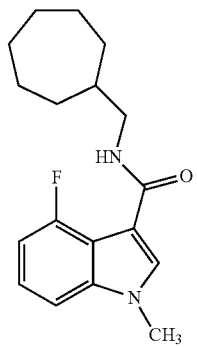

Synthesised according to the procedure disclosed in Example 1 where X is 4-fluoro indole, Y is methyl iodide, and Z is cycloheptylmethyl amine. Formula: $C_{18}H_{23}FN_2O$; Molecular Weight: 302.4; Mass/charge ratio: 302.2 (100.0%), 303.2 (20.5%), 304.2 (2.2%); Elemental analysis: C, 71.50; H, 7.67; F, 6.28; N, 9.26; O, 5.29.

Example 25

4-bromo-N-(cycloheptylmethyl)-1-methyl-1H-indole-3-carboxamide

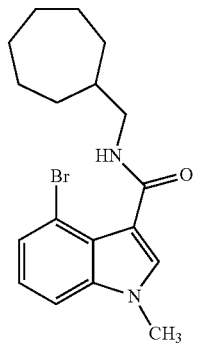

Synthesised according to the procedure disclosed in Example 1 where X is 4-bromo indole, Y is methyl iodide, and Z is cycloheptylmethyl amine. Formula: $C_{18}H_{23}BrN_2O$; Molecular Weight: 363.3; MS: 364.1/365.1; Mass/charge ratio: 362.1 (100.0%), 364.1 (99.5%), 363.1 (20.5%), 365.1 (20.1%), 366.1 (2.2%); Elemental analysis: C, 59.51; H, 6.38; Br, 21.99; N, 7.71; O, 4.40.

Example 26

N-(cycloheptylmethyl)-1,4-dimethyl-1H-indole-3-carboxamide

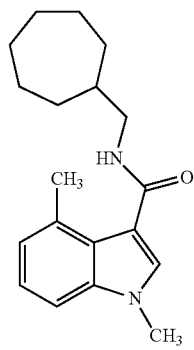 [SMILES: Cc1cccc2c1c(C(=O)NCC1CCCCCC1)cn2C]

Synthesised according to the procedure disclosed in Example 1 where X is 4-methyl indole, Y is methyl iodide, and Z is cycloheptylmethyl amine. Formula: $C_{19}H_{26}N_2O$; Molecular Weight: 298.4; MS: 299.1; Mass/charge ratio: 298.2 (100.0%), 299.2 (21.6%), 300.2 (2.4%); Elemental analysis: C, 76.47; H, 8.78; N, 9.39; O, 5.36.

Example 27

N-(cycloheptylmethyl)-4-methoxy-1-methyl-1H-indole-3-carboxamide

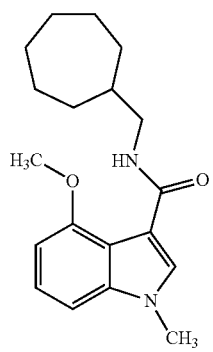 [SMILES: COc1cccc2c1c(C(=O)NCC1CCCCCC1)cn2C]

Synthesised according to the procedure disclosed in Example 1 where X is 4-methoxy indole, Y is methyl iodide, and Z is cycloheptylmethyl amine. Formula: $C_{19}H_{26}N_2O_2$; Molecular Weight: 314.4; Mass/charge ratio: 314.2 (100.0%), 315.2 (21.7%), 316.2 (2.6%); Elemental analysis: C, 72.58; H, 8.33; N, 8.91; O, 10.18.

Example 28

4-cyano-N-(cycloheptylmethyl)-1-methyl-1H-indole-3-carboxamide

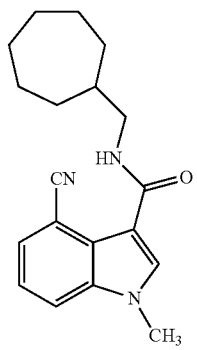 [SMILES: Cn1cc(C(=O)NCC2CCCCCC2)c2c(C#N)cccc21]

Synthesised according to the procedure disclosed in Example 1 where X is 4-cyano indole, Y is methyl iodide, and Z is cycloheptylmethyl amine. Formula: $C_{19}H_{23}N_3O$; Molecular Weight: 309.4; Mass/charge ratio: 309.2 (100.0%), 310.2 (22.0%), 311.2 (2.5%); Elemental analysis: C, 73.76; H, 7.49; N, 13.58; O, 5.17.

Example 29

N-(cycloheptylmethyl)-1-methyl-4-(trifluoromethyl)-1H-indole-3-carboxamide

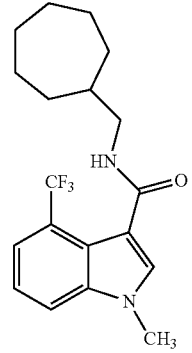 [SMILES: Cn1cc(C(=O)NCC2CCCCCC2)c2c(C(F)(F)F)cccc21]

Synthesised according to the procedure disclosed in Example 1 where X is 4-trifluoro indole, Y is methyl iodide, and Z is cycloheptylmethyl amine. Formula: $C_{19}H_{23}F_3N_2O$; Molecular Weight: 352.4; Mass/charge ratio: 352.2 (100.0%), 353.2 (21.6%), 354.2 (2.4%); Elemental analysis: C, 64.76; H, 6.58; F, 16.17; N, 7.95; O, 4.54.

Example 30

N-(cycloheptylmethyl)-1-ethyl-1H-indole-3-carboxamide

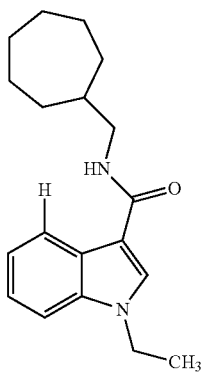 [SMILES: CCn1cc(C(=O)NCC2CCCCCC2)c2ccccc21]

Synthesised according to the procedure disclosed in Example 1 where X is indole, Y is ethyl iodide, and Z is cycloheptylmethyl amine. Formula: $C_{19}H_{26}N_2O$; Molecular Weight: 298.4; Mass/charge ratio: 298.2 (100.0%), 299.2 (21.6%), 300.2 (2.4%); Elemental analysis: C, 76.47; H, 8.78; N, 9.39; O, 5.36.

Example 31

N-(cycloheptylmethyl)-1-ethyl-4-fluoro-1H-indole-3-carboxamide

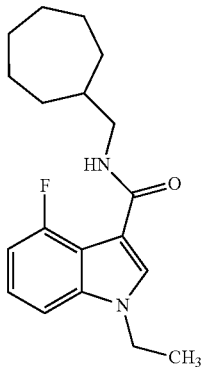 [SMILES: CCn1cc(C(=O)NCC2CCCCCC2)c2c(F)cccc21]

Synthesised according to the procedure disclosed in Example 1 where X is 4-fluoro indole, Y is ethyl iodide, and Z is cycloheptylmethyl amine. Formula: $C_{19}H_{25}FN_2O$; Molecular Weight: 316.4; Mass/charge ratio: 316.2 (100.0%), 317.2 (21.6%), 318.2 (2.4%); Elemental analysis: C, 72.12; H, 7.96; F, 6.00; N, 8.85; O, 5.06.

Example 32

4-chloro-N-(cycloheptylmethyl)-1-ethyl-1H-indole-3-carboxamide

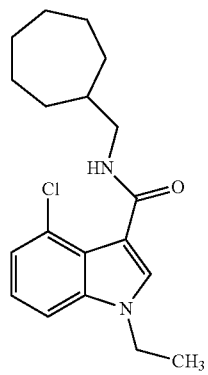 [SMILES: CCn1cc(C(=O)NCC2CCCCCC2)c2c(Cl)cccc21]

Synthesised according to the procedure disclosed in Example 1 where X is 4-chloro indole, Y is ethyl iodide, and Z is cycloheptylmethyl amine. Formula: $C_{19}H_{25}ClN_2O$; Molecular Weight: 332.9; Mass/charge ratio: 332.2 (100.0%), 334.2 (34.4%), 333.2 (21.6%), 335.2 (7.1%); Elemental analysis: C, 68.56; H, 7.57; Cl, 10.65; N, 8.42; O, 4.81.

Example 33

4-bromo-N-(cycloheptylmethyl)-1-ethyl-1H-indole-3-carboxamide

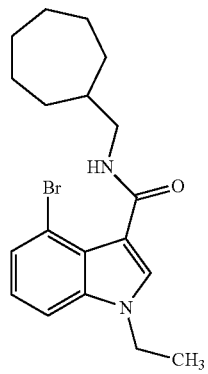 [SMILES: CCn1cc(C(=O)NCC2CCCCCC2)c2c(Br)cccc21]

Synthesised according to the procedure disclosed in Example 1 where X is 4-bromo indole, Y is ethyl iodide, and Z is cycloheptylmethyl amine. Formula: $C_{19}H_{25}BrN_2O$; Molecular Weight: 377.3; Mass/charge ratio: 376.1 (100.0%), 378.1 (99.7%), 377.1 (21.6%), 379.1 (21.2%), 380.1 (2.4%); Elemental analysis: C, 60.48; H, 6.68; Br, 21.18; N, 7.42; O, 4.24.

Example 34

N-(cycloheptylmethyl)-1-ethyl-4-methyl-1H-indole-3-carboxamide

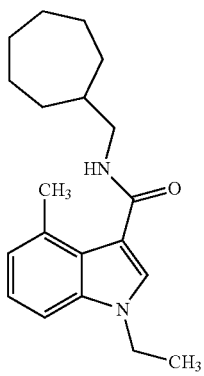

Synthesised according to the procedure disclosed in Example 1 where X is 4-methyl indole, Y is ethyl iodide, and Z is cycloheptylmethyl amine. Formula: $C_{20}H_{28}N_2O$; Molecular Weight: 312.4; Mass/charge ratio: 312.2 (100.0%), 313.2 (22.7%), 314.2 (2.7%); Elemental analysis: C, 76.88; H, 9.03; N, 8.97; O, 5.12.

Example 35

N-(cycloheptylmethyl)-1-ethyl-4-methoxy-1H-indole-3-carboxamide

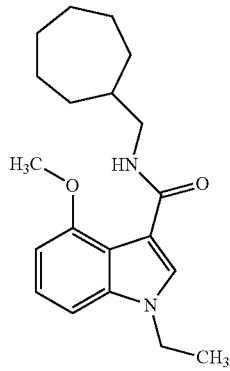 [SMILES: CCn1cc(C(=O)NCC2CCCCCC2)c2c(OC)cccc21]

Synthesised according to the procedure disclosed in Example 1 where X is 4-methoxy indole, Y is ethyl iodide, and Z is cycloheptylmethyl amine. Formula: $C_{20}H_{28}N_2O_2$; Molecular Weight: 328.4; Mass/charge ratio: 328.2 (100.0%), 329.2 (22.8%), 330.2 (2.9%); Elemental analysis: C, 73.14; H, 8.59; N, 8.53; O, 9.74.

Example 36

4-cyano-N-(cycloheptylmethyl)-1-ethyl-1H-indole-3-carboxamide

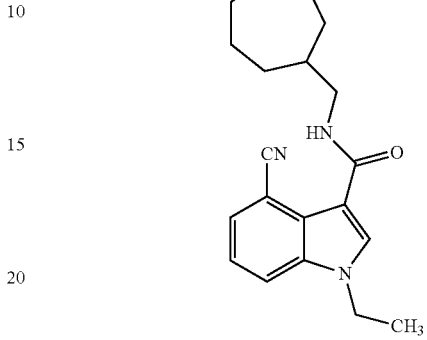

Synthesised according to the procedure disclosed in Example 1 where X is 4-cyano indole, Y is ethyl iodide, and Z is cycloheptylmethyl amine. Formula: $C_{20}H_{25}N_3O$; Molecular Weight: 323.4; Mass/charge ratio: 323.2 (100.0%), 324.2 (23.1%), 325.2 (2.7%); Elemental analysis: C, 74.27; H, 7.79; N, 12.99; O, 4.95.

Example 37

N-(cycloheptylmethyl)-1-ethyl-4-(trifluoromethyl)-1H-indole-3-carboxamide

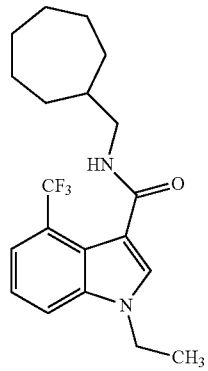 [SMILES: CCn1cc(C(=O)NCC2CCCCCC2)c2c(C(F)(F)F)cccc21]

Synthesised according to the procedure disclosed in Example 1 where X is 4-trifluoro indole, Y is ethyl iodide, and Z is cycloheptylmethyl amine. Formula: $C_{20}H_{25}F_3N_2O$; Molecular Weight: 366.4; Mass/charge ratio: 366.2 (100.0%), 367.2 (22.7%), 368.2 (2.7%); Elemental analysis: C, 65.56; H, 6.88; F, 15.55; N, 7.65; O, 4.37.

Example 38

N-(cycloheptylmethyl)-1-propyl-1H-indole-3-carboxamide

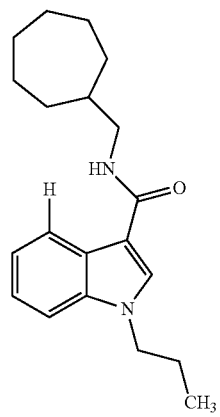

Synthesised according to the procedure disclosed in Example 1 where X is indole, Y is n-propyl bromide, and Z is cycloheptylmethyl amine. Formula: $C_{20}H_{28}N_2O$; Molecular Weight: 312.4; Mass/charge ratio: 312.2 (100.0%), 313.2 (22.7%), 314.2 (2.7%); Elemental analysis: C, 76.88; H, 9.03; N, 8.97; O, 5.12.

Example 39

N-(cycloheptylmethyl)-4-fluoro-1-propyl-1H-indole-3-carboxamide

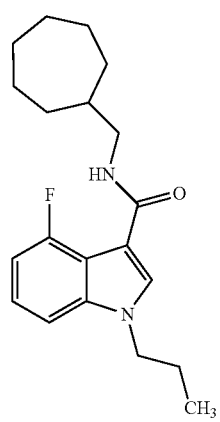 [SMILES: CCCn1cc(C(=O)NCC2CCCCCC2)c2c(F)cccc21]

Synthesised according to the procedure disclosed in Example 1 where X is 4-fluoro indole, Y is n-propyl bromide, and Z is cycloheptylmethyl amine. Formula: $C_{20}H_{27}FN_2O$; Molecular Weight: 330.4; Mass/charge ratio: 330.2 (100.0%), 331.2 (22.7%), 332.2 (2.7%); Elemental analysis: C, 72.70; H, 8.24; F, 5.75; N, 8.48; O, 4.84.

Example 40

4-chloro-N-(cycloheptylmethyl)-1-propyl-1H-indole-3-carboxamide

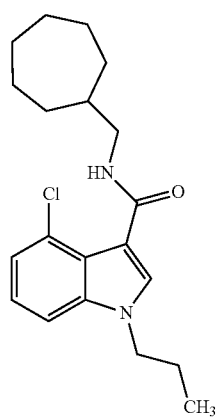 [SMILES: CCCn1cc(C(=O)NCC2CCCCCC2)c2c(Cl)cccc21]

Synthesised according to the procedure disclosed in Example 1 where X is 4-chloro indole, Y is n-propyl bromide, and Z is cycloheptylmethyl amine. Formula: $C_{20}H_{27}ClN_2O$; Molecular Weight: 346.9; Mass/charge ratio: 346.2 (100.0%), 348.2 (34.6%), 347.2 (22.7%), 349.2 (7.5%); Elemental analysis: C, 69.25; H, 7.85; Cl, 10.22; N, 8.08; O, 4.61.

Example 41

4-bromo-N-(cycloheptylmethyl)-1-propyl-1H-indole-3-carboxamide

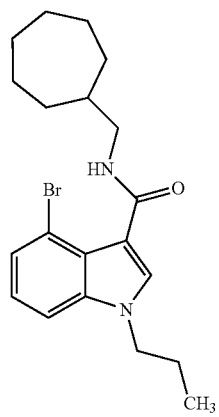

Synthesised according to the procedure disclosed in Example 1 where X is 4-bromo indole, Y is n-propyl bromide, and Z is cycloheptylmethyl amine. Formula: $C_{20}H_{27}BrN_2O$; Molecular Weight: 391.3; Mass/charge ratio: 390.1 (100.0%), 392.1 (99.9%), 391.1 (22.7%), 393.1 (22.3%), 394.1 (2.6%); Elemental analysis: C, 61.38; H, 6.95; Br, 20.42; N, 7.16; O, 4.09.

Example 42

N-(cycloheptylmethyl)-4-methyl-1-propyl-1H-indole-3-carboxamide

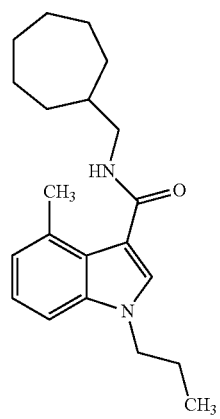 [SMILES: CCCn1cc(C(=O)NCC2CCCCCC2)c2c(C)cccc21]

Synthesised according to the procedure disclosed in Example 1 where X is 4-methyl indole, Y is n-propyl bromide, and Z is cycloheptylmethyl amine. Formula: $C_{21}H_{30}N_2O$; Molecular Weight: 326.5; Mass/charge ratio: 326.2 (100.0%), 327.2 (23.8%), 328.2 (2.9%); Elemental analysis: C, 77.26; H, 9.26; N, 8.58; O, 4.90.

Example 43

N-(cycloheptylmethyl)-4-methoxy-1-propyl-1H-indole-3-carboxamide

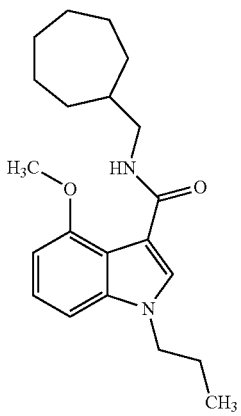 [SMILES: CCCn1cc(C(=O)NCC2CCCCCC2)c2c(OC)cccc21]

Synthesised according to the procedure disclosed in Example 1 where X is 4-methoxy indole, Y is n-propyl bromide, and Z is cycloheptylmethyl amine. Formula: $C_{21}H_{30}N_2O_2$; Molecular Weight: 342.5; Mass/charge ratio: 342.2 (100.0%), 343.2 (23.9%), 344.2 (3.1%); Elemental analysis: C, 73.65; H, 8.83; N, 8.18; O, 9.34.

Example 44

4-cyano-N-(cycloheptylmethyl)-1-propyl-1H-indole-3-carboxamide

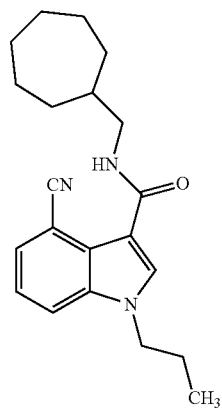 [SMILES: CCCn1cc(C(=O)NCC2CCCCCC2)c2c(C#N)cccc21]

Synthesised according to the procedure disclosed in Example 1 where X is 4-cyano indole, Y is n-propyl bromide, and Z is cycloheptylmethyl amine. Formula: $C_{21}H_{27}N_3O$; Molecular Weight: 337.5; Mass/charge ratio: 337.2 (100.0%), 338.2 (24.2%), 339.2 (3.0%); Elemental analysis: C, 74.74; H, 8.06; N, 12.45; O, 4.74.

Example 45

N-(cycloheptylmethyl)-1-propyl-4-(trifluoromethyl)-1H-indole-3-carboxamide

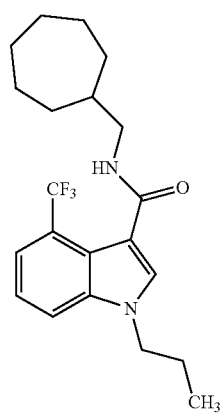 [SMILES: CCCn1cc(C(=O)NCC2CCCCCC2)c2c(C(F)(F)F)cccc21]

Synthesised according to the procedure disclosed in Example 1 where X is 4-trifluoro indole, Y is n-propyl bromide, and Z is cycloheptylmethyl amine. Formula: $C_{21}H_{27}F_3N_2O$; Molecular Weight: 380.4; Mass/charge ratio: 380.2 (100.0%), 381.2 (23.8%), 382.2 (2.9%); Elemental analysis: C, 66.30; H, 7.15; F, 14.98; N, 7.36; O, 4.21.

Example 46

4-chloro-N-(cycloheptylmethyl)-1-isopropyl-1H-indole-3-carboxamide

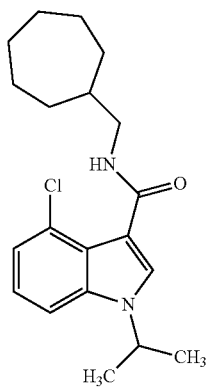 [SMILES: CC(C)n1cc(C(=O)NCC2CCCCCC2)c2c(Cl)cccc21]

Synthesised according to the procedure disclosed in Example 1 where X is 4-chloro indole, Y is isopropyl bromide, and Z is cycloheptylmethyl amine. Formula: $C_{20}H_{27}ClN_2O$; Molecular Weight: 346.9; Mass/charge ratio: 346.2 (100.0%), 348.2 (34.6%), 347.2 (22.7%), 349.2 (7.5%); Elemental analysis: C, 69.25; H, 7.85; Cl, 10.22; N, 8.08; O, 4.61.

Example 47

4-bromo-N-(cycloheptylmethyl)-1-isopropyl-1H-indole-3-carboxamide

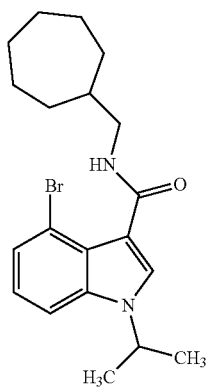 [SMILES: CC(C)n1cc(C(=O)NCC2CCCCCC2)c2c(Br)cccc21]

Synthesised according to the procedure disclosed in Example 1 where X is 4-bromo indole, Y is isopropyl bromide, and Z is cycloheptylmethyl amine. Formula: $C_{20}H_{27}BrN_2O$; Molecular Weight: 391.3; Mass/charge ratio: 390.1 (100.0%), 392.1 (99.9%), 391.1 (22.7%), 393.1 (22.3%), 394.1 (2.6%); Elemental analysis: C, 61.38; H, 6.95; Br, 20.42; N, 7.16; O, 4.09.

Example 48

N-(cycloheptylmethyl)-1-isopropyl-4-methyl-1H-indole-3-carboxamide

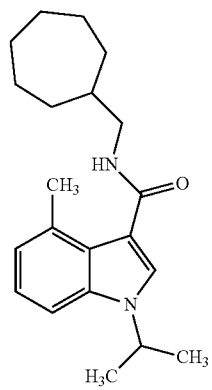 [SMILES: Cc1cccc2c1c(C(=O)NCC1CCCCCC1)cn2C(C)C]

Synthesised according to the procedure disclosed in Example 1 where X is 4-methyl indole, Y is isopropyl bromide, and Z is cycloheptylmethyl amine. Formula: $C_{21}H_{30}N_2O$; Molecular Weight: 326.5; Mass/charge ratio: 326.2 (100.0%), 327.2 (23.8%), 328.2 (2.9%); Elemental analysis: C, 77.26; H, 9.26; N, 8.58; O, 4.90.

Example 49

4-chloro-N-(cycloheptylmethyl)-1-isobutyl-1H-indole-3-carboxamide

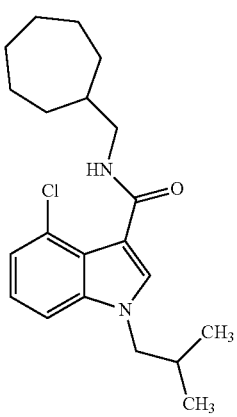 [SMILES: CC(C)Cn1cc(C(=O)NCC2CCCCCC2)c2c(Cl)cccc21]

Synthesised according to the procedure disclosed in Example 1 where X is 4-chloro indole, Y is isobutyl bromide, and Z is cycloheptylmethyl amine. Formula: $C_{21}H_{29}ClN_2O$; Molecular Weight: 360.9; Mass/charge ratio: 360.2 (100.0%), 362.2 (34.9%), 361.2 (23.8%), 363.2 (7.9%); Elemental analysis: C, 69.88; H, 8.10; Cl, 9.82; N, 7.76; O, 4.43.

Example 50

4-bromo-N-(cycloheptylmethyl)-1-isobutyl-1H-indole-3-carboxamide

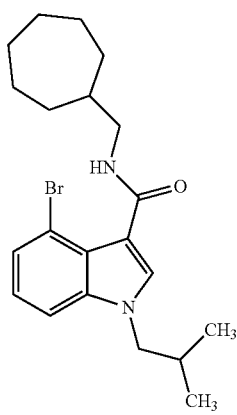 [SMILES: CC(C)Cn1cc(C(=O)NCC2CCCCCC2)c2c(Br)cccc21]

Synthesised according to the procedure disclosed in Example 1 where X is 4-bromo indole, Y is isobutyl bromide, and Z is cycloheptylmethyl amine. Formula: $C_{21}H_{29}BrN_2O$; Molecular Weight: 405.4; Mass/charge ratio: 404.1 (100.0%), 406.1 (97.4%), 405.1 (23.5%), 407.1 (22.9%), 406.2 (2.7%), 408.2 (2.5%); Elemental analysis: C, 62.22; H, 7.21; Br, 19.71; N, 6.91; O, 3.95.

Example 51

N-(cycloheptylmethyl)-1-isobutyl-4-methyl-1H-indole-3-carboxamide

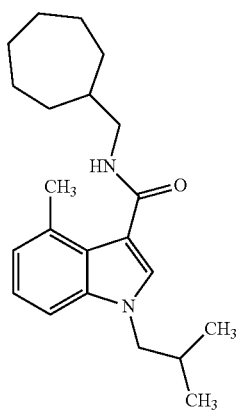 [SMILES: Cc1cccc2c1c(C(=O)NCC1CCCCCC1)cn2CC(C)C]

Synthesised according to the procedure disclosed in Example 1 where X is 4-methyl indole, Y is isobutyl bromide, and Z is cycloheptylmethyl amine. Formula: $C_{22}H_{32}N_2O$; Molecular Weight: 340.5; Mass/charge ratio: 340.3 (100.0%), 341.3 (24.2%), 342.3 (3.2%); Elemental analysis: C, 77.60; H, 9.47; N, 8.23; O, 4.70.

Example 52

N-(cycloheptylmethyl)-1-(2-hydroxyethyl)-1H-indole-3-carboxamide

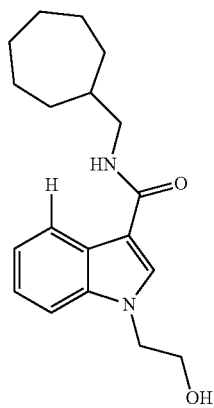 [SMILES: O=C(NCC1CCCCCC1)c1cn(CCO)c2ccccc12]

Synthesised according to the procedure disclosed in Example 1 where X is indole, Y is O-t-butyldimethylsilyl-2-chloroethanol, and Z is cycloheptylmethyl amine. Formula: $C_{19}H_{26}N_2O_2$; Molecular Weight: 314.4; Mass/charge ratio: 314.2 (100.0%), 315.2 (21.7%), 316.2 (2.6%); Elemental analysis: C, 72.58; H, 8.33; N, 8.91; O, 10.18.

Example 53

N-(cycloheptylmethyl)-4-fluoro-1-(2-hydroxyethyl)-1H-indole-3-carboxamide

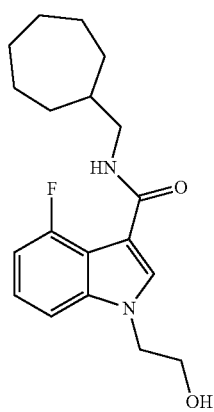 [SMILES: O=C(NCC1CCCCCC1)c1cn(CCO)c2cccc(F)c12]

Synthesised according to the procedure disclosed in Example 1 where X is 4-fluoro indole, Y is O-t-butyldimethylsilyl-2-chloroethanol, and Z is cycloheptylmethyl amine. Formula: $C_{19}H_{25}FN_2O_2$; Molecular Weight: 332.4; Mass/charge ratio: 332.2 (100.0%), 333.2 (21.7%), 334.2 (2.6%); Elemental analysis: C, 68.65; H, 7.58; F, 5.72; N, 8.43; O, 9.63.

Example 54

4-chloro-N-(cycloheptylmethyl)-1-(2-hydroxyethyl)-1H-indole-3-carboxamide

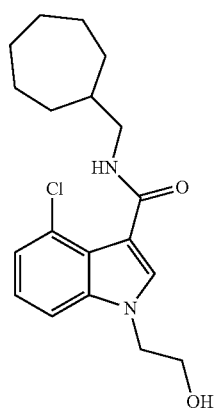 [SMILES: O=C(NCC1CCCCCC1)c1cn(CCO)c2cccc(Cl)c12]

Synthesised according to the procedure disclosed in Example 1 where X is 4-chloro indole, Y is O-t-butyldimethylsilyl-2-chloroethanol, and Z is cycloheptylmethyl amine. Formula: $C_{19}H_{25}ClN_2O_2$; Molecular Weight: 348.9; MS: 349.2/350.2; Mass/charge ratio: 348.2 (100.0%), 350.2 (34.6%), 349.2 (21.7%), 351.2 (7.2%); Elemental analysis: C, 65.41; H, 7.22; Cl, 10.16; N, 8.03; O, 9.17.

Example 55

4-bromo-N-(cycloheptylmethyl)-1-(2-hydroxyethyl)-1H-indole-3-carboxamide

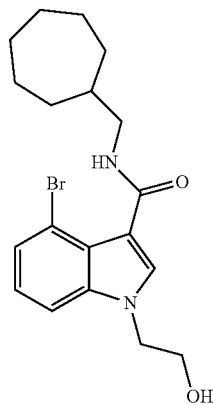 [SMILES: O=C(NCC1CCCCCC1)c1cn(CCO)c2cccc(Br)c12]

Synthesised according to the procedure disclosed in Example 1 where X is 4-bromo indole, Y is O-t-butyldimethylsilyl-2-chloroethanol, and Z is cycloheptylmethyl amine. Formula: $C_{19}H_{25}BrN_2O_2$; Molecular Weight: 393.3; MS: 393.2/394.2; Mass/charge ratio: 392.1 (100.0%), 394.1 (99.9%), 393.1 (21.7%), 395.1 (21.3%), 396.1 (2.6%); Elemental analysis: C, 58.02; H, 6.41; Br, 20.32; N, 7.12; O, 8.14.

Example 56

N-(cycloheptylmethyl)-1-(2-hydroxyethyl)-4-methyl-1H-indole-3-carboxamide

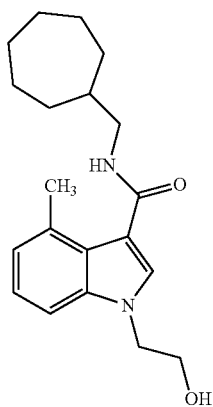 [SMILES: Cc1cccc2c1c(C(=O)NCC1CCCCCC1)cn2CCO]

Synthesised according to the procedure disclosed in Example 1 where X is 4-methyl indole, Y is O-t-butyldimethylsilyl-2-chloroethanol, and Z is cycloheptylmethyl amine. Formula: $C_{20}H_{28}N_2O_2$; Molecular Weight: 328.4; Mass/charge ratio: 328.2 (100.0%), 329.2 (22.8%), 330.2 (2.9%); Elemental analysis: C, 73.14; H, 8.59; N, 8.53; O, 9.74.

Example 57

N-(cycloheptylmethyl)-1-(2-hydroxyethyl)-4-methoxy-1H-indole-3-carboxamide

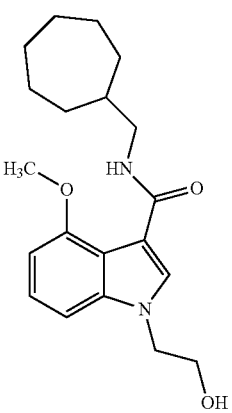 [SMILES: COc1cccc2c1c(C(=O)NCC1CCCCCC1)cn2CCO]

Synthesised according to the procedure disclosed in Example 1 where X is 4-methoxy indole, Y is O-t-butyldimethylsilyl-2-chloroethanol, and Z is cycloheptylmethyl amine. Formula: $C_{20}H_{28}N_2O_3$; Molecular Weight: 344.4; Mass/charge ratio: 344.2 (100.0%), 345.2 (22.8%), 346.2 (3.1%); Elemental analysis: C, 69.74; H, 8.19; N, 8.13; O, 13.93.

Example 58

4-cyano-N-(cycloheptylmethyl)-1-(2-hydroxyethyl)-1H-indole-3-carboxamide

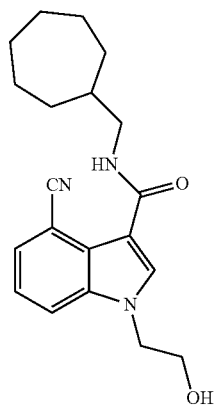 [SMILES: N#Cc1cccc2c1c(C(=O)NCC1CCCCCC1)cn2CCO]

Synthesised according to the procedure disclosed in Example 1 where X is 4-cyano indole, Y is O-t-butyldimethylsilyl-2-chloroethanol, and Z is cycloheptylmethyl amine. Formula: $C_{20}H_{25}N_3O_2$; Molecular Weight: 339.4; Mass/charge ratio: 339.2 (100.0%), 340.2 (23.1%), 341.2 (3.0%); Elemental analysis: C, 70.77; H, 7.42; N, 12.38; O, 9.43.

Example 59

N-(cycloheptylmethyl)-1-(2-hydroxyethyl)-4-(trifluoromethyl)-1H-indole-3-carboxamide

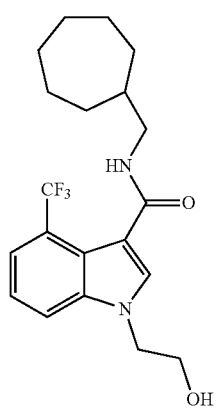 [SMILES: O=C(NCC1CCCCCC1)c1cn(CCO)c2cccc(C(F)(F)F)c12]

Synthesised according to the procedure disclosed in Example 1 where X is 4-trifluoro indole, Y is O-t-butyldimethylsilyl-2-chloroethanol, and Z is cycloheptylmethyl amine. Formula: $C_{20}H_{25}F_3N_2O_2$; Molecular Weight: 382.4; Mass/charge ratio: 382.2 (100.0%), 383.2 (22.7%), 384.2 (2.9%); Elemental analysis: C, 62.81; H, 6.59; F, 14.90; N, 7.33; O, 8.37.

Example 60

1-butyl-N-(cycloheptylmethyl)-1H-indole-3-carboxamide

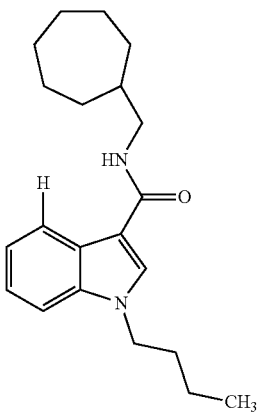 [SMILES: CCCCn1cc(C(=O)NCC2CCCCCC2)c2c(F)cccc21]

Synthesised according to the procedure disclosed in Example 1 where X is indole, Y is n-butyl bromide, and Z is cycloheptylmethyl amine. Formula: $C_{21}H_{30}N_2O$; Molecular Weight: 326.5; Mass/charge ratio: 326.2 (100.0%), 327.2 (23.8%), 328.2 (2.9%); Elemental analysis: C, 77.26; H, 9.26; N, 8.58; O, 4.90.

Example 61

1-butyl-N-(cycloheptylmethyl)-4-fluoro-1H-indole-3-carboxamide

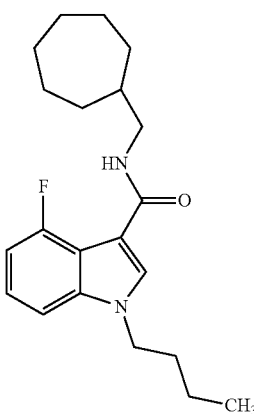

Synthesised according to the procedure disclosed in Example 1 where X is 4-fluoro indole, Y is n-butyl bromide, and Z is cycloheptylmethyl amine. Formula: $C_{21}H_{29}FN_2O$; Molecular Weight: 344.5; Mass/charge ratio: 344.2 (100.0%), 345.2 (23.8%), 346.2 (2.9%); Elemental analysis: C, 73.22; H, 8.49; F, 5.52; N, 8.13; O, 4.64.

Example 62

1-butyl-4-chloro-N-(cycloheptylmethyl)-1H-indole-3-carboxamide

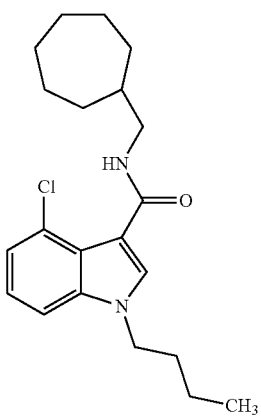

Synthesised according to the procedure disclosed in Example 1 where X is 4-chloro indole, Y is n-butyl bromide, and Z is cycloheptylmethyl amine. Formula: $C_{21}H_{29}ClN_2O$; Molecular Weight: 360.9; Mass/charge ratio: 360.2 (100.0%), 362.2 (34.9%), 361.2 (23.8%), 363.2 (7.9%); Elemental analysis: C, 69.88; H, 8.10; Cl, 9.82; N, 7.76; O, 4.43.

Example 63

4-bromo-1-butyl-N-(cycloheptylmethyl)-1H-indole-3-carboxamide

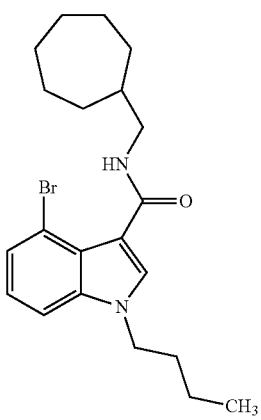

Synthesised according to the procedure disclosed in Example 1 where X is 4-bromo indole, Y is n-butyl bromide, and Z is cycloheptylmethyl amine. Formula: $C_{21}H_{29}BrN_2O$; Molecular Weight: 405.4; Mass/charge ratio: 404.1 (100.0%), 406.1 (97.4%), 405.1 (23.5%), 407.1 (22.9%), 406.2 (2.7%), 408.2; Elemental analysis: C, 62.22; H, 7.21; Br, 19.71; N, 6.91; O, 3.95.

Example 64

1-butyl-N-(cycloheptylmethyl)-4-methyl-1H-indole-3-carboxamide

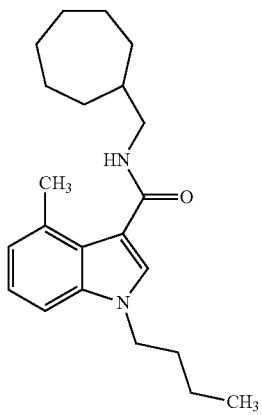 [SMILES: CCCCn1cc(C(=O)NCC2CCCCCC2)c2c(C)cccc21]

Synthesised according to the procedure disclosed in Example 1 where X is 4-methyl indole, Y is n-butyl bromide, and Z is cycloheptylmethyl amine. Formula: $C_{22}H_{32}N_2O$; Molecular Weight: 340.5; Mass/charge ratio: 340.3 (100.0%), 341.3 (24.2%), 342.3 (3.2%); Elemental analysis: C, 77.60; H, 9.47; N, 8.23; O, 4.70.

Example 65

N-(cycloheptylmethyl)-4-fluoro-1-(3-hydroxypropyl)-1H-indole-3-carboxamide

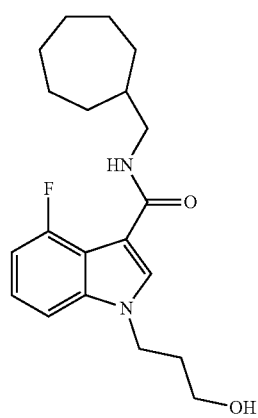 [SMILES: O=C(NCC1CCCCCC1)c1cn(CCCO)c2cccc(F)c12]

Synthesised according to the procedure disclosed in Example 1 where X is 4-fluoro indole, Y is O-t-butyldimethylsilyl-2-chloropropanol, and Z is cycloheptylmethyl amine. Formula: $C_{20}H_{27}FN_2O_2$; Molecular Weight: 346.4; Mass/charge ratio: 346.2 (100.0%), 347.2 (22.8%), 348.2 (2.9%); Elemental analysis: C, 69.34; H, 7.86; F, 5.48; N, 8.09; O, 9.24.

Example 66

4-chloro-N-(cycloheptylmethyl)-1-(3-hydroxypropyl)-1H-indole-3-carboxamide

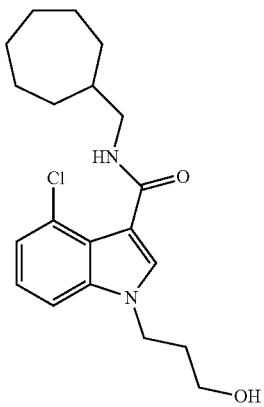 [SMILES: O=C(NCC1CCCCCC1)c1cn(CCCO)c2cccc(Cl)c12]

Synthesised according to the procedure disclosed in Example 1 where X is 4-chloro indole, Y is O-t-butyldimethylsilyl-2-chloropropanol, and Z is cycloheptylmethyl amine. Formula: $C_{20}H_{27}ClN_2O_2$; Molecular Weight: 362.9; Mass/charge ratio: 362.2 (100.0%), 364.2 (34.8%), 363.2 (22.8%), 365.2 (7.5%); Elemental analysis: C, 66.19; H, 7.50; Cl, 9.77; N, 7.72; O, 8.82.

Example 67

4-bromo-N-(cycloheptylmethyl)-1-(3-hydroxypropyl)-1H-indole-3-carboxamide

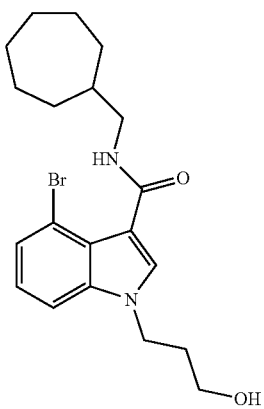 [SMILES: O=C(NCC1CCCCCC1)c1cn(CCCO)c2cccc(Br)c12]

Synthesised according to the procedure disclosed in Example 1 where X is 4-bromo indole, Y is O-t-butyldimethylsilyl-2-chloropropanol, and Z is cycloheptylmethyl amine. Formula: $C_{20}H_{27}BrN_2O_2$; Molecular Weight: 407.3; Mass/charge ratio: 408.1 (100.0%), 406.1 (99.8%), 407.1 (22.7%), 409.1 (22.4%), 410.1 (2.8%); Elemental analysis: C, 58.97; H, 6.68; Br, 19.62; N, 6.88; O, 7.86.

Example 68

N-(bicyclo[2.2.2]octan-1-ylmethyl)-1-methyl-1H-indole-3-carboxamide

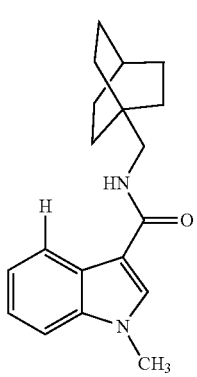 [SMILES: Cn1cc(C(=O)NCC23CCC(CC2)CC3)c2ccccc21]

Synthesised according to the procedure disclosed in Example 1 where X is indole, Y is methyl iodide, and Z is bicyclo[2.2.2]octan-1-ylmethyl amine. Formula: $C_{19}H_{24}N_2O$; Molecular Weight: 296.4; Mass/charge ratio: 296.2 (100.0%), 297.2 (21.6%), 298.2 (2.4%); Elemental analysis: C, 76.99; H, 8.16; N, 9.45; O, 5.40.

Example 69

N-(bicyclo[2.2.2]octan-1-ylmethyl)-4-chloro-1-methyl-1H-indole-3-carboxamide

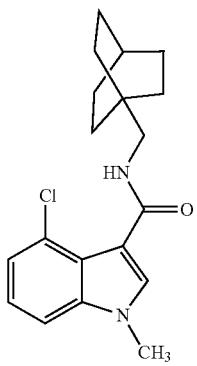 [SMILES: Cn1cc(C(=O)NCC23CCC(CC2)CC3)c2c(Cl)cccc21]

Synthesised according to the procedure disclosed in Example 1 where X is 4-chloro indole, Y is methyl iodide, and Z is bicyclo[2.2.2]octan-1-ylmethyl amine. Formula: $C_{19}H_{23}ClN_2O$; Molecular Weight: 330.9; MS: 331.2/332.2; Mass/charge ratio: 330.1 (100.0%), 332.1 (32.0%), 331.2 (20.9%), 333.2 (6.9%), 332.2 (2.4%); Elemental analysis: C, 68.97; H, 7.01; Cl, 10.72; N, 8.47; O, 4.84.

Example 70

N-(bicyclo[2.2.2]octan-1-ylmethyl)-4-fluoro-1-methyl-1H-indole-3-carboxamide

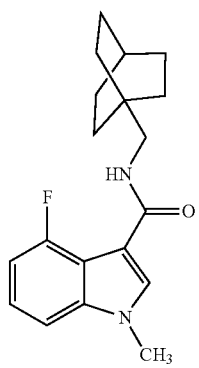 [SMILES: Cn1cc(C(=O)NCC23CCC(CC2)CC3)c2c(F)cccc21]

Synthesised according to the procedure disclosed in Example 1 where X is 4-fluoro indole, Y is methyl iodide, and Z is bicyclo[2.2.2]octan-1-ylmethyl amine. Formula: $C_{19}H_{23}FN_2O$; Molecular Weight: 314.4; Mass/charge ratio: 314.2 (100.0%), 315.2 (21.6%), 316.2 (2.4%); Elemental analysis: C, 72.58; H, 7.37; F, 6.04; N, 8.91; O, 5.09.

Example 71

N-(bicyclo[2.2.2]octan-1-ylmethyl)-4-bromo-1-methyl-1H-indole-3-carboxamide

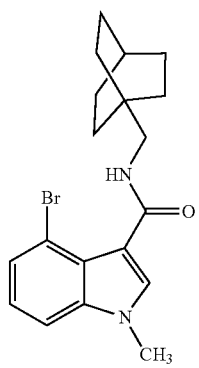 [SMILES: Cn1cc(C(=O)NCC23CCC(CC2)CC3)c2c(Br)cccc21]

Synthesised according to the procedure disclosed in Example 1 where X is 4-bromo indole, Y is methyl iodide, and Z is bicyclo[2.2.2]octan-1-ylmethyl amine. Formula: $C_{19}H_{23}BrN_2O$; Molecular Weight: 375.3; MS: 375.1/376.1; Mass/charge ratio: 374.1 (100.0%), 376.1 (99.7%), 375.1 (21.6%), 377.1 (21.2%), 378.1 (2.4%); Elemental analysis: C, 60.81; H, 6.18; Br, 21.29; N, 7.46; O, 4.26.

Example 72

N-(bicyclo[2.2.2]octan-1-ylmethyl)-1,4-dimethyl-1H-indole-3-carboxamide

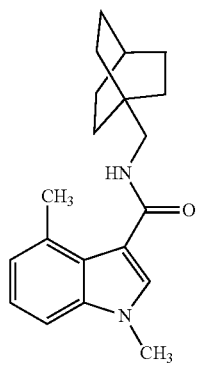 [SMILES: Cc1cccc2c1c(C(=O)NCC13CCC(CC1)CC3)cn2C]

Synthesised according to the procedure disclosed in Example 1 where X is 4-methyl indole, Y is methyl iodide, and Z is bicyclo[2.2.2]octan-1-ylmethyl amine. Formula: $C_{20}H_{26}N_2O$; Molecular Weight: 310.4; MS: 311.1; Mass/charge ratio: 310.2 (100.0%), 311.2 (22.7%), 312.2 (2.7%); Elemental analysis: C, 77.38; H, 8.44; N, 9.02; O, 5.15.

Example 73

N-(bicyclo[2.2.2]octan-1-ylmethyl)-4-methoxy-1-methyl-1H-indole-3-carboxamide

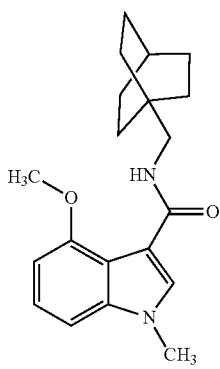 [SMILES: COc1cccc2c1c(C(=O)NCC13CCC(CC1)CC3)cn2C]

Synthesised according to the procedure disclosed in Example 1 where X is 4-methoxy indole, Y is methyl iodide, and Z is bicyclo[2.2.2]octan-1-ylmethyl amine. Formula: $C_{20}H_{26}N_2O_2$; Molecular Weight: 326.4; Mass/charge ratio: 326.2 (100.0%), 327.2 (22.7%), 328.2 (2.9%); Elemental analysis: C, 73.59; H, 8.03; N, 8.58; O, 9.80.

Example 74

N-(bicyclo[2.2.2]octan-1-ylmethyl)-4-cyano-1-methyl-1H-indole-3-carboxamide

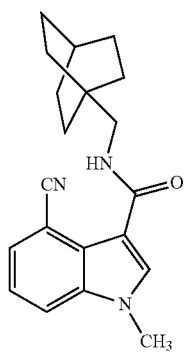 [SMILES: Cn1cc(C(=O)NCC23CCC(CC2)CC3)c2c(C#N)cccc21]

Synthesised according to the procedure disclosed in Example 1 where X is 4-cyano indole, Y is methyl iodide, and Z is bicyclo[2.2.2]octan-1-ylmethyl amine. Formula: $C_{20}H_{23}N_3O$; Molecular Weight: 321.4; Mass/charge ratio: 321.2 (100.0%), 322.2 (23.0%), 323.2 (2.7%); Elemental analysis: C, 74.74; H, 7.21; N, 13.07; O, 4.98.

Example 75

N-(bicyclo[2.2.2]octan-1-ylmethyl)-1-methyl-4-(trifluoromethyl)-1H-indole-3-carboxamide

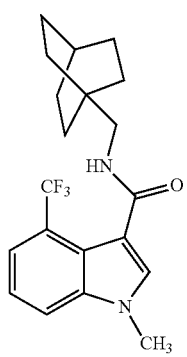 [SMILES: Cn1cc(C(=O)NCC23CCC(CC2)CC3)c2c(C(F)(F)F)cccc21]

Synthesised according to the procedure disclosed in Example 1 where X is 4-trifluoro indole, Y is methyl iodide, and Z is bicyclo[2.2.2]octan-1-ylmethyl amine. Formula: $C_{20}H_{23}F_3N_2O$; Molecular Weight: 364.4; Mass/charge ratio: 364.2 (100.0%), 365.2 (22.7%), 366.2 (2.7%); Elemental analysis: C, 65.92; H, 6.36; F, 15.64; N, 7.69; O, 4.39.

Example 76

N-(bicyclo[2.2.2]octan-1-ylmethyl)-1-ethyl-1H-indole-3-carboxamide

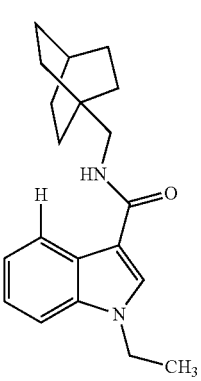 [SMILES: CCn1cc(C(=O)NCC23CCC(CC2)CC3)c2c(F)cccc21]

Synthesised according to the procedure disclosed in Example 1 where X is indole, Y is ethyl iodide, and Z is bicyclo[2.2.2]octan-1-ylmethyl amine. Formula: $C_{20}H_{26}N_2O$; Molecular Weight: 310.4; Mass/charge ratio: 310.2 (100.0%), 311.2 (22.7%), 312.2 (2.7%); Elemental analysis: C, 77.38; H, 8.44; N, 9.02; O, 5.15.

Example 77

N-(bicyclo[2.2.2]octan-1-ylmethyl)-1-ethyl-4-fluoro-1H-indole-3-carboxamide

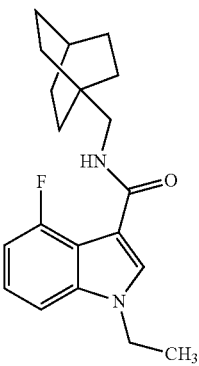

Synthesised according to the procedure disclosed in Example 1 where X is 4-fluoro indole, Y is ethyl iodide, and Z is bicyclo[2.2.2]octan-1-ylmethyl amine. Formula: $C_{20}H_{25}FN_2O$; Molecular Weight: 328.4; Mass/charge ratio: 328.2 (100.0%), 329.2 (22.7%), 330.2 (2.7%); Elemental analysis: C, 73.14; H, 7.67; F, 5.78; N, 8.53; O, 4.87.

Example 78

N-(bicyclo[2.2.2]octan-1-ylmethyl)-4-chloro-1-ethyl-1H-indole-3-carboxamide

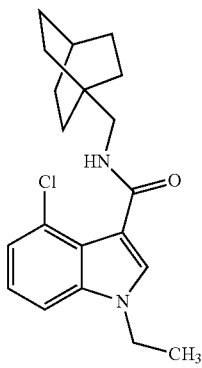 [SMILES: CCn1cc(C(=O)NCC23CCC(CC2)CC3)c2c(Cl)cccc21]

Synthesised according to the procedure disclosed in Example 1 where X is 4-chloro indole, Y is ethyl iodide, and Z is bicyclo[2.2.2]octan-1-ylmethyl amine. Formula: $C_{20}H_{25}ClN_2O$; Molecular Weight: 344.9; Mass/charge ratio: 344.2 (100.0%), 346.2 (34.6%), 345.2 (22.7%), 347.2 (7.5%); Elemental analysis: C, 69.65; H, 7.31; Cl, 10.28; N, 8.12; O, 4.64.

Example 79

N-(bicyclo[2.2.2]octan-1-ylmethyl)-4-bromo-1-ethyl-1H-indole-3-carboxamide

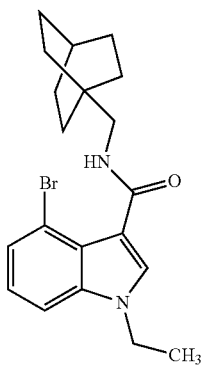 [SMILES: CCn1cc(C(=O)NCC23CCC(CC2)CC3)c2c(Br)cccc21]

Synthesised according to the procedure disclosed in Example 1 where X is 4-bromo indole, Y is ethyl iodide, and Z is bicyclo[2.2.2]octan-1-ylmethyl amine. Formula: $C_{20}H_{25}BrN_2O$; Molecular Weight: 389.3; Mass/charge ratio: 388.1 (100.0%), 390.1 (99.9%), 389.1 (22.7%), 391.1 (22.3%), 392.1 (2.6%); Elemental analysis: C, 61.70; H, 6.47; Br, 20.52; N, 7.20; O, 4.11.

Example 80

N-(bicyclo[2.2.2]octan-1-ylmethyl)-1-ethyl-4-methyl-1H-indole-3-carboxamide

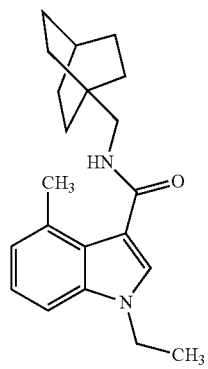 [SMILES: CCn1cc(C(=O)NCC23CCC(CC2)CC3)c2c(C)cccc21]

Synthesised according to the procedure disclosed in Example 1 where X is 4-methyl indole, Y is ethyl iodide, and Z is bicyclo[2.2.2]octan-1-ylmethyl amine. Formula: $C_{21}H_{28}N_2O$; Molecular Weight: 324.5; Mass/charge ratio: 324.2 (100.0%), 325.2 (23.8%), 326.2 (2.9%); Elemental analysis: C, 77.74; H, 8.70; N, 8.63; O, 4.93.

Example 81

N-(bicyclo[2.2.2]octan-1-ylmethyl)-1-ethyl-4-methoxy-1H-indole-3-carboxamide

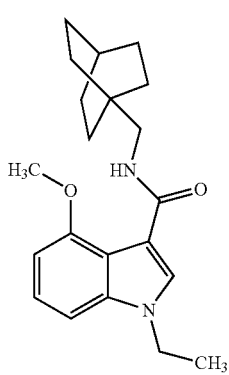 [SMILES: CCn1cc(C(=O)NCC23CCC(CC2)CC3)c2c(OC)cccc21]

Synthesised according to the procedure disclosed in Example 1 where X is 4-methoxy indole, Y is ethyl iodide, and Z is bicyclo[2.2.2]octan-1-ylmethyl amine. Formula: $C_{21}H_{28}N_2O_2$; Molecular Weight: 340.5; Mass/charge ratio: 340.2 (100.0%), 341.2 (23.8%), 342.2 (3.1%); Elemental analysis: C, 74.08; H, 8.29; N, 8.23; O, 9.40.

Example 82

N-(bicyclo[2.2.2]octan-1-ylmethyl)-4-cyano-1-ethyl-1H-indole-3-carboxamide

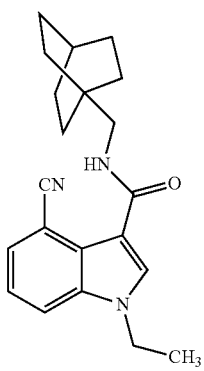 [SMILES: CCn1cc(C(=O)NCC23CCC(CC2)CC3)c2c(C#N)cccc21]

Synthesised according to the procedure disclosed in Example 1 where X is 4-cyano indole, Y is ethyl iodide, and Z is bicyclo[2.2.2]octan-1-ylmethyl amine. Formula: $C_{21}H_{25}N_3O$; Molecular Weight: 335.4; Mass/charge ratio: 335.2 (100.0%), 336.2 (24.1%), 337.2 (3.0%); Elemental analysis: C, 75.19; H, 7.51; N, 12.53; O, 4.77.

Example 83

N-(bicyclo[2.2.2]octan-1-ylmethyl)-1-ethyl-4-(trifluoromethyl)-1H-indole-3-carboxamide

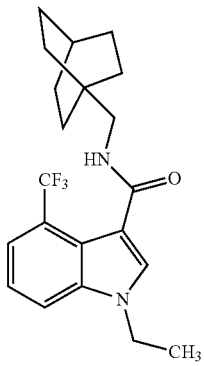 [SMILES: CCn1cc(C(=O)NCC23CCC(CC2)CC3)c2c(C(F)(F)F)cccc21]

Synthesised according to the procedure disclosed in Example 1 where X is 4-trifluoro indole, Y is ethyl iodide, and Z is bicyclo[2.2.2]octan-1-ylmethyl amine. Formula: $C_{21}H_{25}F_3N_2O$; Molecular Weight: 378.4; Mass/charge ratio: 378.2 (100.0%), 379.2 (23.8%), 380.2 (2.9%); Elemental analysis: C, 66.65; H, 6.66; F, 15.06; N, 7.40; O, 4.23.

Example 84

N-(bicyclo[2.2.2]octan-1-ylmethyl)-1-propyl-1H-indole-3-carboxamide

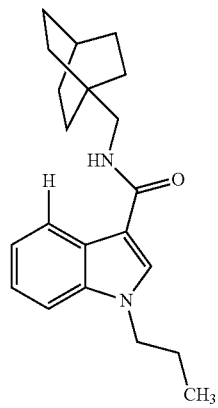

Synthesised according to the procedure disclosed in Example 1 where X is indole, Y is n-propyl bromide, and Z is bicyclo[2.2.2]octan-1-ylmethyl amine. Formula: $C_{21}H_{28}N_2O$; Molecular Weight: 324.5; Mass/charge ratio: 324.2 (100.0%), 325.2 (23.8%), 326.2 (2.9%); Elemental analysis: C, 77.74; H, 8.70; N, 8.63; O, 4.93.

Example 85

N-(bicyclo[2.2.2]octan-1-ylmethyl)-4-fluoro-1-propyl-1H-indole-3-carboxamide

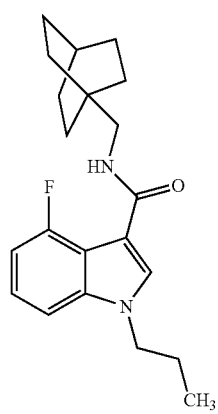 [SMILES: CCCn1cc(C(=O)NCC23CCC(CC2)CC3)c2c(F)cccc21]

Synthesised according to the procedure disclosed in Example 1 where X is 4-fluoro indole, Y is n-propyl bromide, and Z is bicyclo[2.2.2]octan-1-ylmethyl amine. Formula: $C_{21}H_{27}FN_2O$; Molecular Weight: 342.5; Mass/charge ratio: 342.2 (100.0%), 343.2 (23.8%), 344.2 (2.9%); Elemental analysis: C, 73.65; H, 7.95; F, 5.55; N, 8.18; O, 4.67.

Example 86

N-(bicyclo[2.2.2]octan-1-ylmethyl)-4-chloro-1-propyl-1H-indole-3-carboxamide

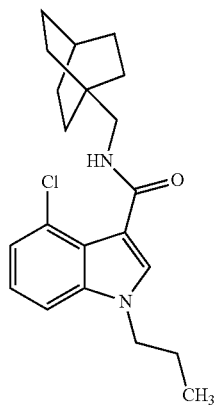 [SMILES: CCCn1cc(C(=O)NCC23CCC(CC2)CC3)c2c(Cl)cccc21]

Synthesised according to the procedure disclosed in Example 1 where X is 4-chloro indole, Y is n-propyl bromide, and Z is bicyclo[2.2.2]octan-1-ylmethyl amine. Formula: $C_{21}H_{27}ClN_2O$; Molecular Weight: 358.9; Mass/charge ratio: 358.2 (100.0%), 360.2 (34.9%), 359.2 (23.8%), 361.2 (7.9%); Elemental analysis: C, 70.28; H, 7.58; Cl, 9.88; N, 7.81; O, 4.46.

Example 87

N-(bicyclo[2.2.2]octan-1-ylmethyl)-4-bromo-1-propyl-1H-indole-3-carboxamide

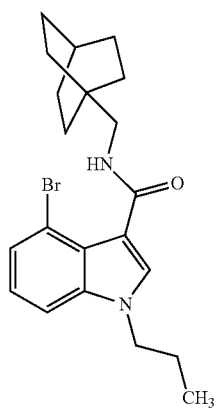 [SMILES: CCCn1cc(C(=O)NCC23CCC(CC2)CC3)c2c(Br)cccc21]

Synthesised according to the procedure disclosed in Example 1 where X is 4-bromo indole, Y is n-propyl bromide, and Z is bicyclo[2.2.2]octan-1-ylmethyl amine. Formula: $C_{21}H_{27}BrN_2O$; Molecular Weight: 403.4; MS: 405.1/406.2; Mass/charge ratio: 404.1 (100.0%), 402.1 (99.8%), 403.1 (23.8%), 405.1 (23.4%), 406.1 (2.8%); Elemental analysis: C, 62.53; H, 6.75; Br, 19.81; N, 6.95; O, 3.97.

Example 88

N-(bicyclo[2.2.2]octan-1-ylmethyl)-4-methyl-1-propyl-1H-indole-3-carboxamide

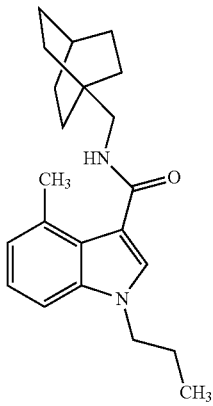 [SMILES: CCCn1cc(C(=O)NCC23CCC(CC2)CC3)c2c(C)cccc21]

Synthesised according to the procedure disclosed in Example 1 where X is 4-methyl indole, Y is n-propyl bromide, and Z is bicyclo[2.2.2]octan-1-ylmethyl amine. Formula: $C_{22}H_{30}N_2O$; Molecular Weight: 338.5; Mass/charge ratio: 338.2 (100.0%), 339.2 (24.9%), 340.2 (3.2%); Elemental analysis: C, 78.06; H, 8.93; N, 8.28; O, 4.73.

Example 89

N-(bicyclo[2.2.2]octan-1-ylmethyl)-4-methoxy-1-propyl-1H-indole-3-carboxamide

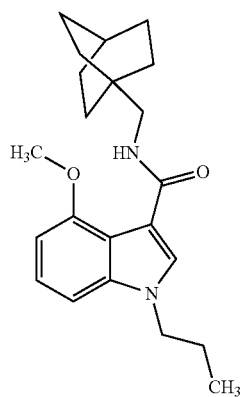 [SMILES: CCCn1cc(C(=O)NCC23CCC(CC2)CC3)c2c(OC)cccc21]

Synthesised according to the procedure disclosed in Example 1 where X is 4-methoxy indole, Y is n-propyl bromide, and Z is bicyclo[2.2.2]octan-1-ylmethyl amine. Formula: $C_{22}H_{30}N_2O_2$; Molecular Weight: 354.5; Mass/charge ratio: 354.2 (100.0%), 355.2 (25.0%), 356.2 (3.4%); Elemental analysis: C, 74.54; H, 8.53; N, 7.90; O, 9.03.

Example 90

N-(bicyclo[2.2.2]octan-1-ylmethyl)-4-cyano-1-propyl-1H-indole-3-carboxamide

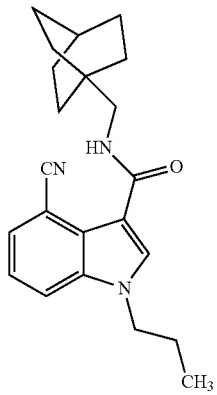 [SMILES: CCCn1cc(C(=O)NCC23CCC(CC2)CC3)c2c(C#N)cccc21]

Synthesised according to the procedure disclosed in Example 1 where X is 4-cyano indole, Y is n-propyl bromide, and Z is bicyclo[2.2.2]octan-1-ylmethyl amine. Formula: $C_{22}H_{27}N_3O$; Molecular Weight: 349.5; Mass/charge ratio: 349.2 (100.0%), 350.2 (25.3%), 351.2 (3.3%); Elemental analysis: C, 75.61; H, 7.79; N, 12.02; O, 4.58.

Example 91

N-(bicyclo[2.2.2]octan-1-ylmethyl)-1-propyl-4-(trifluoromethyl)-1H-indole-3-carboxamide

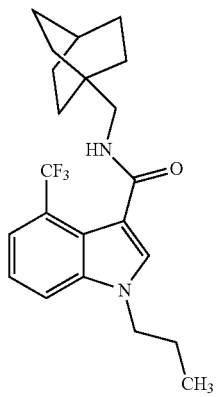 [SMILES: CCCn1cc(C(=O)NCC23CCC(CC2)CC3)c2c(C(F)(F)F)cccc21]

Synthesised according to the procedure disclosed in Example 1 where X is 4-trifluoro indole, Y is n-propyl bromide, and Z is bicyclo[2.2.2]octan-1-ylmethyl amine. Formula: $C_{22}H_{27}F_3N_2O$; Molecular Weight: 392.5; Mass/charge ratio: 392.2 (100.0%), 393.2 (24.9%), 394.2 (3.2%); Elemental analysis: C, 67.33; H, 6.93; F, 14.52; N, 7.14; O, 4.08.

Example 92

N-(bicyclo[2.2.2]octan-1-ylmethyl)-1-isopropyl-1H-indole-3-carboxamide

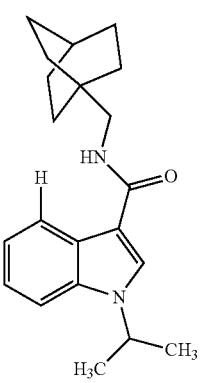

Synthesised according to the procedure disclosed in Example 1 where X is indole, Y is isopropyl bromide, and Z is bicyclo[2.2.2]octan-1-ylmethyl amine. Formula: $C_{21}H_{28}N_2O$; Molecular Weight: 324.5; Mass/charge ratio: 324.2 (100.0%), 325.2 (23.8%), 326.2 (2.9%); Elemental analysis: C, 77.74; H, 8.70; N, 8.63; O, 4.93.

Example 93

N-(bicyclo[2.2.2]octan-1-ylmethyl)-4-fluoro-1-isopropyl-1H-indole-3-carboxamide

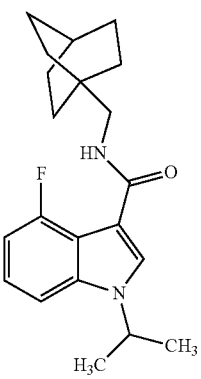 [SMILES: CC(C)n1cc(C(=O)NCC23CCC(CC2)CC3)c2c(F)cccc21]

Synthesised according to the procedure disclosed in Example 1 where X is 4-fluoro indole, Y is isopropyl bromide, and Z is bicyclo[2.2.2]octan-1-ylmethyl amine. Formula: $C_{21}H_{27}FN_2O$; Molecular Weight: 342.5; Mass/charge ratio: 342.2 (100.0%), 343.2 (23.8%), 344.2 (2.9%); Elemental analysis: C, 73.65; H, 7.95; F, 5.55; N, 8.18; O, 4.67.

Example 94

N-(bicyclo[2.2.2]octan-1-ylmethyl)-4-chloro-1-isopropyl-1H-indole-3-carboxamide

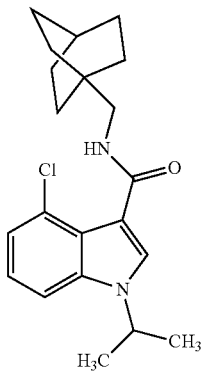 [SMILES: CC(C)n1cc(C(=O)NCC23CCC(CC2)CC3)c2c(Cl)cccc21]

Synthesised according to the procedure disclosed in Example 1 where X is 4-chloro indole, Y is isopropyl bromide, and Z is bicyclo[2.2.2]octan-1-ylmethyl amine. Formula: $C_{21}H_{27}ClN_2O$; Molecular Weight: 358.9; Mass/charge ratio: 358.2 (100.0%), 360.2 (34.9%), 359.2 (23.8%), 361.2 (7.9%); Elemental analysis: C, 70.28; H, 7.58; Cl, 9.88; N, 7.81; O, 4.46.

Example 95

N-(bicyclo[2.2.2]octan-1-ylmethyl)-4-bromo-1-isopropyl-1H-indole-3-carboxamide

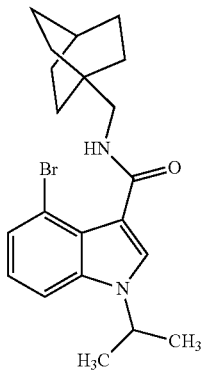 [SMILES: CC(C)n1cc(C(=O)NCC23CCC(CC2)CC3)c2c(Br)cccc21]

Synthesised according to the procedure disclosed in Example 1 where X is 4-bromo indole, Y is isopropyl bromide, and Z is bicyclo[2.2.2]octan-1-ylmethyl amine. Formula: $C_{21}H_{27}BrN_2O$; Molecular Weight: 403.4; Mass/charge ratio: 404.1 (100.0%), 402.1 (99.8%), 403.1 (23.8%), 405.1 (23.4%), 406.1 (2.8%); Elemental analysis: C, 62.53; H, 6.75; Br, 19.81; N, 6.95; O, 3.97.

Example 96

N-(bicyclo[2.2.2]octan-1-ylmethyl)-1-isopropyl-4-methyl-1H-indole-3-carboxamide

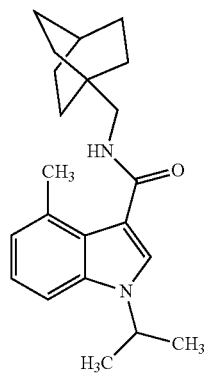 [SMILES: Cc1cccc2c1c(C(=O)NCC13CCC(CC1)CC3)cn2C(C)C]

Synthesised according to the procedure disclosed in Example 1 where X is 4-methyl indole, Y is isopropyl bromide, and Z is bicyclo[2.2.2]octan-1-ylmethyl amine. Formula: $C_{22}H_{30}N_2O$; Molecular Weight: 338.5; Mass/charge ratio: 338.2 (100.0%), 339.2 (24.9%), 340.2 (3.2%); Elemental analysis: C, 78.06; H, 8.93; N, 8.28; O, 4.73.

Example 97

N-(bicyclo[2.2.2]octan-1-ylmethyl)-4-fluoro-1-isobutyl-1H-indole-3-carboxamide

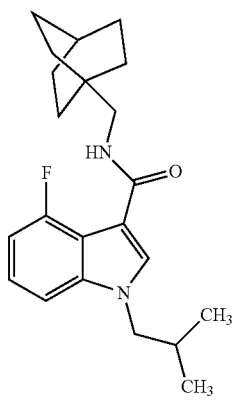 [SMILES: CC(C)Cn1cc(C(=O)NCC23CCC(CC2)CC3)c2c(F)cccc21]

Synthesised according to the procedure disclosed in Example 1 where X is 4-fluoro indole, Y is isobutyl bromide, and Z is bicyclo[2.2.2]octan-1-ylmethyl amine. Formula: $C_{22}H_{29}FN_2O$; Molecular Weight: 356.5; Mass/charge ratio: 356.2 (100.0%), 357.2 (24.9%), 358.2 (3.2%); Elemental analysis: C, 74.12; H, 8.20; F, 5.33; N, 7.86; O, 4.49.

Example 98

N-(bicyclo[2.2.2]octan-1-ylmethyl)-4-chloro-1-isobutyl-1H-indole-3-carboxamide

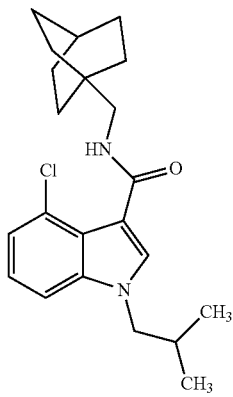 [SMILES: CC(C)Cn1cc(C(=O)NCC23CCC(CC2)CC3)c2c(Cl)cccc21]

Synthesised according to the procedure disclosed in Example 1 where X is 4-chloro indole, Y is isobutyl bromide, and Z is bicyclo[2.2.2]octan-1-ylmethyl amine. Formula: $C_{22}H_{29}ClN_2O$; Molecular Weight: 372.9; Mass/charge ratio: 372.2 (100.0%), 374.2 (35.1%), 373.2 (24.9%), 375.2 (8.2%), 376.2 (1.0%); Elemental analysis: C, 70.85; H, 7.84; Cl, 9.51; N, 7.51; O, 4.29.

Example 99

N-(bicyclo[2.2.2]octan-1-ylmethyl)-4-bromo-1-isobutyl-1H-indole-3-carboxamide

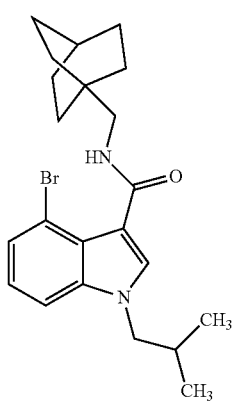 [SMILES: CC(C)Cn1cc(C(=O)NCC23CCC(CC2)CC3)c2c(Br)cccc21]

Synthesised according to the procedure disclosed in Example 1 where X is 4-bromo indole, Y is isobutyl bromide, and Z is bicyclo[2.2.2]octan-1-ylmethyl amine. Formula: $C_{22}H_{29}BrN_2O$; Molecular Weight: 417.4; Mass/charge ratio: 416.1 (100.0%), 418.1 (97.5%), 417.1 (24.5%), 419.1 (23.9%), 418.2 (3.0%), 420.2 (2.7%); Elemental analysis: C, 63.31; H, 7.00; Br, 19.14; N, 6.71; O, 3.83.

Example 100

N-(bicyclo[2.2.2]octan-1-ylmethyl)-1-isobutyl-4-methyl-1H-indole-3-carboxamide

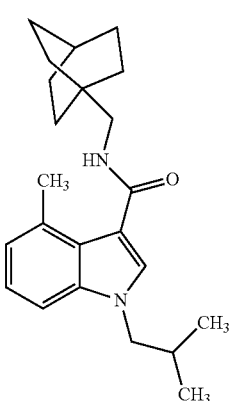

Synthesised according to the procedure disclosed in Example 1 where X is 4-methyl indole, Y is isobutyl bromide, and Z is bicyclo[2.2.2]octan-1-ylmethyl amine. Formula: $C_{23}H_{32}N_2O$; Molecular Weight: 352.5; Mass/charge ratio: 352.3 (100.0%), 353.3 (25.3%), 354.3 (3.5%); Elemental analysis: C, 78.36; H, 9.15; N, 7.95; O, 4.54.

Example 101

N-(bicyclo[2.2.2]octan-1-ylmethyl)-1-(2-hydroxyethyl)-1H-indole-3-carboxamide

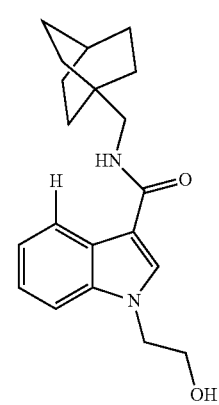 [SMILES: O=C(NCC12CCC(CC1)CC2)c1cn(CCO)c2ccccc12]

Synthesised according to the procedure disclosed in Example 1 where X is indole, Y is O-t-butyldimethylsilyl-2-chloroethanol, and Z is bicyclo[2.2.2]octan-1-ylmethyl amine. Formula: $C_{20}H_{26}N_2O_2$; Molecular Weight: 326.4; Mass/charge ratio: 326.2 (100.0%), 327.2 (22.7%), 328.2 (2.9%); Elemental analysis: C, 73.59; H, 8.03; N, 8.58; O, 9.80.

Example 102

N-(bicyclo[2.2.2]octan-1-ylmethyl)-4-fluoro-1-(2-hydroxyethyl)-1H-indole-3-carboxamide

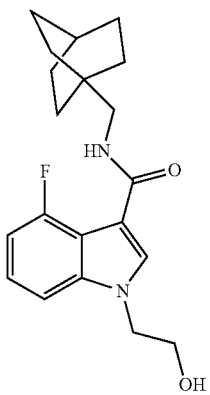 [SMILES: O=C(NCC12CCC(CC1)CC2)c1cn(CCO)c2cccc(F)c12]

Synthesised according to the procedure disclosed in Example 1 where X is 4-fluoro indole, Y is O-t-butyldimethylsilyl-2-chloroethanol, and Z is bicyclo[2.2.2]octan-1-ylmethyl amine. Formula: $C_{20}H_{25}FN_2O_2$; Molecular Weight: 344.4; Mass/charge ratio: 344.2 (100.0%), 345.2 (22.7%), 346.2 (2.9%); Elemental analysis: C, 69.74; H, 7.32; F, 5.52; N, 8.13; O, 9.29.

Example 103

N-(bicyclo[2.2.2]octan-1-ylmethyl)-4-chloro-1-(2-hydroxyethyl)-1H-indole-3-carboxamide

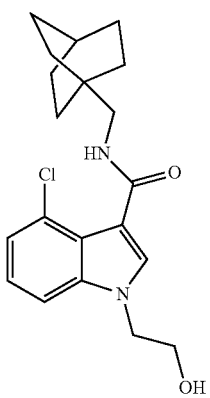 [SMILES: O=C(NCC12CCC(CC1)CC2)c1cn(CCO)c2cccc(Cl)c12]

Synthesised according to the procedure disclosed in Example 1 where X is 4-chloro indole, Y is O-t-butyldimethylsilyl-2-chloroethanol, and Z is bicyclo[2.2.2]octan-1-ylmethyl amine. Formula: $C_{20}H_{25}ClN_2O_2$; Molecular Weight: 360.9; MS: 361.2/362.1; Mass/charge ratio: 360.2 (100.0%), 362.2 (34.8%), 361.2 (22.7%), 363.2 (7.5%); Elemental analysis: C, 66.56; H, 6.98; Cl, 9.82; N, 7.76; O, 8.87.

Example 104

N-(bicyclo[2.2.2]octan-1-ylmethyl)-4-bromo-1-(2-hydroxyethyl)-1H-indole-3-carboxamide

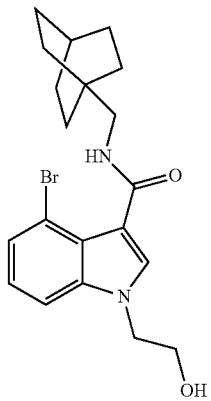 [SMILES: O=C(NCC12CCC(CC1)CC2)c1cn(CCO)c2cccc(Br)c12]

Synthesised according to the procedure disclosed in Example 1 where X is 4-bromo indole, Y is O-t-butyldimethylsilyl-2-chloroethanol, and Z is bicyclo[2.2.2]octan-1-ylmethyl amine. Formula: $C_{20}H_{25}BrN_2O_2$; Molecular Weight: 405.3; Mass/charge ratio: 406.1 (100.0%), 404.1 (99.8%), 405.1 (22.7%), 407.1 (22.3%), 408.1 (2.8%); Elemental analysis: C, 59.26; H, 6.22; Br, 19.71; N, 6.91; O, 7.89.

Example 105

N-(bicyclo[2.2.2]octan-1-ylmethyl)-1-(2-hydroxyethyl)-4-methyl-1H-indole-3-carboxamide

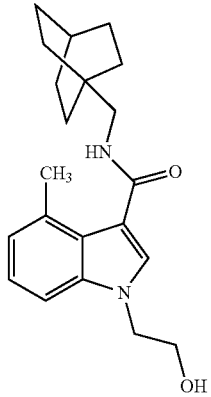 [SMILES: Cc1cccc2c1c(C(=O)NCC13CCC(CC1)CC3)cn2CCO]

Synthesised according to the procedure disclosed in Example 1 where X is 4-methyl indole, Y is O-t-butyldimethylsilyl-2-chloroethanol, and Z is bicyclo[2.2.2]octan-1-ylmethyl amine. Formula: $C_{21}H_{28}N_2O_2$; Molecular Weight: 340.5; Mass/charge ratio: 340.2 (100.0%), 341.2 (23.8%), 342.2 (3.1%); Elemental analysis: C, 74.08; H, 8.29; N, 8.23; O, 9.40.

Example 106

N-(bicyclo[2.2.2]octan-1-ylmethyl)-1-(2-hydroxyethyl)-4-methoxy-1H-indole-3-carboxamide

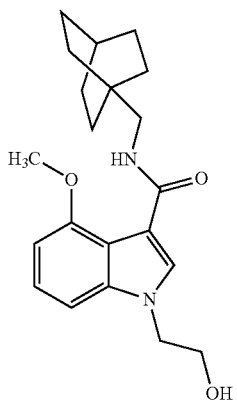 [SMILES: COc1cccc2c1c(C(=O)NCC13CCC(CC1)CC3)cn2CCO]

Synthesised according to the procedure disclosed in Example 1 where X is 4-methoxy indole, Y is O-t-butyldimethylsilyl-2-chloroethanol, and Z is bicyclo[2.2.2]octan-1-ylmethyl amine. Formula: $C_{21}H_{28}N_2O_3$; Molecular Weight: 356.5; Mass/charge ratio: 356.2 (100.0%), 357.2 (23.9%), 358.2 (3.3%); Elemental analysis: C, 70.76; H, 7.92; N, 7.86; O, 13.47.

Example 107

N-(bicyclo[2.2.2]octan-1-ylmethyl)-4-cyano-1-(2-hydroxyethyl)-1H-indole-3-carboxamide

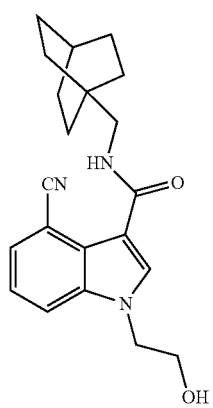 [SMILES: N#Cc1cccc2c1c(C(=O)NCC13CCC(CC1)CC3)cn2CCO]

Synthesised according to the procedure disclosed in Example 1 where X is 4-cyano indole, Y is O-t-butyldimethylsilyl-2-chloroethanol, and Z is bicyclo[2.2.2]octan-1-ylmethyl amine. Formula: $C_{21}H_{25}N_3O_2$; Molecular Weight: 351.4; Mass/charge ratio: 351.2 (100.0%), 352.2 (24.2%), 353.2 (3.2%); Elemental analysis: C, 71.77; H, 7.17; N, 11.96; O, 9.10.

Example 108

N-(bicyclo[2.2.2]octan-1-ylmethyl)-1-(2-hydroxyethyl)-4-(trifluoromethyl)-1H-indole-3-carboxamide

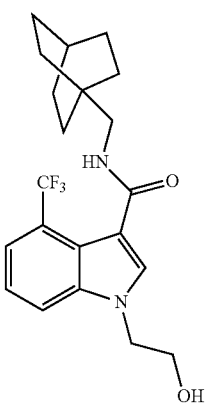 [SMILES: O=C(NCC12CCC(CC1)CC2)c1cn(CCO)c2cccc(C(F)(F)F)c12]

Synthesised according to the procedure disclosed in Example 1 where X is 4-trifluoro indole, Y is O-t-butyldimethylsilyl-2-chloroethanol, and Z is bicyclo[2.2.2]octan-1-ylmethyl amine. Formula: $C_{21}H_{25}F_3N_2O_2$; Molecular Weight: 394.4; Mass/charge ratio: 394.2 (100.0%), 395.2 (23.8%), 396.2 (3.1%); Elemental analysis: C, 63.95; H, 6.39; F, 14.45; N, 7.10; O, 8.11.

Example 109

N-(bicyclo[2.2.2]octan-1-ylmethyl)-1-butyl-4-fluoro-1H-indole-3-carboxamide

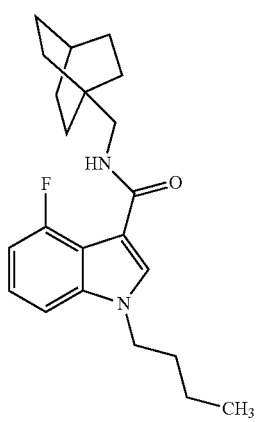 [SMILES: CCCCn1cc(C(=O)NCC23CCC(CC2)CC3)c2c(F)cccc21]

Synthesised according to the procedure disclosed in Example 1 where X is 4-fluoro indole, Y is n-butyl bromide, and Z is bicyclo[2.2.2]octan-1-ylmethyl amine. Formula: $C_{22}H_{29}FN_2O$; Molecular Weight: 356.5; Mass/charge ratio: 356.2 (100.0%), 357.2 (24.9%), 358.2 (3.2%); Elemental analysis: C, 74.12; H, 8.20; F, 5.33; N, 7.86; O, 4.49.

Example 110

N-(bicyclo[2.2.2]octan-1-ylmethyl)-1-butyl-4-chloro-1H-indole-3-carboxamide

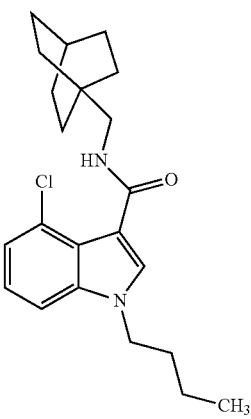 [SMILES: CCCCn1cc(C(=O)NCC23CCC(CC2)CC3)c2c(Cl)cccc21]

Synthesised according to the procedure disclosed in Example 1 where X is 4-chloro indole, Y is n-butyl bromide, and Z is bicyclo[2.2.2]octan-1-ylmethyl amine. Formula: $C_{22}H_{29}ClN_2O$; Molecular Weight: 372.9; Mass/charge ratio: 372.2 (100.0%), 374.2 (35.1%), 373.2 (24.9%), 375.2 (8.2%), 376.2 (1.0%); Elemental analysis: C, 70.85; H, 7.84; Cl, 9.51; N, 7.51; O, 4.29.

Example 111

N-(bicyclo[2.2.2]octan-1-ylmethyl)-4-bromo-1-butyl-1H-indole-3-carboxamide

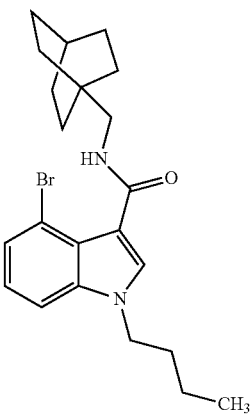 [SMILES: CCCCn1cc(C(=O)NCC23CCC(CC2)CC3)c2c(Br)cccc21]

Synthesised according to the procedure disclosed in Example 1 where X is 4-bromo indole, Y is n-butyl bromide, and Z is bicyclo[2.2.2]octan-1-ylmethyl amine. Formula: $C_{22}H_{29}BrN_2O$; Molecular Weight: 417.4; Mass/charge ratio: 416.1 (100.0%), 418.1 (97.5%), 417.1 (24.5%), 419.1 (23.9%), 418.2 (3.0%), 420.2 (2.7%); Elemental analysis: C, 63.31; H, 7.00; Br, 19.14; N, 6.71; O, 3.83.

Example 112

N-(bicyclo[2.2.2]octan-1-ylmethyl)-1-butyl-4-methyl-1H-indole-3-carboxamide

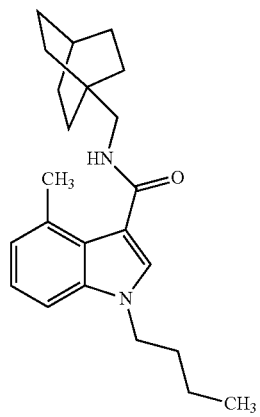 [SMILES: CCCCn1cc(C(=O)NCC23CCC(CC2)CC3)c2c(C)cccc21]

Synthesised according to the procedure disclosed in Example 1 where X is 4-methyl indole, Y is n-butyl bromide, and Z is bicyclo[2.2.2]octan-1-ylmethyl amine. Formula: $C_{23}H_{32}N_2O$; Molecular Weight: 352.5; Mass/charge ratio: 352.3 (100.0%), 353.3 (25.3%), 354.3 (3.5%); Elemental analysis: C, 78.36; H, 9.15; N, 7.95; O, 4.54.

Example 113

N-(bicyclo[2.2.2]octan-1-ylmethyl)-4-fluoro-1-(3-hydroxypropyl)-1H-indole-3-carboxamide

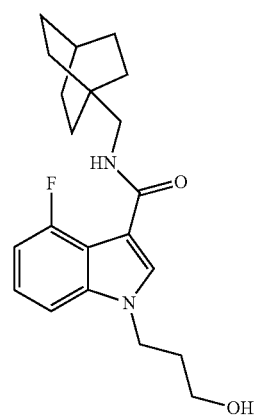 [SMILES: O=C(NCC12CCC(CC1)CC2)c1cn(CCCO)c2cccc(F)c12]

Synthesised according to the procedure disclosed in Example 1 where X is 4-fluoro indole, Y is O-t-butyldimethylsilyl-2-chloropropanol, and Z is bicyclo[2.2.2]octan-1-ylmethyl amine. Formula: $C_{21}H_{27}FN_2O_2$; Molecular Weight: 358.4; Mass/charge ratio: 358.2 (100.0%), 359.2 (23.8%), 360.2 (3.1%); Elemental analysis: C, 70.37; H, 7.59; F, 5.30; N, 7.82; O, 8.93.

Example 114

N-(bicyclo[2.2.2]octan-1-ylmethyl)-4-chloro-1-(3-hydroxypropyl)-1H-indole-3-carboxamide

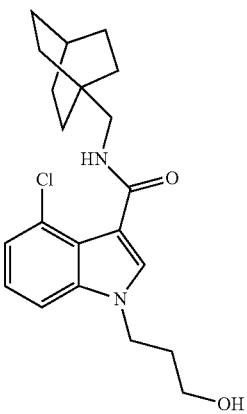 [SMILES: O=C(NCC12CCC(CC1)CC2)c1cn(CCCO)c2cccc(Cl)c12]

Synthesised according to the procedure disclosed in Example 1 where X is 4-chloro indole, Y is O-t-butyldimethylsilyl-2-chloropropanol, and Z is bicyclo[2.2.2]octan-1-ylmethyl amine. Formula: $C_{21}H_{27}ClN_2O_2$; Molecular Weight: 374.9; Mass/charge ratio: 374.2 (100.0%), 376.2 (35.1%), 375.2 (23.8%), 377.2 (7.9%), 378.2 (1.0%); Elemental analysis: C, 67.28; H, 7.26; Cl, 9.46; N, 7.47; O, 8.54.

Example 115

N-(bicyclo[2.2.2]octan-1-ylmethyl)-4-bromo-1-(3-hydroxypropyl)-1H-indole-3-carboxamide

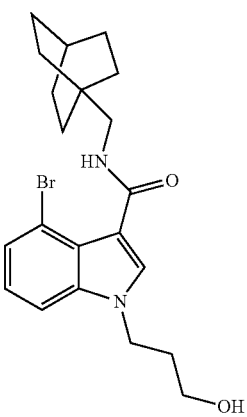

Synthesised according to the procedure disclosed in Example 1 where X is 4-bromo indole, Y is O-t-butyldimethylsilyl-2-chloropropanol, and Z is bicyclo[2.2.2]octan-1-ylmethyl amine. Formula: $C_{21}H_{27}BrN_2O_2$; Molecular Weight: 419.4; Mass/charge ratio: 420.1 (100.0%), 418.1 (99.6%), 419.1 (23.7%), 421.1 (23.4%), 422.1 (3.1%); Elemental analysis: C, 60.15; H, 6.49; Br, 19.05; N, 6.68; O, 7.63.

Example 116

N-(bicyclo[2.2.2]octan-1-ylmethyl)-1-(3-hydroxypropyl)-4-methyl-1H-indole-3-carboxamide

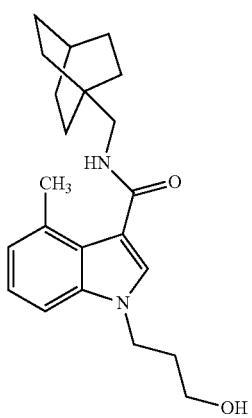 [SMILES: Cc1cccc2c1c(C(=O)NCC13CCC(CC1)CC3)cn2CCCO]

Synthesised according to the procedure disclosed in Example 1 where X is 4-methyl indole, Y is O-t-butyldimethylsilyl-2-chloropropanol, and Z is bicyclo[2.2.2]octan-1-ylmethyl amine. Formula: $C_{22}H_{30}N_2O_2$; Molecular Weight: 354.5; Mass/charge ratio: 354.2 (100.0%), 355.2 (25.0%), 356.2 (3.4%); Elemental analysis: C, 74.54; H, 8.53; N, 7.90; O, 9.03.

Example 117

4-chloro-N-(2-cyclohexylethyl)-1-methyl-1H-indole-3-carboxamide

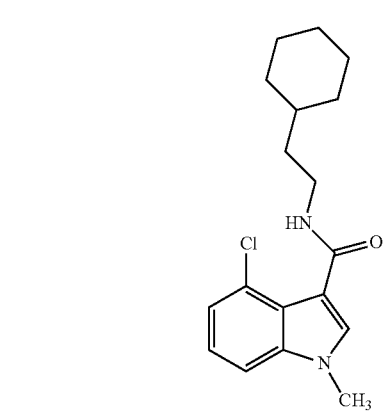 [SMILES: Cn1cc(C(=O)NCCC2CCCCC2)c2c(Cl)cccc21]

Synthesised according to the procedure disclosed in Example 1 where X is 4-chloro indole, Y is methyl iodide, and Z is cyclohexylethyl amine. Formula: $C_{18}H_{23}ClN_2O$; Molecular Weight: 318.8; Mass/charge ratio: 318.1 (100.0%), 320.1 (32.0%), 319.2 (19.8%), 321.2 (6.5%), 320.2 (2.2%); Elemental analysis: C, 67.81; H, 7.27; Cl, 11.12; N, 8.79; O, 5.02.

Example 118

N-(2-cyclohexylethyl)-4-fluoro-1-methyl-1H-indole-3-carboxamide

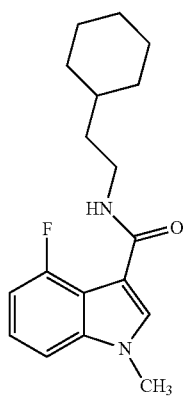

Synthesised according to the procedure disclosed in Example 1 where X is 4-fluoro indole, Y is methyl iodide, and Z is cyclohexylethyl amine. Formula: $C_{18}H_{23}FN_2O$; Molecular Weight: 302.4; Mass/charge ratio: 302.2 (100.0%), 303.2 (20.5%), 304.2 (2.2%); Elemental analysis: C, 71.50; H, 7.67; F, 6.28; N, 9.26; O, 5.29.

Example 119

4-bromo-N-(2-cyclohexylethyl)-1-methyl-1H-indole-3-carboxamide

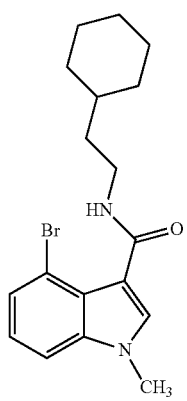 [SMILES: Cn1cc(C(=O)NCCC2CCCCC2)c2c(F)cccc21]

Synthesised according to the procedure disclosed in Example 1 where X is 4-bromo indole, Y is methyl iodide, and Z is cyclohexylethyl amine. Formula: $C_{18}H_{23}BrN_2O$; Molecular Weight: 363.3; Mass/charge ratio: 362.1 (100.0%), 364.1 (99.5%), 363.1 (20.5%), 365.1 (20.1%), 366.1 (2.2%); Elemental analysis: C, 59.51; H, 6.38; Br, 21.99; N, 7.71; O, 4.40.

Example 120

N-(2-cyclohexylethyl)-1,4-dimethyl-1H-indole-3-carboxamide

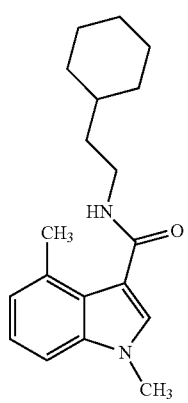

Synthesised according to the procedure disclosed in Example 1 where X is 4-methyl indole, Y is methyl iodide, and Z is cyclohexylethyl amine. Formula: $C_{19}H_{26}N_2O$; Molecular Weight: 298.4; Mass/charge ratio: 298.2 (100.0%), 299.2 (21.6%), 300.2 (2.4%); Elemental analysis: C, 76.47; H, 8.78; N, 9.39; O, 5.36.

Example 121

N-(2-cyclohexylethyl)-1-ethyl-4-fluoro-1H-indole-3-carboxamide

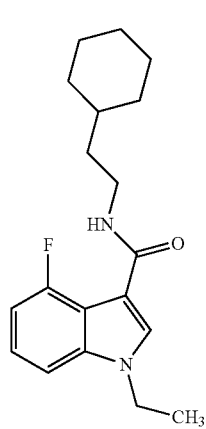 [SMILES: CCn1cc(C(=O)NCCC2CCCCC2)c2c(F)cccc21]

Synthesised according to the procedure disclosed in Example 1 where X is 4-fluoro indole, Y is ethyl iodide, and Z is cyclohexylethyl amine. Formula: $C_{19}H_{25}FN_2O$; Molecular Weight: 316.4; Mass/charge ratio: 316.2 (100.0%), 317.2 (21.6%), 318.2 (2.4%); Elemental analysis: C, 72.12; H, 7.96; F, 6.00; N, 8.85; O, 5.06.

Example 122

4-chloro-N-(2-cyclohexylethyl)-1-ethyl-1H-indole-3-carboxamide

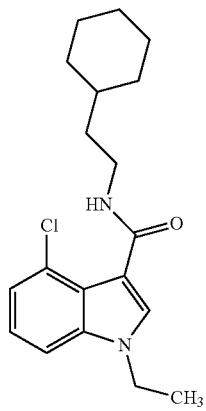 [SMILES: CCn1cc(C(=O)NCCC2CCCCC2)c2c(Cl)cccc21]

Synthesised according to the procedure disclosed in Example 1 where X is 4-chloro indole, Y is ethyl iodide, and Z is cyclohexylethyl amine. Formula: $C_{19}H_{25}ClN_2O$; Molecular Weight: 332.9; Mass/charge ratio: 332.2 (100.0%), 334.2 (34.4%), 333.2 (21.6%), 335.2 (7.1%); Elemental analysis: C, 68.56; H, 7.57; Cl, 10.65; N, 8.42; O, 4.81.

Example 123

4-bromo-N-(2-cyclohexylethyl)-1-ethyl-1H-indole-3-carboxamide

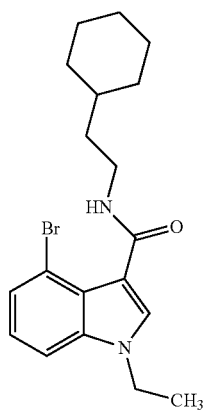 [SMILES: CCn1cc(C(=O)NCCC2CCCCC2)c2c(Br)cccc21]

Synthesised according to the procedure disclosed in Example 1 where X is 4-bromo indole, Y is ethyl iodide, and Z is cyclohexylethyl amine. Formula: $C_{19}H_{25}BrN_2O$; Molecular Weight: 377.3; Mass/charge ratio: 376.1 (100.0%), 378.1 (99.7%), 377.1 (21.6%), 379.1 (21.2%), 380.1 (2.4%); Elemental analysis: C, 60.48; H, 6.68; Br, 21.18; N, 7.42; O, 4.24.

Example 124

N-(2-cyclohexylethyl)-1-ethyl-4-methyl-1H-indole-3-carboxamide

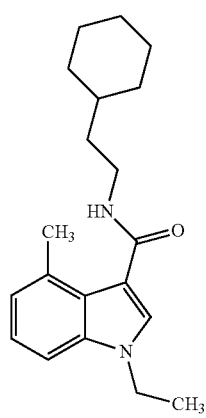 [SMILES: CCn1cc(C(=O)NCCC2CCCCC2)c2c(C)cccc21]

Synthesised according to the procedure disclosed in Example 1 where X is 4-methyl indole, Y is ethyl iodide, and Z is cyclohexylethyl amine. Formula: $C_{20}H_{28}N_2O$; Molecular Weight: 312.4; Mass/charge ratio: 312.2 (100.0%), 313.2 (22.7%), 314.2 (2.7%); Elemental analysis: C, 76.88; H, 9.03; N, 8.97; O, 5.12.

Example 125

N-(2-cyclohexylethyl)-4-fluoro-1-(2-hydroxyethyl)-1H-indole-3-carboxamide

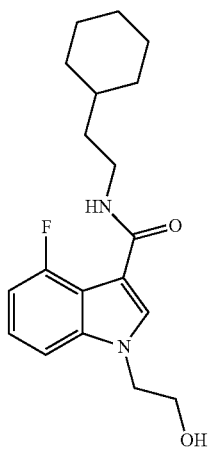 [SMILES: O=C(NCCC1CCCCC1)c1cn(CCO)c2cccc(F)c12]

Synthesised according to the procedure disclosed in Example 1 where X is 4-fluoro indole, Y is O-t-butyldimethylsilyl-2-chloroethanol, and Z is cyclohexylethyl amine. Formula: $C_{19}H_{25}FN_2O_2$; Molecular Weight: 332.4; Mass/charge ratio: 332.2 (100.0%), 333.2 (21.7%), 334.2 (2.6%); Elemental analysis: C, 68.65; H, 7.58; F, 5.72; N, 8.43; O, 9.63.

Example 126

4-chloro-N-(2-cyclohexylethyl)-1-(2-hydroxyethyl)-1H-indole-3-carboxamide

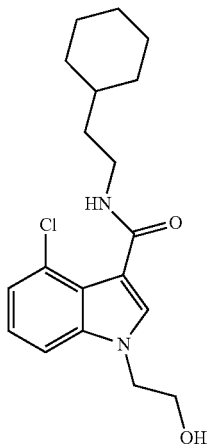 [SMILES: O=C(NCCC1CCCCC1)c1cn(CCO)c2cccc(Cl)c12]

Synthesised according to the procedure disclosed in Example 1 where X is 4-chloro indole, Y is O-t-butyldimethylsilyl-2-chloroethanol, and Z is cyclohexylethyl amine. Formula: $C_{19}H_{25}ClN_2O_2$; Molecular Weight: 348.9; Mass/charge ratio: 348.2 (100.0%), 350.2 (34.6%), 349.2 (21.7%), 351.2 (7.2%); Elemental analysis: C, 65.41; H, 7.22; Cl, 10.16; N, 8.03; O, 9.17.

Example 127

4-bromo-N-(2-cyclohexylethyl)-1-(2-hydroxyethyl)-1H-indole-3-carboxamide

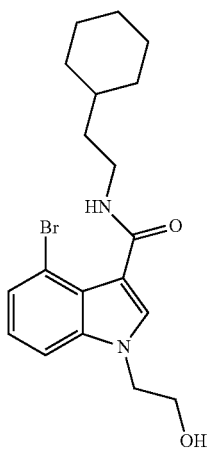 [SMILES: O=C(NCCC1CCCCC1)c1cn(CCO)c2cccc(Br)c12]

Synthesised according to the procedure disclosed in Example 1 where X is 4-bromo indole, Y is O-t-butyldimethylsilyl-2-chloroethanol, and Z is cyclohexylethyl amine. Formula: $C_{19}H_{25}BrN_2O_2$; Molecular Weight: 393.3; Mass/charge ratio: 392.1 (100.0%), 394.1 (99.9%), 393.1 (21.7%), 395.1 (21.3%), 396.1 (2.6%); Elemental analysis: C, 58.02; H, 6.41; Br, 20.32; N, 7.12; O, 8.14.

Example 128

N-(2-cyclohexylethyl)-1-(2-hydroxyethyl)-4-methyl-1H-indole-3-carboxamide

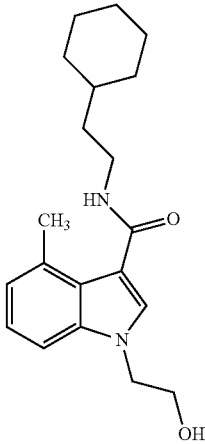 [SMILES: Cc1cccc2c1c(C(=O)NCCC1CCCCC1)cn2CCO]

Synthesised according to the procedure disclosed in Example 1 where X is 4-methyl indole, Y is O-t-butyldimethylsilyl-2-chloroethanol, and Z is cyclohexylethyl amine. Formula: $C_{20}H_{28}N_2O_2$; Molecular Weight: 328.4; Mass/charge ratio: 328.2 (100.0%), 329.2 (22.8%), 330.2 (2.9%); Elemental analysis: C, 73.14; H, 8.59; N, 8.53; O, 9.74.

Example 129

4-chloro-N-(2-cycloheptylethyl)-1-methyl-1H-indole-3-carboxamide

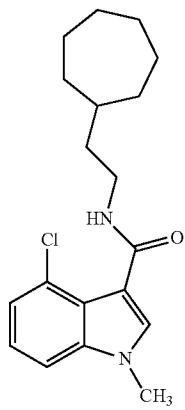 [SMILES: Cn1cc(C(=O)NCCC2CCCCCC2)c2c(Cl)cccc21]

Synthesised according to the procedure disclosed in Example 1 where X is 4-chloro indole, Y is methyl iodide, and Z is cycloheptylethyl amine. Formula: $C_{19}H_{25}ClN_2O$; Molecular Weight: 332.9; Mass/charge ratio: 332.2 (100.0%), 334.2 (34.4%), 333.2 (21.6%), 335.2 (7.1%); Elemental analysis: C, 68.56; H, 7.57; Cl, 10.65; N, 8.42; O, 4.81.

Example 130

4-bromo-N-(2-cycloheptylethyl)-1-methyl-1H-indole-3-carboxamide

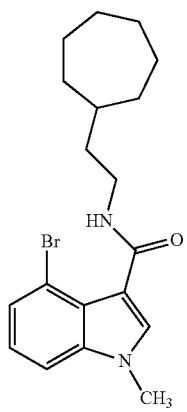

Synthesised according to the procedure disclosed in Example 1 where X is 4-bromo indole, Y is methyl iodide, and Z is cycloheptylethyl amine. Formula: $C_{19}H_{25}BrN_2O$; Molecular Weight: 377.3; Mass/charge ratio: 376.1 (100.0%), 378.1 (99.7%), 377.1 (21.6%), 379.1 (21.2%), 380.1 (2.4%); Elemental analysis: C, 60.48; H, 6.68; Br, 21.18; N, 7.42; O, 4.24.

Example 131

N-(2-cycloheptylethyl)-1,4-dimethyl-1H-indole-3-carboxamide

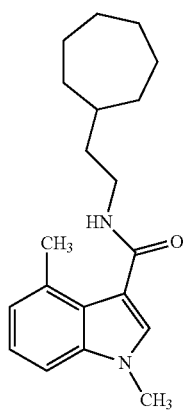

Synthesised according to the procedure disclosed in Example 1 where X is 4-methyl indole, Y is methyl iodide, and Z is cycloheptylethyl amine. Formula: $C_{20}H_{28}N_2O$; Molecular Weight: 312.4; Mass/charge ratio: 312.2 (100.0%), 313.2 (22.7%), 314.2 (2.7%); Elemental analysis: C, 76.88; H, 9.03; N, 8.97; O, 5.12.

Example 132

4-chloro-N-(2-cycloheptylethyl)-1-ethyl-1H-indole-3-carboxamide

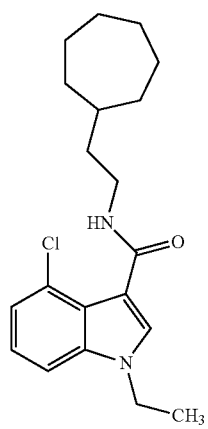 [SMILES: CCn1cc(C(=O)NCCC2CCCCCC2)c2c(Cl)cccc21]

Synthesised according to the procedure disclosed in Example 1 where X is 4-chloro indole, Y is ethyl iodide, and Z is cycloheptylethyl amine. Formula: $C_{20}H_{27}ClN_2O$; Molecular Weight: 346.9; Mass/charge ratio: 346.2 (100.0%), 348.2 (34.6%), 347.2 (22.7%), 349.2 (7.5%); Elemental analysis: C, 69.25; H, 7.85; Cl, 10.22; N, 8.08; O, 4.61.

Example 133

4-bromo-N-(2-cycloheptylethyl)-1-ethyl-1H-indole-3-carboxamide

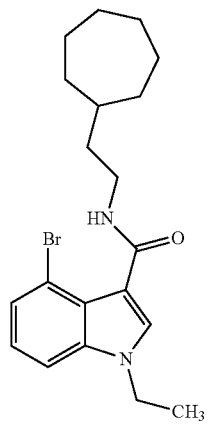 [SMILES: CCn1cc(C(=O)NCCC2CCCCCC2)c2c(Br)cccc21]

Synthesised according to the procedure disclosed in Example 1 where X is 4-bromo indole, Y is ethyl iodide, and Z is cycloheptylethyl amine. Formula: $C_{20}H_{27}ClN_2O$; Molecular Weight: 391.3; Mass/charge ratio: 390.1 (100.0%), 392.1 (99.9%), 391.1 (22.7%), 393.1 (22.3%), 394.1 (2.6%); Elemental analysis: C, 61.38; H, 6.95; Br, 20.42; N, 7.16; O, 4.09.

Example 134

N-(2-cycloheptylethyl)-1-ethyl-4-methyl-1H-indole-3-carboxamide

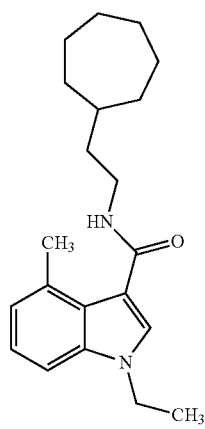

Synthesised according to the procedure disclosed in Example 1 where X is 4-methyl indole, Y is ethyl iodide, and Z is cycloheptylethyl amine. Formula: $C_{21}H_{30}N_2O$; Molecular Weight: 326.5; Mass/charge ratio: 326.2 (100.0%), 327.2 (23.8%), 328.2 (2.9%); Elemental analysis: C, 77.26; H, 9.26; N, 8.58; O, 4.90.

Example 135

4-chloro-N-(2-cycloheptylethyl)-1-(2-hydroxyethyl)-1H-indole-3-carboxamide

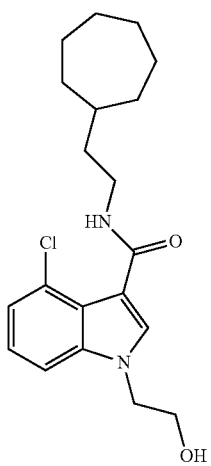 [SMILES: O=C(NCCC1CCCCCC1)c1cn(CCO)c2cccc(Cl)c12]

Synthesised according to the procedure disclosed in Example 1 where X is 4-chloro indole, Y is O-t-butyldimethylsilyl-2-chloroethanol, and Z is cycloheptylethyl amine. Formula: $C_{20}H_{27}ClN_2O_2$; Molecular Weight: 362.9; Mass/charge ratio: 362.2 (100.0%), 364.2 (34.8%), 363.2 (22.8%), 365.2 (7.5%); Elemental analysis: C, 66.19; H, 7.50; Cl, 9.77; N, 7.72; O, 8.82.

Example 136

4-bromo-N-(2-cycloheptylethyl)-1-(2-hydroxyethyl)-1H-indole-3-carboxamide

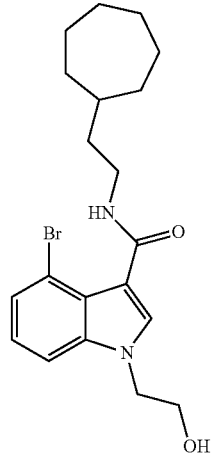 [SMILES: O=C(NCCC1CCCCCC1)c1cn(CCO)c2cccc(Br)c12]

Synthesised according to the procedure disclosed in Example 1 where X is 4-bromo indole, Y is O-t-butyldimethylsilyl-2-chloroethanol, and Z is cycloheptylethyl amine. Formula: $C_{20}H_{27}BrN_2O_2$; Molecular Weight: 407.3; Mass/charge ratio: 408.1 (100.0%), 406.1 (99.8%), 407.1 (22.7%), 409.1 (22.4%), 410.1 (2.8%); Elemental analysis: C, 58.97; H, 6.68; Br, 19.62; N, 6.88; O, 7.86.

Example 137

N-(2-cycloheptylethyl)-1-(2-hydroxyethyl)-4-methyl-1H-indole-3-carboxamide

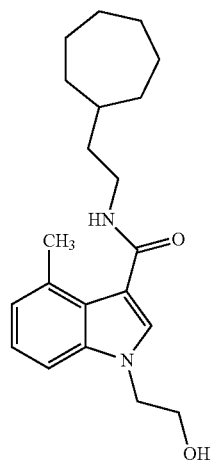 [SMILES: Cc1cccc2c1c(C(=O)NCCC1CCCCCC1)cn2CCO]

Synthesised according to the procedure disclosed in Example 1 where X is 4-methyl indole, Y is O-t-butyldimethylsilyl-2-chloroethanol, and Z is cycloheptylethyl amine. Formula: $C_{21}H_{30}N_2O_2$; Molecular Weight: 342.5; Mass/charge ratio: 342.2 (100.0%), 343.2 (23.9%), 344.2 (3.1%); Elemental analysis: C, 73.65; H, 8.83; N, 8.18; O, 9.34.

Example 138

5-chloro-N-(cycloheptylmethyl)-1-methyl-1H-indole-3-carboxamide

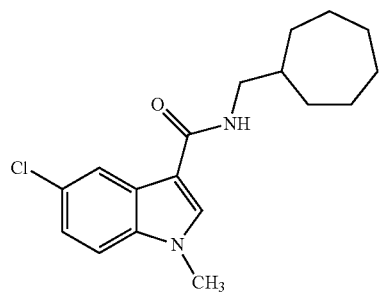 [SMILES: Cn1cc(C(=O)NCC2CCCCCC2)c2cc(Cl)ccc21]

Synthesised according to the procedure disclosed in Example 1 where X is 5-chloro indole, Y is methyl iodide, and Z is cycloheptylmethyl amine. Formula: $C_{18}H_{23}ClN_2O$; Molecular Weight: 318.8; Mass/charge ratio: 318.1 (100.0%), 320.1 (32.0%), 319.2 (19.8%), 321.2 (6.5%), 320.2 (2.2%); Elemental analysis: C, 67.81; H, 7.27; Cl, 11.12; N, 8.79; O, 5.02.

Example 139

5-bromo-N-(cycloheptylmethyl)-1-methyl-1H-indole-3-carboxamide

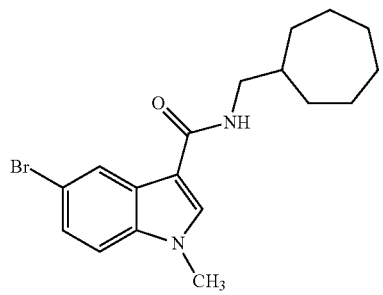

Synthesised according to the procedure disclosed in Example 1 where X is 5-bromo indole, Y is methyl iodide, and Z is cycloheptylmethyl amine. Formula: $C_{18}H_{23}BrN_2O$; Molecular Weight: 363.3; Mass/charge ratio: 362.1 (100.0%), 364.1 (99.5%), 363.1 (20.5%), 365.1 (20.1%), 366.1 (2.2%); Elemental analysis: C, 59.51; H, 6.38; Br, 21.99; N, 7.71; O, 4.40.

Example 140

N-(cycloheptylmethyl)-1,5-dimethyl-1H-indole-3-carboxamide

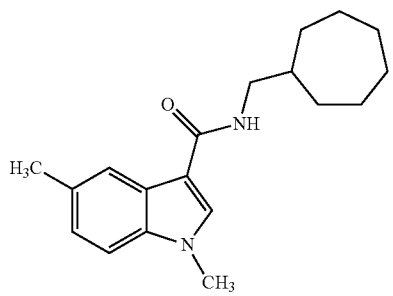 [SMILES: Cc1ccc2c(c1)c(C(=O)NCC1CCCCCC1)cn2C]

Synthesised according to the procedure disclosed in Example 1 where X is 5-methyl indole, Y is methyl iodide, and Z is cycloheptylmethyl amine. Formula: $C_{19}H_{26}N_2O$; Molecular Weight: 298.4; Mass/charge ratio: 298.2 (100.0%), 299.2 (21.6%), 300.2 (2.4%); Elemental analysis: C, 76.47; H, 8.78; N, 9.39; O, 5.36.

Example 141

5-chloro-N-(cycloheptylmethyl)-1-ethyl-1H-indole-3-carboxamide

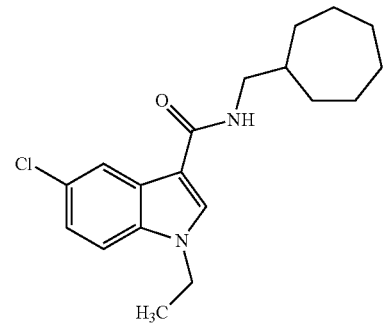

Synthesised according to the procedure disclosed in Example 1 where X is 5-chloro indole, Y is ethyl iodide, and Z is cycloheptylmethyl amine. Formula: $C_{19}H_{25}ClN_2O$; Molecular Weight: 332.9; Mass/charge ratio: 332.2 (100.0%), 334.2 (34.4%), 333.2 (21.6%), 335.2 (7.1%); Elemental analysis: C, 68.56; H, 7.57; Cl, 10.65; N, 8.42; O, 4.81.

Example 142

5-bromo-N-(cycloheptylmethyl)-1-ethyl-1H-indole-3-carboxamide

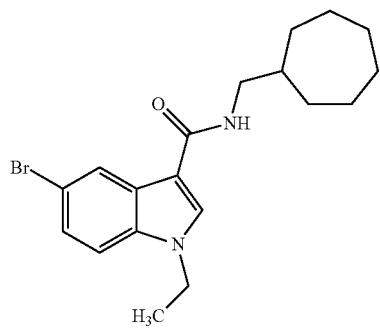 [SMILES: CCn1cc(C(=O)NCC2CCCCCC2)c2cc(Cl)ccc21]

Synthesised according to the procedure disclosed in Example 1 where X is 5-bromo indole, Y is ethyl iodide, and Z is cycloheptylmethyl amine. Formula: $C_{19}H_{28}BrN_2O$; Molecular Weight: 377.3; Mass/charge ratio: 376.1 (100.0%), 378.1 (99.7%), 377.1 (21.6%), 379.1 (21.2%), 380.1 (2.4%); Elemental analysis: C, 60.48; H, 6.68; Br, 21.18; N, 7.42; O, 4.24.

Example 143

N-(cycloheptylmethyl)-1-ethyl-5-methyl-1H-indole-3-carboxamide

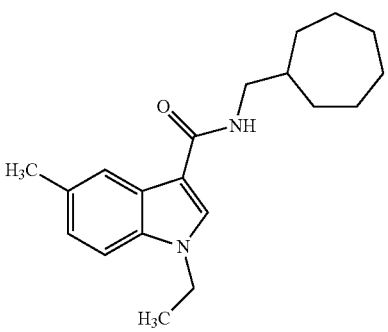 [SMILES: CCn1cc(C(=O)NCC2CCCCCC2)c2cc(C)ccc21]

Synthesised according to the procedure disclosed in Example 1 where X is 5-methyl indole, Y is ethyl iodide, and Z is cycloheptylmethyl amine. Formula: $C_{20}H_{28}N_2O$; Molecular Weight: 312.4; Mass/charge ratio: 312.2 (100.0%), 313.2 (22.7%), 314.2 (2.7%); Elemental analysis: C, 76.88; H, 9.03; N, 8.97; O, 5.12.

Example 144

5-chloro-N-(cycloheptylmethyl)-1-(2-hydroxyethyl)-1H-indole-3-carboxamide

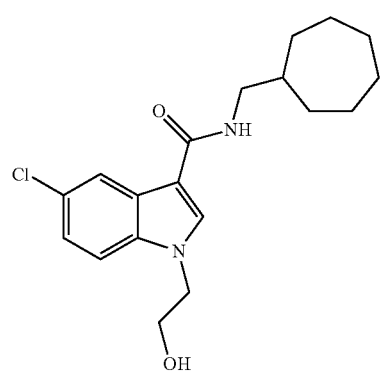

Synthesised according to the procedure disclosed in Example 1 where X is 5-chloro indole, Y is O-t-butyldimethylsilyl-2-chloroethanol, and Z is cycloheptylmethyl amine. Formula: $C_{19}H_{25}ClN_2O_2$; Molecular Weight: 348.9; Mass/charge ratio: 348.2 (100.0%), 350.2 (34.6%), 349.2 (21.7%), 351.2 (7.2%); Elemental analysis: C, 65.41; H, 7.22; Cl, 10.16; N, 8.03; O, 9.17.

Example 145

5-bromo-N-(cycloheptylmethyl)-1-(2-hydroxyethyl)-1H-indole-3-carboxamide

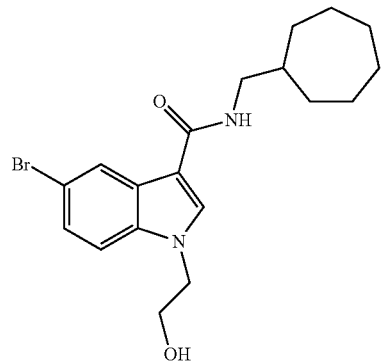 [SMILES: O=C(NCC1CCCCCC1)c1cn(CCO)c2ccc(Cl)cc12]

Synthesised according to the procedure disclosed in Example 1 where X is 5-bromo indole, Y is O-t-butyldimethylsilyl-2-chloroethanol, and Z is cycloheptylmethyl amine. Formula: $C_{19}H_{25}BrN_2O_2$; Molecular Weight: 393.3; Mass/charge ratio: 392.1 (100.0%), 394.1 (99.9%), 393.1 (21.7%), 395.1 (21.3%), 396.1 (2.6%); Elemental analysis: C, 58.02; H, 6.41; Br, 20.32; N, 7.12; O, 8.14.

Example 146

N-(cycloheptylmethyl)-1-(2-hydroxyethyl)-5-methyl-1H-indole-3-carboxamide

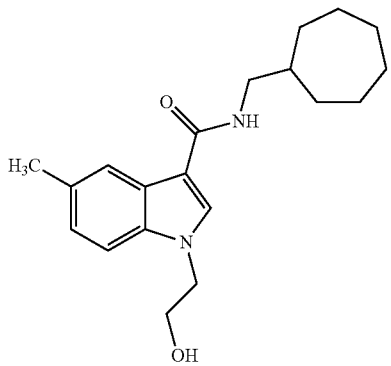 [SMILES: Cc1ccc2c(c1)c(C(=O)NCC1CCCCCC1)cn2CCO]

Synthesised according to the procedure disclosed in Example 1 where X is 5-methyl indole, Y is O-t-butyldimethylsilyl-2-chloroethanol, and Z is cycloheptylmethyl amine. Formula: $C_{20}H_{28}N_2O_2$; Molecular Weight: 328.4; Mass/charge ratio: 328.2 (100.0%), 329.2 (22.8%), 330.2 (2.9%); Elemental analysis: C, 73.14; H, 8.59; N, 8.53; O, 9.74.

Example 147

6-chloro-N-(cycloheptylmethyl)-1-methyl-1H-indole-3-carboxamide

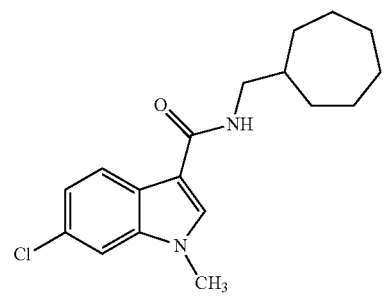

Synthesised according to the procedure disclosed in Example 1 where X is 6-chloro indole, Y is methyl iodide, and Z is cycloheptylmethyl amine. Formula: $C_{18}H_{23}ClN_2O$; Molecular Weight: 318.8; Mass/charge ratio: 318.1 (100.0%), 320.1 (32.0%), 319.2 (19.8%), 321.2 (6.5%), 320.2 (2.2%); Elemental analysis: C, 67.81; H, 7.27; Cl, 11.12; N, 8.79; O, 5.02.

Example 148

6-bromo-N-(cycloheptylmethyl)-1-methyl-1H-indole-3-carboxamide

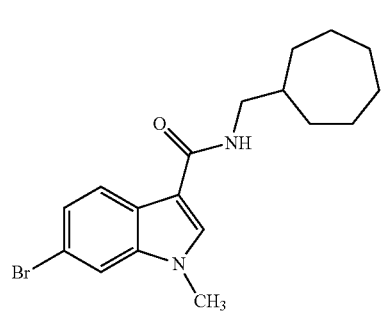 [SMILES: Cn1cc(C(=O)NCC2CCCCCC2)c2ccc(Cl)cc21]

Synthesised according to the procedure disclosed in Example 1 where X is 6-bromo indole, Y is methyl iodide, and Z is cycloheptylmethyl amine. Formula: $C_{18}H_{23}BrN_2O$; Molecular Weight: 363.3; Mass/charge ratio: 362.1 (100.0%), 364.1 (99.5%), 363.1 (20.5%), 365.1 (20.1%), 366.1 (2.2%); Elemental analysis: C, 59.51; H, 6.38; Br, 21.99; N, 7.71; O, 4.40.

Example 149

N-(cycloheptylmethyl)-1,6-dimethyl-1H-indole-3-carboxamide

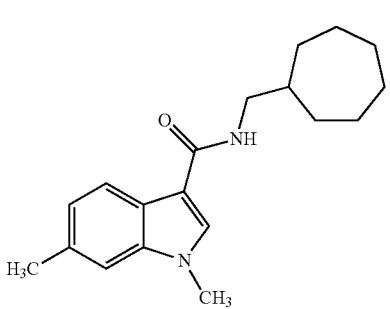 [SMILES: Cc1ccc2c(C(=O)NCC3CCCCCC3)cn(C)c2c1]

Synthesised according to the procedure disclosed in Example 1 where X is 6-methyl indole, Y is methyl iodide, and Z is cycloheptylmethyl amine. Formula: $C_{19}H_{26}N_2O$; Molecular Weight: 298.4; Mass/charge ratio: 298.2 (100.0%), 299.2 (21.6%), 300.2 (2.4%); Elemental analysis: C, 76.47; H, 8.78; N, 9.39; O, 5.36.

Example 150

6-chloro-N-(cycloheptylmethyl)-1-ethyl-1H-indole-3-carboxamide

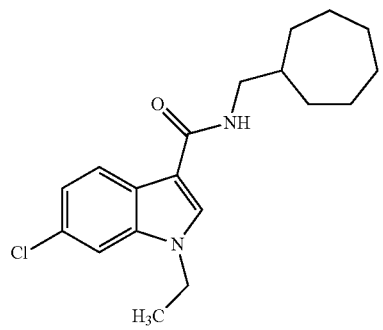 [SMILES: CCn1cc(C(=O)NCC2CCCCCC2)c2ccc(Cl)cc21]

Synthesised according to the procedure disclosed in Example 1 where X is 6-chloro indole, Y is ethyl iodide, and Z is cycloheptylmethyl amine. Formula: $C_{19}H_{25}ClN_2O$; Molecular Weight: 332.9; Mass/charge ratio: 332.2 (100.0%), 334.2 (34.4%), 333.2 (21.6%), 335.2 (7.1%); Elemental analysis: C, 68.56; H, 7.57; Cl, 10.65; N, 8.42; O, 4.81.

Example 151

6-bromo-N-(cycloheptylmethyl)-1-ethyl-1H-indole-3-carboxamide

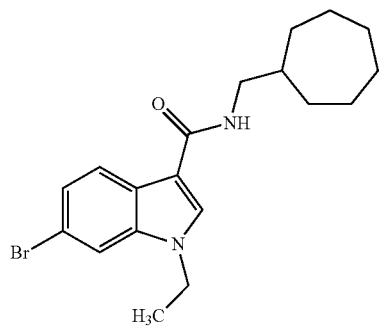

Synthesised according to the procedure disclosed in Example 1 where X is 6-bromo indole, Y is ethyl iodide, and Z is cycloheptylmethyl amine. Formula: $C_{19}H_{25}BrN_2O$; Molecular Weight: 377.3; Mass/charge ratio: 376.1 (100.0%), 378.1 (99.7%), 377.1 (21.6%), 379.1 (21.2%), 380.1 (2.4%); Elemental analysis: C, 60.48; H, 6.68; Br, 21.18; N, 7.42; O, 4.24.

Example 152

N-(cycloheptylmethyl)-1-ethyl-6-methyl-1H-indole-3-carboxamide

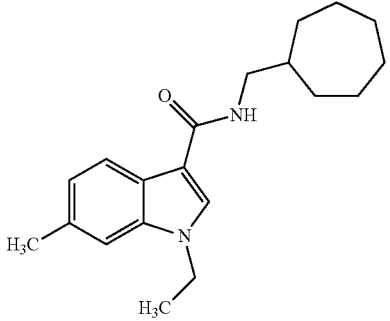 [SMILES: CCn1cc(C(=O)NCC2CCCCCC2)c2ccc(C)cc21]

Synthesised according to the procedure disclosed in Example 1 where X is 6-methyl indole, Y is ethyl iodide, and Z is cycloheptylmethyl amine. Formula: $C_{20}H_{28}N_2O$; Molecular Weight: 312.4; Mass/charge ratio: 312.2 (100.0%), 313.2 (22.7%), 314.2 (2.7%); Elemental analysis: C, 76.88; H, 9.03; N, 8.97; O, 5.12.

Example 153

6-chloro-N-(cycloheptylmethyl)-1-(2-hydroxyethyl)-1H-indole-3-carboxamide)

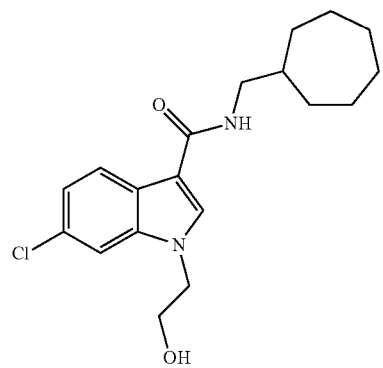

Synthesised according to the procedure disclosed in Example 1 where X is 6-chloro indole, Y is O-t-butyldimethylsilyl-2-chloroethanol, and Z is cycloheptylmethyl amine. Formula: $C_{19}H_{25}ClN_2O_2$; Molecular Weight: 348.9; Mass/charge ratio: 348.2 (100.0%), 350.2 (34.6%), 349.2 (21.7%), 351.2 (7.2%); Elemental analysis: C, 65.41; H, 7.22; Cl, 10.16; N, 8.03; O, 9.17.

Example 154

6-bromo-N-(cycloheptylmethyl)-1-(2-hydroxyethyl)-1H-indole-3-carboxamide

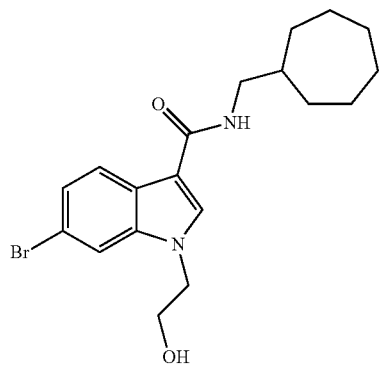 [SMILES: O=C(NCC1CCCCCC1)c1cn(CCO)c2cc(Cl)ccc12]

Synthesised according to the procedure disclosed in Example 1 where X is 6-bromo indole, Y is O-t-butyldimethylsilyl-2-chloroethanol, and Z is cycloheptylmethyl amine. Formula: $C_{19}H_{25}BrN_2O_2$; Molecular Weight: 393.3; Mass/charge ratio: 392.1 (100.0%), 394.1 (99.9%), 393.1 (21.7%), 395.1 (21.3%), 396.1 (2.6%); Elemental analysis: C, 58.02; H, 6.41; Br, 20.32; N, 7.12; O, 8.14.

Example 155

N-(cycloheptylmethyl)-1-(2-hydroxyethyl)-6-methyl-1H-indole-3-carboxamide

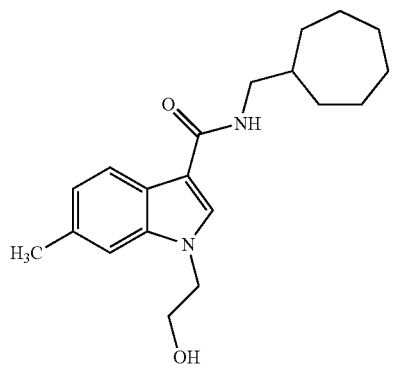 [SMILES: Cc1ccc2c(C(=O)NCC3CCCCCC3)cn(CCO)c2c1]

Synthesised according to the procedure disclosed in Example 1 where X is 6-methyl indole, Y is O-t-butyldimethylsilyl-2-chloroethanol, and Z is cycloheptylmethyl amine. Formula: $C_{20}H_{28}N_2O_2$; Molecular Weight: 328.4; Mass/charge ratio: 328.2 (100.0%), 329.2 (22.8%), 330.2 (2.9%); Elemental analysis: C, 73.14; H, 8.59; N, 8.53; O, 9.74.

Example 156

7-chloro-N-(cycloheptylmethyl)-1-methyl-1H-indole-3-carboxamide

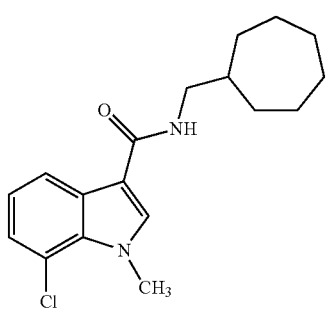 [SMILES: Cn1cc(C(=O)NCC2CCCCCC2)c2cccc(Cl)c21]

Synthesised according to the procedure disclosed in Example 1 where X is 7-chloro indole, Y is methyl iodide, and Z is cycloheptylmethyl amine. Formula: $C_{18}H_{23}ClN_2O$; Molecular Weight: 318.8; Mass/charge ratio: 318.1 (100.0%), 320.1 (32.0%), 319.2 (19.8%), 321.2 (6.5%), 320.2 (2.2%); Elemental analysis: C, 67.81; H, 7.27; Cl, 11.12; N, 8.79; O, 5.02.

Example 157

7-bromo-N-(cycloheptylmethyl)-1-methyl-1H-indole-3-carboxamide

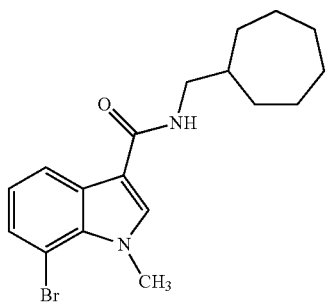 [SMILES: Cn1cc(C(=O)NCC2CCCCCC2)c2cccc(Br)c21]

Synthesised according to the procedure disclosed in Example 1 where X is 7-bromo indole, Y is methyl iodide, and Z is cycloheptylmethyl amine. Formula: $C_{18}H_{23}BrN_2O$; Molecular Weight: 363.3; Mass/charge ratio: 362.1 (100.0%), 364.1 (99.5%), 363.1 (20.5%), 365.1 (20.1%), 366.1 (2.2%); Elemental analysis: C, 59.51; H, 6.38; Br, 21.99; N, 7.71; O, 4.40.

Example 158

N-(cycloheptylmethyl)-1,7-dimethyl-1H-indole-3-carboxamide

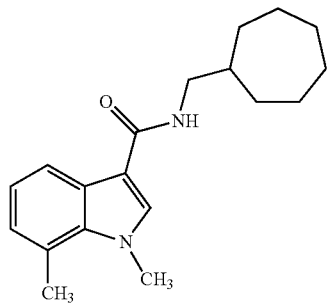 [SMILES: Cc1cccc2c(C(=O)NCC3CCCCCC3)cn(C)c12]

Synthesised according to the procedure disclosed in Example 1 where X is 7-methyl indole, Y is methyl iodide, and Z is cycloheptylmethyl amine. Formula: $C_{19}H_{26}N_2O$; Molecular Weight: 298.4; Mass/charge ratio: 298.2 (100.0%), 299.2 (21.6%), 300.2 (2.4%); Elemental analysis: C, 76.47; H, 8.78; N, 9.39; O, 5.36.

Example 159

7-chloro-N-(cycloheptylmethyl)-1-ethyl-1H-indole-3-carboxamide

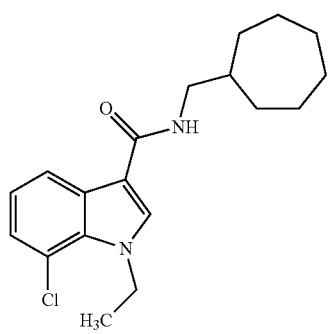 [SMILES: CCn1cc(C(=O)NCC2CCCCCC2)c2cccc(Cl)c21]

Synthesised according to the procedure disclosed in Example 1 where X is 7-chloro indole, Y is ethyl iodide, and Z is cycloheptylmethyl amine. Formula: $C_{19}H_{25}ClN_2O$; Molecular Weight: 332.9; Mass/charge ratio: 332.2 (100.0%), 334.2 (34.4%), 333.2 (21.6%), 335.2 (7.1%); Elemental analysis: C, 68.56; H, 7.57; Cl, 10.65; N, 8.42; O, 4.81.

Example 160

7-bromo-N-(cycloheptylmethyl)-1-ethyl-1H-indole-3-carboxamide

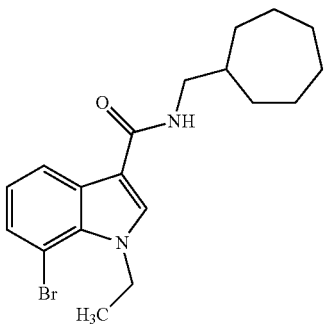 [SMILES: CCn1cc(C(=O)NCC2CCCCCC2)c2cccc(Br)c21]

Synthesised according to the procedure disclosed in Example 1 where X is 7-bromo indole, Y is ethyl iodide, and Z is cycloheptylmethyl amine. Formula: $C_{19}H_{25}BrN_2O$; Molecular Weight: 377.3; Mass/charge ratio: 376.1 (100.0%), 378.1 (99.7%), 377.1 (21.6%), 379.1 (21.2%), 380.1 (2.4%); Elemental analysis: C, 60.48; H, 6.68; Br, 21.18; N, 7.42; O, 4.24.

Example 161

N-(cycloheptylmethyl)-1-ethyl-7-methyl-1H-indole-3-carboxamide

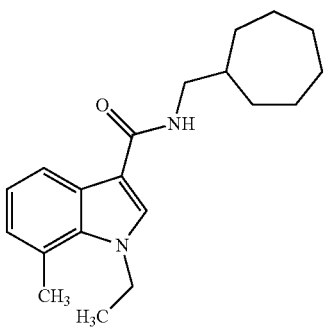 [SMILES: CCn1cc(C(=O)NCC2CCCCCC2)c2cccc(C)c21]

Synthesised according to the procedure disclosed in Example 1 where X is 7-methyl indole, Y is ethyl iodide, and Z is cycloheptylmethyl amine. Formula: $C_{20}H_{28}N_2O$; Molecular Weight: 312.4; Mass/charge ratio: 312.2 (100.0%), 313.2 (22.7%), 314.2 (2.7%); Elemental analysis: C, 76.88; H, 9.03; N, 8.97; O, 5.12.

Example 162

7-chloro-N-(cycloheptylmethyl)-1-(2-hydroxyethyl)-1H-indole-3-carboxamide

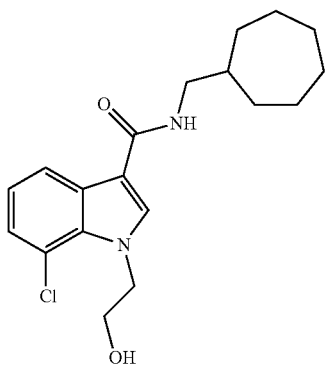 [SMILES: O=C(NCC1CCCCCC1)c1cn(CCO)c2c(Cl)cccc12]

Synthesised according to the procedure disclosed in Example 1 where X is 7-chloro indole, Y is O-t-butyldimethylsilyl-2-chloroethanol, and Z is cycloheptylmethyl amine. Formula: $C_{19}H_{25}ClN_2O_2$; Molecular Weight: 348.9; Mass/charge ratio: 348.2 (100.0%), 350.2 (34.6%), 349.2 (21.7%), 351.2 (7.2%); Elemental analysis: C, 65.41; H, 7.22; Cl, 10.16; N, 8.03; O, 9.17.

Example 163

7-bromo-N-(cycloheptylmethyl)-1-(2-hydroxyethyl)-1H-indole-3-carboxamide

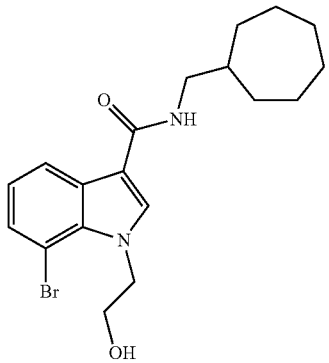 [SMILES: O=C(NCC1CCCCCC1)c1cn(CCO)c2c(Br)cccc12]

Synthesised according to the procedure disclosed in Example 1 where X is 7-bromo indole, Y is O-t-butyldimethylsilyl-2-chloroethanol, and Z is cycloheptylmethyl amine. Formula: $C_{19}H_{25}BrN_2O_2$; Molecular Weight: 393.3; Mass/charge ratio: 392.1 (100.0%), 394.1 (99.9%), 393.1 (21.7%), 395.1 (21.3%), 396.1 (2.6%); Elemental analysis: C, 58.02; H, 6.41; Br, 20.32; N, 7.12; O, 8.14.

Example 164

N-(cycloheptylmethyl)-1-(2-hydroxyethyl)-7-methyl-1H-indole-3-carboxamide

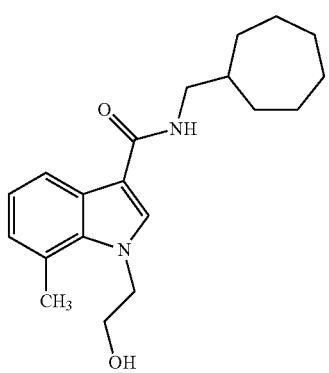 [SMILES: Cc1cccc2c(C(=O)NCC3CCCCCC3)cn(CCO)c12]

Synthesised according to the procedure disclosed in Example 1 where X is 7-methyl indole, Y is O-t-butyldimethylsilyl-2-chloroethanol, and Z is cycloheptylmethyl amine. Formula: $C_{20}H_{28}N_2O_2$; Molecular Weight: 328.4; Mass/charge ratio: 328.2 (100.0%), 329.2 (22.8%), 330.2 (2.9%); Elemental analysis: C, 73.14; H, 8.59; N, 8.53; O, 9.74.

Example 165

N-(bicyclo[2.2.2]octan-1-ylmethyl)-5-chloro-1-methyl-1H-indole-3-carboxamide

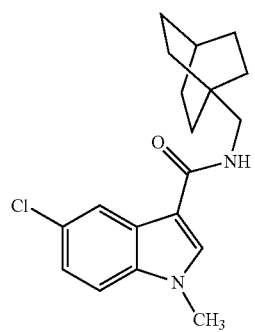 [SMILES: Cn1cc(C(=O)NCC23CCC(CC2)CC3)c2cc(Cl)ccc21]

Synthesised according to the procedure disclosed in Example 1 where X is 5-chloro indole, Y is O-t-butyldimethylsilyl-2-chloroethanol, and Z is bicyclo[2.2.2]octan-1-ylmethyl amine. Formula: $C_{19}H_{23}ClN_2O$; Molecular Weight: 330.9; Mass/charge ratio: 330.1 (100.0%), 332.1 (32.0%), 331.2 (20.9%), 333.2 (6.9%), 332.2 (2.4%); Elemental analysis: C, 68.97; H, 7.01; Cl, 10.72; N, 8.47; O, 4.84.

Example 166

N-(bicyclo[2.2.2]octan-1-ylmethyl)-5-bromo-1-methyl-1H-indole-3-carboxamide

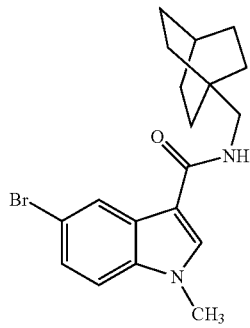

Synthesised according to the procedure disclosed in Example 1 where X is 5-bromo indole, Y is O-t-butyldimethylsilyl-2-chloroethanol, and Z is bicyclo[2.2.2]octan-1-ylmethyl amine. Formula: $C_{19}H_{23}BrN_2O$; Molecular Weight: 375.3; Mass/charge ratio: 374.1 (100.0%), 376.1 (99.7%), 375.1 (21.6%), 377.1 (21.2%), 378.1 (2.4%); Elemental analysis: C, 60.81; H, 6.18; Br, 21.29; N, 7.46; O, 4.26.

Example 167

N-(bicyclo[2.2.2]octan-1-ylmethyl)-1,5-dimethyl-1H-indole-3-carboxamide

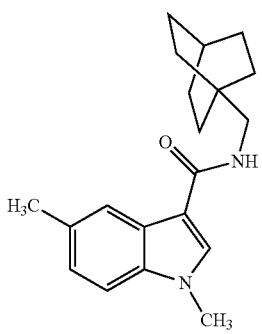 [SMILES: Cc1ccc2c(c1)c(C(=O)NCC13CCC(CC1)CC3)cn2C]

Synthesised according to the procedure disclosed in Example 1 where X is 5-methyl indole, Y is O-t-butyldimethylsilyl-2-chloroethanol, and Z is bicyclo[2.2.2]octan-1-ylmethyl amine. Formula: $C_{20}H_{26}N_2O$; Molecular Weight: 310.4; Mass/charge ratio: 310.2 (100.0%), 311.2 (22.7%), 312.2 (2.7%); Elemental analysis: C, 77.38; H, 8.44; N, 9.02; O, 5.15.

Example 168

N-(bicyclo[2.2.2]octan-1-ylmethyl)-5-chloro-1-ethyl-1H-indole-3-carboxamide

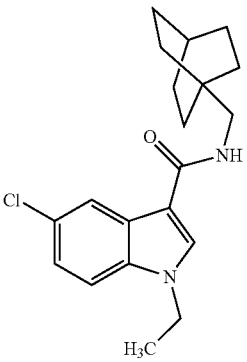

Synthesised according to the procedure disclosed in Example 1 where X is 5-chloro indole, Y is ethyl iodide, and Z is bicyclo[2.2.2]octan-1-ylmethyl amine. Formula: $C_{20}H_{25}ClN_2O$; Molecular Weight: 344.9; Mass/charge ratio: 344.2 (100.0%), 346.2 (34.6%), 345.2 (22.7%), 347.2 (7.5%); Elemental analysis: C, 69.65; H, 7.31; Cl, 10.28; N, 8.12; O, 4.64.

Example 169

N-(bicyclo[2.2.2]octan-1-ylmethyl)-5-bromo-1-ethyl-1H-indole-3-carboxamide

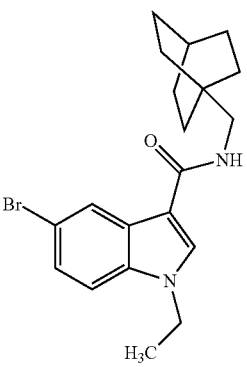 [SMILES: CCn1cc(C(=O)NCC23CCC(CC2)CC3)c2cc(Cl)ccc21]

Synthesised according to the procedure disclosed in Example 1 where X is 5-bromo indole, Y is ethyl iodide, and Z is bicyclo[2.2.2]octan-1-ylmethyl amine. Formula: $C_{20}H_{25}BrN_2O$; Molecular Weight: 389.3; Mass/charge ratio: 388.1 (100.0%), 390.1 (99.9%), 389.1 (22.7%), 391.1 (22.3%), 392.1 (2.6%); Elemental analysis: C, 61.70; H, 6.47; Br, 20.52; N, 7.20; O, 4.11.

Example 170

N-(bicyclo[2.2.2]octan-1-ylmethyl)-1-ethyl-5-methyl-1H-indole-3-carboxamide

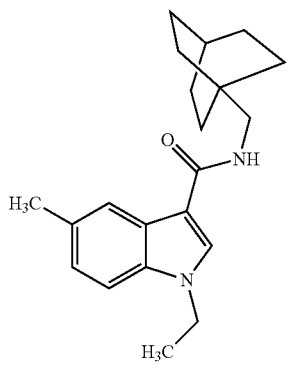 [SMILES: CCn1cc(C(=O)NCC23CCC(CC2)CC3)c2cc(C)ccc21]

Synthesised according to the procedure disclosed in Example 1 where X is 5-methyl indole, Y is ethyl iodide, and Z is bicyclo[2.2.2]octan-1-ylmethyl amine. Formula: $C_{21}H_{28}N_2O$; Molecular Weight: 324.5; Mass/charge ratio: 324.2 (100.0%), 325.2 (23.8%), 326.2 (2.9%); Elemental analysis: C, 77.74; H, 8.70; N, 8.63; O, 4.93.

Example 171

N-(bicyclo[2.2.2]octan-1-ylmethyl)-5-chloro-1-(2-hydroxyethyl)-1H-indole-3-carboxamide

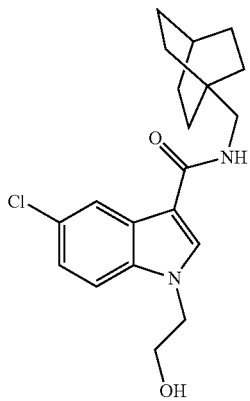 [SMILES: O=C(NCC12CCC(CC1)CC2)c1cn(CCO)c2ccc(Cl)cc12]

Synthesised according to the procedure disclosed in Example 1 where X is 5-chloro indole, Y is O-t-butyldimethylsilyl-2-chloroethanol, and Z is bicyclo[2.2.2]octan-1-ylmethyl amine. Formula: $C_{20}H_{25}ClN_2O_2$; Molecular Weight: 360.9; Mass/charge ratio: 360.2 (100.0%), 362.2 (34.8%), 361.2 (22.7%), 363.2 (7.5%); Elemental analysis: C, 66.56; H, 6.98; Cl, 9.82; N, 7.76; O, 8.87.

Example 172

N-(bicyclo[2.2.2]octan-1-ylmethyl)-5-bromo-1-(2-hydroxyethyl)-1H-indole-3-carboxamide

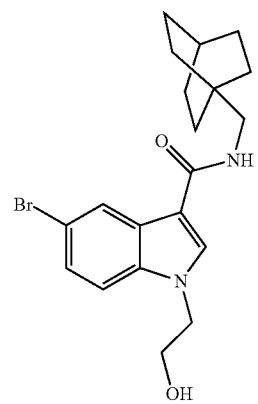 [SMILES: O=C(NCC12CCC(CC1)CC2)c1cn(CCO)c2ccc(Br)cc12]

Synthesised according to the procedure disclosed in Example 1 where X is 5-bromo indole, Y is O-t-butyldimethylsilyl-2-chloroethanol, and Z is bicyclo[2.2.2]octan-1-ylmethyl amine. Formula: $C_{20}H_{25}BrN_2O_2$; Molecular Weight: 405.3; Mass/charge ratio: 406.1 (100.0%), 404.1 (99.8%), 405.1 (22.7%), 407.1 (22.3%), 408.1 (2.8%); Elemental analysis: C, 59.26; H, 6.22; Br, 19.71; N, 6.91; O, 7.89.

Example 173

N-(bicyclo[2.2.2]octan-1-ylmethyl)-1-(2-hydroxyethyl)-5-methyl-1H-indole-3-carboxamide

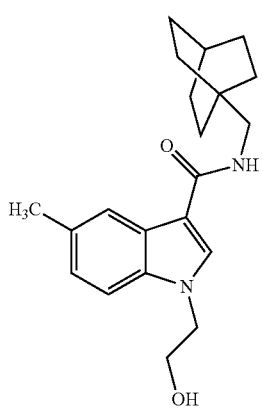 [SMILES: Cc1ccc2c(c1)c(C(=O)NCC13CCC(CC1)CC3)cn2CCO]

Synthesised according to the procedure disclosed in Example 1 where X is 5-methyl indole, Y is O-t-butyldimethylsilyl-2-chloroethanol, and Z is bicyclo[2.2.2]octan-1-ylmethyl amine. Formula: $C_{21}H_{28}N_2O_2$; Molecular Weight: 340.5; Mass/charge ratio: 340.2 (100.0%), 341.2 (23.8%), 342.2 (3.1%); Elemental analysis: C, 74.08; H, 8.29; N, 8.23; O, 9.40.

Example 174

N-(bicyclo[2.2.2]octan-1-ylmethyl)-6-chloro-1-methyl-1H-indole-3-carboxamide

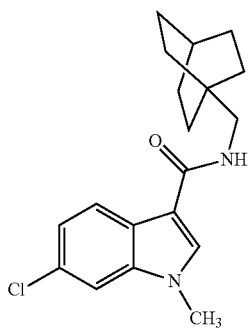 [SMILES: Cn1cc(C(=O)NCC23CCC(CC2)CC3)c2ccc(Cl)cc21]

Synthesised according to the procedure disclosed in Example 1 where X is 6-chloro indole, Y is methyl iodide, and Z is bicyclo[2.2.2]octan-1-ylmethyl amine. Formula: $C_{19}H_{23}ClN_2O$; Molecular Weight: 330.9; Mass/charge ratio: 330.1 (100.0%), 332.1 (32.0%), 331.2 (20.9%), 333.2 (6.9%), 332.2 (2.4%); Elemental analysis: C, 68.97; H, 7.01; Cl, 10.72; N, 8.47; O, 4.84.

Example 175

N-(bicyclo[2.2.2]octan-1-ylmethyl)-6-bromo-1-methyl-1H-indole-3-carboxamide

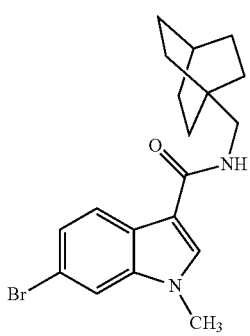

Synthesised according to the procedure disclosed in Example 1 where X is 6-bromo indole, Y is methyl iodide, and Z is bicyclo[2.2.2]octan-1-ylmethyl amine. Formula: $C_{19}H_{23}BrN_2O$; Molecular Weight: 375.3; Mass/charge ratio: 374.1 (100.0%), 376.1 (99.7%), 375.1 (21.6%), 377.1 (21.2%), 378.1 (2.4%); Elemental analysis: C, 60.81; H, 6.18; Br, 21.29; N, 7.46; O, 4.26.

Example 176

N-(bicyclo[2.2.2]octan-1-ylmethyl)-1,6-dimethyl-1H-indole-3-carboxamide

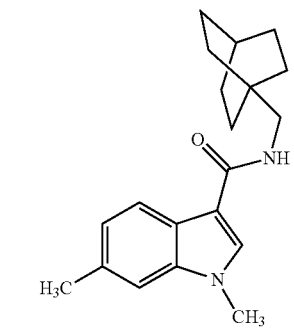 [SMILES: Cc1ccc2c(C(=O)NCC34CCC(CC3)CC4)cn(C)c2c1]

Synthesised according to the procedure disclosed in Example 1 where X is 6-methyl indole, Y is methyl iodide, and Z is bicyclo[2.2.2]octan-1-ylmethyl amine. Formula: $C_{20}H_{26}N_2O$; Molecular Weight: 310.4; Mass/charge ratio: 310.2 (100.0%), 311.2 (22.7%), 312.2 (2.7%); Elemental analysis: C, 77.38; H, 8.44; N, 9.02; O, 5.15.

Example 177

N-(bicyclo[2.2.2]octan-1-ylmethyl)-6-chloro-1-ethyl-1H-indole-3-carboxamide

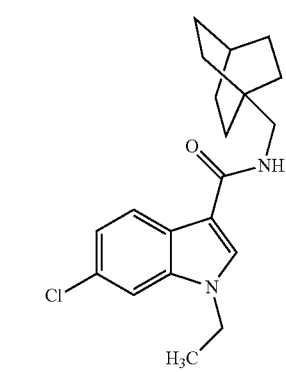 [SMILES: CCn1cc(C(=O)NCC23CCC(CC2)CC3)c2ccc(Cl)cc21]

Synthesised according to the procedure disclosed in Example 1 where X is 6-chloro indole, Y is ethyl iodide, and Z is bicyclo[2.2.2]octan-1-ylmethyl amine. Formula: $C_{20}H_{25}ClN_2O$; Molecular Weight: 344.9; Mass/charge ratio: 344.2 (100.0%), 346.2 (34.6%), 345.2 (22.7%), 347.2 (7.5%); Elemental analysis: C, 69.65; H, 7.31; Cl, 10.28; N, 8.12; O, 4.64.

Example 178

N-(bicyclo[2.2.2]octan-1-ylmethyl)-6-bromo-1-ethyl-1H-indole-3-carboxamide

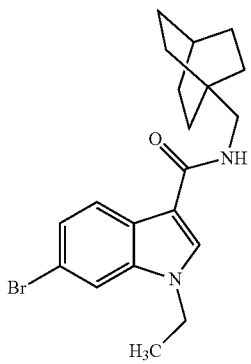

Synthesised according to the procedure disclosed in Example 1 where X is 6-bromo indole, Y is ethyl iodide, and Z is bicyclo[2.2.2]octan-1-ylmethyl amine. Formula: $C_{20}H_{25}BrN_2O$; Molecular Weight: 389.3; Mass/charge ratio: 388.1 (100.0%), 390.1 (99.9%), 389.1 (22.7%), 391.1 (22.3%), 392.1 (2.6%); Elemental analysis: C, 61.70; H, 6.47; Br, 20.52; N, 7.20; O, 4.11.

Example 179

N-(bicyclo[2.2.2]octan-1-ylmethyl)-1-ethyl-6-methyl-1H-indole-3-carboxamide

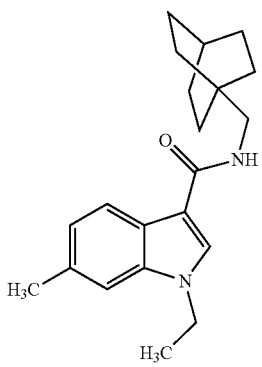 [SMILES: CCn1cc(C(=O)NCC23CCC(CC2)CC3)c2ccc(C)cc21]

Synthesised according to the procedure disclosed in Example 1 where X is 6-methyl indole, Y is ethyl iodide, and Z is bicyclo[2.2.2]octan-1-ylmethyl amine. Formula: $C_{21}H_{28}N_2O$; Molecular Weight: 324.5; Mass/charge ratio: 324.2 (100.0%), 325.2 (23.8%), 326.2 (2.9%); Elemental analysis: C, 77.74; H, 8.70; N, 8.63; O, 4.93.

Example 180

N-(bicyclo[2.2.2]octan-1-ylmethyl)-6-chloro-1-(2-hydroxyethyl)-1H-indole-3-carboxamide

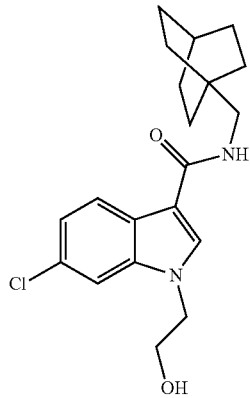 [SMILES: O=C(NCC12CCC(CC1)CC2)c1cn(CCO)c2cc(Cl)ccc12]

Synthesised according to the procedure disclosed in Example 1 where X is 6-chloro indole, Y is O-t-butyldimethylsilyl-2-chloroethanol, and Z is bicyclo[2.2.2]octan-1-ylmethyl amine. Formula: $C_{20}H_{25}ClN_2O_2$; Molecular Weight: 360.9; Mass/charge ratio: 360.2 (100.0%), 362.2 (34.8%), 361.2 (22.7%), 363.2 (7.5%); Elemental analysis: C, 66.56; H, 6.98; Cl, 9.82; N, 7.76; O, 8.87.

Example 181

N-(bicyclo[2.2.2]octan-1-ylmethyl)-6-bromo-1-(2-hydroxyethyl)-1H-indole-3-carboxamide

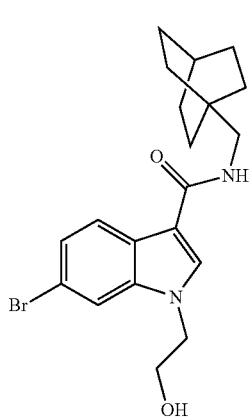

Synthesised according to the procedure disclosed in Example 1 where X is 6-bromo indole, Y is O-t-butyldimethylsilyl-2-chloroethanol, and Z is bicyclo[2.2.2]octan-1-ylmethyl amine. Formula: $C_{20}H_{25}BrN_2O_2$; Molecular Weight: 405.3; Mass/charge ratio: 406.1 (100.0%), 404.1 (99.8%), 405.1 (22.7%), 407.1 (22.3%), 408.1 (2.8%); Elemental analysis: C, 59.26; H, 6.22; Br, 19.71; N, 6.91; O, 7.89.

Example 182

N-(bicyclo[2.2.2]octan-1-ylmethyl)-1-(2-hydroxyethyl)-6-methyl-1H-indole-3-carboxamide

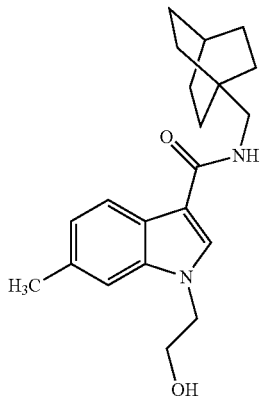 [SMILES: Cc1ccc2c(C(=O)NCC34CCC(CC3)CC4)cn(CCO)c2c1]

Synthesised according to the procedure disclosed in Example 1 where X is 6-methyl indole, Y is O-t-butyldimethylsilyl-2-chloroethanol, and Z is bicyclo[2.2.2]octan-1-ylmethyl amine. Formula: $C_{21}H_{28}N_2O_2$; Molecular Weight: 340.5; Mass/charge ratio: 340.2 (100.0%), 341.2 (23.8%), 342.2 (3.1%); Elemental analysis: C, 74.08; H, 8.29; N, 8.23; O, 9.40.

Example 183

N-(bicyclo[2.2.2]octan-1-ylmethyl)-7-chloro-1-methyl-1H-indole-3-carboxamide

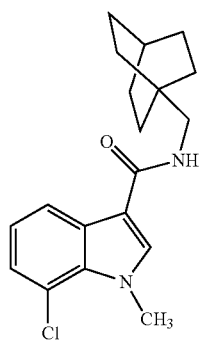 [SMILES: Cn1cc(C(=O)NCC23CCC(CC2)CC3)c2cccc(Cl)c21]

Synthesised according to the procedure disclosed in Example 1 where X is 7-chloro indole, Y is methyl iodide, and Z is bicyclo[2.2.2]octan-1-ylmethyl amine. Formula: $C_{19}H_{23}ClN_2O$; Molecular Weight: 330.9; Mass/charge ratio: 330.1 (100.0%), 332.1 (32.0%), 331.2 (20.9%), 333.2 (6.9%), 332.2 (2.4%); Elemental analysis: C, 68.97; H, 7.01; Cl, 10.72; N, 8.47; O, 4.84.

Example 184

N-(bicyclo[2.2.2]octan-1-ylmethyl)-7-bromo-1-methyl-1H-indole-3-carboxamide

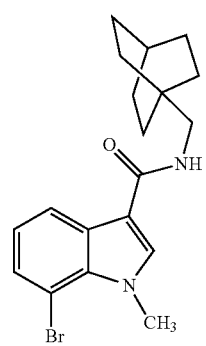 [SMILES: Cn1cc(C(=O)NCC23CCC(CC2)CC3)c2cccc(Br)c21]

Synthesised according to the procedure disclosed in Example 1 where X is 7-bromo indole, Y is methyl iodide, and Z is bicyclo[2.2.2]octan-1-ylmethyl amine. Formula: $C_{19}H_{23}BrN_2O$; Molecular Weight: 375.3; Mass/charge ratio: 374.1 (100.0%), 376.1 (99.7%), 375.1 (21.6%), 377.1 (21.2%), 378.1 (2.4%); Elemental analysis: C, 60.81; H, 6.18; Br, 21.29; N, 7.46; O, 4.26.

Example 185

N-(bicyclo[2.2.2]octan-1-ylmethyl)-1,7-dimethyl-1H-indole-3-carboxamide

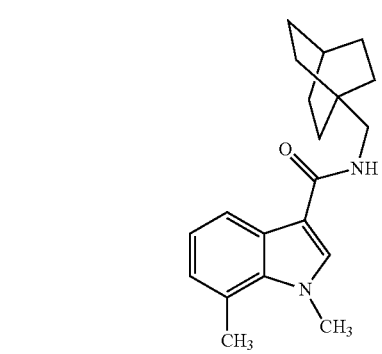 [SMILES: Cc1cccc2c(C(=O)NCC34CCC(CC3)CC4)cn(C)c12]

Synthesised according to the procedure disclosed in Example 1 where X is 7-methyl indole, Y is methyl iodide, and Z is bicyclo[2.2.2]octan-1-ylmethyl amine. Formula: $C_{20}H_{26}N_2O$; Molecular Weight: 310.4; Mass/charge ratio: 310.2 (100.0%), 311.2 (22.7%), 312.2 (2.7%); Elemental analysis: C, 77.38; H, 8.44; N, 9.02; O, 5.15.

Example 186

N-(bicyclo[2.2.2]octan-1-ylmethyl)-7-chloro-1-ethyl-1H-indole-3-carboxamide

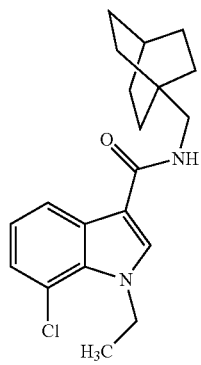

Synthesised according to the procedure disclosed in Example 1 where X is 7-chloro indole, Y is ethyl iodide, and Z is bicyclo[2.2.2]octan-1-ylmethyl amine. Formula: $C_{20}H_{25}ClN_2O$; Molecular Weight: 344.9; Mass/charge ratio: 344.2 (100.0%), 346.2 (34.6%), 345.2 (22.7%), 347.2 (7.5%); Elemental analysis: C, 69.65; H, 7.31; Cl, 10.28; N, 8.12; O, 4.64.

Example 187

N-(bicyclo[2.2.2]octan-1-ylmethyl)-7-bromo-1-ethyl-1H-indole-3-carboxamide

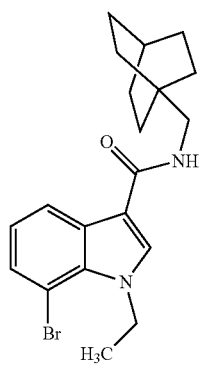 [SMILES: CCn1cc(C(=O)NCC23CCC(CC2)CC3)c2cccc(Br)c21]

Synthesised according to the procedure disclosed in Example 1 where X is 7-bromo indole, Y is ethyl iodide, and Z is bicyclo[2.2.2]octan-1-ylmethyl amine. Formula: $C_{20}H_{25}BrN_2O$; Molecular Weight: 389.3; Mass/charge ratio: 388.1 (100.0%), 390.1 (99.9%), 389.1 (22.7%), 391.1 (22.3%), 392.1 (2.6%); Elemental analysis: C, 61.70; H, 6.47; Br, 20.52; N, 7.20; O, 4.11.

Example 188

N-(bicyclo[2.2.2]octan-1-ylmethyl)-1-ethyl-7-methyl-1H-indole-3-carboxamide

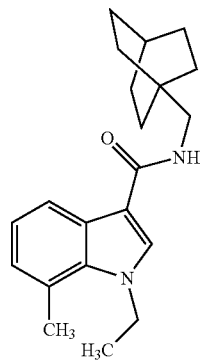 [SMILES: CCn1cc(C(=O)NCC23CCC(CC2)CC3)c2cccc(C)c21]

Synthesised according to the procedure disclosed in Example 1 where X is 7-methyl indole, Y is ethyl iodide, and Z is bicyclo[2.2.2]octan-1-ylmethyl amine. Formula: $C_{21}H_{28}N_2O$; Molecular Weight: 324.5; Mass/charge ratio: 324.2 (100.0%), 325.2 (23.8%), 326.2 (2.9%); Elemental analysis: C, 77.74; H, 8.70; N, 8.63; O, 4.93.

Example 189

N-(bicyclo[2.2.2]octan-1-ylmethyl)-7-chloro-1-(2-hydroxyethyl)-1H-indole-3-carboxamide

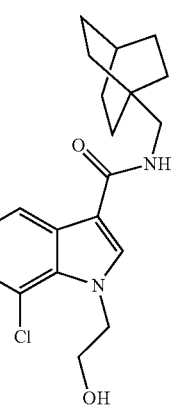

Synthesised according to the procedure disclosed in Example 1 where X is 7-chloro indole, Y is O-t-butyldimethylsilyl-2-chloroethanol, and Z is bicyclo[2.2.2]octan-1-ylmethyl amine. Formula: $C_{20}H_{25}ClN_2O_2$; Molecular Weight: 360.9; Mass/charge ratio: 360.2 (100.0%), 362.2 (34.8%), 361.2 (22.7%), 363.2 (7.5%); Elemental analysis: C, 66.56; H, 6.98; Cl, 9.82; N, 7.76; O, 8.87.

Example 190

N-(bicyclo[2.2.2]octan-1-ylmethyl)-7-bromo-1-(2-hydroxyethyl)-1H-indole-3-carboxamide

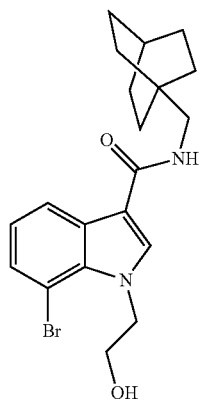 [SMILES: O=C(NCC12CCC(CC1)CC2)c1cn(CCO)c2c(Br)cccc12]

Synthesised according to the procedure disclosed in Example 1 where X is 7-bromo indole, Y is O-t-butyldimethylsilyl-2-chloroethanol, and Z is bicyclo[2.2.2]octan-1-ylmethyl amine. Formula: $C_{20}H_{25}BrN_2O_2$; Molecular Weight: 405.3; Mass/charge ratio: 406.1 (100.0%), 404.1 (99.8%), 405.1 (22.7%), 407.1 (22.3%), 408.1 (2.8%); Elemental analysis: C, 59.26; H, 6.22; Br, 19.71; N, 6.91; O, 7.89.

Example 191

N-(bicyclo[2.2.2]octan-1-ylmethyl)-1-(2-hydroxyethyl)-7-methyl-1H-indole-3-carboxamide

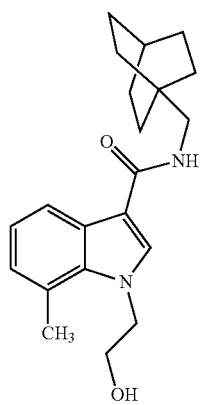 [SMILES: Cc1cccc2c(C(=O)NCC34CCC(CC3)CC4)cn(CCO)c12]

Synthesised according to the procedure disclosed in Example 1 where X is 7-methyl indole, Y is O-t-butyldimethylsilyl-2-chloroethanol, and Z is bicyclo[2.2.2]octan-1-ylmethyl amine. Formula: $C_{21}H_{28}N_2O_2$; Molecular Weight: 340.5; Mass/charge ratio: 340.2 (100.0%), 341.2 (23.8%), 342.2 (3.1%); Elemental analysis: C, 74.08; H, 8.29; N, 8.23; O, 9.40.

Example 192

4-chloro-N-(cycloheptylmethyl)-6-fluoro-1-methyl-1H-indole-3-carboxamide

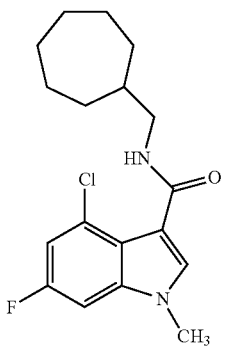 [SMILES: Cn1cc(C(=O)NCC2CCCCCC2)c2c(Cl)cc(F)cc21]

Synthesised according to the procedure disclosed in Example 1 where X is 4-chloro-6-fluoro indole, Y is methyl iodide, and Z is cycloheptylmethyl amine. Formula: C18H22ClFN2O; Molecular Weight: 336.8; Mass/charge ratio: 336.1 (100.0%), 338.1 (34.1%), 337.1 (20.5%), 339.1 (6.6%); Elemental analysis: C, 64.18; H, 6.58; Cl, 10.53; F, 5.64; N, 8.32; O, 4.75.

Example 193

4-bromo-N-(cycloheptylmethyl)-6-fluoro-1-methyl-1H-indole-3-carboxamide

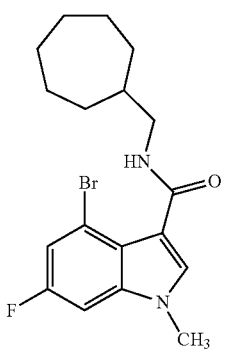 [SMILES: Cn1cc(C(=O)NCC2CCCCCC2)c2c(Br)cc(F)cc21]

Synthesised according to the procedure disclosed in Example 1 where X is 4-bromo-6-fluoro indole, Y is methyl iodide, and Z is cycloheptylmethyl amine. Formula: $C_{18}H_{22}BrFN_2O$; Molecular Weight: 381.3; Mass/charge ratio: 380.1 (100.0%), 382.1 (99.5%), 381.1 (20.5%), 383.1 (20.1%), 384.1 (2.1%); Elemental analysis: C, 56.70; H, 5.82; Br, 20.96; F, 4.98; N, 7.35; O, 4.20.

Example 194

N-(cycloheptylmethyl)-6-fluoro-1,4-dimethyl-1H-indole-3-carboxamide

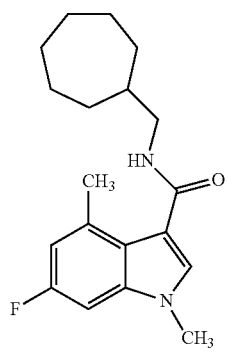

Synthesised according to the procedure disclosed in Example 1 where X is 4-methyl-6-fluoro indole, Y is methyl iodide, and Z is cycloheptylmethyl amine. Formula: $C_{19}H_{25}FN_2O$; Molecular Weight: 316.4; Mass/charge ratio: 316.2 (100.0%), 317.2 (21.6%), 318.2 (2.4%); Elemental analysis: C, 72.12; H, 7.96; F, 6.00; N, 8.85; O, 5.06.

Example 195

4-chloro-N-(cycloheptylmethyl)-1-ethyl-6-fluoro-1H-indole-3-carboxamide

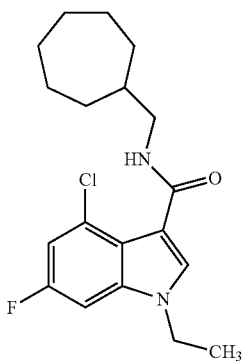 [SMILES: CCn1cc(C(=O)NCC2CCCCCC2)c2c(Cl)cc(F)cc21]

Synthesised according to the procedure disclosed in Example 1 where X is 4-chloro-6-fluoro indole, Y is ethyl iodide, and Z is cycloheptylmethyl amine. Formula: $C_{19}H_{24}ClFN_2O$; Molecular Weight: 350.9; Mass/charge ratio: 350.2 (100.0%), 352.2 (34.4%), 351.2 (21.6%), 353.2 (7.1%); Elemental analysis: C, 65.04; H, 6.89; Cl, 10.10; F, 5.41; N, 7.98; O, 4.56.

Example 196

4-bromo-N-(cycloheptylmethyl)-1-ethyl-6-fluoro-1H-indole-3-carboxamide

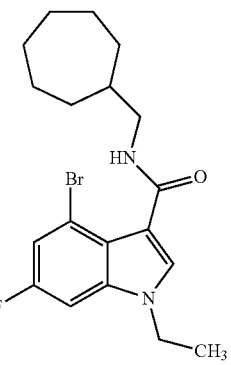

Synthesised according to the procedure disclosed in Example 1 where X is 4-bromo-6-fluoro indole, Y is ethyl iodide, and Z is cycloheptylmethyl amine. Formula: $C_{19}H_{24}BrFN_2O$; Molecular Weight: 395.3; Mass/charge ratio: 394.1 (100.0%), 396.1 (99.7%), 395.1 (21.6%), 397.1 (21.2%), 398.1 (2.4%); Elemental analysis: C, 57.73; H, 6.12; Br, 20.21; F, 4.81; N, 7.09; O, 4.05.

Example 197

N-(cycloheptylmethyl)-1-ethyl-6-fluoro-4-methyl-1H-indole-3-carboxamide

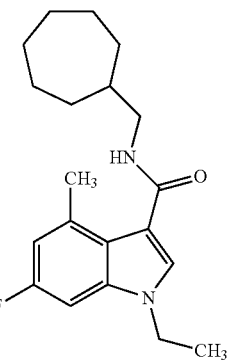

Synthesised according to the procedure disclosed in Example 1 where X is 4-methyl-6-fluoro indole, Y is ethyl iodide, and Z is cycloheptylmethyl amine. Formula: $C_{20}H_{27}FN_2O$; Molecular Weight: 330.4; Mass/charge ratio: 330.2 (100.0%), 331.2 (22.7%), 332.2 (2.7%); Elemental analysis: C, 72.70; H, 8.24; F, 5.75; N, 8.48; O, 4.84.

Example 198

4-chloro-N-(cycloheptylmethyl)-6-fluoro-1-isopropyl-1H-indole-3-carboxamide

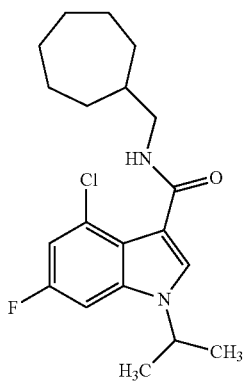 [SMILES: CC(C)n1cc(C(=O)NCC2CCCCCC2)c2c(Cl)cc(F)cc21]

Synthesised according to the procedure disclosed in Example 1 where X is 4-chloro-6-fluoro indole, Y is isopropyl bromide, and Z is cycloheptylmethyl amine. Formula: $C_{20}H_{26}ClFN_2O$; Molecular Weight: 364.9; Mass/charge ratio: 364.2 (100.0%), 366.2 (34.6%), 365.2 (22.7%), 367.2 (7.5%); Elemental analysis: C, 65.83; H, 7.18; Cl, 9.72; F, 5.21; N, 7.68; O, 4.38.

Example 199

4-bromo-N-(cycloheptylmethyl)-6-fluoro-1-isopropyl-1H-indole-3-carboxamide

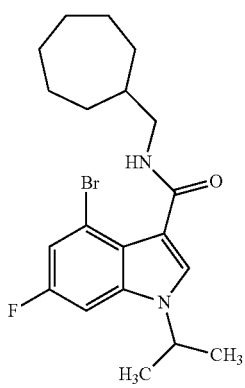 [SMILES: CC(C)n1cc(C(=O)NCC2CCCCCC2)c2c(Br)cc(F)cc21]

Synthesised according to the procedure disclosed in Example 1 where X is 4-bromo-6-fluoro indole, Y is isopropyl bromide, and Z is cycloheptylmethyl amine. Formula: $C_{20}H_{26}BrFN_2O$; Molecular Weight: 409.3; Mass/charge ratio: 408.1 (100.0%), 410.1 (99.9%), 409.1 (22.7%), 411.1 (22.3%), 412.1 (2.6%); Elemental analysis: C, 58.68; H, 6.40; Br, 19.52; F, 4.64; N, 6.84; O, 3.91.

Example 200

4-chloro-N-(cycloheptylmethyl)-6-fluoro-1-(2-hydroxyethyl)-1H-indole-3-carboxamide

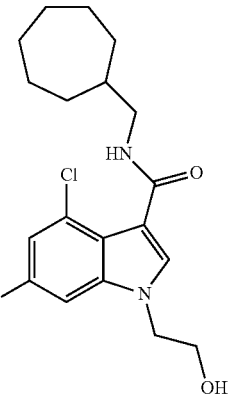

Synthesised according to the procedure disclosed in Example 1 where X is 4-chloro-6-fluoro indole, Y is O-t-butyldimethylsilyl-2-chloroethanol, and Z is cycloheptylmethyl amine. Formula: $C_{19}H_{24}ClFN_2O_2$; Molecular Weight: 366.9; Mass/charge ratio: 366.2 (100.0%), 368.1 (32.0%), 367.2 (20.9%), 369.2 (6.9%), 368.2 (2.6%); Elemental analysis: C, 62.20; H, 6.59; Cl, 9.66; F, 5.18; N, 7.64; O, 8.72.

Example 201

4-bromo-N-(cycloheptylmethyl)-6-fluoro-1-(2-hydroxyethyl)-1H-indole-3-carboxamide

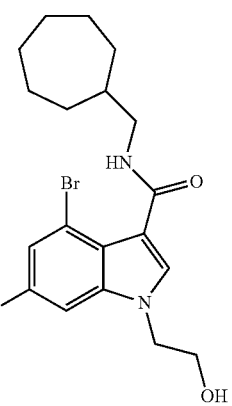

Synthesised according to the procedure disclosed in Example 1 where X is 4-bromo-6-fluoro indole, Y is O-t-butyldimethylsilyl-2-chloroethanol, and Z is cycloheptylmethyl amine. Formula: $C_{19}H_{24}BrFN_2O_2$; Molecular Weight: 411.3; Mass/charge ratio: 410.1 (100.0%), 412.1 (99.9%), 411.1 (21.6%), 413.1 (21.3%), 414.1 (2.6%); Elemental analysis: C, 55.48; H, 5.88; Br, 19.43; F, 4.62; N, 6.81; O, 7.78.

Example 202

N-(cycloheptylmethyl)-6-fluoro-1-(2-hydroxyethyl)-4-methyl-1H-indole-3-carboxamide

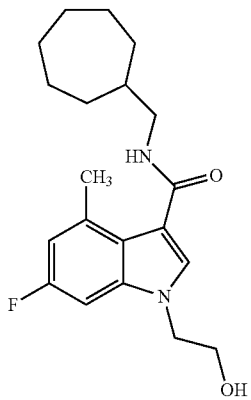 [SMILES: O=C(NCC1CCCCCC1)c1cn(CCO)c2cc(F)cc(Cl)c12]

Synthesised according to the procedure disclosed in Example 1 where X is 4-methyl-6-fluoro indole, Y is O-t-butyldimethylsilyl-2-chloroethanol, and Z is cycloheptylmethyl amine. Formula: $C_{20}H_{27}FN_2O_2$; Molecular Weight: 346.4; Mass/charge ratio: 346.2 (100.0%), 347.2 (22.8%), 348.2 (2.9%); Elemental analysis: C, 69.34; H, 7.86; F, 5.48; N, 8.09; O, 9.24.

Example 203

4,6-dichloro-N-(cycloheptylmethyl)-1-methyl-1H-indole-3-carboxamide

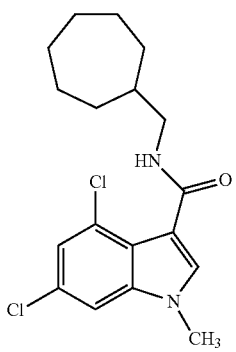 [SMILES: Cn1cc(C(=O)NCC2CCCCCC2)c2c(Cl)cc(Cl)cc21]

Synthesised according to the procedure disclosed in Example 1 where X is 4,6-dichloro indole, Y is methyl iodide, and Z is cycloheptylmethyl amine. Formula: $C_{18}H_{22}Cl_2N_2O$; Molecular Weight: 353.3; Mass/charge ratio: 352.1 (100.0%), 354.1 (66.1%), 353.1 (20.5%), 355.1 (13.3%), 356.1 (11.6%), 357.1 (2.2%); Elemental analysis: C, 61.19; H, 6.28; Cl, 20.07; N, 7.93; O, 4.53.

Example 204

6-chloro-N-(cycloheptylmethyl)-4-fluoro-1-methyl-1H-indole-3-carboxamide

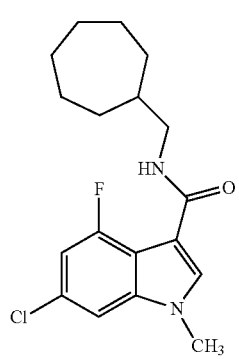 [SMILES: Cn1cc(C(=O)NCC2CCCCCC2)c2c(F)cc(Cl)cc21]

Synthesised according to the procedure disclosed in Example 1 where X is 4-fluoro-6-chloro indole, Y is methyl iodide, and Z is cycloheptylmethyl amine. Formula: $C_{18}H_{22}ClFN_2O$; Molecular Weight: 336.8; Mass/charge ratio: 336.1 (100.0%), 338.1 (34.1%), 337.1 (20.5%), 339.1 (6.6%); Elemental analysis: C, 64.18; H, 6.58; Cl, 10.53; F, 5.64; N, 8.32; O, 4.75.

Example 205

4-bromo-6-chloro-N-(cycloheptylmethyl)-1-methyl-1H-indole-3-carboxamide

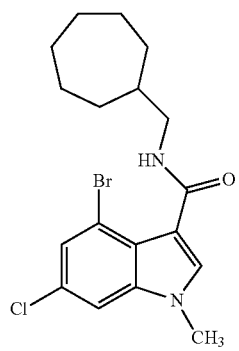 [SMILES: Cn1cc(C(=O)NCC2CCCCCC2)c2c(Br)cc(Cl)cc21]

Synthesised according to the procedure disclosed in Example 1 where X is 4-bromo-6-chloro indole, Y is methyl iodide, and Z is cycloheptylmethyl amine. Formula: $C_{18}H_{22}BrClN_2O$; Molecular Weight: 397.7; Mass/charge ratio: 398.1 (100.0%), 396.1 (76.1%), 400.1 (25.8%), 399.1 (20.3%), 397.1 (15.6%), 401.1 (5.0%); Elemental analysis: C, 54.36; H, 5.58; Br, 20.09; Cl, 8.91; N, 7.04; O, 4.02.

Example 206

6-chloro-N-(cycloheptylmethyl)-1,4-dimethyl-1H-indole-3-carboxamide

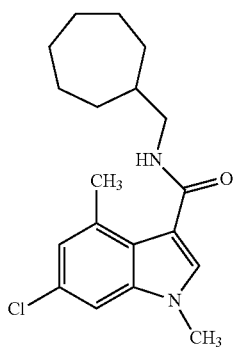 [SMILES: Cc1cc(Cl)cc2c1c(C(=O)NCC1CCCCCC1)cn2C]

Synthesised according to the procedure disclosed in Example 1 where X is 4-methyl-6-chloro indole, Y is methyl iodide, and Z is cycloheptylmethyl amine. Formula: $C_{19}H_{25}ClN_2O$; Molecular Weight: 332.9; Mass/charge ratio: 332.2 (100.0%), 334.2 (34.4%), 333.2 (21.6%), 335.2 (7.1%); Elemental analysis: C, 68.56; H, 7.57; Cl, 10.65; N, 8.42; O, 4.81.

Example 207

6-chloro-N-(cycloheptylmethyl)-1-ethyl-4-fluoro-1H-indole-3-carboxamide

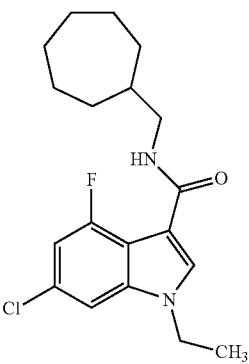 [SMILES: CCn1cc(C(=O)NCC2CCCCCC2)c2c(F)cc(Cl)cc21]

Synthesised according to the procedure disclosed in Example 1 where X is 4-fluoro-6-chloro indole, Y is ethyl iodide, and Z is cycloheptylmethyl amine. Formula: $C_{19}H_{24}ClFN_2O$; Molecular Weight: 350.9; Mass/charge ratio: 350.2 (100.0%), 352.2 (34.4%), 351.2 (21.6%), 353.2 (7.1%); Elemental analysis: C, 65.04; H, 6.89; Cl, 10.10; F, 5.41; N, 7.98; O, 4.56.

Example 208

4,6-dichloro-N-(cycloheptylmethyl)-1-ethyl-1H-indole-3-carboxamide

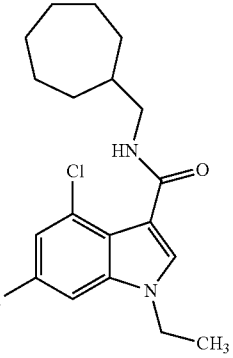

Synthesised according to the procedure disclosed in Example 1 where X is 4,6-dichloro indole, Y is ethyl iodide, and Z is cycloheptylmethyl amine. Formula: $C_{19}H_{24}Cl_2N_2O$; Molecular Weight: 367.3; Mass/charge ratio: 366.1 (100.0%), 368.1 (66.3%), 367.1 (21.6%), 369.1 (14.0%), 370.1 (11.8%), 371.1 (2.3%); Elemental analysis: C, 62.13; H, 6.59; Cl, 19.30; N, 7.63; O, 4.36.

Example 209

4-bromo-6-chloro-N-(cycloheptylmethyl)-1-ethyl-1H-indole-3-carboxamide

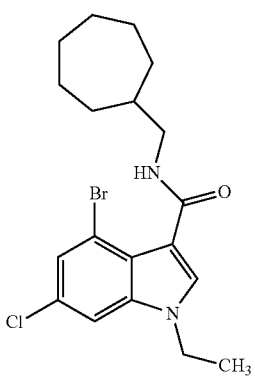

Synthesised according to the procedure disclosed in Example 1 where X is 4-bromo-6-chloro indole, Y is ethyl iodide, and Z is cycloheptylmethyl amine. Formula: $C_{19}H_{24}BrClN_2O$; Molecular Weight: 411.8; Mass/charge ratio: 412.1 (100.0%), 410.1 (76.0%), 414.1 (26.0%), 413.1 (21.3%), 411.1 (16.4%), 415.1 (5.3%); Elemental analysis: C, 55.42; H, 5.87; Br, 19.41; Cl, 8.61; N, 6.80; O, 3.89.

Example 210

6-chloro-N-(cycloheptylmethyl)-1-ethyl-4-methyl-1H-indole-3-carboxamide

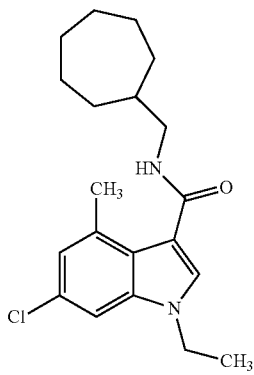 [SMILES: CCn1cc(C(=O)NCC2CCCCCC2)c2c(C)cc(Cl)cc21]

Synthesised according to the procedure disclosed in Example 1 where X is 4-methyl-6-chloro indole, Y is ethyl iodide, and Z is cycloheptylmethyl amine. Formula: $C_{20}H_{27}ClN_2O$; Molecular Weight: 346.9; Mass/charge ratio: 346.2 (100.0%), 348.2 (34.6%), 347.2 (22.7%), 349.2 (7.5%); Elemental analysis: C, 69.25; H, 7.85; Cl, 10.22; N, 8.08; O, 4.61.

Example 211

6-chloro-N-(cycloheptylmethyl)-4-fluoro-1-(2-hydroxyethyl)-1H-indole-3-carboxamide

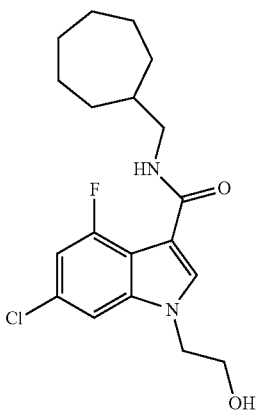 [SMILES: O=C(NCC1CCCCCC1)c1cn(CCO)c2cc(Cl)cc(F)c12]

Synthesised according to the procedure disclosed in Example 1 where X is 4-fluoro-6-chloro indole, Y is O-t-butyldimethylsilyl-2-chloroethanol, and Z is cycloheptylmethyl amine. Formula: $C_{19}H_{24}ClFN_2O_2$; Molecular Weight: 366.9; Mass/charge ratio: 366.2 (100.0%), 368.1 (32.0%), 367.2 (20.9%), 369.2 (6.9%), 368.2 (2.6%); Elemental analysis: C, 62.20; H, 6.59; Cl, 9.66; F, 5.18; N, 7.64; O, 8.72.

Example 212

4,6-dichloro-N-(cycloheptylmethyl)-1-(2-hydroxyethyl)-1H-indole-3-carboxamide

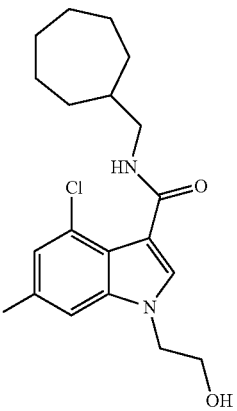

Synthesised according to the procedure disclosed in Example 1 where X is 4,6-dichloro indole, Y is O-t-butyldimethylsilyl-2-chloroethanol, and Z is cycloheptylmethyl amine. Formula: $C_{19}H_{24}Cl_2N_2O_2$; Molecular Weight: 383.3; Mass/charge ratio: 382.1 (100.0%), 384.1 (66.6%), 383.1 (21.6%), 385.1 (14.1%), 386.1 (11.9%), 387.1 (2.4%); Elemental analysis: C, 59.53; H, 6.31; Cl, 18.50; N, 7.31; O, 8.35.

Example 213

4-bromo-6-chloro-N-(cycloheptylmethyl)-1-(2-hydroxyethyl)-1H-indole-3-carboxamide

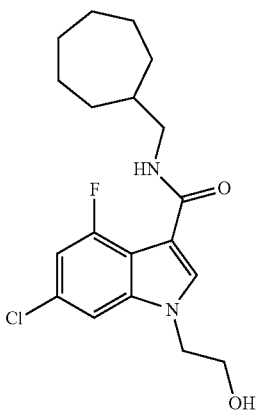 [SMILES: O=C(NCC1CCCCCC1)c1cn(CCO)c2cc(Cl)cc(F)c12]

Synthesised according to the procedure disclosed in Example 1 where X is 4-bromo-6-chloro indole, Y is O-t-butyldimethylsilyl-2-chloroethanol, and Z is cycloheptylmethyl amine. Formula: $C_{19}H_{24}BrClN_2O_2$; Molecular Weight: 427.8; Mass/charge ratio: 428.1 (100.0%), 426.1 (75.8%), 430.1 (26.2%), 429.1 (21.4%), 427.1 (16.4%), 431.1 (5.3%); Elemental analysis: C, 53.35; H, 5.66; Br, 18.68; Cl, 8.29; N, 6.55; O, 7.48.

Example 214

6-chloro-N-(cycloheptylmethyl)-1-(2-hydroxyethyl)-4-methyl-1H-indole-3-carboxamide

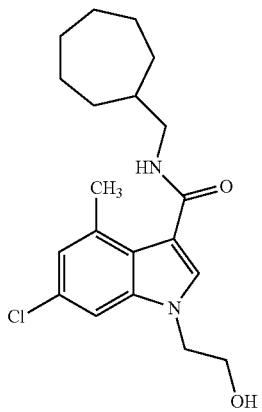 [SMILES: Cc1cc(Cl)cc2c1c(C(=O)NCC1CCCCCC1)cn2CCO]

Synthesised according to the procedure disclosed in Example 1 where X is 4-methyl-6-chloro indole, Y is O-t-butyldimethylsilyl-2-chloroethanol, and Z is cycloheptylmethyl amine. Formula: $C_{20}H_{27}ClN_2O_2$; Molecular Weight: 362.9; Mass/charge ratio: 362.2 (100.0%), 364.2 (34.8%), 363.2 (22.8%), 365.2 (7.5%); Elemental analysis: C, 66.19; H, 7.50; Cl, 9.77; N, 7.72; O, 8.82.

Example 215

6-bromo-4-chloro-N-(cycloheptylmethyl)-1-methyl-1H-indole-3-carboxamide

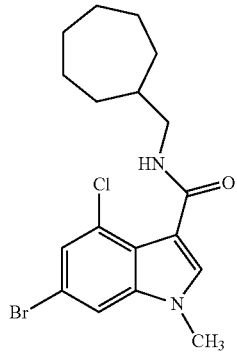

Synthesised according to the procedure disclosed in Example 1 where X is 4-chloro-6-bromo indole, Y is methyl iodide, and Z is cycloheptylmethyl amine. Formula: $C_{18}H_{22}BrClN_2O$; Molecular Weight: 397.7; Mass/charge ratio: 398.1 (100.0%), 396.1 (76.1%), 400.1 (25.8%), 399.1 (20.3%), 397.1 (15.6%), 401.1 (5.0%); Elemental analysis: C, 54.36; H, 5.58; Br, 20.09; Cl, 8.91; N, 7.04; O, 4.02.

Example 216

6-bromo-N-(cycloheptylmethyl)-4-fluoro-1-methyl-1H-indole-3-carboxamide

Synthesised according to the procedure disclosed in Example 1 where X is 4-fluoro-6-bromo indole, Y is methyl iodide, and Z is cycloheptylmethyl amine. Formula: $C_{18}H_{22}BrFN_2O$; Molecular Weight: 381.3; Mass/charge ratio: 380.1 (100.0%), 382.1 (99.5%), 381.1 (20.5%), 383.1 (20.1%), 384.1 (2.1%); Elemental analysis: C, 56.70; H, 5.82; Br, 20.96; F, 4.98; N, 7.35; O, 4.20.

Example 217

4,6-dibromo-N-(cycloheptylmethyl)-1-methyl-1H-indole-3-carboxamide

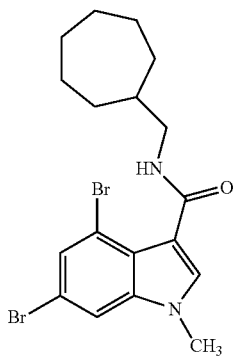 [SMILES: Cn1cc(C(=O)NCC2CCCCCC2)c2c(Br)cc(Br)cc21]

Synthesised according to the procedure disclosed in Example 1 where X is 4,6-dibromo indole, Y is methyl iodide, and Z is cycloheptylmethyl amine. Formula: $C_{18}H_{22}Br_2N_2O$; Molecular Weight: 442.2; Mass/charge ratio: 442.0 (100.0%), 440.0 (50.8%), 444.0 (50.3%), 443.0 (20.4%), 441.0 (10.4%), 445.0 (10.0%), 446.0 (1.1%); Elemental analysis: C, 48.89; H, 5.01; Br, 36.14; N, 6.34; O, 3.62.

Example 218

6-bromo-N-(cycloheptylmethyl)-1,4-dimethyl-1H-indole-3-carboxamide

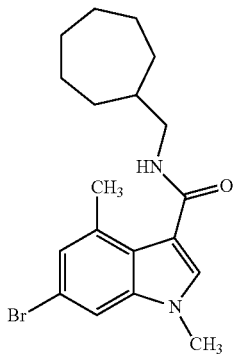 [SMILES: Cc1cc(Br)cc2c1c(C(=O)NCC1CCCCCC1)cn2C]

Synthesised according to the procedure disclosed in Example 1 where X is 4-methyl-6-bromo indole, Y is methyl iodide, and Z is cycloheptylmethyl amine. Formula: $C_{19}H_{25}BrN_2O$; Molecular Weight: 377.3; Mass/charge ratio: 376.1 (100.0%), 378.1 (99.7%), 377.1 (21.6%), 379.1 (21.2%), 380.1 (2.4%); Elemental analysis: C, 60.48; H, 6.68; Br, 21.18; N, 7.42; O, 4.24.

Example 219

6-bromo-N-(cycloheptylmethyl)-1-ethyl-4-fluoro-1H-indole-3-carboxamide

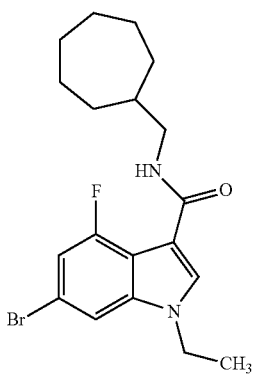 [SMILES: CCn1cc(C(=O)NCC2CCCCCC2)c2c(F)cc(Br)cc21]

Synthesised according to the procedure disclosed in Example 1 where X is 4-fluoro-6-bromo indole, Y is ethyl iodide, and Z is cycloheptylmethyl amine. Formula: $C_{19}H_{24}BrFN_2O$; Molecular Weight: 395.3; Mass/charge ratio: 394.1 (100.0%), 396.1 (99.7%), 395.1 (21.6%), 397.1 (21.2%), 398.1 (2.4%); Elemental analysis: C, 57.73; H, 6.12; Br, 20.21; F, 4.81; N, 7.09; O, 4.05.

Example 220

6-bromo-4-chloro-N-(cycloheptylmethyl)-1-ethyl-1H-indole-3-carboxamide

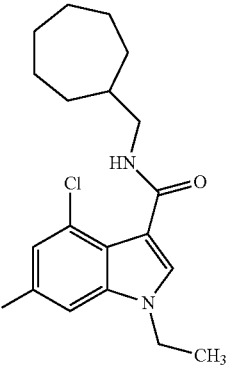

Synthesised according to the procedure disclosed in Example 1 where X is 4-chloro-6-bromo indole, Y is ethyl iodide, and Z is cycloheptylmethyl amine. Formula: $C_{19}H_{24}BrClN_2O$; Molecular Weight: 411.8; Mass/charge ratio: 412.1 (100.0%), 410.1 (76.0%), 414.1 (26.0%), 413.1 (21.3%), 411.1 (16.4%), 415.1 (5.3%); Elemental analysis: C, 55.42; H, 5.87; Br, 19.41; Cl, 8.61; N, 6.80; O, 3.89.

Example 221

4,6-dibromo-N-(cycloheptylmethyl)-1-ethyl-1H-indole-3-carboxamide

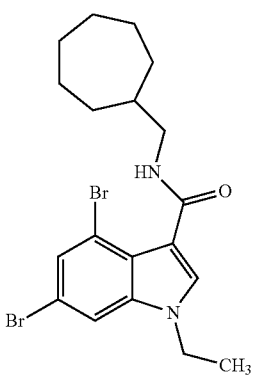

Synthesised according to the procedure disclosed in Example 1 where X is 4,6-dibromo indole, Y is ethyl iodide, and Z is cycloheptylmethyl amine. Formula: $C_{19}H_{24}Br_2N_2O$; Molecular Weight: 456.2; Mass/charge ratio: 456.0 (100.0%), 454.0 (50.8%), 458.0 (50.4%), 457.0 (21.4%), 455.0 (11.0%), 459.0 (10.6%), 460.0 (1.2%); Elemental analysis: C, 50.02; H, 5.30; Br, 35.03; N, 6.14; O, 3.51.

Example 222

6-bromo-N-(cycloheptylmethyl)-1-ethyl-4-methyl-1H-indole-3-carboxamide

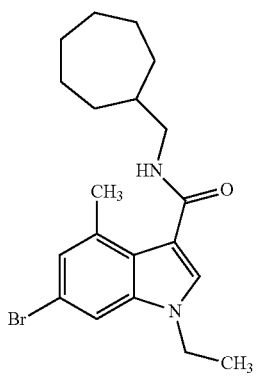

Synthesised according to the procedure disclosed in Example 1 where X is 4-methyl-6-bromo indole, Y is ethyl iodide, and Z is cycloheptylmethyl amine. Formula: $C_{20}H_{27}BrN_2O$; Molecular Weight: 391.3; Mass/charge ratio: 390.1 (100.0%), 392.1 (99.9%), 391.1 (22.7%), 393.1 (22.3%), 394.1 (2.6%); Elemental analysis: C, 61.38; H, 6.95; Br, 20.42; N, 7.16; O, 4.09.

Example 223

6-bromo-N-(cycloheptylmethyl)-4-fluoro-1-(2-hydroxyethyl)-1H-indole-3-carboxamide

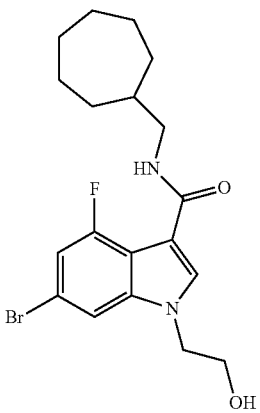

Synthesised according to the procedure disclosed in Example 1 where X is 4-fluoro-6-bromo indole, Y is O-t-butyldimethylsilyl-2-chloroethanol, and Z is cycloheptylmethyl amine. Formula: $C_{19}H_{24}BrFN_2O_2$; Molecular Weight: 411.3; Mass/charge ratio: 410.1 (100.0%), 412.1 (99.9%), 411.1 (21.6%), 413.1 (21.3%), 414.1 (2.6%); Elemental analysis: C, 55.48; H, 5.88; Br, 19.43; F, 4.62; N, 6.81; O, 7.78.

Example 224

6-bromo-4-chloro-N-(cycloheptylmethyl)-1-(2-hydroxyethyl)-1H-indole-3-carboxamide)

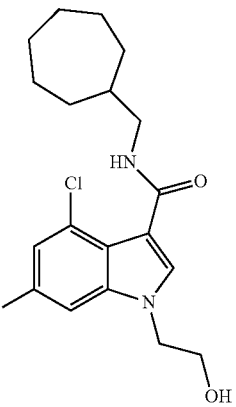

Synthesised according to the procedure disclosed in Example 1 where X is 4-chloro-6-bromo indole, Y is O-t-butyldimethylsilyl-2-chloroethanol, and Z is cycloheptylmethyl amine. Formula: $C_{19}H_{24}BrClN_2O_2$; Molecular Weight: 427.8; Mass/charge ratio: 428.1 (100.0%), 426.1 (75.8%), 430.1 (26.2%), 429.1 (21.4%), 427.1 (16.4%), 431.1 (5.3%); Elemental analysis: C, 53.35; H, 5.66; Br, 18.68; Cl, 8.29; N, 6.55; O, 7.48.

Example 225

4,6-dibromo-N-(cycloheptylmethyl)-1-(2-hydroxyethyl)-1H-indole-3-carboxamide

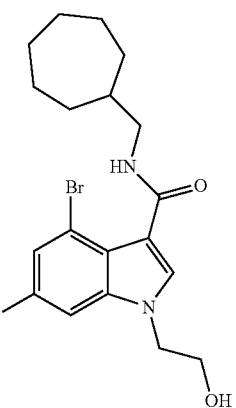

Synthesised according to the procedure disclosed in Example 1 where X is 4,6-dibromo indole, Y is O-t-butyldimethylsilyl-2-chloroethanol, and Z is cycloheptylmethyl amine. Formula: $C_{19}H_{24}Br_2N_2O_2$; Molecular Weight: 472.2; Mass/charge ratio: 472.0 (100.0%), 470.0 (50.7%), 474.0 (50.6%), 473.0 (21.5%), 471.0 (11.0%), 475.0 (10.6%), 476.0 (1.3%); Elemental analysis: C, 48.33; H, 5.12; Br, 33.84; N, 5.93; O, 6.78.

Example 226

6-bromo-N-(cycloheptylmethyl)-1-(2-hydroxyethyl)-4-methyl-1H-indole-3-carboxamide

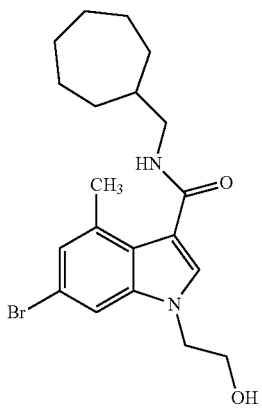 [SMILES: Cc1cc(Br)cc2c1c(C(=O)NCC1CCCCCC1)cn2CCO]

Synthesised according to the procedure disclosed in Example 1 where X is 4-methyl-6-bromo indole, Y is O-t-butyldimethylsilyl-2-chloroethanol, and Z is cycloheptylmethyl amine. Formula: $C_{20}H_{27}BrN_2O_2$; Molecular Weight: 407.3; Mass/charge ratio: 408.1 (100.0%), 406.1 (99.8%), 407.1 (22.7%), 409.1 (22.4%), 410.1 (2.8%); Elemental analysis: C, 58.97; H, 6.68; Br, 19.62; N, 6.88; O, 7.86.

Example 227

N-(bicyclo[2.2.2]octan-1-ylmethyl)-4-chloro-6-fluoro-1-methyl-1H-indole-3-carboxamide

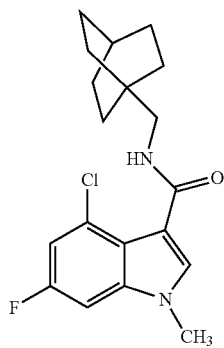

Synthesised according to the procedure disclosed in Example 1 where X is 4-chloro-6-fluoro indole, Y is methyl iodide, and Z is bicyclo[2.2.2]octan-1-ylmethyl amine. Formula: $C_{19}H_{22}ClFN_2O$; Molecular Weight: 348.8; Mass/charge ratio: 348.1 (100.0%), 350.1 (34.3%), 349.1 (21.6%), 351.1 (7.0%); Elemental analysis: C, 65.42; H, 6.36; Cl, 10.16; F, 5.45; N, 8.03; O, 4.59.

Example 228

N-(bicyclo[2.2.2]octan-1-ylmethyl)-4-bromo-6-fluoro-1-methyl-1H-indole-3-carboxamide

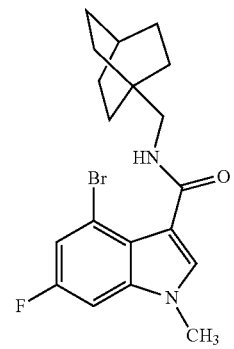

Synthesised according to the procedure disclosed in Example 1 where X is 4-bromo-6-fluoro indole, Y is methyl iodide, and Z is bicyclo[2.2.2]octan-1-ylmethyl amine. Formula: $C_{19}H_{22}BrFN_2O$; Molecular Weight: 393.3; Mass/charge ratio: 392.1 (100.0%), 394.1 (99.7%), 393.1 (21.6%), 395.1 (21.2%), 396.1 (2.4%); Elemental analysis: C, 58.02; H, 5.64; Br, 20.32; F, 4.83; N, 7.12; O, 4.07.

Example 229

N-(bicyclo[2.2.2]octan-1-ylmethyl)-6-fluoro-1,4-dimethyl-1H-indole-3-carboxamide

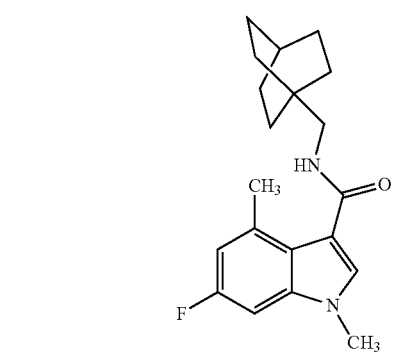

Synthesised according to the procedure disclosed in Example 1 where X is 4-methyl-6-fluoro indole, Y is methyl iodide, and Z is bicyclo[2.2.2]octan-1-ylmethyl amine. Formula: $C_{20}H_{25}FN_2O$; Molecular Weight: 328.4; Mass/charge ratio: 328.2 (100.0%), 329.2 (22.7%), 330.2 (2.7%); Elemental analysis: C, 73.14; H, 7.67; F, 5.78; N, 8.53; O, 4.87.

Example 230

N-(bicyclo[2.2.2]octan-1-ylmethyl)-4-chloro-1-ethyl-6-fluoro-1H-indole-3-carboxamide

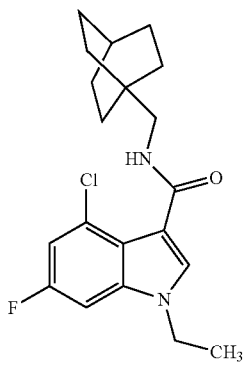

Synthesised according to the procedure disclosed in Example 1 where X is 4-chloro-6-fluoro indole, Y is ethyl iodide, and Z is bicyclo[2.2.2]octan-1-ylmethyl amine. Formula: $C_{20}H_{24}ClFN_2O$; Molecular Weight: 362.9; Mass/charge ratio: 362.2 (100.0%), 364.2 (34.6%), 363.2 (22.7%), 365.2 (7.5%); Elemental analysis: C, 66.20; H, 6.67; Cl, 9.77; F, 5.24; N, 7.72; O, 4.41.

Example 231

N-(bicyclo[2.2.2]octan-1-ylmethyl)-4-bromo-1-ethyl-6-fluoro-1H-indole-3-carboxamide

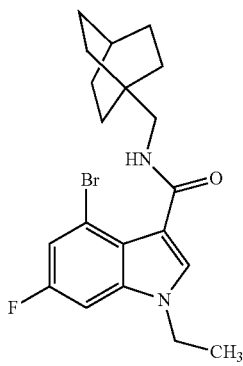 [SMILES: CCn1cc(C(=O)NCC23CCC(CC2)CC3)c2c(Br)cc(F)cc21]

Synthesised according to the procedure disclosed in Example 1 where X is 4-bromo-6-fluoro indole, Y is ethyl iodide, and Z is bicyclo[2.2.2]octan-1-ylmethyl amine. Formula: $C_{20}H_{24}BrFN_2O$; Molecular Weight: 407.3; Mass/charge ratio: 406.1 (100.0%), 408.1 (99.9%), 407.1 (22.7%), 409.1 (22.3%), 410.1 (2.6%); Elemental analysis: C, 58.97; H, 5.94; Br, 19.62; F, 4.66; N, 6.88; O, 3.93.

Example 232

N-(bicyclo[2.2.2]octan-1-ylmethyl)-1-ethyl-6-fluoro-4-methyl-1H-indole-3-carboxamide

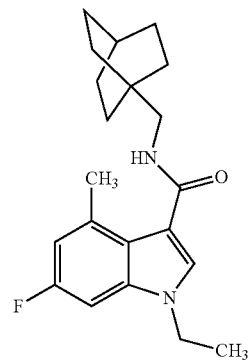

Synthesised according to the procedure disclosed in Example 1 where X is 4-methyl-6-fluoro indole, Y is ethyl iodide, and Z is bicyclo[2.2.2]octan-1-ylmethyl amine. Formula: $C_{21}H_{27}FN_2O$; Molecular Weight: 342.5; Mass/charge ratio: 342.2 (100.0%), 343.2 (23.8%), 344.2 (2.9%); Elemental analysis: C, 73.65; H, 7.95; F, 5.55; N, 8.18; O, 4.67.

Example 233

N-(bicyclo[2.2.2]octan-1-ylmethyl)-4-chloro-6-fluoro-1-(2-hydroxyethyl)-1H-indole-3-carboxamide

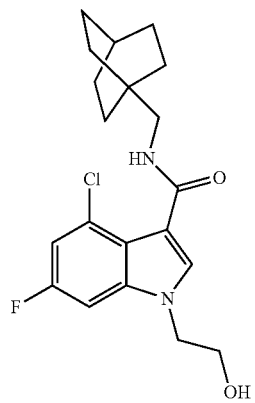 [SMILES: O=C(NCC12CCC(CC1)CC2)c1cn(CCO)c2cc(F)cc(Cl)c12]

Synthesised according to the procedure disclosed in Example 1 where X is 4-chloro-6-fluoro indole, Y is O-t-butyldimethylsilyl-2-chloroethanol, and Z is bicyclo[2.2.2]octan-1-ylmethyl amine. Formula: $C_{20}H_{24}ClFN_2O_2$; Molecular Weight: 378.9; Mass/charge ratio: 378.2 (100.0%), 380.1 (32.0%), 379.2 (22.0%), 381.2 (7.3%), 380.2 (2.9%); Elemental analysis: C, 63.40; H, 6.38; Cl, 9.36; F, 5.01; N, 7.39; O, 8.45.

Example 234

N-(bicyclo[2.2.2]octan-1-ylmethyl)-4-bromo-6-fluoro-1-(2-hydroxyethyl)-1H-indole-3-carboxamide

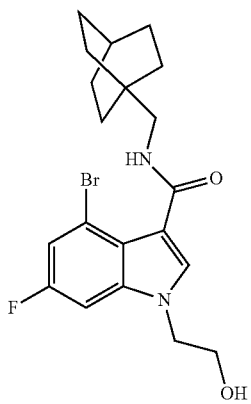 [SMILES: O=C(NCC12CCC(CC1)CC2)c1cn(CCO)c2cc(F)cc(Br)c12]

Synthesised according to the procedure disclosed in Example 1 where X is 4-bromo-6-fluoro indole, Y is O-t-butyldimethylsilyl-2-chloroethanol, and Z is bicyclo[2.2.2]octan-1-ylmethyl amine. Formula: $C_{20}H_{24}BrFN_2O_2$; Molecular Weight: 423.3; Mass/charge ratio: 424.1 (100.0%), 422.1 (99.8%), 423.1 (22.7%), 425.1 (22.3%), 426.1 (2.8%); Elemental analysis: C, 56.75; H, 5.71; Br, 18.88; F, 4.49; N, 6.62; O, 7.56.

Example 235

N-(bicyclo[2.2.2]octan-1-ylmethyl)-6-fluoro-1-(2-hydroxyethyl)-4-methyl-1H-indole-3-carboxamide

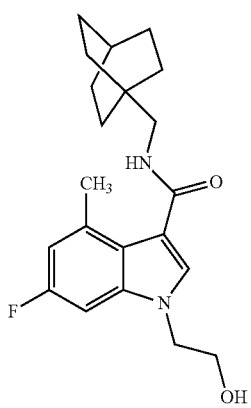 [SMILES: Cc1cc(F)cc2c1c(C(=O)NCC13CCC(CC1)CC3)cn2CCO]

Synthesised according to the procedure disclosed in Example 1 where X is 4-methyl-6-fluoro indole, Y is O-t-butyldimethylsilyl-2-chloroethanol, and Z is bicyclo[2.2.2]octan-1-ylmethyl amine. Formula: $C_{21}H_{27}FN_2O_2$; Molecular Weight: 358.4; Mass/charge ratio: 358.2 (100.0%), 359.2 (23.8%), 360.2 (3.1%); Elemental analysis: C, 70.37; H, 7.59; F, 5.30; N, 7.82; O, 8.93.

Example 236

N-(bicyclo[2.2.2]octan-1-ylmethyl)-4,6-dichloro-1-methyl-1H-indole-3-carboxamide

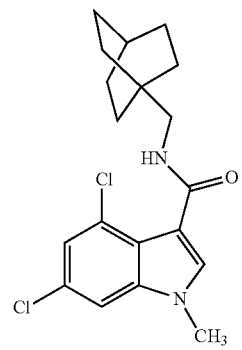

Synthesised according to the procedure disclosed in Example 1 where X is 4,6-dichloro indole, Y is methyl iodide, and Z is bicyclo[2.2.2]octan-1-ylmethyl amine. Formula: $C_{19}H_{22}Cl_2N_2O$; Molecular Weight: 365.3; Mass/charge ratio: 364.1 (100.0%), 366.1 (66.3%), 365.1 (21.6%), 367.1 (14.0%), 368.1 (11.8%), 369.1 (2.3%); Elemental analysis: C, 62.47; H, 6.07; Cl, 19.41; N, 7.67; O, 4.38.

Example 237

N-(bicyclo[2.2.2]octan-1-ylmethyl)-6-chloro-4-fluoro-1-methyl-1H-indole-3-carboxamide

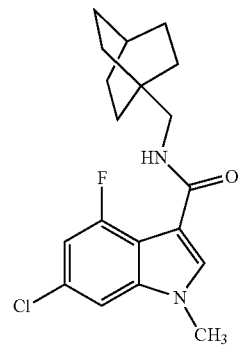

Synthesised according to the procedure disclosed in Example 1 where X is 4-fluoro-6-chloro indole, Y is methyl iodide, and Z is bicyclo[2.2.2]octan-1-ylmethyl amine. Formula: $C_{19}H_{22}ClFN_2O$; Molecular Weight: 348.8; Mass/charge ratio: 348.1 (100.0%), 350.1 (34.3%), 349.1 (21.6%), 351.1 (7.0%); Elemental analysis: C, 65.42; H, 6.36; Cl, 10.16; F, 5.45; N, 8.03; O, 4.59.

Example 238

N-(bicyclo[2.2.2]octan-1-ylmethyl)-4-bromo-6-chloro-1-methyl-1H-indole-3-carboxamide

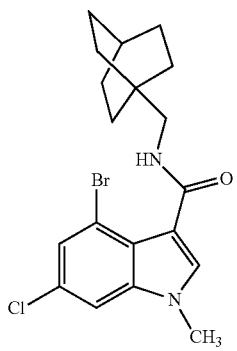

Synthesised according to the procedure disclosed in Example 1 where X is 4-bromo-6-chloro indole, Y is methyl iodide, and Z is bicyclo[2.2.2]octan-1-ylmethyl amine. Formula: $C_{19}H_{22}BrClN_2O$; Molecular Weight: 409.7; Mass/charge ratio: 410.1 (100.0%), 408.1 (76.0%), 412.1 (26.0%), 411.1 (21.3%), 409.1 (16.4%), 413.1 (5.3%); Elemental analysis: C, 55.69; H, 5.41; Br, 19.50; Cl, 8.65; N, 6.84; O, 3.90.

Example 239

N-(bicyclo[2.2.2]octan-1-ylmethyl)-6-chloro-1,4-dimethyl-1H-indole-3-carboxamide

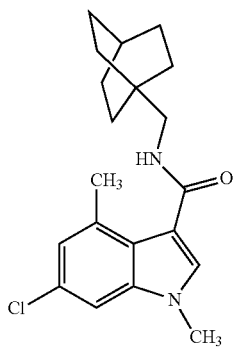

Synthesised according to the procedure disclosed in Example 1 where X is 4-methyl-6-chloro indole, Y is methyl iodide, and Z is bicyclo[2.2.2]octan-1-ylmethyl amine. Formula: $C_{20}H_{25}ClN_2O$; Molecular Weight: 344.9; Mass/charge ratio: 344.2 (100.0%), 346.2 (34.6%), 345.2 (22.7%), 347.2 (7.5%); Elemental analysis: C, 69.65; H, 7.31; Cl, 10.28; N, 8.12; O, 4.64.

Example 240

N-(bicyclo[2.2.2]octan-1-ylmethyl)-6-chloro-1-ethyl-4-fluoro-1H-indole-3-carboxamide

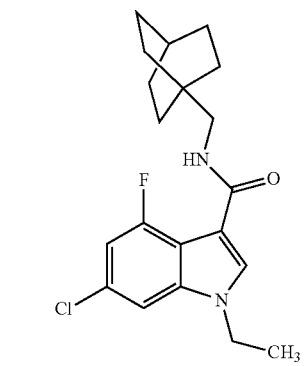

Synthesised according to the procedure disclosed in Example 1 where X is 4-fluoro-6-chloro indole, Y is ethyl iodide, and Z is bicyclo[2.2.2]octan-1-ylmethyl amine. Formula: $C_{20}H_{24}ClFN_2O$; Molecular Weight: 362.9; Mass/charge ratio: 362.2 (100.0%), 364.2 (34.6%), 363.2 (22.7%), 365.2 (7.5%); Elemental analysis: C, 66.20; H, 6.67; Cl, 9.77; F, 5.24; N, 7.72; O, 4.41.

Example 241

N-(bicyclo[2.2.2]octan-1-ylmethyl)-4,6-dichloro-1-ethyl-1H-indole-3-carboxamide

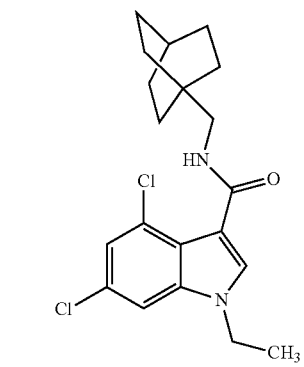

Synthesised according to the procedure disclosed in Example 1 where X is 4,6-dichloro indole, Y is ethyl iodide, and Z is bicyclo[2.2.2]octan-1-ylmethyl amine. Formula: $C_{20}H_{24}Cl_2N_2O$; Molecular Weight: 379.3; Mass/charge ratio: 378.1 (100.0%), 380.1 (66.6%), 379.1 (22.7%), 381.1 (14.7%), 382.1 (11.9%), 383.1 (2.5%); Elemental analysis: C, 63.33; H, 6.38; Cl, 18.69; N, 7.39; O, 4.22.

Example 242

N-(bicyclo[2.2.2]octan-1-ylmethyl)-4-bromo-6-chloro-1-ethyl-1H-indole-3-carboxamide

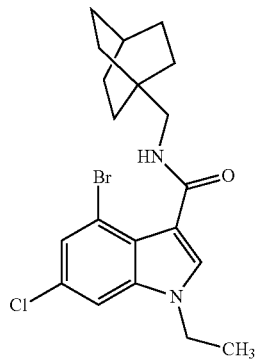

Synthesised according to the procedure disclosed in Example 1 where X is 4-bromo-6-chloro indole, Y is ethyl iodide, and Z is bicyclo[2.2.2]octan-1-ylmethyl amine. Formula: $C_{20}H_{24}BrClN_2O$; Molecular Weight: 423.8; Mass/charge ratio: 424.1 (100.0%), 422.1 (75.8%), 426.1 (26.2%), 425.1 (22.4%), 423.1 (17.2%), 427.1 (5.6%); Elemental analysis: C, 56.68; H, 5.71; Br, 18.86; Cl, 8.37; N, 6.61; O, 3.78.

Example 243

N-(bicyclo[2.2.2]octan-1-ylmethyl)-6-chloro-1-ethyl-4-methyl-1H-indole-3-carboxamide

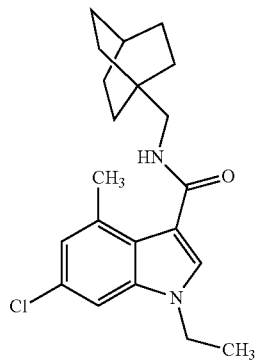

Synthesised according to the procedure disclosed in Example 1 where X is 4-methyl-6-chloro indole, Y is ethyl iodide, and Z is bicyclo[2.2.2]octan-1-ylmethyl amine. Formula: $C_{21}H_{27}ClN_2O$, Molecular Weight: 358.9; Mass/charge ratio: 358.2 (100.0%), 360.2 (34.9%), 359.2 (23.8%), 361.2 (7.9%); Elemental analysis: C, 70.28; H, 7.58; Cl, 9.88; N, 7.81; O, 4.46.

Example 244

N-(bicyclo[2.2.2]octan-1-ylmethyl)-6-chloro-4-fluoro-1-(2-hydroxyethyl)-1H-indole-3-carboxamide

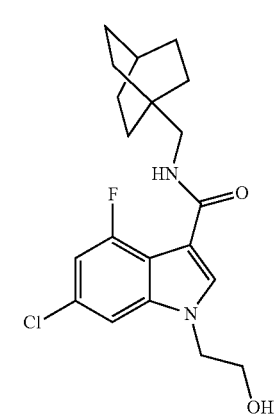

Synthesised according to the procedure disclosed in Example 1 where X is 4-fluoro-6-chloro indole, Y is O-t-butyldimethylsilyl-2-chloroethanol, and Z is bicyclo[2.2.2]octan-1-ylmethyl amine. Formula: $C_{20}H_{24}ClFN_2O_2$; Molecular Weight: 378.9; Mass/charge ratio: 378.2 (100.0%), 380.1 (32.0%), 379.2 (22.0%), 381.2 (7.3%), 380.2 (2.9%); Elemental analysis: C, 63.40; H, 6.38; Cl, 9.36; F, 5.01; N, 7.39; O, 8.45.

Example 245

N-(bicyclo[2.2.2]octan-1-ylmethyl)-4,6-dichloro-1-(2-hydroxyethyl)-1H-indole-3-carboxamide

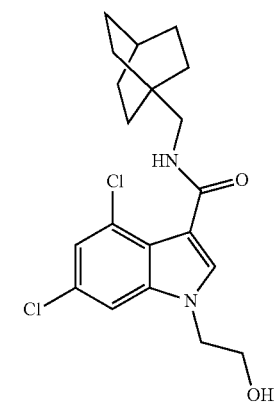

Synthesised according to the procedure disclosed in Example 1 where X is 4,6-dichloro indole, Y is O-t-butyldimethylsilyl-2-chloroethanol, and Z is bicyclo[2.2.2]octan-1-ylmethyl amine. Formula: $C_{20}H_{24}Cl_2N_2O_2$; Molecular Weight: 395.3; Mass/charge ratio: 394.1 (100.0%), 396.1 (66.8%), 395.1 (22.7%), 397.1 (14.8%), 398.1 (12.1%), 399.1 (2.5%); Elemental analysis: C, 60.76; H, 6.12; Cl, 17.94; N, 7.09; O, 8.09.

Example 246

N-(bicyclo[2.2.2]octan-1-ylmethyl)-4-bromo-6-chloro-1-(2-hydroxyethyl)-1H-indole-3-carboxamide

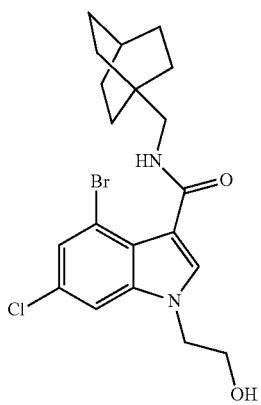

Synthesised according to the procedure disclosed in Example 1 where X is 4-bromo-6-chloro indole, Y is O-t-butyldimethylsilyl-2-chloroethanol, and Z is bicyclo[2.2.2]octan-1-ylmethyl amine. Formula: $C_{20}H_{24}BrClN_2O_2$; Molecular Weight: 439.8; Mass/charge ratio: 440.1 (100.0%), 438.1 (75.7%), 442.1 (26.4%), 441.1 (22.4%), 439.1 (17.2%), 443.1 (5.6%); Elemental analysis: C, 54.62; H, 5.50; Br, 18.17; Cl, 8.06; N, 6.37; O, 7.28.

Example 247

N-(bicyclo[2.2.2]octan-1-ylmethyl)-6-chloro-1-(2-hydroxyethyl)-4-methyl-1H-indole-3-carboxamide

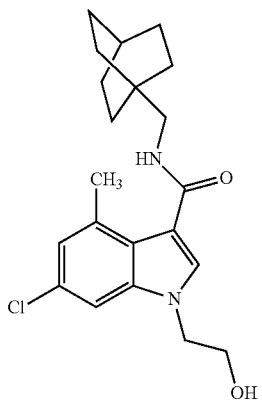

Synthesised according to the procedure disclosed in Example 1 where X is 4-methyl-6-chloro indole, Y is O-t-butyldimethylsilyl-2-chloroethanol, and Z is bicyclo[2.2.2]octan-1-ylmethyl amine. Formula: $C_{21}H_{27}ClN_2O_2$; Molecular Weight: 374.9; Mass/charge ratio: 374.2 (100.0%), 376.2 (35.1%), 375.2 (23.8%), 377.2 (7.9%), 378.2 (1.0%); Elemental analysis: C, 67.28; H, 7.26; Cl, 9.46; N, 7.47; O, 8.54.

Example 248

N-(bicyclo[2.2.2]octan-1-ylmethyl)-6-bromo-4-chloro-1-methyl-1H-indole-3-carboxamide

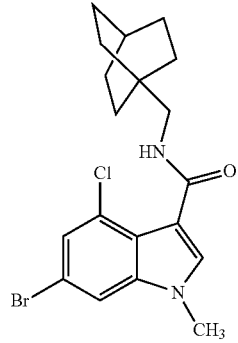

Synthesised according to the procedure disclosed in Example 1 where X is 4-chloro-6-bromo indole, Y is methyl iodide, and Z is bicyclo[2.2.2]octan-1-ylmethyl amine. Formula: $C_{19}H_{22}BrClN_2O$; Molecular Weight: 409.7; Mass/charge ratio: 410.1 (100.0%), 408.1 (76.0%), 412.1 (26.0%), 411.1 (21.3%), 409.1 (16.4%), 413.1 (5.3%); Elemental analysis: C, 55.69; H, 5.41; Br, 19.50; Cl, 8.65; N, 6.84; O, 3.90.

Example 249

N-(bicyclo[2.2.2]octan-1-ylmethyl)-6-bromo-4-fluoro-1-methyl-1H-indole-3-carboxamide

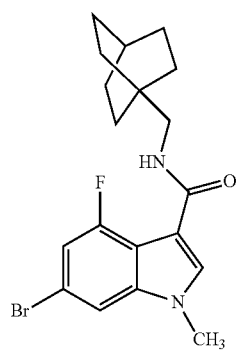 [SMILES: Cn1cc(C(=O)NCC23CCC(CC2)CC3)c2c(F)cc(Cl)cc21]

Synthesised according to the procedure disclosed in Example 1 where X is 4-fluoro-6-bromo indole, Y is methyl iodide, and Z is bicyclo[2.2.2]octan-1-ylmethyl amine. Formula: $C_{19}H_{22}BrFN_2O$; Molecular Weight: 393.3; Mass/charge ratio: 392.1 (100.0%), 394.1 (99.7%), 393.1 (21.6%), 395.1 (21.2%), 396.1 (2.4%); Elemental analysis: C, 58.02; H, 5.64; Br, 20.32; F, 4.83; N, 7.12; O, 4.07.

Example 250

N-(bicyclo[2.2.2]octan-1-ylmethyl)-4,6-dibromo-1-methyl-1H-indole-3-carboxamide

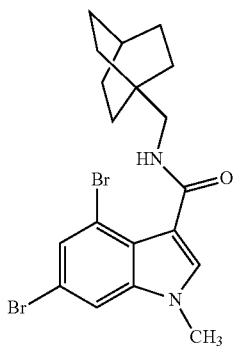 [SMILES: Cn1cc(C(=O)NCC23CCC(CC2)CC3)c2c(Br)cc(Cl)cc21]

Synthesised according to the procedure disclosed in Example 1 where X is 4,6-dibromo indole, Y is methyl iodide, and Z is bicyclo[2.2.2]octan-1-ylmethyl amine. Formula: $C_{19}H_{22}Br_2N_2O$; Molecular Weight: 454.2; Mass/charge ratio: 454.0 (100.0%), 452.0 (50.8%), 456.0 (50.4%), 455.0 (21.4%), 453.0 (11.0%), 457.0 (10.6%), 458.0 (1.2%); Elemental analysis: C, 50.24; H, 4.88; Br, 35.18; N, 6.17; O, 3.52.

Example 251

N-(bicyclo[2.2.2]octan-1-ylmethyl)-6-bromo-1,4-dimethyl-1H-indole-3-carboxamide

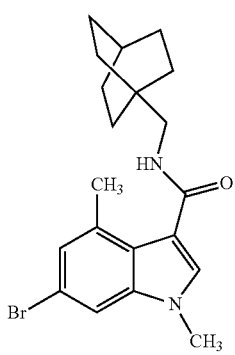 [SMILES: Cc1cc(Cl)cc2c1c(C(=O)NCC13CCC(CC1)CC3)cn2C]

Synthesised according to the procedure disclosed in Example 1 where X is 4-methyl-6-bromo indole, Y is methyl iodide, and Z is bicyclo[2.2.2]octan-1-ylmethyl amine. Formula: $C_{20}H_{25}BrN_2O$; Molecular Weight: 389.3; Mass/charge ratio: 388.1 (100.0%), 390.1 (99.9%), 389.1 (22.7%), 391.1 (22.3%), 392.1 (2.6%); Elemental analysis: C, 61.70; H, 6.47; Br, 20.52; N, 7.20; O, 4.11.

Example 252

N-(bicyclo[2.2.2]octan-1-ylmethyl)-6-bromo-1-ethyl-4-fluoro-1H-indole-3-carboxamide

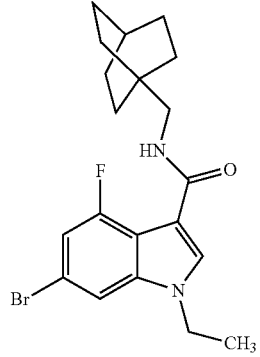 [SMILES: CCn1cc(C(=O)NCC23CCC(CC2)CC3)c2c(F)cc(Cl)cc21]

Synthesised according to the procedure disclosed in Example 1 where X is 4-fluoro-6-bromo indole, Y is ethyl iodide, and Z is bicyclo[2.2.2]octan-1-ylmethyl amine. Formula: $C_{20}H_{24}BrFN_2O$; Molecular Weight: 407.3; Mass/charge ratio: 406.1 (100.0%), 408.1 (99.9%), 407.1 (22.7%), 409.1 (22.3%), 410.1 (2.6%); Elemental analysis: C, 58.97; H, 5.94; Br, 19.62; F, 4.66; N, 6.88; O, 3.93.

Example 253

N-(bicyclo[2.2.2]octan-1-ylmethyl)-6-bromo-4-chloro-1-ethyl-1H-indole-3-carboxamide

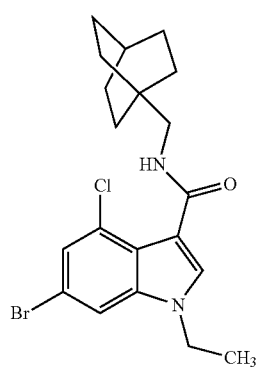 [SMILES: CCn1cc(C(=O)NCC23CCC(CC2)CC3)c2c(Cl)cc(Cl)cc21]

Synthesised according to the procedure disclosed in Example 1 where X is 4-chloro-6-bromo indole, Y is ethyl iodide, and Z is bicyclo[2.2.2]octan-1-ylmethyl amine. Formula: $C_{20}H_{24}BrClN_2O$; Molecular Weight: 423.8; Mass/charge ratio: 424.1 (100.0%), 422.1 (75.8%), 426.1 (26.2%), 425.1 (22.4%), 423.1 (17.2%), 427.1 (5.6%); Elemental analysis: C, 56.68; H, 5.71; Br, 18.86; Cl, 8.37; N, 6.61; O, 3.78.

Example 254

N-(bicyclo[2.2.2]octan-1-ylmethyl)-4,6-dibromo-1-ethyl-1H-indole-3-carboxamide

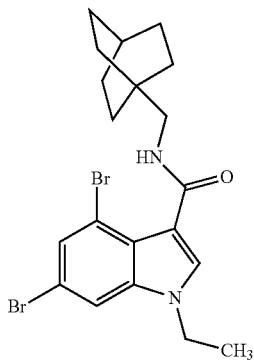 [SMILES: CCn1cc(C(=O)NCC23CCC(CC2)CC3)c2c(Br)cc(Cl)cc21]

Synthesised according to the procedure disclosed in Example 1 where X is 4,6-dibromo indole, Y is ethyl iodide, and Z is bicyclo[2.2.2]octan-1-ylmethyl amine. Formula: $C_{20}H_{24}Br_2N_2O$; Molecular Weight: 468.2; Mass/charge ratio: 468.0 (100.0%), 466.0 (50.7%), 470.0 (50.6%), 469.0 (22.5%), 467.0 (11.5%), 471.0 (11.1%), 472.0 (1.3%); Elemental analysis: C, 51.30; H, 5.17; Br, 34.13; N, 5.98; O, 3.42.

Example 255

N-(bicyclo[2.2.2]octan-1-ylmethyl)-6-bromo-1-ethyl-4-methyl-1H-indole-3-carboxamide

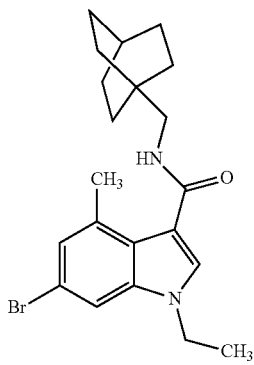 [SMILES: CCn1cc(C(=O)NCC23CCC(CC2)CC3)c2c(C)cc(Cl)cc21]

Synthesised according to the procedure disclosed in Example 1 where X is 4-methyl-6-bromo indole, Y is ethyl iodide, and Z is bicyclo[2.2.2]octan-1-ylmethyl amine. Formula: $C_{21}H_{27}BrN_2O$; Molecular Weight: 403.4; Mass/charge ratio: 404.1 (100.0%), 402.1 (99.8%), 403.1 (23.8%), 405.1 (23.4%), 406.1 (2.8%); Elemental analysis: C, 62.53; H, 6.75; Br, 19.81; N, 6.95; O, 3.97.

Example 256

N-(bicyclo[2.2.2]octan-1-ylmethyl)-6-bromo-4-fluoro-1-(2-hydroxyethyl)-1H-indole-3-carboxamide

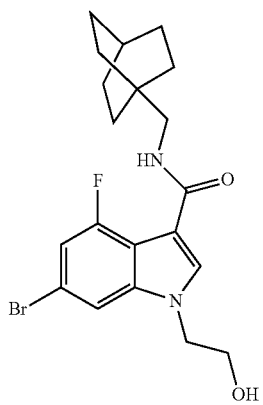 [SMILES: O=C(NCC12CCC(CC1)CC2)c1cn(CCO)c2cc(Cl)cc(F)c12]

Synthesised according to the procedure disclosed in Example 1 where X is 4-fluoro-6-bromo indole, Y is O-t-butyldimethylsilyl-2-chloroethanol, and Z is bicyclo[2.2.2]octan-1-ylmethyl amine. Formula: $C_{20}H_{24}BrFN_2O_2$; Molecular Weight: 423.3; Mass/charge ratio: 424.1 (100.0%), 422.1 (99.8%), 423.1 (22.7%), 425.1 (22.3%), 426.1 (2.8%); Elemental analysis: C, 56.75; H, 5.71; Br, 18.88; F, 4.49; N, 6.62; O, 7.56.

Example 257

N-(bicyclo[2.2.2]octan-1-ylmethyl)-6-bromo-4-chloro-1-(2-hydroxyethyl)-1H-indole-3-carboxamide

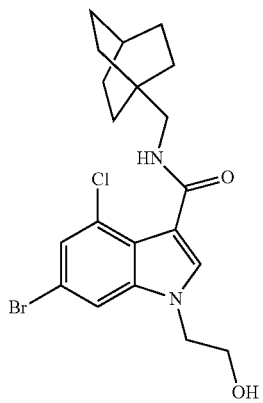

Synthesised according to the procedure disclosed in Example 1 where X is 4-chloro-6-bromo indole, Y is O-t-butyldimethylsilyl-2-chloroethanol, and Z is bicyclo[2.2.2]octan-1-ylmethyl amine. Formula: $C_{20}H_{24}BrClN_2O_2$; Molecular Weight: 439.8; Mass/charge ratio: 440.1 (100.0%), 438.1 (75.7%), 442.1 (26.4%), 441.1 (22.4%), 439.1 (17.2%), 443.1 (5.6%); Elemental analysis: C, 54.62; H, 5.50; Br, 18.17; Cl, 8.06; N, 6.37; O, 7.28.

Example 258

N-(bicyclo[2.2.2]octan-1-ylmethyl)-4,6-dibromo-1-(2-hydroxyethyl)-1H-indole-3-carboxamide)

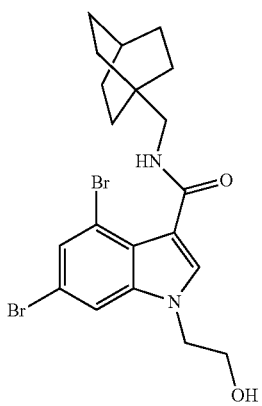 [SMILES: O=C(NCC12CCC(CC1)CC2)c1cn(CCO)c2cc(Cl)cc(Br)c12]

Synthesised according to the procedure disclosed in Example 1 where X is 4,6-dibromo indole, Y is O-t-butyldimethylsilyl-2-chloroethanol, and Z is bicyclo[2.2.2]octan-1-ylmethyl amine. Formula: $C_{20}H_{24}Br_2N_2O_2$; Molecular Weight: 484.2; Mass/charge ratio: 484.0 (100.0%), 486.0 (50.8%), 482.0 (50.7%), 485.0 (22.5%), 483.0 (11.5%), 487.0 (11.2%), 488.0 (1.4%); Elemental analysis: C, 49.61; H, 5.00; Br, 33.00; N, 5.79; O, 6.61.

Example 259

N-(bicyclo[2.2.2]octan-1-ylmethyl)-6-bromo-1-(2-hydroxyethyl)-4-methyl-1H-indole-3-carboxamide

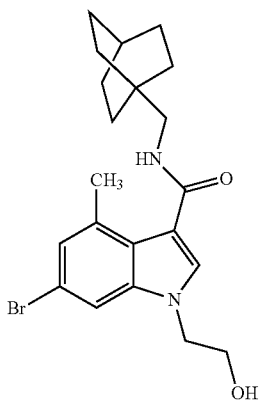 [SMILES: Cc1cc(Cl)cc2c1c(C(=O)NCC13CCC(CC1)CC3)cn2CCO]

Synthesised according to the procedure disclosed in Example 1 where X is 4-methyl-6-bromo indole, Y is O-t-butyldimethylsilyl-2-chloroethanol, and Z is bicyclo[2.2.2]octan-1-ylmethyl amine. Formula: $C_{21}H_{27}BrN_2O_2$; Molecular Weight: 419.4; Mass/charge ratio: 420.1 (100.0%), 418.1 (99.6%), 419.1 (23.7%), 421.1 (23.4%), 422.1 (3.1%); Elemental analysis: C, 60.15; H, 6.49; Br, 19.05; N, 6.68; O, 7.63.

Example 260

4-chloro-N-(cycloheptylmethyl)-1-methyl-1H-indazole-3-carboxamide)

Formula: $C_{17}H_{22}ClN_3O$; Molecular Weight: 319.8; Mass/charge ratio: 319.1 (100.0%), 321.1 (32.4%), 320.1 (19.5%), 322.1 (6.3%), 321.2 (1.6%); Elemental analysis: C, 63.84; H, 6.93; Cl, 11.08; N, 13.14; O, 5.00.

Example 261

4-bromo-N-(cycloheptylmethyl)-1-methyl-1H-indazole-3-carboxamide

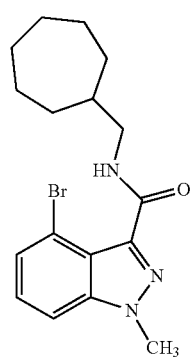

Formula: $C_{17}H_{22}BrN_3O$; Molecular Weight: 364.3; Mass/charge ratio: 363.1 (100.0%), 365.1 (99.3%), 364.1 (19.8%), 366.1 (19.4%), 367.1 (2.0%); Elemental analysis: C, 56.05; H, 6.09; Br, 21.93; N, 11.54; O, 4.39.

Example 262

N-(bicyclo[2.2.2]octan-1-ylmethyl)-4-chloro-1-methyl-1H-indazole-3-carboxamide

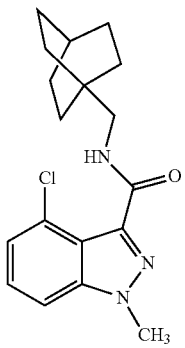 [SMILES: Cn1nc(C(=O)NCC23CCC(CC2)CC3)c2c(Cl)cccc21]

Formula: $C_{18}H_{22}ClN_3O$; Molecular Weight: 331.8; Mass/charge ratio: 331.1 (100.0%), 333.1 (32.4%), 332.1 (20.6%), 334.1 (6.7%), 333.2 (1.8%); Elemental analysis: C, 65.15; H, 6.68; Cl, 10.68; N, 12.66; O, 4.82.

Example 263

N-(bicyclo[2.2.2]octan-1-ylmethyl)-4-bromo-1-methyl-1H-indazole-3-carboxamide

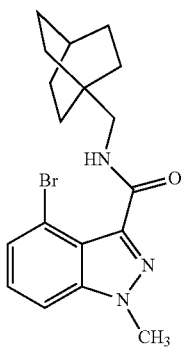 [SMILES: Cn1nc(C(=O)NCC23CCC(CC2)CC3)c2c(Br)cccc21]

Formula: $C_{18}H_{22}BrN_3O$; Molecular Weight: 376.3; Mass/charge ratio: 375.1 (100.0%), 377.1 (99.6%), 376.1 (20.9%), 378.1 (20.5%), 379.1 (2.2%); Elemental analysis: C, 57.45; H, 5.89; Br, 21.23; N, 11.17; O, 4.25.

Example 264

4-chloro-N-(cycloheptylmethyl)-1-methyl-1H-pyrrolo[2,3-b]pyridine-3-carboxamide)

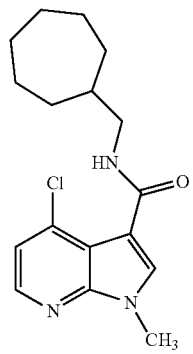

Synthesised according to the procedure disclosed in Example 2 where X is 4-chloro-7-azaindole, Y is methyl iodide, and Z is cycloheptylmethyl amine. Formula: $C_{17}H_{22}ClN_3O$; Molecular Weight: 319.8; Mass/charge ratio: 319.1 (100.0%), 321.1 (32.4%), 320.1 (19.5%), 322.1 (6.3%), 321.2 (1.6%); Elemental analysis: C, 63.84; H, 6.93; Cl, 11.08; N, 13.14; O, 5.00.

Example 265

4-bromo-N-(cycloheptylmethyl)-1-methyl-1H-pyrrolo[2,3-b]pyridine-3-carboxamide

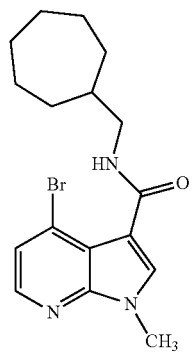

Synthesised according to the procedure disclosed in Example 2 where X is 4-bromo-7-azaindole, Y is methyl iodide, and Z is cycloheptylmethyl amine. Formula: $C_{17}H_{22}BrN_3O$; Molecular Weight: 364.3; Mass/charge ratio: 363.1 (100.0%), 365.1 (99.3%), 364.1 (19.8%), 366.1 (19.4%), 367.1 (2.0%); Elemental analysis: C, 56.05; H, 6.09; Br, 21.93; N, 11.54; O, 4.39.

Example 266

N-(bicyclo[2.2.2]octan-1-ylmethyl)-4-chloro-1-methyl-1H-pyrrolo[2,3-b]pyridine-3-carboxamide

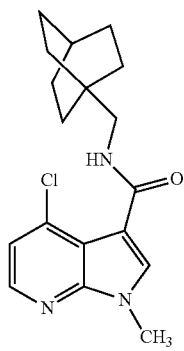 [SMILES: Cn1cc(C(=O)NCC23CCC(CC2)CC3)c2c(Cl)ccnc21]

Synthesised according to the procedure disclosed in Example 2 where X is 4-chloro-7-azaindole, Y is methyl iodide, and Z is bicyclo[2.2.2]octan-1-ylmethyl amine. Formula: $C_{18}H_{22}ClN_3O$; Molecular Weight: 331.8; Mass/charge ratio: 331.1 (100.0%), 333.1 (32.4%), 332.1 (20.6%), 334.1 (6.7%), 333.2 (1.8%); Elemental analysis: C, 65.15; H, 6.68; Cl, 10.68; N, 12.66; O, 4.82.

Example 267

N-(bicyclo[2.2.2]octan-1-ylmethyl)-4-bromo-1-methyl-1H-pyrrolo[2,3-b]pyridine-3-carboxamide

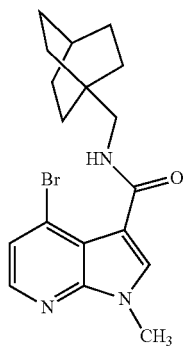 [SMILES: Cn1cc(C(=O)NCC23CCC(CC2)CC3)c2c(Br)ccnc21]

Synthesised according to the procedure disclosed in Example 2 where X is 4-bromo-7-azaindole, Y is methyl iodide, and Z is bicyclo[2.2.2]octan-1-ylmethyl amine. Formula: $C_{18}H_{22}BrN_3O$; Molecular Weight: 376.3; Mass/charge ratio: 375.1 (100.0%), 377.1 (99.6%), 376.1 (20.9%), 378.1 (20.5%), 379.1 (2.2%); Elemental analysis: C, 57.45; H, 5.89; Br, 21.23; N, 11.17; O, 4.25.

Example 268

4-chloro-N-(cycloheptylmethyl)-1-methyl-1H-pyrrolo[3,2-c]pyridine-3-carboxamide

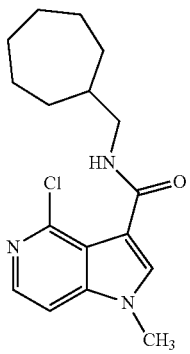 [SMILES: Cn1cc(C(=O)NCC2CCCCCC2)c2c(Cl)nccc21]

Synthesised according to the procedure disclosed in Example 2 where X is 4-chloro-5-azaindole, Y is methyl iodide, and Z is cycloheptylmethyl amine. Formula: $C_{17}H_{22}ClN_3O$; Molecular Weight: 319.1 (100.0%), 321.1 (32.4%), 320.1 (19.5%), 322.1 (6.3%), 321.2 (1.6%); Mass/charge ratio: Elemental analysis: C, 63.84; H, 6.93; Cl, 11.08; N, 13.14; O, 5.00.

Example 269

4-bromo-N-(cycloheptylmethyl)-1-methyl-1H-pyrrolo[3,2-c]pyridine-3-carboxamide)

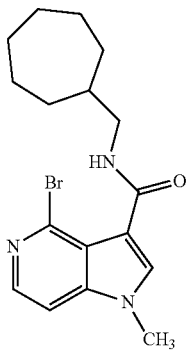

Synthesised according to the procedure disclosed in Example 2 where X is 4-bromo-5-azaindole, Y is methyl iodide, and Z is cycloheptylmethyl amine. Formula: $C_{17}H_{22}BrN_3O$; Molecular Weight: 364.3; Mass/charge ratio: 363.1 (100.0%), 365.1 (99.3%), 364.1 (19.8%), 366.1 (19.4%), 367.1 (2.0%); Elemental analysis: C, 56.05; H, 6.09; Br, 21.93; N, 11.54; O, 4.39.

Example 270

N-(bicyclo[2.2.2]octan-1-ylmethyl)-4-chloro-1-methyl-1H-pyrrolo[3,2-c]pyridine-3-carboxamide

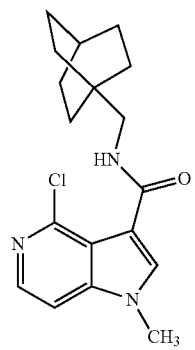 [SMILES: Cn1cc(C(=O)NCC23CCC(CC2)CC3)c2c(Cl)cncc21]

Synthesised according to the procedure disclosed in Example 2 where X is 4-chloro-5-azaindole, Y is methyl iodide, and Z is bicyclo[2.2.2]octan-1-ylmethyl amine. Formula: $C_{18}H_{22}ClN_3O$; Molecular Weight: 331.8; Mass/charge ratio: 331.1 (100.0%), 333.1 (32.4%), 332.1 (20.6%), 334.1 (6.7%), 333.2 (1.8%); Elemental analysis: C, 65.15; H, 6.68; Cl, 10.68; N, 12.66; O, 4.82.

Example 271

N-(bicyclo[2.2.2]octan-1-ylmethyl)-4-bromo-1-methyl-1H-pyrrolo[3,2-c]pyridine-3-carboxamide

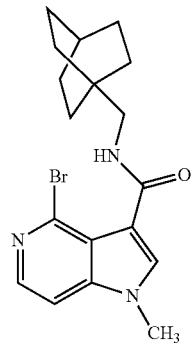

Synthesised according to the procedure disclosed in Example 2 where X is 4-bromo-5-azaindole, Y is methyl iodide, and Z is bicyclo[2.2.2]octan-1-ylmethyl amine. Formula: $C_{18}H_{22}BrN_3O$; Molecular Weight: 376.3; Mass/charge ratio: 375.1 (100.0%), 377.1 (99.6%), 376.1 (20.9%), 378.1 (20.5%), 379.1 (2.2%); Elemental analysis: C, 57.45; H, 5.89; Br, 21.23; N, 11.17; O, 4.25.

Example 272

4-chloro-N-(cycloheptylmethyl)-1-methyl-1H-pyrrolo[2,3-c]pyridine-3-carboxamide

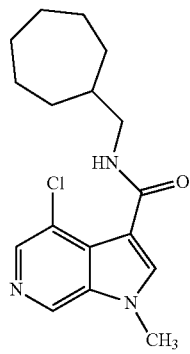

Synthesised according to the procedure disclosed in Example 2 where X is 4-chloro-6-azaindole, Y is methyl iodide, and Z is cycloheptylmethyl amine. Formula: $C_{17}H_{22}ClN_3O$; Molecular Weight: 319.8; Mass/charge ratio: 319.1 (100.0%), 321.1 (32.4%), 320.1 (19.5%), 322.1 (6.3%), 321.2 (1.6%); Elemental analysis: C, 63.84; H, 6.93; Cl, 11.08; N, 13.14; O, 5.00.

Example 273

4-bromo-N-(cycloheptylmethyl)-1-methyl-1H-pyrrolo[2,3-c]pyridine-3-carboxamide

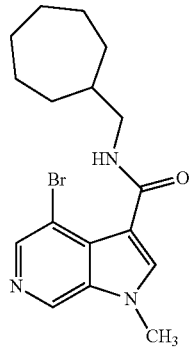

Synthesised according to the procedure disclosed in Example 2 where X is 4-bromo-6-azaindole, Y is methyl iodide, and Z is cycloheptylmethyl amine. Formula: $C_{17}H_{22}BrN_3O$; Molecular Weight: 364.3; Mass/charge ratio: 363.1 (100.0%), 365.1 (99.3%), 364.1 (19.8%), 366.1 (19.4%), 367.1 (2.0%); Elemental analysis: C, 56.05; H, 6.09; Br, 21.93; N, 11.54; O, 4.39.

Example 274

N-(bicyclo[2.2.2]octan-1-ylmethyl)-4-chloro-1-methyl-1H-pyrrolo[2,3-c]pyridine-3-carboxamide

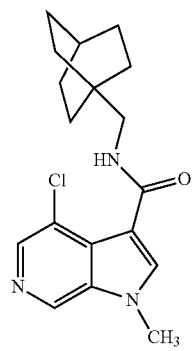

Synthesised according to the procedure disclosed in Example 2 where X is 4-chloro-6-azaindole, Y is methyl iodide, and Z is bicyclo[2.2.2]octan-1-ylmethyl amine. Formula: $C_{18}H_{22}ClN_3O$; Molecular Weight: 331.8; Mass/charge ratio: 331.1 (100.0%), 333.1 (32.4%), 332.1 (20.6%), 334.1 (6.7%), 333.2 (1.8%); Elemental analysis: C, 65.15; H, 6.68; Cl, 10.68; N, 12.66; O, 4.82.

Example 275

N-(bicyclo[2.2.2]octan-1-ylmethyl)-4-bromo-1-methyl-1H-pyrrolo[2,3-c]pyridine-3-carboxamide

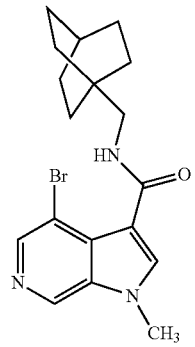 [SMILES: Cn1cc(C(=O)NCC23CCC(CC2)CC3)c2c(Br)cncc21]

Synthesised according to the procedure disclosed in Example 2 where X is 4-bromo-6-azaindole, Y is methyl iodide, and Z is bicyclo[2.2.2]octan-1-ylmethyl amine. Formula: $C_{18}H_{22}BrN_3O$; Molecular Weight: 376.3; Mass/charge ratio: 375.1 (100.0%), 377.1 (99.6%), 376.1 (20.9%), 378.1 (20.5%), 379.1 (2.2%); Elemental analysis: C, 57.45; H, 5.89; Br, 21.23; N, 11.17; O, 4.25.

Example 276

General Synthetic Procedure III

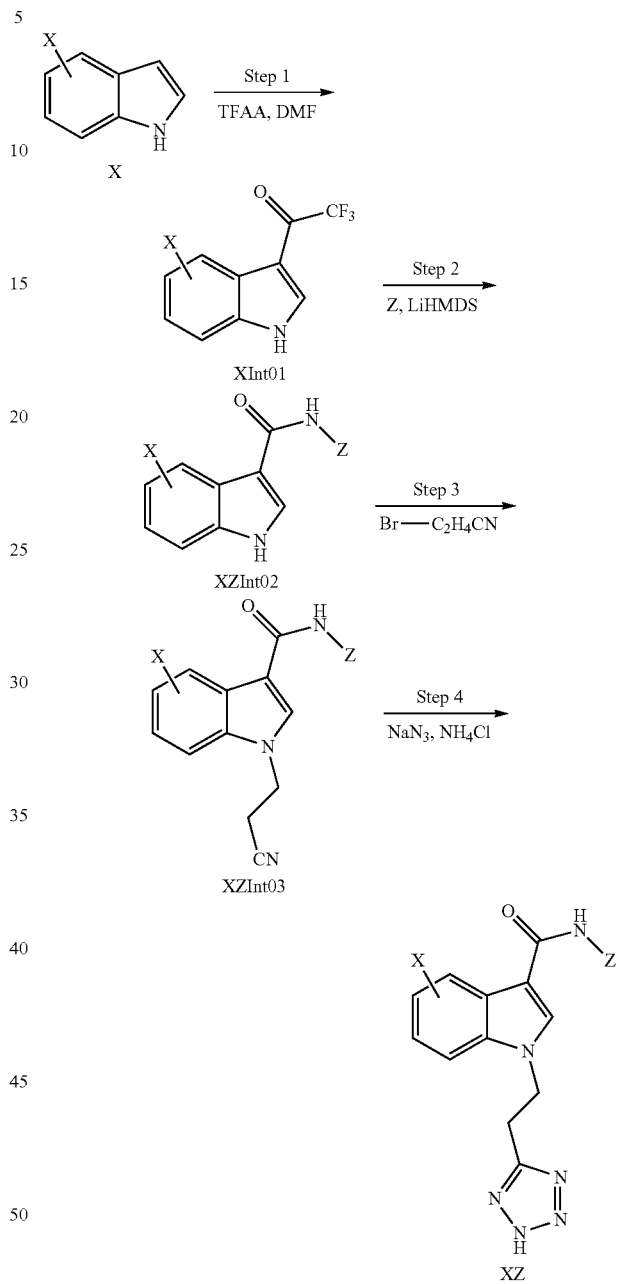

General Procedure for Preparation of XInt01:

A solution of the indole derivative X (1 eq) in dry dimethylformamide at 0° C. was added to trifluoroacetic anhydride (1.5 eq), stirred, and slowly warmed to room temperature. After completion of the reaction (1 h), the mixture was treated with ice-cold water to obtain a solid. The solid was separated by filtration and washed with water and n-pentane and dried under high vacuum to afford compound XInt01 (80-94% yield).

General Procedure for Preparation of XZInt02:

To a mixture of XInt01 (1 eq) and a cycloalkyl amine Z (1.5 eq) like cyclopentylmethyl amine, cyclopentylethyl amine, cyclohexylmethyl amine, cyclohexylethyl amine, cycloheptylmethyl amine, cycloheptylethyl amine, bicyclo[2.2.2]octan-1-ylmethyl amine) prepared according to the procedures disclosed in Unig and Kahanek (1957) Chem Ber 90:236, Delany and Berchtold (1988) J Org Chem 53:3262-3265, Grob et al. (1958) Hely Chim Acta 41:1191-1197, Whitney et al. (1970) J Med Chem 13:254-260), or bicyclo[2.2.2]octan-1-ylethyl amine, in dry THF at −78° C. was added lithium hexamethyldisilazide (3.5 eq). The resulting solution was warmed to room temperature and subsequently heated to reflux for 3 hours. Ice-cold water was then added to the reaction mixture and extracted 3 times with EtOAc. The combined organic layer was dried over anhydrous $Na_2SO_4$, concentrated under reduced pressure. The residue obtained was purified by flash chromatography ($SiO_2$, 100-200 mesh) to afford XZInt02 as a solid.

General Procedure for Preparation of XZInt03:

To a solution of XZInt02 in dimethylformamide, were added 3-bromopropionitrile and $K_2CO_3$ and the resultant reaction mixture was heated to 60° C. After 16 hours, the reaction mixture was diluted with ice water and extracted 3 times with EtOAc. The combined organic layer was dried over $Na_2SO_4$ and concentrated under reduced pressure to afford XZInt03 as a solid.

General Procedure for Preparation of XZ:

To a solution of XZInt03 in dimethylformamide were added $NH_4Cl$ and $NaN_3$ and the resultant reaction mixture was heated to 125° C. After 8 hours, the reaction mixture was diluted with ice water and extracted 3 times with EtOAc. The combined EtOAc layers were washed with brine, dried over anhydrous $Na_2SO_4$ and concentrated under reduced pressure. Purification by flash chromatography ($SiO_2$, 100-200 mesh, 4% MeOH in DCM) afforded XZ as a solid.

Example 277

1-(2-(2H-tetrazol-5-yl)ethyl)-4-chloro-N-(cycloheptylmethyl)-1H-indole-3-carboxamide

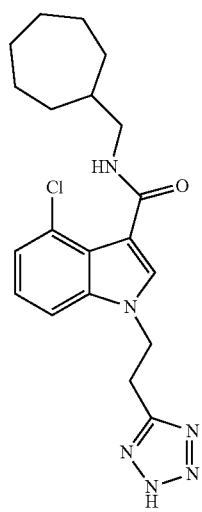 [SMILES: O=C(NCC1CCCCCC1)c1cn(CCc2nn[nH]n2)c2cccc(Cl)c12]

Synthesised according to the procedure disclosed in Example 276 where X is 4-chloro indole, and Z is cycloheptylmethyl amine. Formula: $C_{20}H_{25}ClN_6O$; Molecular Weight: 400.9; Mass/charge ratio: 400.2 (100.0%), 402.2 (35.0%), 401.2 (24.2%), 403.2 (8.0%); Elemental analysis: C, 59.92; H, 6.29; Cl, 8.84; N, 20.96; O, 3.99.

Example 278

1-(2-(2H-tetrazol-5-yl)ethyl)-4-bromo-N-(cycloheptylmethyl)-1H-indole-3-carboxamide

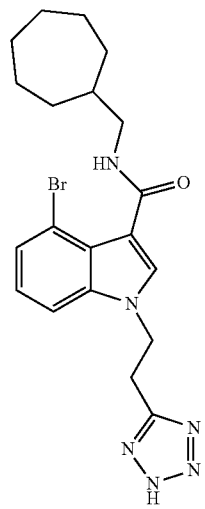

Synthesised according to the procedure disclosed in Example 276 where X is 4-bromo indole, and Z is cycloheptylmethyl amine. Formula: $C_{20}H_{25}BrN_6O$; Molecular Weight: 445.4; Mass/charge ratio: 446.1 (100.0%), 444.1 (99.7%), 445.1 (24.1%), 447.1 (23.7%), 448.1 (2.9%); Elemental analysis: C, 53.94; H, 5.66; Br, 17.94; N, 18.87; O, 3.59.

Example 279

1-(2-(2H-tetrazol-5-yl)ethyl)-N-(cycloheptylmethyl)-4-methyl-1H-indole-3-carboxamide

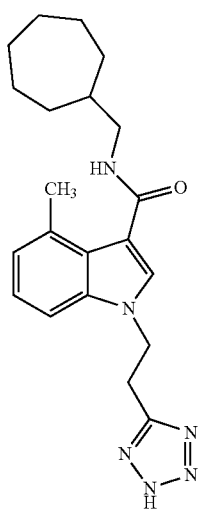

Synthesised according to the procedure disclosed in Example 276 where X is 4-methyl indole, and Z is cycloheptylmethyl amine. Formula: $C_{21}H_{28}N_6O$; Molecular Weight:

380.5; Mass/charge ratio: 380.2 (100.0%), 381.2 (25.3%), 382.2 (3.3%); Elemental analysis: C, 66.29; H, 7.42; N, 22.09; O, 4.20.

Example 280

1-(2-(2H-tetrazol-5-yl)ethyl)-N-(bicyclo[2.2.2]octan-1-ylmethyl)-4-chloro-1H-indole-3-carboxamide

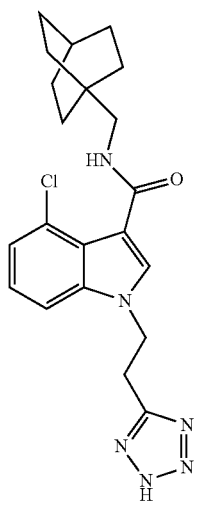 [SMILES: O=C(NCC12CCC(CC1)CC2)c1cn(CCc2nn[nH]n2)c2cccc(Cl)c12]

Synthesised according to the procedure disclosed in Example 276 where X is 4-chloro indole, and Z is bicyclo[2.2.2]octan-1-ylmethyl amine. Formula: $C_{21}H_{25}ClN_6O$; Molecular Weight: 412.9; Mass/charge ratio: 412.2 (100.0%), 414.2 (35.2%), 413.2 (25.3%), 415.2 (8.4%), 416.2 (1.1%); Elemental analysis: C, 61.08; H, 6.10; Cl, 8.59; N, 20.35; O, 3.87.

Example 281

1-(2-(2H-tetrazol-5-yl)ethyl)-N-(bicyclo[2.2.2]octan-1-ylmethyl)-4-bromo-1H-indole-3-carboxamide

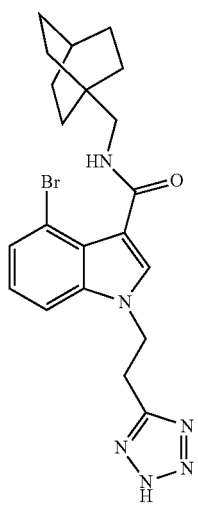 [SMILES: O=C(NCC12CCC(CC1)CC2)c1cn(CCc2nn[nH]n2)c2cccc(Br)c12]

Synthesised according to the procedure disclosed in Example 276 where X is 4-bromo indole, and Z is bicyclo[2.2.2]octan-1-ylmethyl amine. Formula: $C_{21}H_{25}BrN_6O$; Molecular Weight: 457.4; Mass/charge ratio: 458.1 (100.0%), 456.1 (99.5%), 457.1 (25.1%), 459.1 (24.7%), 460.1 (3.2%); Elemental analysis: C, 55.15; H, 5.51; Br, 17.47; N, 18.37; O, 3.50.

Example 282

1-(2-(2H-tetrazol-5-yl)ethyl)-N-(bicyclo[2.2.2]octan-1-ylmethyl)-4-methyl-1H-indole-3-carboxamide

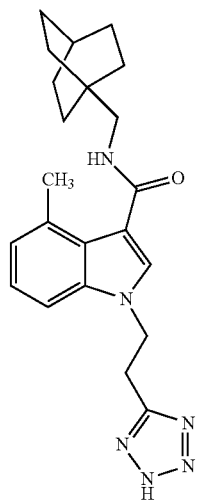 [SMILES: Cc1cccc2c1c(C(=O)NCC13CCC(CC1)CC3)cn2CCc1nn[nH]n1]

Synthesised according to the procedure disclosed in Example 276 where X is 4-methyl indole, and Z is bicyclo[2.2.2]octan-1-ylmethyl amine. Formula: $C_{22}H_{28}N_6O$; Molecular Weight: 392.5; Mass/charge ratio: 392.2 (100.0%), 393.2 (26.4%), 394.2 (3.5%); Elemental analysis: C, 67.32; H, 7.19; N, 21.41; O, 4.08.

Example 283

General Synthetic Procedure IV

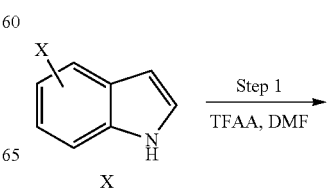

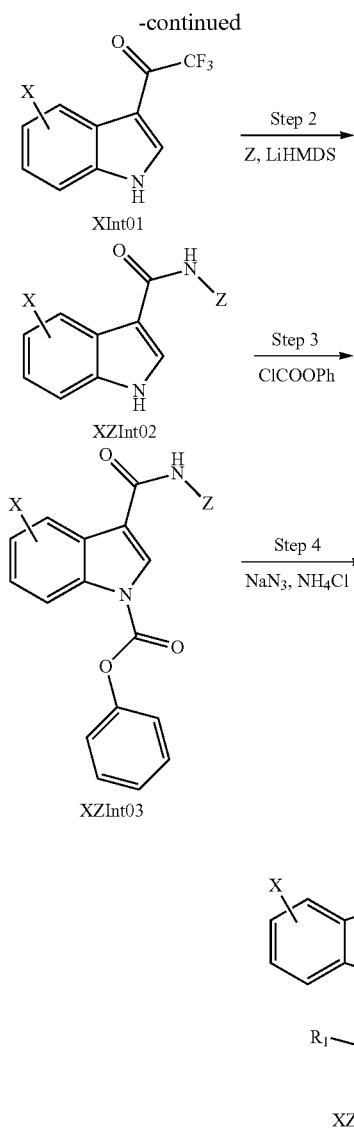

hexamethyldisilazide (3.5 eq). The resulting solution was warmed to room temperature and subsequently heated to reflux for 3 hours. Ice-cold water was then added to the reaction mixture and extracted 3 times with EtOAc. The combined organic layer was dried over anhydrous $Na_2SO_4$, concentrated under reduced pressure. The residue obtained was purified by flash chromatography ($SiO_2$, 100-200 mesh) to afford XZInt02 as a solid.

General Procedure for Preparation of XZInt03:

To a solution of XZInt02 in THF at 0-5° C. were added Et3N and phenyl chloroformate (ClCOOPh). The resultant reaction mixture was slowly warmed to room temperature and stirred further. After 2 hours, the reaction mixture was concentrated under reduced pressure. The residue obtained was diluted with water and extracted 3 times with EtOAc. The combined EtOAc layer was washed with brine and dried over anhydrous $Na_2SO_4$ and concentrated under reduced pressure to afford the title XZInt03 as a solid.

General Procedure for Preparation of $XZNR_1R_2$

To solution of XZInt03, Et3N, and methylamine hydrochloride, dimethylamine hydrochloride, or N-ethyl methylamine in DMSO was stirred at room temperature for 16 hours. After completion of reaction (TLC), the reaction mixture was diluted with ice water and 3 times with EtOAc. The combined EtOAc layer was washed with brine, dried over anhydrous $Na_2SO_4$ and concentrated under reduced pressure. Purification by flash chromatography afforded the title compound $XZNR_1R_2$ as a solid.

Example 284

4-chloro-N3-(cycloheptylmethyl)-N1-methyl-1H-indole-1,3-dicarboxamide

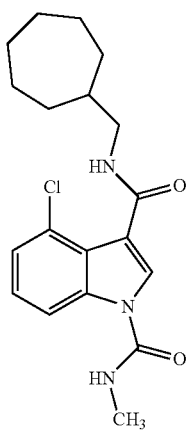

General Procedure for Preparation of XInt01:

A solution of the indole derivative X (1 eq) in dry dimethylformamide at 0° C. was added to trifluoroacetic anhydride (1.5 eq), stirred, and slowly warmed to room temperature. After completion of the reaction (1 h), the mixture was treated with ice-cold water to obtain a solid. The solid was separated by filtration and washed with water and n-pentane and dried under high vacuum to afford compound XInt01 (80-94% yield).

General Procedure for Preparation of XZInt02:

To a mixture of XInt01 (1 eq) and a cycloalkyl amine Z (1.5 eq) like cyclopentylmethyl amine, cyclopentylethyl amine, cyclohexylmethyl amine, cyclohexylethyl amine, cycloheptylmethyl amine, cycloheptylethyl amine, bicyclo[2.2.2]octan-1-ylmethyl amine (prepared according to the procedures disclosed in Unig and Kahanek (1957) Chem Ber 90:236, Delany and Berchtold (1988) J Org Chem 53:3262-3265, Grob et al. (1958) Hely Chim Acta 41:1191-1197, Whitney et al. (1970) J Med Chem 13:254-260), or bicyclo[2.2.2]octan-1-ylethyl amine, in dry THF at −78° C. was added lithium Synthesised according to the procedure disclosed in Example 283 where X is 4-chloro indole, Z is cycloheptylmethyl amine, and methylamine hydrochloride was used. Formula: $C_{19}H_{24}ClN_3O_2$; Molecular Weight: 361.9; Mass/charge ratio: 361.2 (100.0%), 363.2 (34.7%), 362.2 (22.0%), 364.2 (6.9%); Elemental analysis: C, 63.06; H, 6.68; Cl, 9.80; N, 11.61; O, 8.84.

Example 285

4-bromo-N3-(cycloheptylmethyl)-N1-methyl-1H-indole-1,3-dicarboxamide

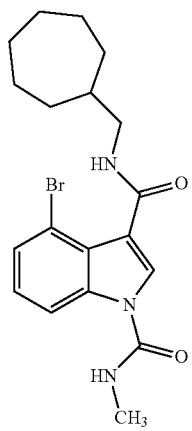 [SMILES: CNC(=O)n1cc(C(=O)NCC2CCCCCC2)c2c(Br)cccc21]

Synthesised according to the procedure disclosed in Example 283 where X is 4-bromo indole, Z is cycloheptylmethyl amine, and methylamine hydrochloride was used. Formula: $C_{19}H_{24}BrN_3O_2$; Molecular Weight: 406.3; Mass/charge ratio: 405.1 (100.0%), 407.1 (100.0%), 406.1 (22.0%), 408.1 (21.7%), 409.1 (2.7%); Elemental analysis: C, 56.16; H, 5.95; Br, 19.67; N, 10.34; O, 7.88.

Example 286

N3-(bicyclo[2.2.2]octan-1-ylmethyl)-4-chloro-N1-methyl-1H-indole-1,3-dicarboxamide

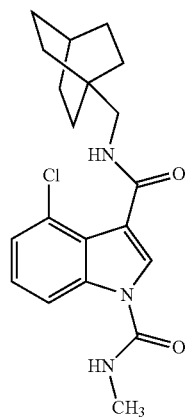 [SMILES: CNC(=O)n1cc(C(=O)NCC23CCC(CC2)CC3)c2c(Cl)cccc21]

Synthesised according to the procedure disclosed in Example 283 where X is 4-chloro indole, Z is bicyclo[2.2.2]octan-1-ylmethyl amine, and methylamine hydrochloride was used. Formula: $C_{20}H_{24}ClN_3O_2$; Molecular Weight: 373.9; Mass/charge ratio: 373.2 (100.0%), 375.2 (34.9%), 374.2 (23.1%), 376.2 (7.3%); Elemental analysis: C, 64.25; H, 6.47; Cl, 9.48; N, 11.24; O, 8.56.

Example 287

N3-(bicyclo[2.2.2]octan-1-ylmethyl)-4-bromo-N1-methyl-1H-indole-1,3-dicarboxamide

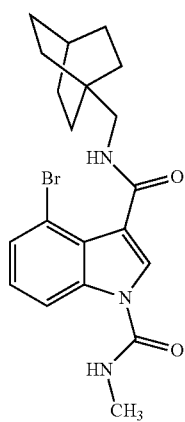 [SMILES: CNC(=O)n1cc(C(=O)NCC23CCC(CC2)CC3)c2c(Br)cccc21]

Synthesised according to the procedure disclosed in Example 283 where X is 4-bromo indole, Z is bicyclo[2.2.2]octan-1-ylmethyl amine, and methylamine hydrochloride was used. Formula: $C_{20}H_{24}BrN_3O_2$; Molecular Weight: 418.3; Mass/charge ratio: 419.1 (100.0%), 417.1 (99.8%), 418.1 (23.0%), 420.1 (22.7%), 421.1 (2.9%); Elemental analysis: C, 57.42; H, 5.78; Br, 19.10; N, 10.04; O, 7.65.

Example 288

4-chloro-N3-(cycloheptylmethyl)-N1,N1-dimethyl-1H-indole-1,3-dicarboxamide

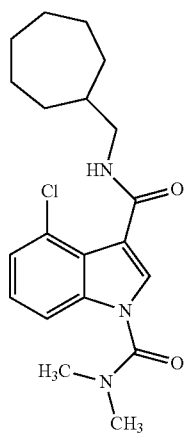 [SMILES: CN(C)C(=O)n1cc(C(=O)NCC2CCCCCC2)c2c(Cl)cccc21]

Synthesised according to the procedure disclosed in Example 283 where X is 4-chloro indole, Z is cycloheptylmethyl amine, and dimethylamine hydrochloride was used. Formula: $C_{20}H_{26}ClN_3O_2$; Molecular Weight: 375.9; Mass/charge ratio: 375.2 (100.0%), 377.2 (34.9%), 376.2 (23.1%), 378.2 (7.7%); Elemental analysis: C, 63.91; H, 6.97; Cl, 9.43; N, 11.18; O, 8.51.

Example 289

4-bromo-N3-(cycloheptylmethyl)-N1,N1-dimethyl-1H-indole-1,3-dicarboxamide

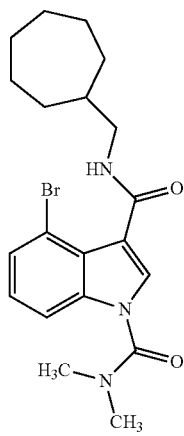 [SMILES: CN(C)C(=O)n1cc(C(=O)NCC2CCCCCC2)c2c(Br)cccc21]

Synthesised according to the procedure disclosed in Example 283 where X is 4-bromo indole, Z is cycloheptylmethyl amine, and dimethylamine hydrochloride was used. Formula: $C_{20}H_{26}BrN_3O_2$; Molecular Weight: 420.3; Mass/charge ratio: 421.1 (100.0%), 419.1 (99.8%), 420.1 (23.1%), 422.1 (22.7%), 423.1 (2.9%); Elemental analysis: C, 57.15; H, 6.23; Br, 19.01; N, 10.00; O, 7.61.

Example 290

N3-(bicyclo[2.2.2]octan-1-ylmethyl)-4-chloro-N1,N1-dimethyl-1H-indole-1,3-dicarboxamide

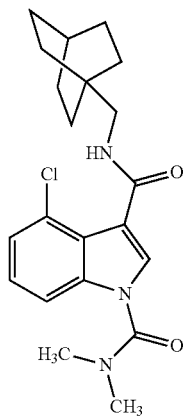 [SMILES: CN(C)C(=O)n1cc(C(=O)NCC23CCC(CC2)CC3)c2c(Cl)cccc21]

Synthesised according to the procedure disclosed in Example 283 where X is 4-chloro indole, Z is bicyclo[2.2.2]octan-1-ylmethyl amine, and dimethylamine hydrochloride was used. Formula: $C_{21}H_{26}ClN_3O_2$; Molecular Weight: 387.9; Mass/charge ratio: 387.2 (100.0%), 389.2 (35.2%), 388.2 (24.2%), 390.2 (8.0%), 391.2 (1.0%); Elemental analysis: C, 65.02; H, 6.76; Cl, 9.14; N, 10.83; O, 8.25.

Example 291

N3-(bicyclo[2.2.2]octan-1-ylmethyl)-4-bromo-N1,N1-dimethyl-1H-indole-1,3-dicarboxamide

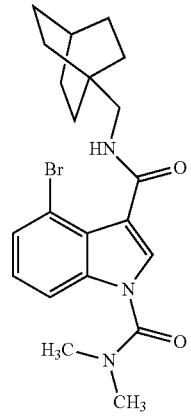 [SMILES: CN(C)C(=O)n1cc(C(=O)NCC23CCC(CC2)CC3)c2c(Br)cccc21]

Synthesised according to the procedure disclosed in Example 283 where X is 4-bromo indole, Z is bicyclo[2.2.2]octan-1-ylmethyl amine, and dimethylamine hydrochloride was used. Formula: $C_{21}H_{26}BrN_3O_2$; Molecular Weight: 432.4; Mass/charge ratio: 433.1 (100.0%), 431.1 (99.5%), 432.1 (24.1%), 434.1 (23.7%), 435.1 (3.1%); Elemental analysis: C, 58.34; H, 6.06; Br, 18.48; N, 9.72; O, 7.40.

Example 292

4-chloro-N3-(cycloheptylmethyl)-N1-ethyl-N1-methyl-1H-indole-1,3-dicarboxamide

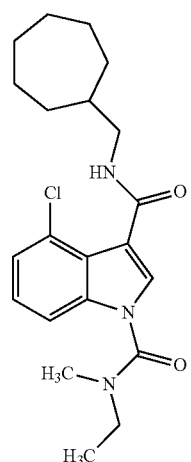

Synthesised according to the procedure disclosed in Example 283 where X is 4-chloro indole, Z is cycloheptylmethyl amine, and N-ethyl methylamine was used. Formula: $C_{21}H_{28}ClN_3O_2$, Molecular Weight: 389.9; Mass/charge ratio: 389.2 (100.0%), 391.2 (35.2%), 390.2 (24.2%), 392.2 (8.0%), 393.2 (1.1%); Elemental analysis: C, 64.69; H, 7.24; Cl, 9.09; N, 10.78; O, 8.21.

Example 293

4-bromo-N3-(cycloheptylmethyl)-N1-ethyl-N1-methyl-1H-indole-1,3-dicarboxamide

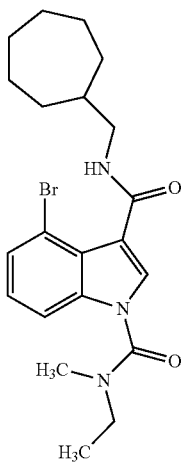 [SMILES: CCN(C)C(=O)n1cc(C(=O)NCC2CCCCCC2)c2c(Br)cccc21]

Synthesised according to the procedure disclosed in Example 283 where X is 4-bromo indole, Z is cycloheptylmethyl amine, and N-ethyl methylamine was used. Formula: $C_{21}H_{28}BrN_3O_2$; Molecular Weight: 434.4; Mass/charge ratio: 435.1 (100.0%), 433.1 (99.5%), 434.1 (24.1%), 436.1 (23.7%), 437.1 (3.1%); Elemental analysis: C, 58.07; H, 6.50; Br, 18.40; N, 9.67; O, 7.37.

Example 294

N3-(bicyclo[2.2.2]octan-1-ylmethyl)-4-chloro-N1-ethyl-N1-methyl-1H-indole-1,3-dicarboxamide

Synthesised according to the procedure disclosed in Example 283 where X is 4-chloro indole, Z is bicyclo[2.2.2]octan-1-ylmethyl amine, and N-ethyl methylamine was used. Formula: $C_{22}H_{28}ClN_3O_2$; Molecular Weight: 401.9; Mass/charge ratio: 401.2 (100.0%), 403.2 (35.4%), 402.2 (25.3%), 404.2 (8.4%), 405.2 (1.1%); Elemental analysis: C, 65.74; H, 7.02; Cl, 8.82; N, 10.45; O, 7.96.

Example 295

N3-(bicyclo[2.2.2]octan-1-ylmethyl)-4-bromo-N1-ethyl-N1-methyl-1H-indole-1,3-dicarboxamide

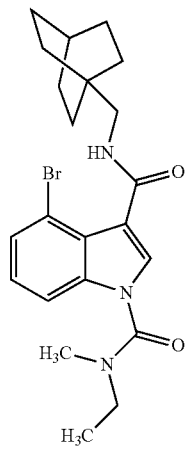 [SMILES: CCN(C)C(=O)n1cc(C(=O)NCC23CCC(CC2)CC3)c2c(Br)cccc21]

Synthesised according to the procedure disclosed in Example 283 where X is 4-bromo indole, Z is bicyclo[2.2.2]octan-1-ylmethyl amine, and N-ethyl methylamine was used. Formula: $C_{22}H_{28}BrN_3O_2$; Molecular Weight: 446.4; Mass/charge ratio: 447.1 (100.0%), 445.1 (99.2%), 446.1 (25.1%), 448.1 (24.8%), 449.1 (3.4%); Elemental analysis: C, 59.20; H, 6.32; Br, 17.90; N, 9.41; O, 7.17.

Example 296

4-chloro-N-(cycloheptylmethyl)-1-(1,3-dihydroxypropan-2-yl)-1H-indole-3-carboxamide

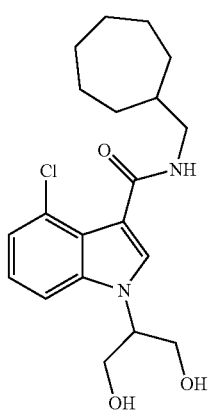 [SMILES: O=C(NCC1CCCCCC1)c1cn(C(CO)CO)c2cccc(Cl)c12]

Synthesised similar to the procedure disclosed in Example 1 where X is 4-chloro indole, Y is 2-chloroethylmalonate, and Z is cycloheptylmethyl amine. The resulting product XYZ is stirred for 30 minutes at −10° C. in methanol and NaBH4 and then slowly warmed to room temperature and stirred for 2 hour. The reaction mixture is then treated with a 1N aqueous HCl solution (pH ~8) and concentrated to obtain a residue that is taken up in water and acidified with 1N aqueous HCl solution (pH ~6.5 to 7). The formed precipitate is then collected by filtration, washed with water, pet ether, ethyl acetate and finally with n-Pentane, then dried under vacuum. Formula: $C_{20}H_{27}ClN_2O_3$; Molecular Weight: 378.89; Mass/charge ratio: 378.17 (100.0%), 380.17 (32.1%), 379.17 (22.4%), 381.17 (7.3%), 380.18 (2.9%); Elemental analysis: C, 63.40; H, 7.18; Cl, 9.36; N, 7.39; O, 12.67.

Example 297

Therapeutic Effect in Multiple Sclerosis

The therapeutic effects of the compounds of the present invention were assessed in a mouse model of relapsing-remitting multiple sclerosis MS. The relapsing-remitting experimental autoimmune encephalomyelitis (EAE) which develops in SJL mice after immunization with the Proteolipid Protein $PLP_{139-151}$ and Complete Freund's Adjuvant (CFA) is the mouse model which most closely resembles human remitting/relapsing MS (see Webb et al (2004) J Neuroimmunol 153:108-121). In this example, a representative compound of the invention, 4-chloro-N-(cycloheptylmethyl)-1-(2-hydroxyethyl)-1H-indole-3-carboxamide (Example 54), was tested.

EAE was induced in SJL female mice (Jackson Labs), using a $PLP_{139-151}$/CFA Emulsion (Hooke Laboratories, Lawrence Mass.) according to the manufacturer's recommended protocol. Mice were injected subcutaneously at four sites (0.05 mL at each site) in the back with the emulsion. Two sites of injection were in the area of the upper back, approximately 1 cm caudal of the neck line. The other two sites were in the area of the lower back, approximately 2 cm cranial of the base of the tail. Individual animals were then examined daily for clinical signs of neurological deficits scored on a 0 to 5 scale as follows: 0, no abnormality; 0.5, stiff tail; 1, limp tail; 1.5, limp tail with inability to right; 2, paralysis of one limb; 2.5, paralysis of one limb and weakness of one other limb; 3, complete paralysis of both hind limbs; 4, moribund; 5, death. Daily scoring for signs of EAE started on Day 7 after immunization with the first symptoms observed between Days 11 and 15 after immunization. Treatment for each animal began on the second day that the animal developed EAE symptoms. Vehicle (0.5% methylcellulose) or between 125 to 500 mg/kg of a compound of the present invention were administered twice daily by oral gavage. Dosing of all mice was at the same time (+/−1 hour) each day. There were at least 10 hours between morning and evening dose and not more than 14 hours between evening and morning dose. The effect of treatment on development of EAE relapses was evaluated by comparing incidence and severity of relapses, and the end scores between the compound-treated groups and the vehicle group. Incidence of relapse were compared using two-tailed Fisher's exact test and the end scores between vehicle and treatment groups were calculated using Wilcoxon's non-parametric test. Results are illustrated in FIGS. 3 and 4.

In the vehicle group, the mean day of EAE onset was 12 days after immunization. Mice subsequently developed severe EAE (FIG. 3). After partial or full recovery from the first wave, 50.0% of mice relapsed (FIG. 4). The criterion for relapse was an increase in EAE score of at least 1 point over the lowest score reached after the first wave of disease. The mean day of relapse for the mice that experienced a relapse was 22 days from immunisation. The average EAE score at the end of the study (on Day 40, the last day of scoring) for the vehicle group was 1.34. A low average score at the end of the study is expected in this model, because only a few mice are severely sick at any one time during the relapse phase of disease.

In the treatment group, the mean day of EAE onset was 12 days after immunization. Mice subsequently developed severe EAE (FIG. 3). As expected, there was no significant different between vehicle and treatment group since treatment began only two day after animals had developed EAE symptoms. After partial or full recovery from the first wave, only 6% of treated animal developed relapses (p=0.0038). Only one mouse from the group relapsed on day 40 (FIG. 4). The delay in relapse compared to the vehicle group was statistically significant (p=0.0039). The average EAE score on Day 40 (end of the study) was 0.50 for the treatment group. This was significantly lower compared to the vehicle group (p=0.0021). These results support the use of the compounds of the present invention for treatment of multiple sclerosis in humans.

Example 298

Therapeutic Effect in Neuropathic Pain

The therapeutic effects of the compounds of the present invention were assessed in the lysophosphatidic acid (LPA)-induced neuropathy in mice. This model is commonly used to evaluate the potential analgesic activity of compounds designed to treat neuropathic pain in humans (Inoue et al. (2004) Nat Med 10: 712-718; Inoue et al. (2008). Mol Pain 4(6) doi:10.1186/1744-8069-4-6). In this example, a representative compound of the invention, 4-chloro-N-(cycloheptylmethyl)-1-(2-hydroxyethyl)-1H-indole-3-carboxamide (Example 54), was tested.

Neuropathic pain was induced in male, C57/Bl6 mice (Harlan) by an intrathecal injection of 1 nmol LPA (prepared in saline; ENZO) in a 5 µL volume into the spinal cord. Pre-LPA injection, post-LPA injection and post-treatment values for mechanical hyperalgesia were evaluated using a digital Randall-Selitto device (dRS; IITC Life Sciences). Paw compression threshold was measured once at each time point for the left and right paws. The stimulus was applied to the plantar surface of the hind paw by a dome-shaped tip placed between the 3rd and 4th metatarsus, and pressure was applied gradually over approximately 10 seconds. Measurements are taken from the first observed nocifensive behavior of vocalization, struggle or withdrawal. A cut-off value of 300 g was used to prevent injury to the animal. The readings from the left and right paws were averaged at each time point. Animals were assigned to vehicle and treatment group following the post-LPA paw compression threshold measurements so that each group had approximately the same pre-treatment paw compression thresholds.

Vehicle (0.5% carboxymethylcellulose (CMC)) or between 125-500 mg/kg of a compound of the present invention (dissolved in 0.5% CMC) were administered via oral gavage two days after LPA injection. As a comparator, 100 mg/kg of the analgesic gabapentin (dissolved in water; Letco) was administered via intraperitoneal injection two days after LPA injection. Mechanical hyperalgesia was measured 1 hour after treatment and efficacy was assessed using a one-way ANOVA at each time point comparing paw compression thresholds. If a significant main effect was detected, Dunnetts' post hoc test was used to compare treatment to vehicle treated animals. Results are illustrated in FIG. 5.

Two days after LPA injection, paw compression thresholds were measured and the behavioral responses were similar among vehicle, compound and gabapentin groups (FIG. 5; p=0.9995). The mean pre-treatment baseline paw compression thresholds for the vehicle treated group were significantly lower than the mean pre-LPA baseline paw compression thresholds, indicating the presence of mechanical hyperalgesia as a result of LPA injection. Oral administration of vehicle had no significant effect on mean paw compression thresholds compared to pre-treatment baseline values at any time point tested. A slight decrease in mechanical hyperalgesia was observed with gabapentin as indicated by increased paw compression thresholds 1 hour after dosing compared to pre-treatment baseline values. Oral administration of compounds of the present invention significantly increased mean paw compression thresholds 1 hour after dosing compared to pre-treatment baseline values (p<0.05) demonstrating analgesic effects against neuropathic pain.

Figure 1:
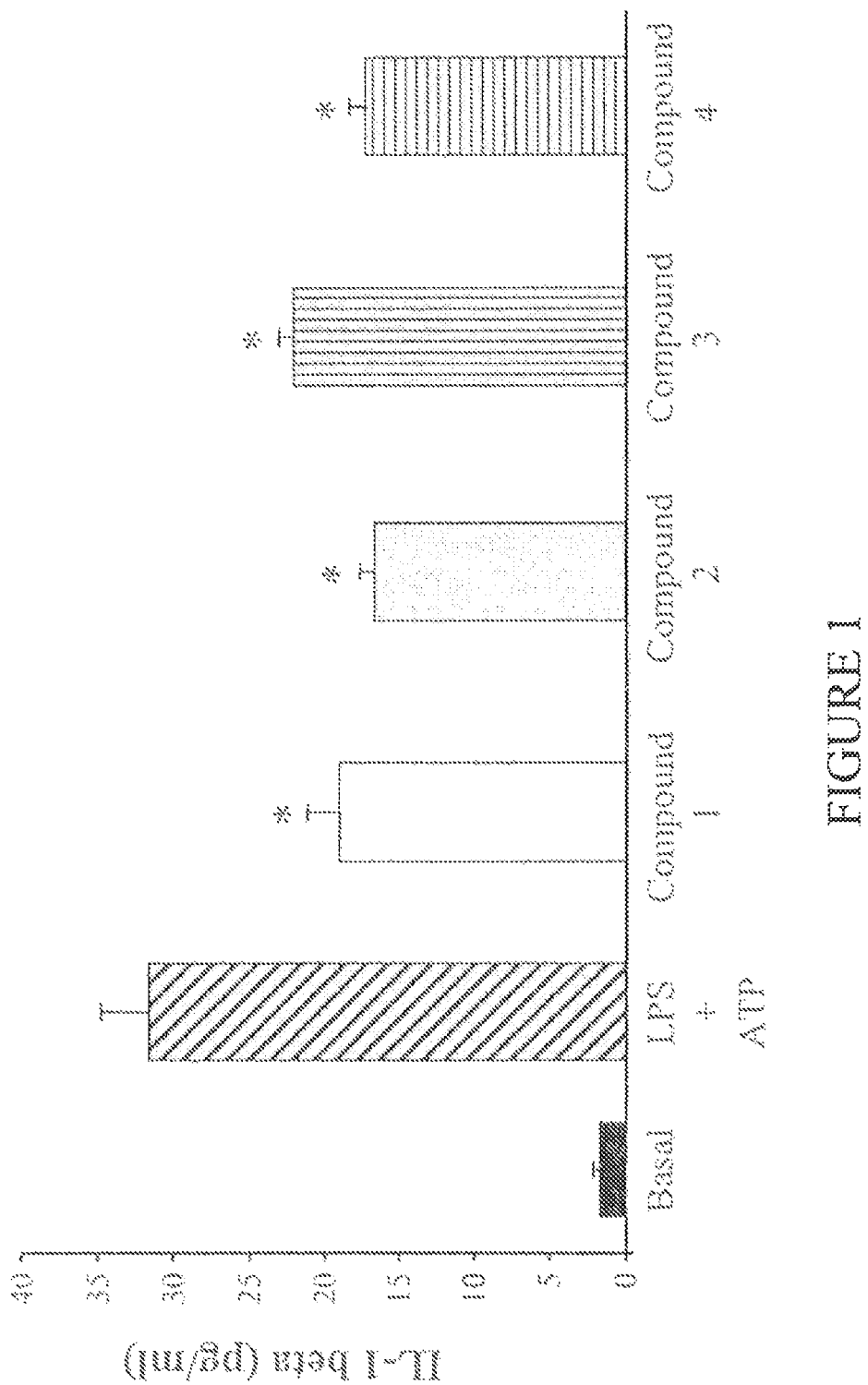
FIG. 1. Inhibition of IL-1 beta Secretion (* p<0.01).
Figure 2:
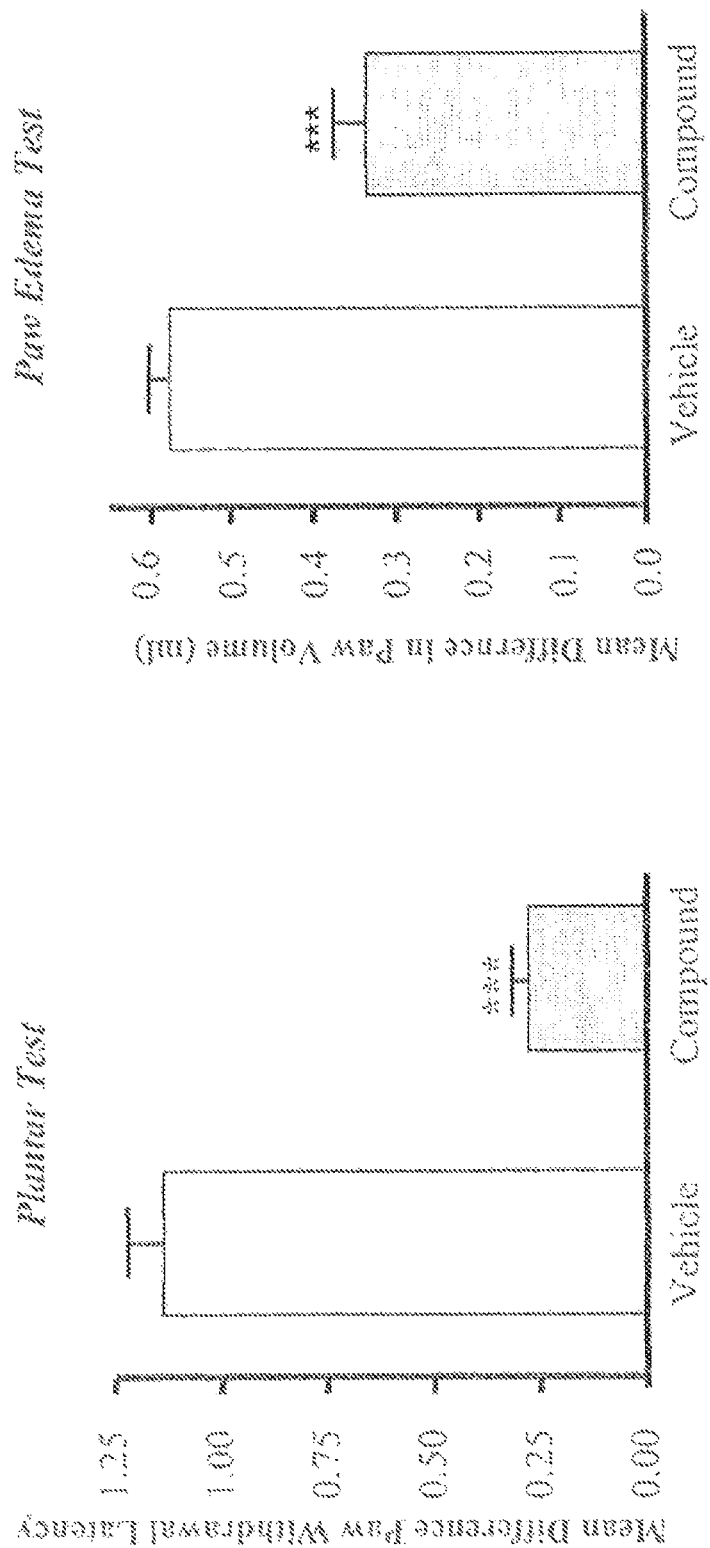
FIG. 2. Analgesic and Anti-inflammatory Effects on a Model of Inflammation (*** p<0.001).
Figure 3:
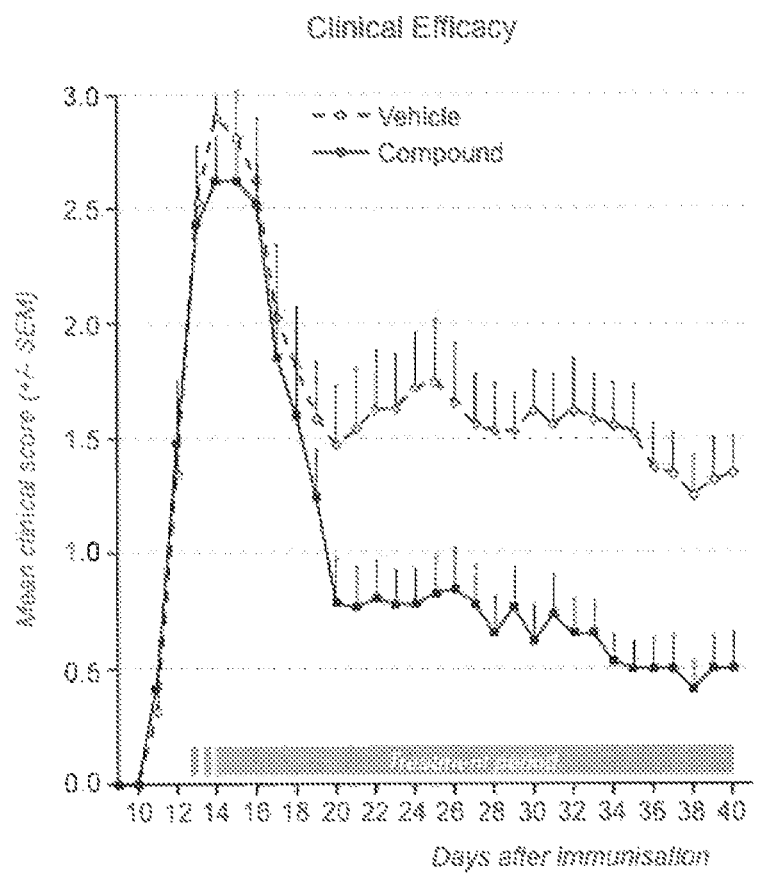
FIG. 3. EAE severity (mean clinical score) vs. time
Figure 4:
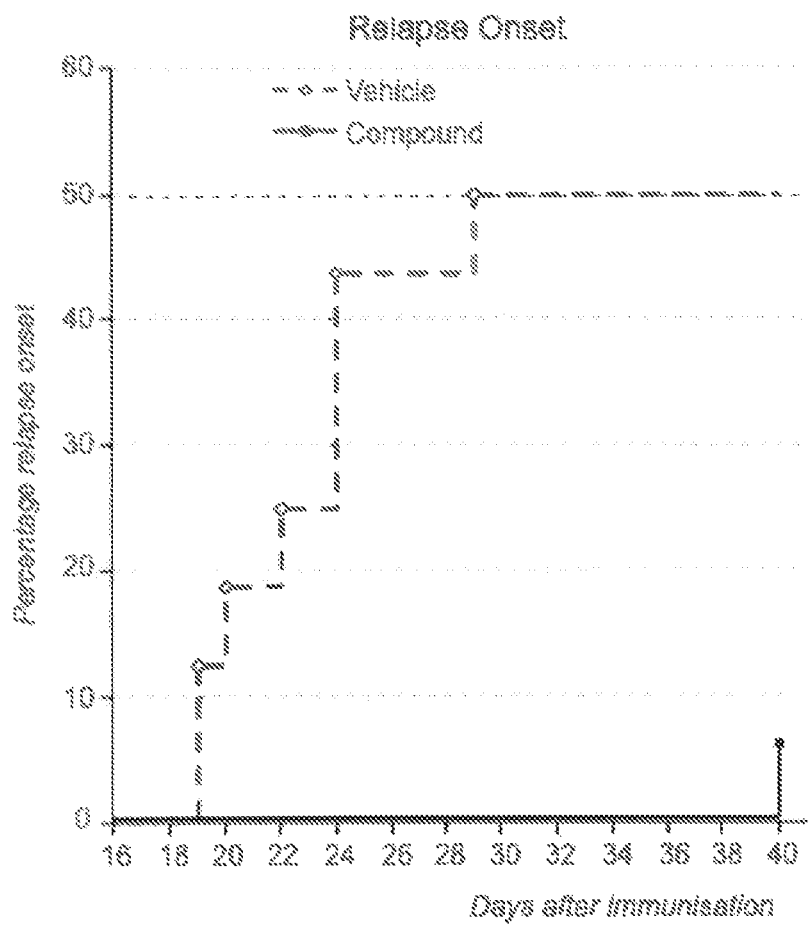
FIG. 4. Percentage of relapse vs. time
Figure 5:
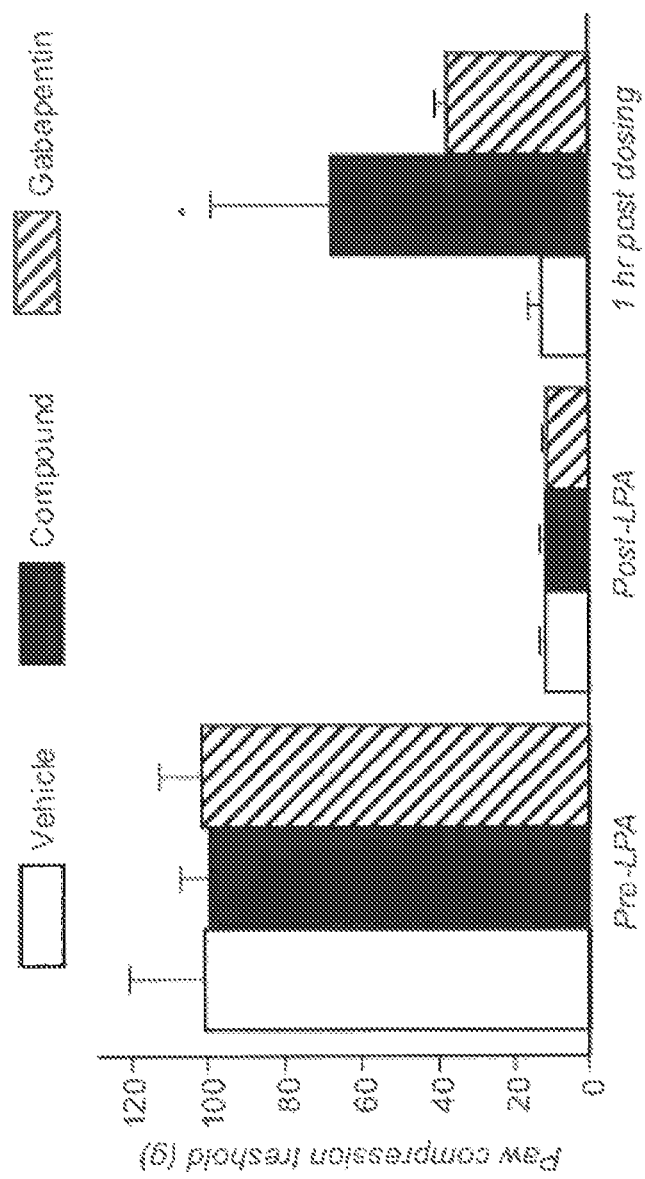
FIG. 5. Effect of vehicle, gabapentin and a compound of the present invention on LPA-induced mechanical hyperalgesia in the mice

The invention claimed is:

1. A method for treating multiple sclerosis, comprising administering to a subject in need thereof a therapeutically effective amount of a compound of compound of formula (I):

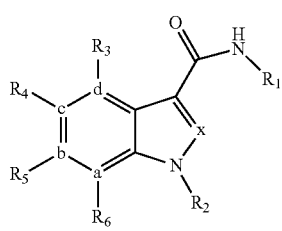

wherein $R_1$ is a cycloheptylmethyl, cycloheptylethyl, bicyclo[2.2.2]octan-1-ylmethyl, or bicyclo[2.2.2]octan-1-ylethyl group;

$R_2$ is selected from straight or branched $C_1$-$C_5$ alkyl which may optionally substituted with —OH, $C_1$-$C_5$ alkoxy, NH$_2$—, N(R$_a$)$_2$—, NHR$_a$—, CN—, CF$_3$, halogen, piperidino, morpholino, pyrrolidino, 5H-tetrazolylpropyl, methylcarbamoyl, dimethylcarbamoyl, or ethylmethylcarbamoyl, wherein Ra is hydrogen or $C_1$-$C_5$ alkyl;

$R_3$, $R_4$, $R_5$, $R_6$ are at each occurrence independently selected from hydrogen, halogen, methyl, hydroxy, methoxy, cyano, or trifluoromethyl; and a, b, c, d, x are carbon;

or a pharmaceutically acceptable salt or solvate thereof.

2. A method according to claim 1, wherein $R_1$ is bicyclo[2.2.2]octan-1-ylmethyl or bicyclo[2.2.2]octan-1-ylethyl.

3. A method according to claim 1, wherein $R_2$ is $C_1$-$C_5$ alkyl or $C_2$-$C_5$ hydroxyalkyl.

4. A method according to claim 1, wherein at least two of $R_3$, $R_4$, $R_5$ and $R_6$ are hydrogen.

5. A method for treating neuropathic pain, comprising administering to a subject in need thereof a therapeutically effective amount of a compound of compound of formula (I):

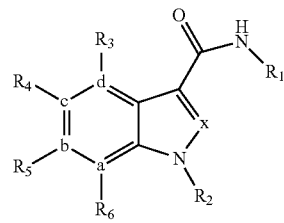

wherein $R_1$ is a cycloheptylmethyl, cycloheptylethyl, bicyclo[2.2.2]octan-1-ylmethyl, or bicyclo[2.2.2]octan-1-ylethyl group;

$R_2$ is selected from straight or branched $C_1$-$C_5$ alkyl which may optionally substituted with —OH, $C_1$-$C_5$ alkoxy, NH$_2$—, N(R$_a$)$_2$—, NHR$_a$—, CN—, CF$_3$, halogen, piperidino, morpholino, pyrrolidino, 5H-tetrazolylpropyl, methylcarbamoyl, dimethylcarbamoyl, or ethylmethylcarbamoyl, wherein Ra is hydrogen or $C_1$-$C_5$ alkyl;

$R_3$, $R_4$, $R_5$, $R_6$ are at each occurrence independently selected from hydrogen, halogen, methyl, hydroxy, methoxy, cyano, or trifluoromethyl; and a, b, c, d, x are carbon;

or a pharmaceutically acceptable salt or solvate thereof.

6. A method according to claim 5, wherein $R_1$ is bicyclo[2.2.2]octan-1-ylmethyl or bicyclo[2.2.2]octan-1-ylethyl.

7. A method according to claim 5, wherein $R_2$ is $C_1$-$C_5$ alkyl or $C_2$-$C_5$ hydroxyalkyl.

8. A method according to claim 5, wherein at least two of $R_3$, $R_4$, $R_5$ and $R_6$ are hydrogen.

9. A method for treating osteoporosis, comprising administering to a subject in need thereof a therapeutically effective amount of a compound of compound of formula (I):

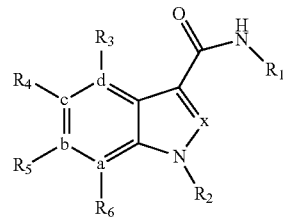

wherein $R_1$ is a cycloheptylmethyl, cycloheptylethyl, bicyclo[2.2.2]octan-1-ylmethyl, or bicyclo[2.2.2]octan-1-ylethyl group;

$R_2$ is selected from straight or branched $C_1$-$C_5$ alkyl which may optionally substituted with —OH, $C_1$-$C_5$ alkoxy, NH$_2$—, N(R$_a$)$_2$—, NHR$_a$—, CN—, CF$_3$, halogen, piperidino, morpholino, pyrrolidino, 5H-tetrazolylpropyl, methylcarbamoyl, dimethylcarbamoyl, or ethylmethylcarbamoyl, wherein Ra is hydrogen or $C_1$-$C_5$ alkyl;

$R_3$, $R_4$, $R_5$, $R_6$ are at each occurrence independently selected from hydrogen, halogen, methyl, hydroxy, methoxy, cyano, or trifluoromethyl; and a, b, c, d, x are carbon;

or a pharmaceutically acceptable salt or solvate thereof.

10. A method according to claim 9, wherein $R_1$ is bicyclo[2.2.2]octan-1-ylmethyl or bicyclo[2.2.2]octan-1-ylethyl.

11. A method according to claim 9, wherein $R_2$ is $C_1$-$C_5$ alkyl or $C_2$-$C_5$ hydroxyalkyl.

12. A method according to claim 9, wherein at least two of $R_3$, $R_4$, $R_5$ and $R_6$ are hydrogen.

13. A method for treating rheumatoid arthritis, chronic obstructive pulmonary disease, glaucoma, amyotrophic lateral sclerosis, Parkinson's disease, or Alzheimer disease, comprising administering to a subject in need thereof a therapeutically effective amount of a compound of compound of formula (I):

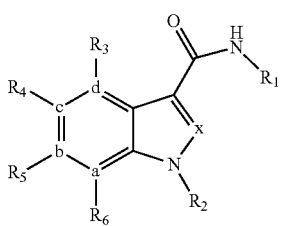

(I)

wherein
$R_1$ is a cycloheptylmethyl, cycloheptylethyl, bicyclo[2.2.2]octan-1-ylmethyl, or bicyclo[2.2.2]octan-1-ylethyl group;
$R_2$ is selected from straight or branched $C_1$-$C_5$ alkyl which may optionally substituted with —OH, $C_1$-$C_5$ alkoxy, $NH_2$—, $N(R_a)_2$—, $NHR_a$—, CN—, $CF_3$, halogen, piperidino, morpholino, pyrrolidino, 5H-tetrazolylpropyl, methylcarbamoyl, dimethylcarbamoyl, or ethylmethylcarbamoyl, wherein Ra is hydrogen or $C_1$-$C_5$ alkyl;
$R_3$, $R_4$, $R_5$, $R_6$ are at each occurrence independently selected from hydrogen, halogen, methyl, hydroxy, methoxy, cyano, or trifluoromethyl; and
a, b, c, d, x are carbon;
or a pharmaceutically acceptable salt or solvate thereof.

14. A method according to claim 13, wherein $R_1$ is bicyclo[2.2.2]octan-1-ylmethyl or bicyclo[2.2.2]octan-1-ylethyl.

15. A method according to claim 13, wherein $R_2$ is $C_1$-$C_5$ alkyl or $C_2$-$C_5$ hydroxyalkyl.

16. A method according to claim 13, wherein at least two of $R_3$, $R_4$, $R_5$ and $R_6$ are hydrogen.

* * * * *